(12) United States Patent
Lu et al.

(10) Patent No.: US 7,595,151 B2
(45) Date of Patent: Sep. 29, 2009

(54) METHODS AND COMPOSITIONS FOR DIAGNOSIS AND TREATMENT OF INFLUENZA

(75) Inventors: Peter S. Lu, Palo Alto, CA (US);
Michael P. Belmares, San Jose, CA (US); Dave Garman, San Jose, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 0 days.

(21) Appl. No.: 11/481,411

(22) Filed: Jul. 3, 2006

(65) Prior Publication Data

US 2007/0161078 A1    Jul. 12, 2007

Related U.S. Application Data

(60) Provisional application No. 60/792,274, filed on Apr. 14, 2006, provisional application No. 60/765,292, filed on Feb. 2, 2006, provisional application No. 60/726,377, filed on Oct. 13, 2005, provisional application No. 60/696,221, filed on Jul. 1, 2005.

(51) Int. Cl.
*C12Q 1/70* (2006.01)
*G01N 33/53* (2006.01)
*G01N 33/542* (2006.01)
*G01N 33/00* (2006.01)
*C12M 1/34* (2006.01)

(52) U.S. Cl. ............................. 435/5; 435/7.1; 435/7.9; 435/7.92; 435/287.1

(58) Field of Classification Search ....................... None
See application file for complete search history.

(56) References Cited

U.S. PATENT DOCUMENTS

2007/0224594 A1* 9/2007 Lu et al. ...................... 435/5

FOREIGN PATENT DOCUMENTS

| EP | 0 726 316 A2 | 8/1996 |
| EP | 0 293 184 A2 | 11/1998 |
| JP | 2006-067979 A | 3/2006 |
| JP | 2006 067979 A | 3/2006 |

OTHER PUBLICATIONS

Dundon, et al. Progressive truncation of the Non-Structural 1 gene of H7N1 avian influenza viruses following extensive circulation in poultry. Virus Research 119 (2006) 171-176.*

(Continued)

*Primary Examiner*—Mary E Mosher
*Assistant Examiner*—Stuart W Snyder
(74) *Attorney, Agent, or Firm*—Townsend and Townsend and Crew, LLP

(57) ABSTRACT

The invention provides method and compositions for determining the presence and amount of an influenza virus in a sample including high risk strains of Influenza A. Also provided are methods for determining whether a subject is infected with a influenza virus, as well as, the type and strain of the influenza virus. The methods involve contacting a sample from the subject with a PDZ polypeptides (PDZ) and/or PDZ ligands (PL) and determining whether binding interactions occur between PDZ and PL. Assays for identifying anti-viral agents are also provided, as well as, methods for using the compositions to alter PDZ binding to PL in influenza infected cells.

32 Claims, 14 Drawing Sheets

OTHER PUBLICATIONS

Birch-Machin, et al. Expression of the nonstructural protein NS1 of equine influenza A virus: Detection of Anti-NS1 antibody in post infection equine sera. Journal of Virological Methods 65 (1997) 255-263.*

Rozek, et al. Evaluation of Immunological Status of Horses Against Influenza Virus Based on the Presence of Antibodies Against NS1 and M1 Proteins. Bull. Vet. Inst. Pulawy 47, 315-324, 2003.*

Songyang, et al. Recognition of Unique Carboxyl-Terminal Motifs by Distinct PDZ Domains. Science 275, 73 (1997); 73-77.*

Basler, et al. Sequence of the 1918 pandemic influenza virus nonstructural gene (NS) segment and characterization of recombinant viruses bearing the 1918 NS genes. PNAS 2001; 98(5):2746-2751.*

Lipatov, et al. Neurovirulence in Mice of H5N1 Influenza Virus Genotypes Isolated from Hong Kong Poultry in 2001. Journal of Virology, 2003; 77(6):3816-3823.*

Obenauer, et al. Large-Scale Sequence Analysis of Avian Influenza Isolates. Science. 2006;311:1576-1580.*

Jackson, et al. A new influenza virus virulence determinant: the NS1 protein four C-terminal residues modulate pathogenicity. Proc Natl Acad Sci U S A. Mar. 18, 2008;105(11):4381-6.*

Cheng, et al. Genetic analysis of NS1 fragment of human H5N1 influenza virus isolated in Anhui province and its expression in *Escherichia coli*. Wei Sheng Wu Xue Bao. Jun. 4, 2007;47(3):418-22. Abstract Only.*

Nakajima, K., et al., "Evolution of the NS Genes of the Influenza A Viruses II Characteristics of the Amino Acid Changes in the NS1 Proteins of the Influenza A Viruses", *Virus Genes*, 1990, vol. 4, No. 1, pp. 15-26.

Obenauer, John C., et al., "Large-Scale Sequence Analysis of Avian Influenza Isolates", *Science*, Mar. 17, 2006, vol. 311, pp. 1576-1580.

Ozaki, H., et al., "Detection of antibodies to the nonstructural protein (NS1) of influenza A virus allows distinction between vaccinated and infected horses", *Veterinary Microbiology*, Sep. 20, 2001, vol. 82, No. 2, pp. 111-119.

Ozaki, H., "A Rapid and Highly Sensitive Method for Diagnosis of Equine Influenza by Antigen Detection Using Immino-PCR", *Jpn. J. Vet. Res.*, 48 (4) 187-195 (2001).

Shaw, M. W., et al., "Immunologic Studies on the Influenza A Virus Nonstructural Protein NS1", *Journal of Experimental Medicine*, Jul. 1982, vol. 156, pp. 243-254.

Songyang, Z., et al., "Recognition of Unique Carboxyl-Terminal Motifs by Distinct PDZ Domains", *Science*, Jan. 3, 1997, vol. 275, pp. 73-77.

Tumpey, Terrence M., et al., "Diagnostic Approach for Differentiating Infected from Vaccinated Poultry on the Basis of Antibodies to NS1, the Nonstructural Protein of Influenza A Virus", *Journal of Clinical Microbiology*, Feb. 2005, vol. 43, No. 2, pp. 676-683.

PCT International Preliminary Report on Patentability and Written Opinion of Jan. 10, 2008 for application No. PCT/US2006/026155.

Basler, C.F.., et al., "Sequence of the 1918 pandemic influenza virus nonstructural gene (NS) segment and characterization of the recombinant viruses bearing the 1918 NS genes," 2001, *PNAS*, 98(5): 2746-2751.

Bezprozvanny, I., et al., "Classification of PDZ domains," *FEBS Letters*, 2001, 509: 457-462.

Binns, M. M., et al., "Genetic and antigenic analysis of an equine influenza H3 isolate from the 1989 epidemic," *Archives of Virology*, 1993, 130: 33-43.

Birch-Machin, et al., "Expression of the nonstructural protein NS1 or equine influenza A virus: detection of Anti-NS1 antibody in the post infection equine sera," 1997, *Journal of Virological Methods*, 65:255-263.

Brown, L. E., et al., "Antigenic Variation in the Influenza A Virus Nonstructural Protein, NS1," *Virology*, 1983, 130:134-143.

Burrows, R., "Laboratory Diagnosis of Some Virus Infections of the Upper Respiratory Tract of the Horse," *Equine Vet J.*, 1968, 1, 32-38.

Dimmock, N. J., "New Virus-Specific Antigens in Cells Infected with Influenza Virus," 1969, *Virology*, 1969, 39:224-234.

Dundon, W. et al., "Progressive truncation of the Non-Structural 1 gene of H7N1 avian influenza viruses following extensive circulation in poultry," *Virus Research*, 2006, 119:171-176.

Lazarowitz, S. G., et al., "Influenza Virus Structural and Nonstructural Proteins in Infected Cells and Their Plasma Membranes," *Virology*, 1971, 46: 830-843.

Lin, D., et al., "Structure and Function of the NS1 Protein of Influenza A Virus," *Acta Biochimica et Biophysica Sinica*, Mar. 2007, 39(3):155-162.

Lipatov, A. et al., "Neurovirulence in Mice of H5N1 Influenza Virus Genotypes Isolated from Hong Kong Poultry in 2001," *Journal of Virology*, Mar. 2003, 77(6):3816-3823.

Marion, R.M., et al., "Influenza virus NS1 protein interacts with viral transcription-replication complexes in vivo," *Journal of General Virology*, 1997, 78:2447-2451.

Marion, R.M.,et al., "The N-terminal half of the influenza virus NS1 protein is sufficient to nuclear retention of mRNA and enhancement of viral nRNA translation," *Nucleic Acids Research*, 1997, 25(21):4271-4277.

Nakijima, K., et al., "Evolution of the NS Genes of the Influenza A Viruses. I. The Genetic Relatedness of the NS Genes of Animal Influenza Viruses," 1990, *Genes* 4:1, 5-13.

Obernauer, J., et al., "Large-Scale Sequence Analysis of Avian Influenza Isolates," *Science*, Mar. 17, 2006, 311: 1576-1580..

Rozek, W. et al., "Evaluation of Immunological Status of Horses Against Influenza Virus Based on the Presence of Antibodies Against NS1 and M1 Proteins," 2003, *Bull. Vet. Inst. Pulaway*, 47:315-324.

Satterly, N., et al., "Influenza virus targets the mRNA export machinery and the nuclear pore complex," *PNAS*, Feb. 6, 2007, 104(6)1853-1858.

Shaw, M. W., et al., "Immunologic studies on the influenza A virus nonstructural protein NS1," *Journal of Experimental Medicine*, 1982, 156:243-254.

Songyang, Z., et al., "Recognition of Unique Carbonxyl-Terminal Motifs by Distinct PDZ Domains," Jan. 3, 1997, *Science*, 275:73-77.

Wolff, T. et al., "NS1-Binding Protein (NS1-BP): a Novel Human Protein That Interacts with the Influenza A Virus Nonstructural NS1 Protein Is Relocalized in the Nuclei of Infected Cells," *Journal of Virology*, Sep. 1998, pp. 7170-7180.

Zezula, J., et al., "The $A_{2A}$-adenosine receptor: a GPCR with unique features?" *British Journal of Pharmacology*, 2008, 153:S184-S190.

Zhang, Y., et al., "Structures of a Human Papillomavirus (HPV) E6 Polypeptide Bound to MAGUK Proteins: Mechanism of Targeting Tumor Suppressors by a High-Risk HPV Oncoprotein," *Journal of Virology*, Apr. 2007, 81(7):3618-3626.

Non-Final Office Action mailed Aug. 30, 2006 in U.S. Appl. No. 10/847,818.

Response to Non-Final Office Action filed Jul. 05, 2007 in U.S. Appl. No. 10/847,818 (redacted).

Final Office Action mailed Jul. 27, 2007 in U.S. Appl. No. 10/847,818.

Response to Office Action filed Oct. 30, 2007 in U.S. Appl. No. 10/847,818 (redacted).

U.S. Appl. No. 10/847,818, unpublished, Lu, Peter S.

* cited by examiner

FIG. 7

SEQUENCE LISTING

```
<160> NUMBER OF SEQ ID NOS: 997

<210> SEQ ID NO 1
<211> LENGTH: 104
<212> TYPE: PRT
<213> ORGANISM: Artificial
<220> FEATURE:
<223> OTHER INFORMATION: PDZ domain PSD95 d2

<400> SEQUENCE: 1

Val Met Arg Arg Lys Pro Pro Ala Glu Lys Val Met Glu Ile Lys Leu
1               5                   10                  15

Ile Lys Gly Pro Lys Gly Leu Gly Phe Ser Ile Ala Gly Gly Val Gly
                20                  25                  30

Asn Gln His Ile Pro Gly Asp Asn Ser Ile Tyr Val Thr Lys Ile Ile
            35                  40                  45

Glu Gly Gly Ala Ala His Lys Asp Gly Arg Leu Gln Ile Gly Asp Lys
        50                  55                  60

Ile Leu Ala Val Asn Ser Val Gly Leu Glu Asp Val Met His Glu Asp
65                  70                  75                  80

Ala Val Ala Ala Leu Lys Asn Thr Tyr Asp Val Val Tyr Leu Lys Val
                85                  90                  95
```

```
Ala Lys Pro Ser Asn Ala Tyr Leu
            100

<210> SEQ ID NO 2
<211> LENGTH: 4
<212> TYPE: PRT
<213> ORGANISM: Artificial
<220> FEATURE:
<223> OTHER INFORMATION: PDZ Ligand Motif

<400> SEQUENCE: 2

Glu Ser Glu Val
1

<210> SEQ ID NO 3
<211> LENGTH: 4
<212> TYPE: PRT
<213> ORGANISM: Artificial
<220> FEATURE:
<223> OTHER INFORMATION: PDZ Ligand Motif

<400> SEQUENCE: 3

Glu Ser Glu Ile
1

<210> SEQ ID NO 4
<211> LENGTH: 4
<212> TYPE: PRT
<213> ORGANISM: Artificial
<220> FEATURE:
<223> OTHER INFORMATION: PDZ Ligand Motif

<400> SEQUENCE: 4

Glu Ser Lys Val
1

<210> SEQ ID NO 5
<211> LENGTH: 4
<212> TYPE: PRT
<213> ORGANISM: Artificial
<220> FEATURE:
<223> OTHER INFORMATION: PDZ Ligand Motif

<400> SEQUENCE: 5

Thr Ser Glu Val
1

<210> SEQ ID NO 6
<211> LENGTH: 4
<212> TYPE: PRT
<213> ORGANISM: Artificial
<220> FEATURE:
<223> OTHER INFORMATION: PDZ Ligand Motif

<400> SEQUENCE: 6

Gly Ser Glu Val
1

<210> SEQ ID NO 7
<211> LENGTH: 4
<212> TYPE: PRT
<213> ORGANISM: Artificial
<220> FEATURE:
<223> OTHER INFORMATION: PDZ Ligand Motif

<400> SEQUENCE: 7
```

```
Arg Ser Glu Val
1

<210> SEQ ID NO 8
<211> LENGTH: 4
<212> TYPE: PRT
<213> ORGANISM: Artificial
<220> FEATURE:
<223> OTHER INFORMATION: PDZ Ligand Motif

<400> SEQUENCE: 8

Arg Ser Lys Val
1

<210> SEQ ID NO 9
<211> LENGTH: 4
<212> TYPE: PRT
<213> ORGANISM: Artificial
<220> FEATURE:
<223> OTHER INFORMATION: PDZ Ligand Motif

<400> SEQUENCE: 9

Gly Ser Glu Ile
1

<210> SEQ ID NO 10
<211> LENGTH: 4
<212> TYPE: PRT
<213> ORGANISM: Artificial
<220> FEATURE:
<223> OTHER INFORMATION: PDZ Ligand Motif

<400> SEQUENCE: 10

Gly Ser Lys Val
1

<210> SEQ ID NO 11
<211> LENGTH: 4
<212> TYPE: PRT
<213> ORGANISM: Artificial
<220> FEATURE:
<223> OTHER INFORMATION: PDZ Ligand Motif

<400> SEQUENCE: 11

Asn Ile Cys Ile
1

<210> SEQ ID NO 12
<211> LENGTH: 4
<212> TYPE: PRT
<213> ORGANISM: Artificial
<220> FEATURE:
<223> OTHER INFORMATION: PDZ Ligand Motif

<400> SEQUENCE: 12

Thr Ile Cys Ile
1

<210> SEQ ID NO 13
<211> LENGTH: 4
<212> TYPE: PRT
<213> ORGANISM: Artificial
<220> FEATURE:
<223> OTHER INFORMATION: PDZ Ligand Motif

<400> SEQUENCE: 13

Arg Ile Cys Ile
```

```
<210> SEQ ID NO 14
<211> LENGTH: 4
<212> TYPE: PRT
<213> ORGANISM: Artificial
<220> FEATURE:
<223> OTHER INFORMATION: PDZ Ligand Motif

<400> SEQUENCE: 14

Asp Met Ala Leu
1

<210> SEQ ID NO 15
<211> LENGTH: 4
<212> TYPE: PRT
<213> ORGANISM: Artificial
<220> FEATURE:
<223> OTHER INFORMATION: PDZ Ligand Motif

<400> SEQUENCE: 15

Asp Met Thr Leu
1

<210> SEQ ID NO 16
<211> LENGTH: 4
<212> TYPE: PRT
<213> ORGANISM: Artificial
<220> FEATURE:
<223> OTHER INFORMATION: PDZ Ligand Motif

<400> SEQUENCE: 16

Asp Ile Ala Leu
1

<210> SEQ ID NO 17
<211> LENGTH: 4
<212> TYPE: PRT
<213> ORGANISM: Artificial
<220> FEATURE:
<223> OTHER INFORMATION: PDZ Ligand Motif

<400> SEQUENCE: 17

Asp Leu Asp Tyr
1

<210> SEQ ID NO 18
<211> LENGTH: 4
<212> TYPE: PRT
<213> ORGANISM: Artificial
<220> FEATURE:
<223> OTHER INFORMATION: PDZ Ligand Motif

<400> SEQUENCE: 18

Ser Ile Cys Leu
1

<210> SEQ ID NO 19
<211> LENGTH: 4
<212> TYPE: PRT
<213> ORGANISM: Artificial
<220> FEATURE:
<223> OTHER INFORMATION: PDZ Ligand Motif
<220> FEATURE:
<221> NAME/KEY: MISC_FEATURE
<222> LOCATION: (4)..(4)
<223> OTHER INFORMATION: X may be V, I or A
```

-continued

<400> SEQUENCE: 19

Glu Ser Glu Xaa
1

<210> SEQ ID NO 20
<211> LENGTH: 10
<212> TYPE: PRT
<213> ORGANISM: Artificial
<220> FEATURE:
<223> OTHER INFORMATION: HA0 cleavage site sequence

<400> SEQUENCE: 20

Pro Glu Ile Pro Lys Gly Arg Gly Leu Phe
1               5                   10

<210> SEQ ID NO 21
<211> LENGTH: 10
<212> TYPE: PRT
<213> ORGANISM: Artificial
<220> FEATURE:
<223> OTHER INFORMATION: HA0 cleavage site sequence

<400> SEQUENCE: 21

Pro Glu Asn Pro Lys Gly Arg Gly Leu Phe
1               5                   10

<210> SEQ ID NO 22
<211> LENGTH: 12
<212> TYPE: PRT
<213> ORGANISM: Artificial
<220> FEATURE:
<223> OTHER INFORMATION: HA0 cleavage site sequence

<400> SEQUENCE: 22

Pro Glu Ile Pro Lys Lys Lys Lys Arg Gly Leu Phe
1               5                   10

<210> SEQ ID NO 23
<211> LENGTH: 14
<212> TYPE: PRT
<213> ORGANISM: Artificial
<220> FEATURE:
<223> OTHER INFORMATION: HA0 cleavage site sequence

<400> SEQUENCE: 23

Pro Glu Thr Pro Lys Arg Lys Arg Lys Arg Gly Leu Ser Phe
1               5                   10

<210> SEQ ID NO 24
<211> LENGTH: 13
<212> TYPE: PRT
<213> ORGANISM: Artificial
<220> FEATURE:
<223> OTHER INFORMATION: HA0 cleavage site sequence

<400> SEQUENCE: 24

Pro Glu Ile Pro Lys Lys Arg Glu Lys Arg Gly Leu Phe
1               5                   10

<210> SEQ ID NO 25
<211> LENGTH: 12
<212> TYPE: PRT
<213> ORGANISM: Artificial
<220> FEATURE:
<223> OTHER INFORMATION: HA0 cleavage site sequence

<400> SEQUENCE: 25

```
Pro Glu Thr Pro Lys Arg Arg Arg Gly Leu Phe
1               5                   10
```

```
<210> SEQ ID NO 26
<211> LENGTH: 4
<212> TYPE: PRT
<213> ORGANISM: Artificial
<220> FEATURE:
<223> OTHER INFORMATION: PDZ domain motif

<400> SEQUENCE: 26

Gly Leu Gly Phe
1

<210> SEQ ID NO 27
<211> LENGTH: 4
<212> TYPE: PRT
<213> ORGANISM: Artificial
<220> FEATURE:
<223> OTHER INFORMATION: PL motif

<400> SEQUENCE: 27

Glu Pro Glu Val
1

<210> SEQ ID NO 28
<211> LENGTH: 4
<212> TYPE: PRT
<213> ORGANISM: Artificial
<220> FEATURE:
<223> OTHER INFORMATION: PL motif

<400> SEQUENCE: 28

Lys Met Ala Asp
1

<210> SEQ ID NO 29
<211> LENGTH: 4
<212> TYPE: PRT
<213> ORGANISM: Artificial
<220> FEATURE:
<223> OTHER INFORMATION: PDZ ligand motif

<400> SEQUENCE: 29

Arg Lys Tyr Leu
1

<210> SEQ ID NO 30
<211> LENGTH: 4
<212> TYPE: PRT
<213> ORGANISM: Artificial
<220> FEATURE:
<223> OTHER INFORMATION: PDZ ligand motif

<400> SEQUENCE: 30

Lys Lys Tyr Leu
1

<210> SEQ ID NO 31
<211> LENGTH: 4
<212> TYPE: PRT
<213> ORGANISM: Artificial
<220> FEATURE:
<223> OTHER INFORMATION: Putative C-terminal PL motif

<400> SEQUENCE: 31
```

```
Gln Asp Phe Val
1

<210> SEQ ID NO 32
<211> LENGTH: 4
<212> TYPE: PRT
<213> ORGANISM: Artificial
<220> FEATURE:
<223> OTHER INFORMATION: Putative C-terminal PL motif

<400> SEQUENCE: 32

Lys Ser Arg Val
1

<210> SEQ ID NO 33
<211> LENGTH: 4
<212> TYPE: PRT
<213> ORGANISM: Artificial
<220> FEATURE:
<223> OTHER INFORMATION: Putative C-terminal PL motif

<400> SEQUENCE: 33

Lys Ile Glu Leu
1

<210> SEQ ID NO 34
<211> LENGTH: 4
<212> TYPE: PRT
<213> ORGANISM: Artificial
<220> FEATURE:
<223> OTHER INFORMATION: Putative C-terminal PL motif

<400> SEQUENCE: 34

Lys Leu Ser Val
1

<210> SEQ ID NO 35
<211> LENGTH: 4
<212> TYPE: PRT
<213> ORGANISM: Artificial
<220> FEATURE:
<223> OTHER INFORMATION: Putative C-terminal PL motif

<400> SEQUENCE: 35

Ser Ala Val Ala
1

<210> SEQ ID NO 36
<211> LENGTH: 4
<212> TYPE: PRT
<213> ORGANISM: Artificial
<220> FEATURE:
<223> OTHER INFORMATION: Putative C-terminal PL motif

<400> SEQUENCE: 36

Lys Val Leu Leu
1

<210> SEQ ID NO 37
<211> LENGTH: 4
<212> TYPE: PRT
<213> ORGANISM: Artificial
<220> FEATURE:
<223> OTHER INFORMATION: Putative C-terminal PL motif

<400> SEQUENCE: 37

Arg His Thr Cys
```

```
<210> SEQ ID NO 38
<211> LENGTH: 4
<212> TYPE: PRT
<213> ORGANISM: Artificial
<220> FEATURE:
<223> OTHER INFORMATION: Putative C-terminal PL motif

<400> SEQUENCE: 38

Leu Ser Leu Val
1

<210> SEQ ID NO 39
<211> LENGTH: 4
<212> TYPE: PRT
<213> ORGANISM: Artificial
<220> FEATURE:
<223> OTHER INFORMATION: Putative C-terminal PL motif

<400> SEQUENCE: 39

Val Lys Ser Cys
1

<210> SEQ ID NO 40
<211> LENGTH: 4
<212> TYPE: PRT
<213> ORGANISM: Artificial
<220> FEATURE:
<223> OTHER INFORMATION: Human PL sequence motif

<400> SEQUENCE: 40

Arg Ser Lys Ile
1

<210> SEQ ID NO 41
<211> LENGTH: 4
<212> TYPE: PRT
<213> ORGANISM: Artificial
<220> FEATURE:
<223> OTHER INFORMATION: Human PL sequence motif

<400> SEQUENCE: 41

Lys Ser Glu Val
1

<210> SEQ ID NO 42
<211> LENGTH: 230
<212> TYPE: PRT
<213> ORGANISM: Influenza virus

<400> SEQUENCE: 42

Met Asp Ser Asn Thr Leu Ser Ser Phe Gln Val Asp Cys Phe Leu Trp
1               5                   10                  15

His Val Arg Lys Gln Val Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asn Ile Glu Thr Ala Thr Cys Val Gly Lys Gln Ile
    50                  55                  60

Val Glu Arg Ile Leu Lys Glu Glu Ser Asp Glu Ala Phe Lys Met Thr
65                  70                  75                  80

Met Ala Ser Ala Leu Ala Ser Arg Tyr Leu Thr Asp Met Thr Ile Glu
                85                  90                  95
```

```
Glu Met Ser Arg Asp Trp Phe Ile Val Met Pro Lys Gln Lys Val Ala
                100                 105                 110
Gly Pro Leu Cys Val Arg Met Asp Gln Ala Ile Thr Asp Lys Asn Ile
            115                 120                 125
Ile Leu Lys Ala Asn Phe Ser Val Ile Phe Asn Arg Leu Glu Thr Leu
        130                 135                 140
Thr Leu Leu Arg Ala Phe Thr Glu Glu Gly Ala Ile Val Gly Glu Ile
145                 150                 155                 160
Ser Pro Leu Pro Ser Leu Pro Gly His Thr Asn Glu Asp Val Lys Asn
                165                 170                 175
Ala Ile Gly Ile Leu Ile Gly Gly Leu Glu Trp Asn Asp Asn Thr Val
            180                 185                 190
Arg Val Ser Glu Ala Leu Gln Arg Phe Ala Trp Arg Ser Ser Asn Glu
        195                 200                 205
Asn Gly Arg Pro Pro Leu Thr Pro Thr Gln Lys Arg Lys Met Ala Gly
    210                 215                 220
Thr Ile Arg Ser Glu Val
225                 230

<210> SEQ ID NO 43
<211> LENGTH: 230
<212> TYPE: PRT
<213> ORGANISM: Influenza virus

<400> SEQUENCE: 43

Met Asp Ser Asn Thr Val Ser Ser Phe Gln Val Asp Cys Phe Leu Trp
1               5                   10                  15
His Ile Arg Lys Gln Val Asp Gln Glu Leu Ser Asp Ala Pro Phe
            20                  25                  30
Leu Asp Arg Leu Arg Arg Asp Gln Arg Ser Leu Arg Gly Arg Gly Asn
        35                  40                  45
Thr Leu Gly Leu Asp Ile Lys Ala Ala Thr His Val Gly Lys Gln Ile
50                  55                  60
Val Glu Lys Ile Leu Lys Gly Glu Ser Asp Glu Ala Leu Lys Met Thr
65                  70                  75                  80
Met Ala Ser Thr Pro Ala Ser Arg Tyr Ile Thr Asp Met Thr Ile Glu
            85                  90                  95
Glu Leu Ser Arg Asn Trp Phe Met Leu Met Pro Lys Gln Lys Met Glu
            100                 105                 110
Gly Pro Leu Cys Ile Arg Met Asp Gln Ala Ile Met Glu Lys Asn Ile
            115                 120                 125
Met Leu Lys Ala Asn Phe Ser Val Ile Phe Asp Arg Leu Glu Asn Ile
        130                 135                 140
Val Leu Leu Arg Ala Phe Thr Glu Glu Gly Ala Ile Val Gly Glu Ile
145                 150                 155                 160
Ser Pro Leu Pro Ser Phe Pro Gly His Thr Ile Glu Asp Val Lys Asn
                165                 170                 175
Ala Ile Gly Val Leu Ile Gly Gly Leu Glu Trp Asn Asp Asn Thr Val
            180                 185                 190
Arg Val Ser Lys Asn Leu Gln Arg Phe Ala Trp Arg Ser Ser Asn Glu
        195                 200                 205
Asn Gly Gly Pro Pro Leu Thr Pro Lys Gln Lys Arg Lys Met Ala Arg
    210                 215                 220
Thr Ala Arg Ser Lys Val
```

<210> SEQ ID NO 44
<211> LENGTH: 230
<212> TYPE: PRT
<213> ORGANISM: Influenza virus

<400> SEQUENCE: 44

```
Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Met Glu Arg
    210                 215                 220

Thr Ile Glu Pro Glu Val
225                 230
```

<210> SEQ ID NO 45
<211> LENGTH: 225
<212> TYPE: PRT
<213> ORGANISM: Influenza virus

<400> SEQUENCE: 45

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Tyr Leu Thr Asp Met Thr Leu Glu Glu Met Ser Arg Asp
```

-continued

```
                    85                  90                  95
Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
        195                 200                 205

Leu Pro Pro Asn Gln Lys Arg Lys Met Ala Arg Thr Ile Glu Ser Glu
    210                 215                 220

Val
225

<210> SEQ ID NO 46
<211> LENGTH: 20
<212> TYPE: PRT
<213> ORGANISM: Influenza virus

<400> SEQUENCE: 46

Tyr Gly Arg Lys Lys Arg Arg Gln Arg Arg Met Glu Arg Thr Ile
1               5                   10                  15

Glu Pro Glu Val
            20

<210> SEQ ID NO 47
<211> LENGTH: 20
<212> TYPE: PRT
<213> ORGANISM: Influenza virus

<400> SEQUENCE: 47

Tyr Gly Arg Lys Lys Arg Arg Gln Arg Arg Met Ala Arg Thr Ile
1               5                   10                  15

Glu Ser Glu Val
            20

<210> SEQ ID NO 48
<211> LENGTH: 4
<212> TYPE: PRT
<213> ORGANISM: Artificial
<220> FEATURE:
<223> OTHER INFORMATION: PSD95 binding peptide motif
<220> FEATURE:
<221> NAME/KEY: MISC_FEATURE
<222> LOCATION: (1)..(1)
<223> OTHER INFORMATION: X is E or D or N or Q
<220> FEATURE:
<221> NAME/KEY: MISC_FEATURE
<222> LOCATION: (2)..(2)
<223> OTHER INFORMATION: X is S or T
<220> FEATURE:
<221> NAME/KEY: MISC_FEATURE
<222> LOCATION: (3)..(3)
<223> OTHER INFORMATION: X is D or E or Q or N
<220> FEATURE:
<221> NAME/KEY: MISC_FEATURE
<222> LOCATION: (4)..(4)
```

```
<223> OTHER INFORMATION: X is V or L

<400> SEQUENCE: 48

Xaa Xaa Xaa Xaa
1

<210> SEQ ID NO 49
<211> LENGTH: 4
<212> TYPE: PRT
<213> ORGANISM: Artificial
<220> FEATURE:
<223> OTHER INFORMATION: Preferred C-terminal sequence

<400> SEQUENCE: 49

Glu Ser Asp Val
1

<210> SEQ ID NO 50
<211> LENGTH: 4
<212> TYPE: PRT
<213> ORGANISM: Artificial
<220> FEATURE:
<223> OTHER INFORMATION: Preferred C-terminal sequence

<400> SEQUENCE: 50

Glu Thr Asp Val
1

<210> SEQ ID NO 51
<211> LENGTH: 4
<212> TYPE: PRT
<213> ORGANISM: Artificial
<220> FEATURE:
<223> OTHER INFORMATION: Preferred C-terminal sequence

<400> SEQUENCE: 51

Glu Thr Glu Val
1

<210> SEQ ID NO 52
<211> LENGTH: 4
<212> TYPE: PRT
<213> ORGANISM: Artificial
<220> FEATURE:
<223> OTHER INFORMATION: Preferred C-terminal sequence

<400> SEQUENCE: 52

Asp Thr Asp Val
1

<210> SEQ ID NO 53
<211> LENGTH: 4
<212> TYPE: PRT
<213> ORGANISM: Artificial
<220> FEATURE:
<223> OTHER INFORMATION: Preferred C-terminal sequence

<400> SEQUENCE: 53

Asp Thr Glu Val
1

<210> SEQ ID NO 54
<211> LENGTH: 20
<212> TYPE: PRT
<213> ORGANISM: Artificial
<220> FEATURE:
<223> OTHER INFORMATION: PL sequence
```

```
<400> SEQUENCE: 54

Gly Arg Trp Thr Gly Arg Ser Met Ser Ser Trp Lys Pro Thr Arg Arg
1               5                   10                  15

Glu Thr Glu Val
            20

<210> SEQ ID NO 55
<211> LENGTH: 20
<212> TYPE: PRT
<213> ORGANISM: Artificial
<220> FEATURE:
<223> OTHER INFORMATION: PL sequence

<400> SEQUENCE: 55

Gln Ile Ser Pro Gly Gly Leu Glu Pro Pro Ser Glu Lys His Phe Arg
1               5                   10                  15

Glu Thr Glu Val
            20

<210> SEQ ID NO 56
<211> LENGTH: 20
<212> TYPE: PRT
<213> ORGANISM: Artificial
<220> FEATURE:
<223> OTHER INFORMATION: PL sequence

<400> SEQUENCE: 56

Tyr Gly Arg Lys Lys Arg Arg Gln Arg Arg Tyr Ile Pro Glu Ala
1               5                   10                  15

Gln Thr Arg Leu
            20

<210> SEQ ID NO 57
<211> LENGTH: 20
<212> TYPE: PRT
<213> ORGANISM: Artificial
<220> FEATURE:
<223> OTHER INFORMATION: PL sequence

<400> SEQUENCE: 57

Tyr Gly Arg Lys Lys Arg Arg Gln Arg Arg Arg Ile Ser Ser Ile
1               5                   10                  15

Glu Thr Asp Val
            20

<210> SEQ ID NO 58
<211> LENGTH: 20
<212> TYPE: PRT
<213> ORGANISM: Artificial
<220> FEATURE:
<223> OTHER INFORMATION: PL sequence

<400> SEQUENCE: 58

Tyr Gly Arg Lys Lys Arg Arg Gln Arg Arg Lys Leu Ser Ser Ile
1               5                   10                  15

Glu Ser Asp Val
            20

<210> SEQ ID NO 59
<211> LENGTH: 20
<212> TYPE: PRT
<213> ORGANISM: Artificial
<220> FEATURE:
```

<223> OTHER INFORMATION: PL sequence

<400> SEQUENCE: 59

Tyr Gly Arg Lys Lys Arg Arg Gln Arg Arg Thr Lys Asn Tyr Lys
1               5                   10                  15

Gln Thr Ser Val
            20

<210> SEQ ID NO 60
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 60

Ala Ala Gly Gly Arg Ser Ala Arg Gly Gly Arg Leu Gln Gly Arg Arg
1               5                   10                  15

Glu Thr Ala Leu
            20

<210> SEQ ID NO 61
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 61

Ala Gly Ala Val Arg Thr Pro Leu Ser Gln Val Asn Lys Val Trp Asp
1               5                   10                  15

Gln Ser Ser Val
            20

<210> SEQ ID NO 62
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 62

Ala Val Gly Gly Arg Pro Ala Arg Gly Gly Arg Leu Gln Gly Arg Arg
1               5                   10                  15

Gln Thr Gln Val
            20

<210> SEQ ID NO 63
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 63

Asp Phe Arg Pro Ser Phe Lys His Ile Leu Phe Arg Arg Ala Arg Arg
1               5                   10                  15

Gly Phe Arg Gln
            20

<210> SEQ ID NO 64
<211> LENGTH: 20
<212> TYPE: PRT
<213> ORGANISM: Artificial

-continued

```
<220> FEATURE:
<223> OTHER INFORMATION: PL sequence binding DLG2 d1

<400> SEQUENCE: 64

Asp Thr Leu Leu Leu Thr Glu Asn Glu Gly Asp Lys Thr Glu Glu Gln
1               5                   10                  15

Val Ser Tyr Val
            20

<210> SEQ ID NO 65
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 65

Gly Arg Trp Thr Gly Arg Ala Met Ser Ala Trp Lys Pro Thr Arg Arg
1               5                   10                  15

Glu Thr Glu Val
            20

<210> SEQ ID NO 66
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 66

His His Leu Val Ala Gln Arg Asp Ile Arg Gln Phe Gln Leu Gln His
1               5                   10                  15

Trp Leu Ala Ile
            20

<210> SEQ ID NO 67
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 67

Lys His Ser Arg Lys Ser Ser Tyr Ser Ser Ser Ser Thr Thr Val
1               5                   10                  15

Lys Thr Ser Tyr
            20

<210> SEQ ID NO 68
<211> LENGTH: 23
<212> TYPE: PRT
<213> ORGANISM: Artificial
<220> FEATURE:
<223> OTHER INFORMATION: PL sequence binding DLG2 d1

<400> SEQUENCE: 68

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 69
<211> LENGTH: 20
<212> TYPE: PRT
```

-continued

<213> ORGANISM: Artificial
<220> FEATURE:
<223> OTHER INFORMATION: PL sequence binding DLG2 d1

<400> SEQUENCE: 69

Leu Ala Val Leu Ala Tyr Ser Ile Thr Leu Val Met Leu Trp Ser Ile
1               5                   10                  15

Trp Gln Tyr Ala
            20

<210> SEQ ID NO 70
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 70

Leu Asn Ser Cys Ser Asn Arg Arg Val Tyr Lys Lys Met Pro Ser Ile
1               5                   10                  15

Glu Ser Asp Val
            20

<210> SEQ ID NO 71
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 71

Leu Asn Ser Ser Ser Asn Arg Arg Val Tyr Lys Lys Met Pro Ser Ile
1               5                   10                  15

Glu Ser Asp Val
            20

<210> SEQ ID NO 72
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 72

Pro Ile Pro Ala Gly Gly Cys Thr Phe Ser Gly Ile Phe Pro Thr Leu
1               5                   10                  15

Thr Ser Pro Leu
            20

<210> SEQ ID NO 73
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 73

Pro Tyr Ser Glu Leu Asn Tyr Glu Thr Ser His Tyr Pro Ala Ser Pro
1               5                   10                  15

Asp Ser Trp Val
            20

<210> SEQ ID NO 74
<211> LENGTH: 20

```
<212> TYPE: PRT
<213> ORGANISM: Artificial
<220> FEATURE:
<223> OTHER INFORMATION: PL sequence binding DLG2 d1

<400> SEQUENCE: 74

Gln Asp Phe Arg Arg Ala Phe Arg Arg Ile Leu Ala Arg Pro Trp Thr
1               5                   10                  15

Gln Thr Ala Trp
            20

<210> SEQ ID NO 75
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 75

Gln Ile Ser Pro Gly Gly Leu Glu Pro Pro Ser Glu Lys His Phe Arg
1               5                   10                  15

Glu Thr Glu Val
            20

<210> SEQ ID NO 76
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 76

Arg Glu Leu Val Asp Arg Gly Glu Val Arg Gln Phe Thr Leu Arg His
1               5                   10                  15

Trp Leu Lys Val
            20

<210> SEQ ID NO 77
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 77

Ser Phe Thr Ser Ile Leu Thr Cys His Gln Arg Arg Thr Gln Arg Lys
1               5                   10                  15

Glu Thr Val Ala
            20

<210> SEQ ID NO 78
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 78

Ser Leu Lys Pro Gly Thr Val Leu Pro Pro Pro Tyr Arg His Arg
1               5                   10                  15

Asn Thr Val Val
            20

<210> SEQ ID NO 79
```

```
<211> LENGTH: 19
<212> TYPE: PRT
<213> ORGANISM: Artificial
<220> FEATURE:
<223> OTHER INFORMATION: PL sequence binding DLG2 d1

<400> SEQUENCE: 79

Ser Ser Lys Ser Lys Ser Ser Glu Glu Ser Gln Thr Phe Phe Gly Leu
1               5                   10                  15

Tyr Lys Leu

<210> SEQ ID NO 80
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 80

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 81
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 81

Thr Gly Ser Ala Leu Gln Ala Trp Arg His Thr Ser Arg Gln Ala Thr
1               5                   10                  15

Glu Ser Thr Val
            20

<210> SEQ ID NO 82
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 82

Thr Gln Gly Phe Pro Gly Pro Ala Thr Trp Arg Arg Ile Ser Ser Leu
1               5                   10                  15

Glu Ser Glu Val
            20

<210> SEQ ID NO 83
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 83

Val Gly Thr Leu Leu Leu Glu Arg Val Ile Phe Pro Ser Val Lys Ile
1               5                   10                  15

Ala Thr Leu Val
            20

<210> SEQ ID NO 84
```

```
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 84

Val His Lys Val Arg Asn Lys Phe Lys Ala Lys Cys Ser Leu Cys Arg
1               5                   10                  15

Leu Tyr Ile Ile
            20

<210> SEQ ID NO 85
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 85

Tyr Gly Arg Lys Lys Arg Arg Gln Arg Arg Gly Ala Ser Ala Asp
1               5                   10                  15

Ser Thr Gln Ala
            20

<210> SEQ ID NO 86
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 86

Tyr Gly Arg Lys Lys Arg Arg Gln Arg Arg Lys Leu Ser Ser Ile
1               5                   10                  15

Glu Ser Asp Val
            20

<210> SEQ ID NO 87
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 87

Tyr Gly Arg Lys Lys Arg Arg Gln Arg Arg Asn Asp Asn Ile Ala
1               5                   10                  15

Leu Leu Val Gln
            20

<210> SEQ ID NO 88
<211> LENGTH: 20
<212> TYPE: PRT
<213> ORGANISM: Artificial
<220> FEATURE:
<223> OTHER INFORMATION: PL sequence binding DLG2 d1

<400> SEQUENCE: 88

Tyr Gly Arg Lys Lys Arg Arg Gln Arg Arg Ser Glu Gly Val Pro
1               5                   10                  15

Asp Leu Leu Val
            20
```

```
<210> SEQ ID NO 89
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 89

Asp Phe Ser Arg Gln Leu Gln Asn Ser Met Ser Gly Ala Ser Ala Asp
1               5                   10                  15

Ser Thr Gln Ala
            20

<210> SEQ ID NO 90
<211> LENGTH: 23
<212> TYPE: PRT
<213> ORGANISM: Artificial
<220> FEATURE:
<223> OTHER INFORMATION: PL sequence binding GORASP d1

<400> SEQUENCE: 90

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 91
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 91

Asn Tyr Lys Leu Asn Thr Asp His Ala Gly Ser Asn Asp Asn Ile Ala
1               5                   10                  15

Leu Leu Val Gln
            20

<210> SEQ ID NO 92
<211> LENGTH: 19
<212> TYPE: PRT
<213> ORGANISM: Artificial
<220> FEATURE:
<223> OTHER INFORMATION: PL sequence binding GORASP d1

<400> SEQUENCE: 92

Ser Gly Gly Asn Arg Ala Arg Gln Glu Arg Leu Gln Arg Arg Arg Glu
1               5                   10                  15

Thr Gln Val

<210> SEQ ID NO 93
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 93

Tyr Gly Arg Lys Lys Arg Arg Gln Arg Arg Ala Arg Gly Asp Arg
1               5                   10                  15

Lys Arg Ile Val
            20
```

```
<210> SEQ ID NO 94
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 94

Tyr Gly Arg Lys Lys Arg Arg Gln Arg Arg Ala Val Ala Ala Thr
1               5                   10                  15

Ser Ile Asn Leu
            20

<210> SEQ ID NO 95
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 95

Tyr Gly Arg Lys Lys Arg Arg Gln Arg Arg Glu Met Gln Val Thr
1               5                   10                  15

Leu Gly Leu His
            20

<210> SEQ ID NO 96
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 96

Tyr Gly Arg Lys Lys Arg Arg Gln Arg Arg Gly Ala Ser Ala Asp
1               5                   10                  15

Ser Thr Gln Ala
            20

<210> SEQ ID NO 97
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 97

Tyr Gly Arg Lys Lys Arg Arg Gln Arg Arg Ile Gly Glu Leu Gln
1               5                   10                  15

Leu Ser Ile Ala
            20

<210> SEQ ID NO 98
<211> LENGTH: 20
<212> TYPE: PRT
<213> ORGANISM: Artificial
<220> FEATURE:
<223> OTHER INFORMATION: PL sequence binding GORASP d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 98

Tyr Gly Arg Lys Lys Arg Arg Gln Arg Arg Lys Leu Ser Ser Ile
1               5                   10                  15
```

Glu Ser Asp Xaa
            20

<210> SEQ ID NO 99
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 99

Tyr Gly Arg Lys Lys Arg Arg Gln Arg Arg Asn Asp Asn Ile Ala
1               5                   10                  15

Leu Leu Val Gln
            20

<210> SEQ ID NO 100
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 100

Tyr Gly Arg Lys Lys Arg Arg Gln Arg Arg Gln Asp Glu Glu Glu
1               5                   10                  15

Gly Ile Trp Ala
            20

<210> SEQ ID NO 101
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 101

Tyr Gly Arg Lys Lys Arg Arg Gln Arg Arg Ser Glu Gly Val Pro
1               5                   10                  15

Asp Leu Leu Val
            20

<210> SEQ ID NO 102
<211> LENGTH: 20
<212> TYPE: PRT
<213> ORGANISM: Artificial
<220> FEATURE:
<223> OTHER INFORMATION: PL sequence binding GORASP d1

<400> SEQUENCE: 102

Tyr Val Tyr Ser Arg Val Lys Asn Leu Asn Ser Ser Glu Gly Val Pro
1               5                   10                  15

Asp Leu Leu Val
            20

<210> SEQ ID NO 103
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 103

Ala Val Gly Gly Arg Pro Ala Arg Gly Gly Arg Leu Gln Gly Arg Arg

```
1               5                  10                  15

Gln Thr Gln Val
            20

<210> SEQ ID NO 104
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 104

Asp Phe Arg Pro Ser Phe Lys His Ile Leu Phe Arg Arg Ala Arg Arg
1               5                  10                  15

Gly Phe Arg Gln
            20

<210> SEQ ID NO 105
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 105

His His Leu Val Ala Gln Arg Asp Ile Arg Gln Phe Gln Leu Gln His
1               5                  10                  15

Trp Leu Ala Ile
            20

<210> SEQ ID NO 106
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 106

His Ser Cys Cys Asn Arg Ala Arg Gln Glu Arg Leu Gln Arg Arg
1               5                  10                  15

Glu Thr Gln Val
            20

<210> SEQ ID NO 107
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 107

Lys His Ser Arg Lys Ser Ser Ser Tyr Ser Ser Ser Thr Thr Val
1               5                  10                  15

Lys Thr Ser Tyr
            20

<210> SEQ ID NO 108
<211> LENGTH: 23
<212> TYPE: PRT
<213> ORGANISM: Artificial
<220> FEATURE:
<223> OTHER INFORMATION: PL sequence binding GRIP1 d4

<400> SEQUENCE: 108
```

-continued

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 109
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 109

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 110
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 110

Leu Ala Val Leu Ala Tyr Ser Ile Thr Leu Val Met Leu Trp Ser Ile
1               5                   10                  15

Trp Gln Tyr Ala
            20

<210> SEQ ID NO 111
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 111

Gln Asp Phe Arg Arg Ala Phe Arg Arg Ile Leu Ala Arg Pro Trp Thr
1               5                   10                  15

Gln Thr Ala Trp
            20

<210> SEQ ID NO 112
<211> LENGTH: 19
<212> TYPE: PRT
<213> ORGANISM: Artificial
<220> FEATURE:
<223> OTHER INFORMATION: PL sequence binding GRIP1 d4

<400> SEQUENCE: 112

Ser Ser Lys Ser Lys Ser Ser Glu Glu Ser Gln Thr Phe Phe Gly Leu
1               5                   10                  15

Tyr Lys Leu

<210> SEQ ID NO 113
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 113

```
Ser Ser Pro Asp Ser Ser Tyr Gln Gly Lys Gly Phe Val Met Ser Arg
1               5                   10                  15

Ala Met Tyr Val
            20

<210> SEQ ID NO 114
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 114

Val Asp Pro Asn Ser Pro Ala Ala Lys Lys Lys Tyr Val Ser Tyr Asn
1               5                   10                  15

Asn Leu Val Ile
            20

<210> SEQ ID NO 115
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 115

Val His Lys Val Arg Asn Lys Phe Lys Ala Lys Cys Ser Leu Cys Arg
1               5                   10                  15

Leu Tyr Ile Ile
            20

<210> SEQ ID NO 116
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 116

Tyr Gly Arg Lys Lys Arg Arg Gln Arg Arg Gly Ala Ser Ala Asp
1               5                   10                  15

Ser Thr Gln Ala
            20

<210> SEQ ID NO 117
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 117

Tyr Gly Arg Lys Lys Arg Arg Gln Arg Arg Asn Asp Asn Ile Ala
1               5                   10                  15

Leu Leu Val Gln
            20

<210> SEQ ID NO 118
<211> LENGTH: 20
<212> TYPE: PRT
<213> ORGANISM: Artificial
<220> FEATURE:
<223> OTHER INFORMATION: PL sequence binding GRIP1 d4

<400> SEQUENCE: 118
```

Tyr Gly Arg Lys Lys Arg Arg Gln Arg Arg Ser Glu Gly Val Pro
1               5                   10                  15

Asp Leu Leu Val
            20

<210> SEQ ID NO 119
<211> LENGTH: 20
<212> TYPE: PRT
<213> ORGANISM: Artificial
<220> FEATURE:
<223> OTHER INFORMATION: PL sequence binding INADL d8

<400> SEQUENCE: 119

Ala Gly Ala Val Arg Thr Pro Leu Ser Gln Val Asn Lys Val Trp Asp
1               5                   10                  15

Gln Ser Ser Val
            20

<210> SEQ ID NO 120
<211> LENGTH: 20
<212> TYPE: PRT
<213> ORGANISM: Artificial
<220> FEATURE:
<223> OTHER INFORMATION: PL sequence binding INADL d8

<400> SEQUENCE: 120

Ala Leu Val Leu Ile Ala Phe Cys Ile Ile Arg Arg Arg Pro Ser Ala
1               5                   10                  15

Tyr Gln Ala Leu
            20

<210> SEQ ID NO 121
<211> LENGTH: 20
<212> TYPE: PRT
<213> ORGANISM: Artificial
<220> FEATURE:
<223> OTHER INFORMATION: PL sequence binding INADL d8

<400> SEQUENCE: 121

Ala Thr Asp Tyr Leu Val Gln Pro Phe Met Asp Gln Leu Ala Phe His
1               5                   10                  15

Gln Phe Tyr Ile
            20

<210> SEQ ID NO 122
<211> LENGTH: 20
<212> TYPE: PRT
<213> ORGANISM: Artificial
<220> FEATURE:
<223> OTHER INFORMATION: PL sequence binding INADL d8

<400> SEQUENCE: 122

Ala Val Gly Gly Arg Pro Ala Arg Gly Gly Arg Leu Gln Gly Arg Arg
1               5                   10                  15

Gln Thr Gln Val
            20

<210> SEQ ID NO 123
<211> LENGTH: 20
<212> TYPE: PRT
<213> ORGANISM: Artificial
<220> FEATURE:
<223> OTHER INFORMATION: PL sequence binding INADL d8

-continued

```
<400> SEQUENCE: 123

Asp Phe Arg Pro Ser Phe Lys His Ile Leu Phe Arg Arg Ala Arg Arg
1               5                   10                  15

Gly Phe Arg Gln
            20

<210> SEQ ID NO 124
<211> LENGTH: 20
<212> TYPE: PRT
<213> ORGANISM: Artificial
<220> FEATURE:
<223> OTHER INFORMATION: PL sequence binding INADL d8

<400> SEQUENCE: 124

Asp Ser Asp Pro Glu Asn Glu Pro Phe Asp Glu Asp Gln His Thr Gln
1               5                   10                  15

Ile Thr Lys Val
            20

<210> SEQ ID NO 125
<211> LENGTH: 20
<212> TYPE: PRT
<213> ORGANISM: Artificial
<220> FEATURE:
<223> OTHER INFORMATION: PL sequence binding INADL d8

<400> SEQUENCE: 125

Asp Thr Leu Leu Leu Thr Glu Asn Gly Asp Lys Thr Gln Glu Gln
1               5                   10                  15

Val Ser Tyr Val
            20

<210> SEQ ID NO 126
<211> LENGTH: 20
<212> TYPE: PRT
<213> ORGANISM: Artificial
<220> FEATURE:
<223> OTHER INFORMATION: PL sequence binding INADL d8

<400> SEQUENCE: 126

Glu Leu Leu Gln Phe Cys Arg Thr Pro Asn Pro Ala Leu Lys Asn Gly
1               5                   10                  15

Gln Tyr Trp Val
            20

<210> SEQ ID NO 127
<211> LENGTH: 20
<212> TYPE: PRT
<213> ORGANISM: Artificial
<220> FEATURE:
<223> OTHER INFORMATION: PL sequence binding INADL d8

<400> SEQUENCE: 127

Glu Ser Ser Gly Thr Gln Ser Pro Lys Arg His Ser Gly Ser Tyr Leu
1               5                   10                  15

Val Thr Ser Val
            20

<210> SEQ ID NO 128
<211> LENGTH: 20
<212> TYPE: PRT
<213> ORGANISM: Artificial
<220> FEATURE:
<223> OTHER INFORMATION: PL sequence binding INADL d8
```

```
<400> SEQUENCE: 128

Gly Gly Gly Gly Gly Ser Gly Gly Gly Ser Gly Leu Pro His Ser
1               5                   10                  15

Thr Thr Arg Val
            20

<210> SEQ ID NO 129
<211> LENGTH: 20
<212> TYPE: PRT
<213> ORGANISM: Artificial
<220> FEATURE:
<223> OTHER INFORMATION: PL sequence binding INADL d8

<400> SEQUENCE: 129

Gly Gly Gly Gly Gly Ser Gly Gly Gly Ser Gly Ser Arg Arg Pro
1               5                   10                  15

Lys Thr Arg Val
            20

<210> SEQ ID NO 130
<211> LENGTH: 20
<212> TYPE: PRT
<213> ORGANISM: Artificial
<220> FEATURE:
<223> OTHER INFORMATION: PL sequence binding INADL d8

<400> SEQUENCE: 130

Gly Arg Trp Thr Gly Arg Ala Met Ser Ala Trp Lys Pro Thr Arg Arg
1               5                   10                  15

Glu Thr Glu Val
            20

<210> SEQ ID NO 131
<211> LENGTH: 20
<212> TYPE: PRT
<213> ORGANISM: Artificial
<220> FEATURE:
<223> OTHER INFORMATION: PL sequence binding INADL d8

<400> SEQUENCE: 131

His His Leu Val Ala Gln Arg Asp Ile Arg Gln Phe Gln Leu Gln His
1               5                   10                  15

Trp Leu Ala Ile
            20

<210> SEQ ID NO 132
<211> LENGTH: 20
<212> TYPE: PRT
<213> ORGANISM: Artificial
<220> FEATURE:
<223> OTHER INFORMATION: PL sequence binding INADL d8

<400> SEQUENCE: 132

His Ser Cys Cys Asn Arg Ala Arg Gln Glu Arg Leu Gln Arg Arg
1               5                   10                  15

Glu Thr Gln Val
            20

<210> SEQ ID NO 133
<211> LENGTH: 20
<212> TYPE: PRT
<213> ORGANISM: Artificial
<220> FEATURE:
```

```
<223> OTHER INFORMATION: PL sequence binding INADL d8

<400> SEQUENCE: 133

Ile Asn Ser Val Gly Ser Thr Ala Ser Ser Gln Pro Leu Leu Val
1               5                   10                  15

His Asp Asp Val
            20

<210> SEQ ID NO 134
<211> LENGTH: 20
<212> TYPE: PRT
<213> ORGANISM: Artificial
<220> FEATURE:
<223> OTHER INFORMATION: PL sequence binding INADL d8

<400> SEQUENCE: 134

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 135
<211> LENGTH: 20
<212> TYPE: PRT
<213> ORGANISM: Artificial
<220> FEATURE:
<223> OTHER INFORMATION: PL sequence binding INADL d8

<400> SEQUENCE: 135

Lys His Ser Arg Lys Ser Ser Ser Tyr Ser Ser Ser Ser Thr Thr Val
1               5                   10                  15

Lys Thr Ser Tyr
            20

<210> SEQ ID NO 136
<211> LENGTH: 23
<212> TYPE: PRT
<213> ORGANISM: Artificial
<220> FEATURE:
<223> OTHER INFORMATION: PL sequence binding INADL d8

<400> SEQUENCE: 136

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 137
<211> LENGTH: 20
<212> TYPE: PRT
<213> ORGANISM: Artificial
<220> FEATURE:
<223> OTHER INFORMATION: PL sequence binding INADL d8

<400> SEQUENCE: 137

Lys Thr Met Pro Ala Ala Met Tyr Arg Leu Leu Thr Ala Gln Glu Gln
1               5                   10                  15

Pro Val Tyr Ile
            20

<210> SEQ ID NO 138
<211> LENGTH: 20
<212> TYPE: PRT
<213> ORGANISM: Artificial
```

```
<220> FEATURE:
<223> OTHER INFORMATION: PL sequence binding INADL d8

<400> SEQUENCE: 138

Leu Ala Val Leu Ala Tyr Ser Ile Thr Leu Val Met Leu Trp Ser Ile
1               5                   10                  15

Trp Gln Tyr Ala
            20

<210> SEQ ID NO 139
<211> LENGTH: 20
<212> TYPE: PRT
<213> ORGANISM: Artificial
<220> FEATURE:
<223> OTHER INFORMATION: PL sequence binding INADL d8

<400> SEQUENCE: 139

Leu Gly Tyr Ser Ile Pro Ser Arg Ser Gly Ala Ser Gly Leu Asp Lys
1               5                   10                  15

Arg Asp Tyr Val
            20

<210> SEQ ID NO 140
<211> LENGTH: 20
<212> TYPE: PRT
<213> ORGANISM: Artificial
<220> FEATURE:
<223> OTHER INFORMATION: PL sequence binding INADL d8

<400> SEQUENCE: 140

Leu Asn Ser Cys Ser Asn Arg Arg Val Tyr Lys Lys Met Pro Ser Ile
1               5                   10                  15

Glu Ser Asp Val
            20

<210> SEQ ID NO 141
<211> LENGTH: 20
<212> TYPE: PRT
<213> ORGANISM: Artificial
<220> FEATURE:
<223> OTHER INFORMATION: PL sequence binding INADL d8

<400> SEQUENCE: 141

Leu Asn Ser Ser Ser Asn Arg Arg Val Tyr Lys Lys Met Pro Ser Ile
1               5                   10                  15

Glu Ser Asp Val
            20

<210> SEQ ID NO 142
<211> LENGTH: 20
<212> TYPE: PRT
<213> ORGANISM: Artificial
<220> FEATURE:
<223> OTHER INFORMATION: PL sequence binding INADL d8

<400> SEQUENCE: 142

Pro Ile Pro Ala Gly Gly Cys Thr Phe Ser Gly Ile Phe Pro Thr Leu
1               5                   10                  15

Thr Ser Pro Leu
            20

<210> SEQ ID NO 143
<211> LENGTH: 20
<212> TYPE: PRT
```

```
<213> ORGANISM: Artificial
<220> FEATURE:
<223> OTHER INFORMATION: PL sequence binding INADL d8

<400> SEQUENCE: 143

Pro Tyr Ser Glu Leu Asn Tyr Glu Thr Ser His Tyr Pro Ala Ser Pro
1               5                   10                  15

Asp Ser Trp Val
            20

<210> SEQ ID NO 144
<211> LENGTH: 20
<212> TYPE: PRT
<213> ORGANISM: Artificial
<220> FEATURE:
<223> OTHER INFORMATION: PL sequence binding INADL d8

<400> SEQUENCE: 144

Gln Asp Phe Arg Arg Ala Phe Arg Arg Ile Leu Ala Arg Pro Trp Thr
1               5                   10                  15

Gln Thr Ala Trp
            20

<210> SEQ ID NO 145
<211> LENGTH: 20
<212> TYPE: PRT
<213> ORGANISM: Artificial
<220> FEATURE:
<223> OTHER INFORMATION: PL sequence binding INADL d8

<400> SEQUENCE: 145

Arg Glu Leu Val Asp Arg Gly Glu Val Arg Gln Phe Thr Leu Arg His
1               5                   10                  15

Trp Leu Lys Val
            20

<210> SEQ ID NO 146
<211> LENGTH: 20
<212> TYPE: PRT
<213> ORGANISM: Artificial
<220> FEATURE:
<223> OTHER INFORMATION: PL sequence binding INADL d8

<400> SEQUENCE: 146

Arg Asn Ile Glu Glu Val Tyr Val Gly Gly Lys Gln Val Val Pro Phe
1               5                   10                  15

Ser Ser Ser Val
            20

<210> SEQ ID NO 147
<211> LENGTH: 20
<212> TYPE: PRT
<213> ORGANISM: Artificial
<220> FEATURE:
<223> OTHER INFORMATION: PL sequence binding INADL d8

<400> SEQUENCE: 147

Ser Phe Thr Ser Ile Leu Thr Cys His Gln Arg Arg Thr Gln Arg Lys
1               5                   10                  15

Glu Thr Val Ala
            20

<210> SEQ ID NO 148
<211> LENGTH: 18
```

<212> TYPE: PRT
<213> ORGANISM: Artificial
<220> FEATURE:
<223> OTHER INFORMATION: PL sequence binding INADL d8

<400> SEQUENCE: 148

Ser Pro Gln Pro Asp Ser Thr Asp Asn Asp Asp Tyr Asp Asp Ile Ser
1               5                   10                  15

Ala Ala

<210> SEQ ID NO 149
<211> LENGTH: 19
<212> TYPE: PRT
<213> ORGANISM: Artificial
<220> FEATURE:
<223> OTHER INFORMATION: PL sequence binding INADL d8

<400> SEQUENCE: 149

Ser Ser Lys Ser Lys Ser Ser Glu Glu Ser Gln Thr Phe Phe Gly Leu
1               5                   10                  15

Tyr Lys Leu

<210> SEQ ID NO 150
<211> LENGTH: 20
<212> TYPE: PRT
<213> ORGANISM: Artificial
<220> FEATURE:
<223> OTHER INFORMATION: PL sequence binding INADL d8

<400> SEQUENCE: 150

Ser Ser Pro Asp Ser Ser Tyr Gln Gly Lys Gly Phe Val Met Ser Arg
1               5                   10                  15

Ala Met Tyr Val
            20

<210> SEQ ID NO 151
<211> LENGTH: 20
<212> TYPE: PRT
<213> ORGANISM: Artificial
<220> FEATURE:
<223> OTHER INFORMATION: PL sequence binding INADL d8

<400> SEQUENCE: 151

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 152
<211> LENGTH: 18
<212> TYPE: PRT
<213> ORGANISM: Artificial
<220> FEATURE:
<223> OTHER INFORMATION: PL sequence binding INADL d8

<400> SEQUENCE: 152

Thr Phe Ala Ala Gly Phe Asn Ser Thr Gly Leu Pro His Ser Thr Thr
1               5                   10                  15

Arg Val

<210> SEQ ID NO 153
<211> LENGTH: 20
<212> TYPE: PRT
<213> ORGANISM: Artificial

```
<220> FEATURE:
<223> OTHER INFORMATION: PL sequence binding INADL d8

<400> SEQUENCE: 153

Thr Phe Lys Gly Thr Pro Thr Ala Glu Asn Pro Glu Tyr Leu Gly Leu
1               5                   10                  15

Asp Val Pro Val
            20

<210> SEQ ID NO 154
<211> LENGTH: 20
<212> TYPE: PRT
<213> ORGANISM: Artificial
<220> FEATURE:
<223> OTHER INFORMATION: PL sequence binding INADL d8

<400> SEQUENCE: 154

Thr Gly Ser Ala Leu Gln Ala Trp Arg His Thr Ser Arg Gln Ala Thr
1               5                   10                  15

Glu Ser Thr Val
            20

<210> SEQ ID NO 155
<211> LENGTH: 20
<212> TYPE: PRT
<213> ORGANISM: Artificial
<220> FEATURE:
<223> OTHER INFORMATION: PL sequence binding INADL d8

<400> SEQUENCE: 155

Thr Gln Gly Phe Pro Gly Pro Ala Thr Trp Arg Arg Ile Ser Ser Leu
1               5                   10                  15

Glu Ser Glu Val
            20

<210> SEQ ID NO 156
<211> LENGTH: 20
<212> TYPE: PRT
<213> ORGANISM: Artificial
<220> FEATURE:
<223> OTHER INFORMATION: PL sequence binding INADL d8

<400> SEQUENCE: 156

Thr Arg Glu Asp Ile Tyr Val Asn Tyr Pro Thr Phe Ser Arg Arg Pro
1               5                   10                  15

Lys Thr Arg Val
            20

<210> SEQ ID NO 157
<211> LENGTH: 19
<212> TYPE: PRT
<213> ORGANISM: Artificial
<220> FEATURE:
<223> OTHER INFORMATION: PL sequence binding INADL d8

<400> SEQUENCE: 157

Thr Thr Asn Asn Asn Pro Asn Ser Ala Val Asn Ile Lys Lys Ile Phe
1               5                   10                  15

Thr Asp Val

<210> SEQ ID NO 158
<211> LENGTH: 20
<212> TYPE: PRT
<213> ORGANISM: Artificial
```

<220> FEATURE:
<223> OTHER INFORMATION: PL sequence binding INADL d8

<400> SEQUENCE: 158

Val Asp Pro Asn Ser Pro Ala Ala Lys Lys Tyr Val Ser Tyr Asn
1               5                   10                  15

Asn Leu Val Ile
            20

<210> SEQ ID NO 159
<211> LENGTH: 20
<212> TYPE: PRT
<213> ORGANISM: Artificial
<220> FEATURE:
<223> OTHER INFORMATION: PL sequence binding INADL d8

<400> SEQUENCE: 159

Val Gly Thr Leu Leu Leu Glu Arg Val Ile Phe Pro Ser Val Lys Ile
1               5                   10                  15

Ala Thr Leu Val
            20

<210> SEQ ID NO 160
<211> LENGTH: 20
<212> TYPE: PRT
<213> ORGANISM: Artificial
<220> FEATURE:
<223> OTHER INFORMATION: PL sequence binding INADL d8

<400> SEQUENCE: 160

Val His Lys Val Arg Asn Lys Phe Lys Ala Lys Cys Ser Leu Cys Arg
1               5                   10                  15

Leu Tyr Ile Ile
            20

<210> SEQ ID NO 161
<211> LENGTH: 20
<212> TYPE: PRT
<213> ORGANISM: Artificial
<220> FEATURE:
<223> OTHER INFORMATION: PL sequence binding INADL d8

<400> SEQUENCE: 161

Tyr Gly Arg Lys Lys Arg Arg Gln Arg Arg Gly Ala Ser Ala Asp
1               5                   10                  15

Ser Thr Gln Ala
            20

<210> SEQ ID NO 162
<211> LENGTH: 20
<212> TYPE: PRT
<213> ORGANISM: Artificial
<220> FEATURE:
<223> OTHER INFORMATION: PL sequence binding INADL d8

<400> SEQUENCE: 162

Tyr Gly Arg Lys Lys Arg Arg Gln Arg Arg Lys Leu Ser Ser Ile
1               5                   10                  15

Glu Ser Asp Val
            20

<210> SEQ ID NO 163
<211> LENGTH: 20
<212> TYPE: PRT

-continued

<213> ORGANISM: Artificial
<220> FEATURE:
<223> OTHER INFORMATION: PL sequence binding INADL d8

<400> SEQUENCE: 163

Tyr Gly Arg Lys Lys Arg Arg Gln Arg Arg Met Ala Arg Thr Ala
1               5                   10                  15

Arg Ser Lys Val
            20

<210> SEQ ID NO 164
<211> LENGTH: 20
<212> TYPE: PRT
<213> ORGANISM: Artificial
<220> FEATURE:
<223> OTHER INFORMATION: PL sequence binding INADL d8

<400> SEQUENCE: 164

Tyr Gly Arg Lys Lys Arg Arg Gln Arg Arg Asn Asp Asn Ile Ala
1               5                   10                  15

Leu Leu Val Gln
            20

<210> SEQ ID NO 165
<211> LENGTH: 20
<212> TYPE: PRT
<213> ORGANISM: Artificial
<220> FEATURE:
<223> OTHER INFORMATION: PL sequence binding KIAA1284 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 165

Tyr Gly Arg Lys Lys Arg Arg Gln Arg Arg Lys Leu Ser Ser Ile
1               5                   10                  15

Glu Ser Asp Xaa
            20

<210> SEQ ID NO 166
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 166

Ala Val Gly Gly Arg Pro Ala Arg Gly Gly Arg Leu Gln Gly Arg
1               5                   10                  15

Gln Thr Gln Val
            20

<210> SEQ ID NO 167
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 167

Asp Phe Arg Pro Ser Phe Lys His Ile Leu Phe Arg Arg Ala Arg Arg
1               5                   10                  15

Gly Phe Arg Gln
            20

```
<210> SEQ ID NO 168
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 168

Asp Gly Gly Ala Arg Thr Glu Asp Glu Val Gln Ser Tyr Pro Ser Lys
1               5                   10                  15

His Asp Tyr Val
            20

<210> SEQ ID NO 169
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 169

Phe His Ser Lys Thr Ala Gly Ala Asn Thr Thr Asp Lys Glu Leu Glu
1               5                   10                  15

Val Leu Ser Leu
            20

<210> SEQ ID NO 170
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 170

Gly Gly Glu Asp Phe Lys Thr Thr Asn Pro Ser Lys Gln Phe Asp Lys
1               5                   10                  15

Asn Ala Tyr Val
            20

<210> SEQ ID NO 171
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 171

Gly Arg Trp Thr Gly Arg Ala Met Ser Ala Trp Lys Pro Thr Arg Arg
1               5                   10                  15

Glu Thr Glu Val
            20

<210> SEQ ID NO 172
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 172

His Asp Phe Arg Arg Ala Phe Lys Lys Ile Leu Ala Arg Gly Asp Arg
1               5                   10                  15

Lys Arg Ile Val
```

```
                 20

<210> SEQ ID NO 173
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 173

His His Leu Val Ala Gln Arg Asp Ile Arg Gln Phe Gln Leu Gln His
1               5                  10                  15

Trp Leu Ala Ile
            20

<210> SEQ ID NO 174
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 174

His Ser Cys Cys Asn Arg Ala Arg Gln Glu Arg Leu Gln Arg Arg Arg
1               5                  10                  15

Glu Thr Gln Val
            20

<210> SEQ ID NO 175
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 175

Ile Leu Asn Ser Ile Gln Val Met Arg Ala Gln Met Asn Gln Ile Gln
1               5                  10                  15

Ser Val Glu Val
            20

<210> SEQ ID NO 176
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 176

Lys Ala Gly Tyr Arg Ala Pro Arg Ser Tyr Pro Lys Ser Asn Ser Ser
1               5                  10                  15

Lys Glu Tyr Val
            20

<210> SEQ ID NO 177
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 177

Lys His Ser Arg Lys Ser Ser Ser Tyr Ser Ser Ser Ser Thr Thr Val
1               5                  10                  15
```

-continued

```
Lys Thr Ser Tyr
            20

<210> SEQ ID NO 178
<211> LENGTH: 23
<212> TYPE: PRT
<213> ORGANISM: Artificial
<220> FEATURE:
<223> OTHER INFORMATION: PL sequence binding KIAA1284 d1

<400> SEQUENCE: 178

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 179
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 179

Leu Ala Val Leu Ala Tyr Ser Ile Thr Leu Val Met Leu Trp Ser Ile
1               5                   10                  15

Trp Gln Tyr Ala
            20

<210> SEQ ID NO 180
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 180

Leu Gly Tyr Ser Ile Pro Ser Arg Ser Gly Ala Ser Gly Leu Asp Lys
1               5                   10                  15

Arg Asp Tyr Val
            20

<210> SEQ ID NO 181
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 181

Leu Asn Ser Cys Ser Asn Arg Arg Val Tyr Lys Lys Met Pro Ser Ile
1               5                   10                  15

Glu Ser Asp Val
            20

<210> SEQ ID NO 182
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 182

Leu Ser Glu Lys Lys Thr Ser Gln Ser Pro His Arg Phe Gln Lys Thr
1               5                   10                  15
```

```
Ala Ser Pro Ile
            20

<210> SEQ ID NO 183
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 183

Pro Gly Gln Pro Pro Lys Val Lys Ser Glu Phe Asn Ser Tyr Ser Leu
1               5                   10                  15

Thr Gly Tyr Val
            20

<210> SEQ ID NO 184
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 184

Pro Ile Pro Ala Gly Gly Cys Thr Phe Ser Gly Ile Phe Pro Thr Leu
1               5                   10                  15

Thr Ser Pro Leu
            20

<210> SEQ ID NO 185
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 185

Gln Asp Phe Arg Arg Ala Phe Arg Arg Ile Leu Ala Arg Pro Trp Thr
1               5                   10                  15

Gln Thr Ala Trp
            20

<210> SEQ ID NO 186
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 186

Arg Glu Leu Val Asp Arg Gly Glu Val Arg Gln Phe Thr Leu Arg His
1               5                   10                  15

Trp Leu Lys Val
            20

<210> SEQ ID NO 187
<211> LENGTH: 19
<212> TYPE: PRT
<213> ORGANISM: Artificial
<220> FEATURE:
<223> OTHER INFORMATION: PL sequence binding KIAA1284 d1

<400> SEQUENCE: 187

Ser Ser Lys Ser Lys Ser Ser Glu Glu Ser Gln Thr Phe Phe Gly Leu
```

```
                  1               5                  10                  15

Tyr Lys Leu

<210> SEQ ID NO 188
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 188

Ser Ser Pro Asp Ser Ser Tyr Gln Gly Lys Gly Phe Val Met Ser Arg
1               5                  10                  15

Ala Met Tyr Val
            20

<210> SEQ ID NO 189
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 189

Thr Phe Lys Gly Thr Pro Thr Ala Glu Asn Pro Glu Tyr Leu Gly Leu
1               5                  10                  15

Asp Val Pro Val
            20

<210> SEQ ID NO 190
<211> LENGTH: 19
<212> TYPE: PRT
<213> ORGANISM: Artificial
<220> FEATURE:
<223> OTHER INFORMATION: PL sequence binding KIAA1284 d1

<400> SEQUENCE: 190

Thr Thr Asn Asn Asn Pro Asn Ser Ala Val Asn Ile Lys Lys Ile Phe
1               5                  10                  15

Thr Asp Val

<210> SEQ ID NO 191
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 191

Val Asp Pro Asn Ser Pro Ala Ala Lys Lys Lys Tyr Val Ser Tyr Asn
1               5                  10                  15

Asn Leu Val Ile
            20

<210> SEQ ID NO 192
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 192

Val His Lys Val Arg Asn Lys Phe Lys Ala Lys Cys Ser Leu Cys Arg
1               5                  10                  15
```

Leu Tyr Ile Ile
            20

<210> SEQ ID NO 193
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 193

Tyr Gly Arg Lys Lys Arg Arg Gln Arg Arg Glu Met Gln Val Thr
1               5                   10                  15

Leu Gly Leu His
            20

<210> SEQ ID NO 194
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 194

Tyr Gly Arg Lys Lys Arg Arg Gln Arg Arg Gly Ala Ser Ala Asp
1               5                   10                  15

Ser Thr Gln Ala
            20

<210> SEQ ID NO 195
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 195

Tyr Gly Arg Lys Lys Arg Arg Gln Arg Arg Ile Gly Glu Leu Gln
1               5                   10                  15

Leu Ser Ile Ala
            20

<210> SEQ ID NO 196
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 196

Tyr Gly Arg Lys Lys Arg Arg Gln Arg Arg Lys Leu Ser Ser Ile
1               5                   10                  15

Glu Ser Asp Val
            20

<210> SEQ ID NO 197
<211> LENGTH: 20
<212> TYPE: PRT
<213> ORGANISM: Artificial
<220> FEATURE:
<223> OTHER INFORMATION: PL sequence binding KIAA1284 d1
<220> FEATURE:
<221> NAME/KEY: misc_feature
<222> LOCATION: (20)..(20)
<223> OTHER INFORMATION: Xaa can be any naturally occurring amino acid

```
<400> SEQUENCE: 197

Tyr Gly Arg Lys Lys Arg Arg Gln Arg Arg Lys Leu Ser Ser Ile
1               5                   10                  15

Glu Ser Asp Xaa
            20

<210> SEQ ID NO 198
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 198

Tyr Gly Arg Lys Lys Arg Arg Gln Arg Arg Asn Asp Asn Ile Ala
1               5                   10                  15

Leu Leu Val Gln
            20

<210> SEQ ID NO 199
<211> LENGTH: 20
<212> TYPE: PRT
<213> ORGANISM: Artificial
<220> FEATURE:
<223> OTHER INFORMATION: PL sequence binding KIAA1284 d1

<400> SEQUENCE: 199

Tyr Gly Arg Lys Lys Arg Arg Gln Arg Arg Ser Glu Gly Val Pro
1               5                   10                  15

Asp Leu Leu Val
            20

<210> SEQ ID NO 200
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 200

Asp Phe Arg Pro Ser Phe Lys His Ile Leu Phe Arg Arg Ala Arg Arg
1               5                   10                  15

Gly Phe Arg Gln
            20

<210> SEQ ID NO 201
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 201

Asp Gly Gly Ala Arg Thr Glu Asp Glu Val Gln Ser Tyr Pro Ser Lys
1               5                   10                  15

His Asp Tyr Val
            20

<210> SEQ ID NO 202
<211> LENGTH: 20
<212> TYPE: PRT
<213> ORGANISM: Artificial
<220> FEATURE:
```

```
<223> OTHER INFORMATION: PL sequence binding KIAA1415 d1

<400> SEQUENCE: 202

Glu Ala Leu Gln Pro Glu Pro Gly Arg Lys Arg Ile Pro Leu Thr Arg
1               5                   10                  15

Thr Thr Thr Phe
            20

<210> SEQ ID NO 203
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 203

Phe His Ser Lys Thr Ala Gly Ala Asn Thr Thr Asp Lys Glu Leu Glu
1               5                   10                  15

Val Leu Ser Leu
            20

<210> SEQ ID NO 204
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 204

Gly Gly Glu Asp Phe Lys Thr Thr Asn Pro Ser Lys Gln Phe Asp Lys
1               5                   10                  15

Asn Ala Tyr Val
            20

<210> SEQ ID NO 205
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 205

His His Leu Val Ala Gln Arg Asp Ile Arg Gln Phe Gln Leu Gln His
1               5                   10                  15

Trp Leu Ala Ile
            20

<210> SEQ ID NO 206
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 206

His Ser Cys Cys Asn Arg Ala Arg Gln Glu Arg Leu Gln Arg Arg Arg
1               5                   10                  15

Glu Thr Gln Val
            20

<210> SEQ ID NO 207
<211> LENGTH: 20
<212> TYPE: PRT
<213> ORGANISM: Artificial
```

-continued

```
<220> FEATURE:
<223> OTHER INFORMATION: PL sequence binding KIAA1415 d1

<400> SEQUENCE: 207

Ile Leu Asn Ser Ile Gln Val Met Arg Ala Gln Met Asn Gln Ile Gln
1               5                   10                  15

Ser Val Glu Val
            20

<210> SEQ ID NO 208
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 208

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 209
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 209

Lys His Ser Arg Lys Ser Ser Tyr Ser Ser Ser Ser Thr Thr Val
1               5                   10                  15

Lys Thr Ser Tyr
            20

<210> SEQ ID NO 210
<211> LENGTH: 23
<212> TYPE: PRT
<213> ORGANISM: Artificial
<220> FEATURE:
<223> OTHER INFORMATION: PL sequence binding KIAA1415 d1

<400> SEQUENCE: 210

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 211
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 211

Leu Ala Val Leu Ala Tyr Ser Ile Thr Leu Val Met Leu Trp Ser Ile
1               5                   10                  15

Trp Gln Tyr Ala
            20

<210> SEQ ID NO 212
<211> LENGTH: 20
<212> TYPE: PRT
```

```
<213> ORGANISM: Artificial
<220> FEATURE:
<223> OTHER INFORMATION: PL sequence binding KIAA1415 d1

<400> SEQUENCE: 212

Leu Gly Tyr Ser Ile Pro Ser Arg Ser Gly Ala Ser Gly Leu Asp Lys
 1               5                  10                  15

Arg Asp Tyr Val
            20

<210> SEQ ID NO 213
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 213

Leu Asn Ser Cys Ser Asn Arg Arg Val Tyr Lys Lys Met Pro Ser Ile
 1               5                  10                  15

Glu Ser Asp Val
            20

<210> SEQ ID NO 214
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 214

Pro Gly Gln Pro Pro Lys Val Lys Ser Glu Phe Asn Ser Tyr Ser Leu
 1               5                  10                  15

Thr Gly Tyr Val
            20

<210> SEQ ID NO 215
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 215

Pro Ile Pro Ala Gly Gly Cys Thr Phe Ser Gly Ile Phe Pro Thr Leu
 1               5                  10                  15

Thr Ser Pro Leu
            20

<210> SEQ ID NO 216
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 216

Gln Asp Phe Arg Arg Ala Phe Arg Arg Ile Leu Ala Arg Pro Trp Thr
 1               5                  10                  15

Gln Thr Ala Trp
            20

<210> SEQ ID NO 217
<211> LENGTH: 20
```

```
<212> TYPE: PRT
<213> ORGANISM: Artificial
<220> FEATURE:
<223> OTHER INFORMATION: PL sequence binding KIAA1415 d1

<400> SEQUENCE: 217

Arg Glu Leu Val Asp Arg Gly Glu Val Arg Gln Phe Thr Leu Arg His
1               5                   10                  15

Trp Leu Lys Val
            20

<210> SEQ ID NO 218
<211> LENGTH: 19
<212> TYPE: PRT
<213> ORGANISM: Artificial
<220> FEATURE:
<223> OTHER INFORMATION: PL sequence binding KIAA1415 d1

<400> SEQUENCE: 218

Ser Ser Lys Ser Lys Ser Ser Glu Glu Ser Gln Thr Phe Phe Gly Leu
1               5                   10                  15

Tyr Lys Leu

<210> SEQ ID NO 219
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 219

Ser Ser Pro Asp Ser Ser Tyr Gln Gly Lys Gly Phe Val Met Ser Arg
1               5                   10                  15

Ala Met Tyr Val
            20

<210> SEQ ID NO 220
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 220

Ser Ser Ser Arg Arg Asp Ser Ser Trp Ser Glu Thr Ser Glu Ala Ser
1               5                   10                  15

Tyr Ser Gly Leu
            20

<210> SEQ ID NO 221
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 221

Thr Ala Glu Asn Ala Glu Tyr Leu Arg Val Ala Pro Gln Ser Ser Glu
1               5                   10                  15

Phe Ile Gly Ala
            20

<210> SEQ ID NO 222
<211> LENGTH: 19
```

<212> TYPE: PRT
<213> ORGANISM: Artificial
<220> FEATURE:
<223> OTHER INFORMATION: PL sequence binding KIAA1415 d1

<400> SEQUENCE: 222

Thr Thr Asn Asn Asn Pro Asn Ser Ala Val Asn Ile Lys Lys Ile Phe
1               5                   10                  15

Thr Asp Val

<210> SEQ ID NO 223
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 223

Val Asp Pro Asn Ser Pro Ala Ala Lys Lys Lys Tyr Val Ser Tyr Asn
1               5                   10                  15

Asn Leu Val Ile
            20

<210> SEQ ID NO 224
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 224

Val His Lys Val Arg Asn Lys Phe Lys Ala Lys Cys Ser Leu Cys Arg
1               5                   10                  15

Leu Tyr Ile Ile
            20

<210> SEQ ID NO 225
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 225

Tyr Gly Arg Lys Lys Arg Arg Gln Arg Arg Gly Ala Ser Ala Asp
1               5                   10                  15

Ser Thr Gln Ala
            20

<210> SEQ ID NO 226
<211> LENGTH: 20
<212> TYPE: PRT
<213> ORGANISM: Artificial
<220> FEATURE:
<223> OTHER INFORMATION: PL sequence binding KIAA1415 d1

<400> SEQUENCE: 226

Tyr Gly Arg Lys Lys Arg Arg Gln Arg Arg Asn Asp Asn Ile Ala
1               5                   10                  15

Leu Leu Val Gln
            20

<210> SEQ ID NO 227
<211> LENGTH: 20

```
<212> TYPE: PRT
<213> ORGANISM: Artificial
<220> FEATURE:
<223> OTHER INFORMATION: PL sequence binding KIAA1415 d1

<400> SEQUENCE: 227

Tyr Gly Arg Lys Lys Arg Arg Gln Arg Arg Ser Glu Gly Val Pro
1               5                   10                  15

Asp Leu Leu Val
            20

<210> SEQ ID NO 228
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 228

Asp Gly Gly Ala Arg Thr Glu Asp Glu Val Gln Ser Tyr Pro Ser Lys
1               5                   10                  15

His Asp Tyr Val
            20

<210> SEQ ID NO 229
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 229

Phe His Ser Lys Thr Ala Gly Ala Asn Thr Thr Asp Lys Glu Leu Glu
1               5                   10                  15

Val Leu Ser Leu
            20

<210> SEQ ID NO 230
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 230

His Asp Phe Arg Arg Ala Phe Lys Lys Ile Leu Ala Arg Gly Asp Arg
1               5                   10                  15

Lys Arg Ile Val
            20

<210> SEQ ID NO 231
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 231

His His Leu Val Ala Gln Arg Asp Ile Arg Gln Phe Gln Leu Gln His
1               5                   10                  15

Trp Leu Ala Ile
            20

<210> SEQ ID NO 232
```

-continued

```
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 232

His Ser Cys Cys Asn Arg Ala Arg Gln Glu Arg Leu Gln Arg Arg Arg
1               5                   10                  15

Glu Thr Gln Val
            20

<210> SEQ ID NO 233
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 233

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 234
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 234

Lys His Ser Arg Lys Ser Ser Ser Tyr Ser Ser Ser Ser Thr Thr Val
1               5                   10                  15

Lys Thr Ser Tyr
            20

<210> SEQ ID NO 235
<211> LENGTH: 23
<212> TYPE: PRT
<213> ORGANISM: Artificial
<220> FEATURE:
<223> OTHER INFORMATION: PL sequence binding KIAA1719 d4

<400> SEQUENCE: 235

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 236
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 236

Leu Ala Val Leu Ala Tyr Ser Ile Thr Leu Val Met Leu Trp Ser Ile
1               5                   10                  15

Trp Gln Tyr Ala
            20
```

-continued

```
<210> SEQ ID NO 237
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 237

Asn Ser Tyr Val Arg Asp Asp Ala Ile Phe Ile Lys Ala Ile Val Asp
1               5                   10                  15

Leu Thr Gly Leu
            20

<210> SEQ ID NO 238
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 238

Pro Gly Gln Pro Pro Lys Val Lys Ser Glu Phe Asn Ser Tyr Ser Leu
1               5                   10                  15

Thr Gly Tyr Val
            20

<210> SEQ ID NO 239
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 239

Gln Asp Phe Arg Arg Ala Phe Arg Arg Ile Leu Ala Arg Pro Trp Thr
1               5                   10                  15

Gln Thr Ala Trp
            20

<210> SEQ ID NO 240
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 240

Ser Pro Ala Ser Ile Pro His Ser Pro Gly Ala Phe Ala Tyr Glu Gly
1               5                   10                  15

Ala Ser Phe Tyr
            20

<210> SEQ ID NO 241
<211> LENGTH: 19
<212> TYPE: PRT
<213> ORGANISM: Artificial
<220> FEATURE:
<223> OTHER INFORMATION: PL sequence binding KIAA1719 d4

<400> SEQUENCE: 241

Ser Ser Lys Ser Lys Ser Ser Glu Glu Ser Gln Thr Phe Phe Gly Leu
1               5                   10                  15

Tyr Lys Leu
```

```
<210> SEQ ID NO 242
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 242

Ser Ser Ser Arg Arg Asp Ser Ser Trp Ser Glu Thr Ser Glu Ala Ser
1               5                   10                  15

Tyr Ser Gly Leu
            20

<210> SEQ ID NO 243
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 243

Val His Lys Val Arg Asn Lys Phe Lys Ala Lys Cys Ser Leu Cys Arg
1               5                   10                  15

Leu Tyr Ile Ile
            20

<210> SEQ ID NO 244
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 244

Tyr Gly Arg Lys Lys Arg Arg Gln Arg Arg Arg Glu Met Gln Val Thr
1               5                   10                  15

Leu Gly Leu His
            20

<210> SEQ ID NO 245
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 245

Tyr Gly Arg Lys Lys Arg Arg Gln Arg Arg Arg Asn Asp Asn Ile Ala
1               5                   10                  15

Leu Leu Val Gln
            20

<210> SEQ ID NO 246
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 246

Tyr Gly Arg Lys Lys Arg Arg Gln Arg Arg Arg Ile Ser Ser Ile
1               5                   10                  15

Glu Thr Asp Val
            20
```

```
<210> SEQ ID NO 247
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 247

Tyr Gly Arg Lys Lys Arg Arg Gln Arg Arg Arg Ile Ser Ser Leu
1               5                   10                  15

Glu Thr Gln Val
            20

<210> SEQ ID NO 248
<211> LENGTH: 20
<212> TYPE: PRT
<213> ORGANISM: Artificial
<220> FEATURE:
<223> OTHER INFORMATION: PL sequence binding KIAA1719 d4

<400> SEQUENCE: 248

Tyr Gly Arg Lys Lys Arg Arg Gln Arg Arg Arg Ser Glu Gly Val Pro
1               5                   10                  15

Asp Leu Leu Val
            20

<210> SEQ ID NO 249
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 249

Ala Ala Gly Gly Arg Ser Ala Arg Gly Gly Arg Leu Gln Gly Arg Arg
1               5                   10                  15

Glu Thr Ala Leu
            20

<210> SEQ ID NO 250
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 250

Ala Thr Asp Tyr Leu Val Gln Pro Phe Met Asp Gln Leu Ala Phe His
1               5                   10                  15

Gln Phe Tyr Ile
            20

<210> SEQ ID NO 251
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 251

Asp Phe Arg Pro Ser Phe Lys His Ile Leu Phe Arg Arg Ala Arg Arg
1               5                   10                  15

Gly Phe Arg Gln
            20
```

<210> SEQ ID NO 252
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 252

Glu Asp Pro Lys Asp Arg Pro Ser Ala Ala His Ile Val Glu Ala Leu
1               5                   10                  15

Glu Thr Asp Val
            20

<210> SEQ ID NO 253
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 253

Glu Leu Leu Gln Phe Cys Arg Thr Pro Asn Pro Ala Leu Lys Asn Gly
1               5                   10                  15

Gln Tyr Trp Val
            20

<210> SEQ ID NO 254
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 254

Phe His Ser Lys Thr Ala Gly Ala Asn Thr Thr Asp Lys Glu Leu Glu
1               5                   10                  15

Val Leu Ser Leu
            20

<210> SEQ ID NO 255
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 255

Phe Asn Gly Ser Ser Asn Gly His Val Tyr Glu Lys Leu Ser Ser Ile
1               5                   10                  15

Glu Ser Asp Val
            20

<210> SEQ ID NO 256
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 256

Gly Arg Trp Thr Gly Arg Ala Met Ser Ala Trp Lys Pro Thr Arg Arg
1               5                   10                  15

Glu Thr Glu Val

-continued

```
                20

<210> SEQ ID NO 257
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 257

His Asp Phe Arg Arg Ala Phe Lys Lys Ile Leu Ala Arg Gly Asp Arg
1               5                   10                  15

Lys Arg Ile Val
            20

<210> SEQ ID NO 258
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 258

His His Leu Val Ala Gln Arg Asp Ile Arg Gln Phe Gln Leu Gln His
1               5                   10                  15

Trp Leu Ala Ile
            20

<210> SEQ ID NO 259
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 259

His Ser Cys Cys Asn Arg Ala Arg Gln Glu Arg Leu Gln Arg Arg Arg
1               5                   10                  15

Glu Thr Gln Val
            20

<210> SEQ ID NO 260
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 260

Ile Leu Asn Ser Ile Gln Val Met Arg Ala Gln Met Asn Gln Ile Gln
1               5                   10                  15

Ser Val Glu Val
            20

<210> SEQ ID NO 261
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 261

Lys His Ser Arg Lys Ser Ser Ser Tyr Ser Ser Ser Ser Thr Thr Val
1               5                   10                  15
```

```
Lys Thr Ser Tyr
            20

<210> SEQ ID NO 262
<211> LENGTH: 23
<212> TYPE: PRT
<213> ORGANISM: Artificial
<220> FEATURE:
<223> OTHER INFORMATION: PL sequence binding Lim Mystique d1

<400> SEQUENCE: 262

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 263
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 263

Leu Ala Ser Lys Ser Ala Glu Glu Gly Lys Gln Ile Pro Asp Ser Leu
1               5                   10                  15

Ser Thr Asp Leu
            20

<210> SEQ ID NO 264
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 264

Leu Ala Val Leu Ala Tyr Ser Ile Thr Leu Val Met Leu Trp Ser Ile
1               5                   10                  15

Trp Gln Tyr Ala
            20

<210> SEQ ID NO 265
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 265

Leu Met Asp Gly Leu Pro Pro Gly Asp Ser Asn Gln Leu Ala Trp Phe
1               5                   10                  15

Asp Thr Asp Leu
            20

<210> SEQ ID NO 266
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 266

Leu Asn Ser Cys Ser Asn Arg Arg Val Tyr Lys Lys Met Pro Ser Ile
1               5                   10                  15
```

```
Glu Ser Asp Val
            20

<210> SEQ ID NO 267
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 267

Leu Asn Ser Ser Ser Asn Arg Arg Val Tyr Lys Lys Met Pro Ser Ile
1               5                   10                  15

Glu Ser Asp Val
            20

<210> SEQ ID NO 268
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 268

Pro Ile Pro Ala Gly Gly Cys Thr Phe Ser Gly Ile Phe Pro Thr Leu
1               5                   10                  15

Thr Ser Pro Leu
            20

<210> SEQ ID NO 269
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 269

Pro Tyr Ser Glu Leu Asn Tyr Glu Thr Ser His Tyr Pro Ala Ser Pro
1               5                   10                  15

Asp Ser Trp Val
            20

<210> SEQ ID NO 270
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 270

Gln Asp Phe Arg Arg Ala Phe Arg Arg Ile Leu Ala Arg Pro Trp Thr
1               5                   10                  15

Gln Thr Ala Trp
            20

<210> SEQ ID NO 271
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 271

Gln Ile Ser Pro Gly Gly Leu Glu Pro Pro Ser Glu Lys His Phe Arg
```

-continued

```
               1               5                  10                 15
Glu Thr Glu Val
            20

<210> SEQ ID NO 272
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 272

Arg Glu Leu Val Asp Arg Gly Glu Val Arg Gln Phe Thr Leu Arg His
1               5                   10                  15

Trp Leu Lys Val
            20

<210> SEQ ID NO 273
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 273

Ser Pro Ala Ser Ile Pro His Ser Pro Gly Ala Phe Ala Tyr Glu Gly
1               5                   10                  15

Ala Ser Phe Tyr
            20

<210> SEQ ID NO 274
<211> LENGTH: 19
<212> TYPE: PRT
<213> ORGANISM: Artificial
<220> FEATURE:
<223> OTHER INFORMATION: PL sequence binding Lim Mystique d1

<400> SEQUENCE: 274

Ser Ser Lys Ser Lys Ser Ser Glu Glu Ser Gln Thr Phe Phe Gly Leu
1               5                   10                  15

Tyr Lys Leu

<210> SEQ ID NO 275
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 275

Ser Ser Ser Arg Arg Asp Ser Ser Trp Ser Glu Thr Ser Glu Ala Ser
1               5                   10                  15

Tyr Ser Gly Leu
            20

<210> SEQ ID NO 276
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 276

Ser Tyr Pro Thr Pro Arg Pro Tyr Pro Lys Pro Ala Pro Ser Ser Gly
```

```
                1               5                  10                  15

Lys Asp Tyr Val
            20

<210> SEQ ID NO 277
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 277

Thr Phe Lys Gly Thr Pro Thr Ala Glu Asn Pro Glu Tyr Leu Gly Leu
1               5                   10                  15

Asp Val Pro Val
            20

<210> SEQ ID NO 278
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 278

Thr Gln Gly Phe Pro Gly Pro Ala Thr Trp Arg Arg Ile Ser Ser Leu
1               5                   10                  15

Glu Ser Glu Val
            20

<210> SEQ ID NO 279
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 279

Val Asp Pro Asn Ser Pro Ala Ala Lys Lys Lys Tyr Val Ser Tyr Asn
1               5                   10                  15

Asn Leu Val Ile
            20

<210> SEQ ID NO 280
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 280

Val His Asp Ala Glu Ser Ser Asp Glu Asp Gly Tyr Asp Trp Gly Pro
1               5                   10                  15

Ala Thr Asp Leu
            20

<210> SEQ ID NO 281
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 281
```

-continued

Val His Lys Val Arg Asn Lys Phe Lys Ala Lys Cys Ser Leu Cys Arg
1               5                   10                  15

Leu Tyr Ile Ile
            20

<210> SEQ ID NO 282
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 282

Val Pro Gly Ala Leu Asp Tyr Ala Ala Phe Ser Ser Ala Leu Tyr Gly
1               5                   10                  15

Glu Ser Asp Leu
            20

<210> SEQ ID NO 283
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 283

Tyr Gly Arg Lys Lys Arg Arg Gln Arg Arg Ala Val Ala Ala Ala
1               5                   10                  15

Ser Ala Asn Leu
            20

<210> SEQ ID NO 284
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 284

Tyr Gly Arg Lys Lys Arg Arg Gln Arg Arg Ala Val Ala Ala Thr
1               5                   10                  15

Ser Ala Asn Leu
            20

<210> SEQ ID NO 285
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 285

Tyr Gly Arg Lys Lys Arg Arg Gln Arg Arg Ala Val Ala Ala Thr
1               5                   10                  15

Ser Ile Asn Leu
            20

<210> SEQ ID NO 286
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 286

```
Tyr Gly Arg Lys Lys Arg Arg Gln Arg Arg Glu Tyr Leu Gly Leu
1               5                   10                  15

Asp Val Pro Val
            20

<210> SEQ ID NO 287
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 287

Tyr Gly Arg Lys Lys Arg Arg Gln Arg Arg Lys Leu Ser Ser Ile
1               5                   10                  15

Glu Ser Asp Val
            20

<210> SEQ ID NO 288
<211> LENGTH: 20
<212> TYPE: PRT
<213> ORGANISM: Artificial
<220> FEATURE:
<223> OTHER INFORMATION: PL sequence binding Lim Mystique d1

<400> SEQUENCE: 288

Tyr Gly Arg Lys Lys Arg Arg Gln Arg Arg Asn Asp Asn Ile Ala
1               5                   10                  15

Leu Leu Val Gln
            20

<210> SEQ ID NO 289
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 289

Ala Ala Gly Gly Arg Ser Ala Arg Gly Gly Arg Leu Gln Gly Arg Arg
1               5                   10                  15

Glu Thr Ala Leu
            20

<210> SEQ ID NO 290
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 290

Ala Leu Val Leu Ile Ala Phe Cys Ile Ile Arg Arg Arg Pro Ser Ala
1               5                   10                  15

Tyr Gln Ala Leu
            20

<210> SEQ ID NO 291
<211> LENGTH: 19
<212> TYPE: PRT
<213> ORGANISM: Artificial
<220> FEATURE:
<223> OTHER INFORMATION: PL sequence binding MAGI1 d1
```

-continued

```
<400> SEQUENCE: 291

Ala Arg His Arg Val Thr Ser Tyr Thr Ser Ser Ser Val Asn Val Ser
1               5                   10                  15

Ser Asn Leu

<210> SEQ ID NO 292
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 292

Ala Thr Asp Tyr Leu Val Gln Pro Phe Met Asp Gln Leu Ala Phe His
1               5                   10                  15

Gln Phe Tyr Ile
            20

<210> SEQ ID NO 293
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 293

Ala Val Gly Gly Arg Pro Ala Arg Gly Gly Arg Leu Gln Gly Arg Arg
1               5                   10                  15

Gln Thr Gln Val
            20

<210> SEQ ID NO 294
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 294

Ala Trp Asp Asp Ser Ala Arg Ala Ala Gly Gln Gly Leu His Val
1               5                   10                  15

Thr Ala Leu

<210> SEQ ID NO 295
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 295

Asp Phe Arg Pro Ser Phe Lys His Ile Leu Phe Arg Arg Ala Arg Arg
1               5                   10                  15

Gly Phe Arg Gln
            20

<210> SEQ ID NO 296
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 296
```

-continued

```
Glu Leu Leu Gln Phe Cys Arg Thr Pro Asn Pro Ala Leu Lys Asn Gly
1               5                   10                  15

Gln Tyr Trp Val
            20

<210> SEQ ID NO 297
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 297

Glu Ser Ser Gly Thr Gln Ser Pro Lys Arg His Ser Gly Ser Tyr Leu
1               5                   10                  15

Val Thr Ser Val
            20

<210> SEQ ID NO 298
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 298

Phe Asn Gly Ser Ser Asn Gly His Val Tyr Glu Lys Leu Ser Ser Ile
1               5                   10                  15

Glu Ser Asp Val
            20

<210> SEQ ID NO 299
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 299

Gly Gly Gly Gly Gly Ser Gly Gly Gly Gly Ser Gly Ile Glu Ser
1               5                   10                  15

Val Lys Ile

<210> SEQ ID NO 300
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 300

Gly Gly Gly Gly Gly Ser Gly Gly Gly Ser Gly Gly Gly His Ser
1               5                   10                  15

Thr Thr Arg Val
            20

<210> SEQ ID NO 301
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 301
```

-continued

```
Gly Gly Gly Gly Gly Ser Gly Gly Gly Ser Gly Leu Pro His Ser
1               5                   10                  15

Thr Thr Arg Val
            20

<210> SEQ ID NO 302
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 302

Gly Gly Gly Gly Gly Ser Gly Gly Gly Ser Gly Ser Arg Pro
1               5                   10                  15

Lys Thr Arg Val
            20

<210> SEQ ID NO 303
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 303

Gly Gly Gly Gly Gly Ser Gly Gly Gly Thr Phe Ser Arg Pro
1               5                   10                  15

Lys Thr Arg Val
            20

<210> SEQ ID NO 304
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 304

Gly Arg Trp Ala Gly Arg Ser Ala Ala Ser Trp Ser Arg Arg
1               5                   10                  15

Glu Thr Ala Leu
            20

<210> SEQ ID NO 305
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 305

Gly Arg Trp Thr Gly Arg Ala Met Ser Ala Trp Lys Pro Thr Arg Arg
1               5                   10                  15

Glu Thr Glu Val
            20

<210> SEQ ID NO 306
<211> LENGTH: 20
<212> TYPE: PRT
<213> ORGANISM: Artificial
<220> FEATURE:
<223> OTHER INFORMATION: PL sequence binding MAGI1 d1
```

-continued

```
<400> SEQUENCE: 306

Gly Arg Trp Thr Gly Arg Ser Ala Val Ser Trp Arg Pro Arg Arg Arg
1               5                   10                  15

Gln Thr Gln Val
            20

<210> SEQ ID NO 307
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 307

Gly Arg Trp Thr Gly Arg Ser Met Ser Ser Trp Lys Pro Thr Arg Arg
1               5                   10                  15

Glu Thr Glu Val
            20

<210> SEQ ID NO 308
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 308

His His Leu Val Ala Gln Arg Asp Ile Arg Gln Phe Gln Leu Gln His
1               5                   10                  15

Trp Leu Ala Ile
            20

<210> SEQ ID NO 309
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 309

His Ser Cys Cys Asn Arg Ala Arg Gln Glu Arg Leu Gln Arg Arg Arg
1               5                   10                  15

Glu Thr Gln Val
            20

<210> SEQ ID NO 310
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 310

Ile Ser Gly Thr Pro Thr Ser Thr Met Val His Gly Met Thr Ser Ser
1               5                   10                  15

Ser Ser Val Val
            20

<210> SEQ ID NO 311
<211> LENGTH: 20
<212> TYPE: PRT
<213> ORGANISM: Artificial
<220> FEATURE:
<223> OTHER INFORMATION: PL sequence binding MAGI1 d1
```

<400> SEQUENCE: 311

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 312
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 312

Lys Asp Ser Arg Pro Ser Phe Val Gly Ser Ser Ser Gly His Thr Ser
1               5                   10                  15

Thr Thr Leu

<210> SEQ ID NO 313
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 313

Lys His Ser Arg Lys Ser Ser Ser Tyr Ser Ser Ser Ser Thr Thr Val
1               5                   10                  15

Lys Thr Ser Tyr
            20

<210> SEQ ID NO 314
<211> LENGTH: 23
<212> TYPE: PRT
<213> ORGANISM: Artificial
<220> FEATURE:
<223> OTHER INFORMATION: PL sequence binding MAGI1 d1

<400> SEQUENCE: 314

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 315
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 315

Leu Ala Val Leu Ala Tyr Ser Ile Thr Leu Val Met Leu Trp Ser Ile
1               5                   10                  15

Trp Gln Tyr Ala
            20

<210> SEQ ID NO 316
<211> LENGTH: 20
<212> TYPE: PRT
<213> ORGANISM: Artificial
<220> FEATURE:
<223> OTHER INFORMATION: PL sequence binding MAGI1 d1

```
<400> SEQUENCE: 316

Leu His Asn Gln Ala Ser Val Pro Leu Glu Pro Arg Pro Leu Arg Arg
1               5                   10                  15

Glu Ser Glu Ile
            20

<210> SEQ ID NO 317
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 317

Leu Asn Glu Thr Thr Glu Thr Gln Arg Thr Leu Leu Asn Gly Asp Leu
1               5                   10                  15

Gln Thr Ser Ile
            20

<210> SEQ ID NO 318
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 318

Leu Asn Ser Cys Ser Asn Arg Arg Val Tyr Lys Lys Met Pro Ser Ile
1               5                   10                  15

Glu Ser Asp Val
            20

<210> SEQ ID NO 319
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 319

Leu Asn Ser Ser Ser Asn Arg Arg Val Tyr Lys Lys Met Pro Ser Ile
1               5                   10                  15

Glu Ser Asp Val
            20

<210> SEQ ID NO 320
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 320

Met Gly Arg Trp Thr Gly Arg Ser Ser Glu Ser Trp Arg Pro Arg Pro
1               5                   10                  15

Val Thr Gln Val
            20

<210> SEQ ID NO 321
<211> LENGTH: 20
<212> TYPE: PRT
<213> ORGANISM: Artificial
<220> FEATURE:
```

```
<223> OTHER INFORMATION: PL sequence binding MAGI1 d1

<400> SEQUENCE: 321

Asn Thr Ser Ser Asp Gln Ala Arg Gln Glu Arg Leu Arg Arg Arg Arg
1               5                   10                  15

Glu Thr Gln Val
            20

<210> SEQ ID NO 322
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 322

Pro Gly Gln Pro Pro Lys Val Lys Ser Glu Phe Asn Ser Tyr Ser Leu
1               5                   10                  15

Thr Gly Tyr Val
            20

<210> SEQ ID NO 323
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 323

Pro Ile Pro Ala Gly Gly Cys Thr Phe Ser Gly Ile Phe Pro Thr Leu
1               5                   10                  15

Thr Ser Pro Leu
            20

<210> SEQ ID NO 324
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 324

Gln Asp Phe Arg Arg Ala Phe Arg Arg Ile Leu Ala Arg Pro Trp Thr
1               5                   10                  15

Gln Thr Ala Trp
            20

<210> SEQ ID NO 325
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 325

Gln Ile Ser Pro Gly Gly Leu Glu Pro Pro Ser Glu Lys His Phe Arg
1               5                   10                  15

Glu Thr Glu Val
            20

<210> SEQ ID NO 326
<211> LENGTH: 20
<212> TYPE: PRT
<213> ORGANISM: Artificial
```

-continued

```
<220> FEATURE:
<223> OTHER INFORMATION: PL sequence binding MAGI1 d1

<400> SEQUENCE: 326

Gln Gln Tyr Gln Gln Arg Gln Ser Val Ile Phe His Lys Arg Ala Pro
1               5                   10                  15

Glu Gln Ala Leu
            20

<210> SEQ ID NO 327
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 327

Arg Glu Leu Val Asp Arg Gly Glu Val Arg Gln Phe Thr Leu Arg His
1               5                   10                  15

Trp Leu Lys Val
            20

<210> SEQ ID NO 328
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 328

Arg Asn Ile Glu Glu Val Tyr Val Gly Gly Lys Gln Val Val Pro Phe
1               5                   10                  15

Ser Ser Ser Val
            20

<210> SEQ ID NO 329
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 329

Ser Glu Gly Gly Arg Pro Thr Arg Gly Pro Arg Leu Gln Gly Arg Arg
1               5                   10                  15

Val Thr Gln Val
            20

<210> SEQ ID NO 330
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 330

Ser Phe Thr Ser Ile Leu Thr Cys His Gln Arg Arg Thr Gln Arg Lys
1               5                   10                  15

Glu Thr Val Ala
            20

<210> SEQ ID NO 331
<211> LENGTH: 19
<212> TYPE: PRT
```

```
<213> ORGANISM: Artificial
<220> FEATURE:
<223> OTHER INFORMATION: PL sequence binding MAGI1 d1

<400> SEQUENCE: 331

Ser Gly Gly Asn Arg Ala Arg Gln Glu Arg Leu Gln Arg Arg Arg Glu
1               5                   10                  15

Thr Gln Val

<210> SEQ ID NO 332
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 332

Ser Leu Ile Gly Pro Val Gln Lys Glu Tyr Gln Arg Glu Leu Gly Lys
1               5                   10                  15

Leu Ser Ser Pro
            20

<210> SEQ ID NO 333
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 333

Ser Leu Lys Pro Gly Thr Val Leu Pro Pro Pro Pro Tyr Arg His Arg
1               5                   10                  15

Asn Thr Val Val
            20

<210> SEQ ID NO 334
<211> LENGTH: 18
<212> TYPE: PRT
<213> ORGANISM: Artificial
<220> FEATURE:
<223> OTHER INFORMATION: PL sequence binding MAGI1 d1

<400> SEQUENCE: 334

Ser Pro Gln Pro Asp Ser Thr Asp Asn Asp Tyr Asp Asp Ile Ser
1               5                   10                  15

Ala Ala

<210> SEQ ID NO 335
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 335

Ser Ser Lys Ser Lys Ser Ser Glu Glu Ser Gln Thr Phe Phe Gly Leu
1               5                   10                  15

Tyr Lys Leu

<210> SEQ ID NO 336
<211> LENGTH: 20
<212> TYPE: PRT
<213> ORGANISM: Artificial
<220> FEATURE:
```

```
<223> OTHER INFORMATION: PL sequence binding MAGI1 d1

<400> SEQUENCE: 336

Ser Ser Pro Asp Ser Ser Tyr Gln Gly Lys Gly Phe Val Met Ser Arg
1               5                   10                  15
Ala Met Tyr Val
            20

<210> SEQ ID NO 337
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 337

Ser Ser Ser Arg Arg Asp Ser Ser Trp Ser Glu Thr Ser Glu Ala Ser
1               5                   10                  15
Tyr Ser Gly Leu
            20

<210> SEQ ID NO 338
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 338

Ser Tyr Pro Thr Pro Arg Pro Tyr Pro Lys Pro Ala Pro Ser Ser Gly
1               5                   10                  15
Lys Asp Tyr Val
            20

<210> SEQ ID NO 339
<211> LENGTH: 18
<212> TYPE: PRT
<213> ORGANISM: Artificial
<220> FEATURE:
<223> OTHER INFORMATION: PL sequence binding MAGI1 d1

<400> SEQUENCE: 339

Thr Phe Ala Ala Gly Phe Asn Ser Thr Gly Leu Pro His Ser Thr Thr
1               5                   10                  15
Arg Val

<210> SEQ ID NO 340
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 340

Thr Gly Arg Gly Met Ser Gly Gly Arg Ser Ser Arg Thr Arg Glu
1               5                   10                  15
Thr Gln Leu

<210> SEQ ID NO 341
<211> LENGTH: 20
<212> TYPE: PRT
<213> ORGANISM: Artificial
<220> FEATURE:
<223> OTHER INFORMATION: PL sequence binding MAGI1 d1
```

<400> SEQUENCE: 341

Thr Gly Ser Ala Leu Gln Ala Trp Arg His Thr Ser Arg Gln Ala Thr
1               5                   10                  15

Glu Ser Thr Val
            20

<210> SEQ ID NO 342
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 342

Thr Gln Gly Phe Pro Gly Pro Ala Thr Trp Arg Arg Ile Ser Ser Leu
1               5                   10                  15

Glu Ser Glu Val
            20

<210> SEQ ID NO 343
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 343

Thr Arg Glu Asp Ile Tyr Val Asn Tyr Pro Thr Phe Ser Arg Arg Pro
1               5                   10                  15

Lys Thr Arg Val
            20

<210> SEQ ID NO 344
<211> LENGTH: 19
<212> TYPE: PRT
<213> ORGANISM: Artificial
<220> FEATURE:
<223> OTHER INFORMATION: PL sequence binding MAGI1 d1

<400> SEQUENCE: 344

Thr Thr Asn Asn Asn Pro Asn Ser Ala Val Asn Ile Lys Lys Ile Phe
1               5                   10                  15

Thr Asp Val

<210> SEQ ID NO 345
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 345

Val Asp Pro Asn Ser Pro Ala Ala Lys Lys Lys Tyr Val Ser Tyr Asn
1               5                   10                  15

Asn Leu Val Ile
            20

<210> SEQ ID NO 346
<211> LENGTH: 20
<212> TYPE: PRT
<213> ORGANISM: Artificial
<220> FEATURE:
<223> OTHER INFORMATION: PL sequence binding MAGI1 d1

```
<400> SEQUENCE: 346

Val Gly Thr Leu Leu Glu Arg Val Ile Phe Pro Ser Val Lys Ile
1               5                   10                  15

Ala Thr Leu Val
            20

<210> SEQ ID NO 347
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 347

Val His Lys Val Arg Asn Lys Phe Lys Ala Lys Cys Ser Leu Cys Arg
1               5                   10                  15

Leu Tyr Ile Ile
            20

<210> SEQ ID NO 348
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 348

Trp Thr Gly Gln Ser Ala Asn Ser Arg Lys Pro Pro Arg Gln Arg Ser
1               5                   10                  15

Glu Thr Gln Val
            20

<210> SEQ ID NO 349
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 349

Tyr Gly Arg Lys Lys Arg Arg Gln Arg Arg Glu Lys His Phe Arg
1               5                   10                  15

Glu Thr Glu Val
            20

<210> SEQ ID NO 350
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 350

Tyr Gly Arg Lys Lys Arg Arg Gln Arg Arg Gly Ala Ser Ala Asp
1               5                   10                  15

Ser Thr Gln Ala
            20

<210> SEQ ID NO 351
<211> LENGTH: 20
<212> TYPE: PRT
<213> ORGANISM: Artificial
<220> FEATURE:
```

```
<223> OTHER INFORMATION: PL sequence binding MAGI1 d1

<400> SEQUENCE: 351

Tyr Gly Arg Lys Lys Arg Arg Gln Arg Arg Lys Leu Ser Ser Ile
1               5                   10                  15

Glu Ser Asp Val
            20

<210> SEQ ID NO 352
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 352

Tyr Gly Arg Lys Lys Arg Arg Gln Arg Arg Asn Asp Asn Ile Ala
1               5                   10                  15

Leu Leu Val Gln
            20

<210> SEQ ID NO 353
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 353

Tyr Gly Arg Lys Lys Arg Arg Gln Arg Arg Arg Ile Ser Ser Ile
1               5                   10                  15

Glu Thr Asp Val
            20

<210> SEQ ID NO 354
<211> LENGTH: 20
<212> TYPE: PRT
<213> ORGANISM: Artificial
<220> FEATURE:
<223> OTHER INFORMATION: PL sequence binding MAGI1 d1

<400> SEQUENCE: 354

Tyr Ser Ala Thr Tyr Ser Glu Leu Glu Asp Pro Gly Glu Met Ser Pro
1               5                   10                  15

Pro Ile Asp Leu
            20

<210> SEQ ID NO 355
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 355

Ala Ala Gly Gly Arg Ser Ala Arg Gly Gly Arg Leu Gln Gly Arg Arg
1               5                   10                  15

Glu Thr Ala Leu
            20

<210> SEQ ID NO 356
<211> LENGTH: 20
<212> TYPE: PRT
<213> ORGANISM: Artificial
```

```
<220> FEATURE:
<223> OTHER INFORMATION: PL sequence binding MAGI2 d5

<400> SEQUENCE: 356

Ala Thr Asp Tyr Leu Val Gln Pro Phe Met Asp Gln Leu Ala Phe His
1               5                   10                  15

Gln Phe Tyr Ile
            20

<210> SEQ ID NO 357
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 357

Ala Val Gly Gly Arg Pro Ala Arg Gly Gly Arg Leu Gln Gly Arg Arg
1               5                   10                  15

Gln Thr Gln Val
            20

<210> SEQ ID NO 358
<211> LENGTH: 19
<212> TYPE: PRT
<213> ORGANISM: Artificial
<220> FEATURE:
<223> OTHER INFORMATION: PL sequence binding MAGI2 d5

<400> SEQUENCE: 358

Ala Trp Asp Asp Ser Ala Arg Ala Ala Gly Gly Gln Gly Leu His Val
1               5                   10                  15

Thr Ala Leu

<210> SEQ ID NO 359
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 359

Asp Phe Arg Pro Ser Phe Lys His Ile Leu Phe Arg Arg Ala Arg Arg
1               5                   10                  15

Gly Phe Arg Gln
            20

<210> SEQ ID NO 360
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 360

Asp Gly Gly Ala Arg Thr Glu Asp Glu Val Gln Ser Tyr Pro Ser Lys
1               5                   10                  15

His Asp Tyr Val
            20

<210> SEQ ID NO 361
<211> LENGTH: 20
<212> TYPE: PRT
<213> ORGANISM: Artificial
```

```
<220> FEATURE:
<223> OTHER INFORMATION: PL sequence binding MAGI2 d5

<400> SEQUENCE: 361

Asp Ser Asp Pro Glu Asn Glu Pro Phe Asp Glu Asp Gln His Thr Gln
1               5                   10                  15

Ile Thr Lys Val
            20

<210> SEQ ID NO 362
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 362

Glu Leu Leu Gln Phe Cys Arg Thr Pro Asn Pro Ala Leu Lys Asn Gly
1               5                   10                  15

Gln Tyr Trp Val
            20

<210> SEQ ID NO 363
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 363

Glu Ser Ser Gly Thr Gln Ser Pro Lys Arg His Ser Gly Ser Tyr Leu
1               5                   10                  15

Val Thr Ser Val
            20

<210> SEQ ID NO 364
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 364

Phe His Ser Lys Thr Ala Gly Ala Asn Thr Thr Asp Lys Glu Leu Glu
1               5                   10                  15

Val Leu Ser Leu
            20

<210> SEQ ID NO 365
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 365

Phe Asn Gly Ser Ser Asn Gly His Val Tyr Glu Lys Leu Ser Ser Ile
1               5                   10                  15

Glu Ser Asp Val
            20

<210> SEQ ID NO 366
<211> LENGTH: 20
<212> TYPE: PRT
```

```
<213> ORGANISM: Artificial
<220> FEATURE:
<223> OTHER INFORMATION: PL sequence binding MAGI2 d5

<400> SEQUENCE: 366

Gly Gly Glu Asp Phe Lys Thr Thr Asn Pro Ser Lys Gln Phe Asp Lys
1               5                   10                  15

Asn Ala Tyr Val
            20

<210> SEQ ID NO 367
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 367

Gly Arg Trp Thr Gly Arg Ala Met Ser Ala Trp Lys Pro Thr Arg Arg
1               5                   10                  15

Glu Thr Glu Val
            20

<210> SEQ ID NO 368
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 368

His Asp Phe Arg Arg Ala Phe Lys Lys Ile Leu Ala Arg Gly Asp Arg
1               5                   10                  15

Lys Arg Ile Val
            20

<210> SEQ ID NO 369
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 369

His His Leu Val Ala Gln Arg Asp Ile Arg Gln Phe Gln Leu Gln His
1               5                   10                  15

Trp Leu Ala Ile
            20

<210> SEQ ID NO 370
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 370

His Ser Cys Cys Asn Arg Ala Arg Gln Glu Arg Leu Gln Arg Arg Arg
1               5                   10                  15

Glu Thr Gln Val
            20

<210> SEQ ID NO 371
<211> LENGTH: 20
```

```
<212> TYPE: PRT
<213> ORGANISM: Artificial
<220> FEATURE:
<223> OTHER INFORMATION: PL sequence binding MAGI2 d5

<400> SEQUENCE: 371

Ile Leu Asn Ser Ile Gln Val Met Arg Ala Gln Met Asn Gln Ile Gln
1               5                   10                  15

Ser Val Glu Val
            20

<210> SEQ ID NO 372
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 372

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 373
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 373

Lys His Ser Arg Lys Ser Ser Ser Tyr Ser Ser Ser Ser Thr Thr Val
1               5                   10                  15

Lys Thr Ser Tyr
            20

<210> SEQ ID NO 374
<211> LENGTH: 23
<212> TYPE: PRT
<213> ORGANISM: Artificial
<220> FEATURE:
<223> OTHER INFORMATION: PL sequence binding MAGI2 d5

<400> SEQUENCE: 374

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 375
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 375

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 376
```

-continued

```
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 376

Leu Ala Ser Lys Ser Ala Glu Glu Gly Lys Gln Ile Pro Asp Ser Leu
1               5                   10                  15

Ser Thr Asp Leu
            20

<210> SEQ ID NO 377
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 377

Leu Ala Val Leu Ala Tyr Ser Ile Thr Leu Val Met Leu Trp Ser Ile
1               5                   10                  15

Trp Gln Tyr Ala
            20

<210> SEQ ID NO 378
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 378

Leu Gly Tyr Ser Ile Pro Ser Arg Ser Gly Ala Ser Gly Leu Asp Lys
1               5                   10                  15

Arg Asp Tyr Val
            20

<210> SEQ ID NO 379
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 379

Leu Met Asp Gly Leu Pro Pro Gly Asp Ser Asn Gln Leu Ala Trp Phe
1               5                   10                  15

Asp Thr Asp Leu
            20

<210> SEQ ID NO 380
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 380

Leu Asn Ser Cys Ser Asn Arg Arg Val Tyr Lys Lys Met Pro Ser Ile
1               5                   10                  15

Glu Ser Asp Val
            20
```

```
<210> SEQ ID NO 381
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 381

Leu Asn Ser Ser Ser Asn Arg Arg Val Tyr Lys Lys Met Pro Ser Ile
1               5                   10                  15

Glu Ser Asp Val
            20

<210> SEQ ID NO 382
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 382

Pro Gly Gln Pro Pro Lys Val Lys Ser Glu Phe Asn Ser Tyr Ser Leu
1               5                   10                  15

Thr Gly Tyr Val
            20

<210> SEQ ID NO 383
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 383

Pro Ile Pro Ala Gly Gly Cys Thr Phe Ser Gly Ile Phe Pro Thr Leu
1               5                   10                  15

Thr Ser Pro Leu
            20

<210> SEQ ID NO 384
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 384

Pro Tyr Ser Glu Leu Asn Tyr Glu Thr Ser His Tyr Pro Ala Ser Pro
1               5                   10                  15

Asp Ser Trp Val
            20

<210> SEQ ID NO 385
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 385

Gln Ala Thr Ser Arg Asn Gly His Ser Ala Arg Gln His Val Val Ala
1               5                   10                  15

Asp Thr Glu Leu
            20
```

-continued

<210> SEQ ID NO 386
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 386

Gln Asp Phe Arg Arg Ala Phe Arg Arg Ile Leu Ala Arg Pro Trp Thr
1               5                   10                  15

Gln Thr Ala Trp
            20

<210> SEQ ID NO 387
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 387

Gln Ile Ser Pro Gly Gly Leu Glu Pro Pro Ser Glu Lys His Phe Arg
1               5                   10                  15

Glu Thr Glu Val
            20

<210> SEQ ID NO 388
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 388

Arg Glu Leu Val Asp Arg Gly Glu Val Arg Gln Phe Thr Leu Arg His
1               5                   10                  15

Trp Leu Lys Val
            20

<210> SEQ ID NO 389
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 389

Arg Asn Ile Glu Glu Val Tyr Val Gly Gly Lys Gln Val Val Pro Phe
1               5                   10                  15

Ser Ser Ser Val
            20

<210> SEQ ID NO 390
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 390

Ser Pro Ala Ser Ile Pro His Ser Pro Gly Ala Phe Ala Tyr Glu Gly
1               5                   10                  15

Ala Ser Phe Tyr
            20

<210> SEQ ID NO 391
<211> LENGTH: 19
<212> TYPE: PRT
<213> ORGANISM: Artificial
<220> FEATURE:
<223> OTHER INFORMATION: PL sequence binding MAGI2 d5

<400> SEQUENCE: 391

Ser Ser Lys Ser Lys Ser Ser Glu Glu Ser Gln Thr Phe Phe Gly Leu
1               5                   10                  15

Tyr Lys Leu

<210> SEQ ID NO 392
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 392

Ser Ser Pro Asp Ser Ser Tyr Gln Gly Lys Gly Phe Val Met Ser Arg
1               5                   10                  15

Ala Met Tyr Val
            20

<210> SEQ ID NO 393
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 393

Ser Ser Ser Arg Arg Asp Ser Ser Trp Ser Glu Thr Ser Glu Ala Ser
1               5                   10                  15

Tyr Ser Gly Leu
            20

<210> SEQ ID NO 394
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 394

Thr Gly Ser Ala Leu Gln Ala Trp Arg His Thr Ser Arg Gln Ala Thr
1               5                   10                  15

Glu Ser Thr Val
            20

<210> SEQ ID NO 395
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 395

Thr Gln Gly Phe Pro Gly Pro Ala Thr Trp Arg Arg Ile Ser Ser Leu
1               5                   10                  15

Glu Ser Glu Val
            20

```
<210> SEQ ID NO 396
<211> LENGTH: 19
<212> TYPE: PRT
<213> ORGANISM: Artificial
<220> FEATURE:
<223> OTHER INFORMATION: PL sequence binding MAGI2 d5

<400> SEQUENCE: 396

Thr Thr Asn Asn Asn Pro Asn Ser Ala Val Asn Ile Lys Lys Ile Phe
1               5                   10                  15

Thr Asp Val

<210> SEQ ID NO 397
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 397

Val Asp Pro Asn Ser Pro Ala Ala Lys Lys Lys Tyr Val Ser Tyr Asn
1               5                   10                  15

Asn Leu Val Ile
            20

<210> SEQ ID NO 398
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 398

Val Gly Thr Leu Leu Leu Glu Arg Val Ile Phe Pro Ser Val Lys Ile
1               5                   10                  15

Ala Thr Leu Val
            20

<210> SEQ ID NO 399
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 399

Val His Asp Ala Glu Ser Ser Asp Glu Asp Gly Tyr Asp Trp Gly Pro
1               5                   10                  15

Ala Thr Asp Leu
            20

<210> SEQ ID NO 400
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 400

Val His Lys Val Arg Asn Lys Phe Lys Ala Lys Cys Ser Leu Cys Arg
1               5                   10                  15

Leu Tyr Ile Ile
            20
```

<210> SEQ ID NO 401
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 401

Val Pro Gly Ala Leu Asp Tyr Ala Ala Phe Ser Ser Ala Leu Tyr Gly
1               5                   10                  15
Glu Ser Asp Leu
            20

<210> SEQ ID NO 402
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 402

Tyr Gly Arg Lys Lys Arg Arg Gln Arg Arg Ala Val Ala Ala Thr
1               5                   10                  15
Ser Ala Asn Leu
            20

<210> SEQ ID NO 403
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 403

Tyr Gly Arg Lys Lys Arg Arg Gln Arg Arg Glu Tyr Leu Gly Leu
1               5                   10                  15
Asp Val Pro Val
            20

<210> SEQ ID NO 404
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 404

Tyr Gly Arg Lys Lys Arg Arg Gln Arg Arg Gly Ala Ser Ala Asp
1               5                   10                  15
Ser Thr Gln Ala
            20

<210> SEQ ID NO 405
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 405

Tyr Gly Arg Lys Lys Arg Arg Gln Arg Arg Lys Leu Ser Ser Ile
1               5                   10                  15
Glu Ser Asp Val

-continued

```
            20

<210> SEQ ID NO 406
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 406

Tyr Gly Arg Lys Lys Arg Arg Gln Arg Arg Arg Asn Asp Asn Ile Ala
1               5                   10                  15

Leu Leu Val Gln
            20

<210> SEQ ID NO 407
<211> LENGTH: 20
<212> TYPE: PRT
<213> ORGANISM: Artificial
<220> FEATURE:
<223> OTHER INFORMATION: PL sequence binding MAGI2 d5

<400> SEQUENCE: 407

Tyr Gly Arg Lys Lys Arg Arg Gln Arg Arg Arg Ser Glu Gly Val Pro
1               5                   10                  15

Asp Leu Leu Val
            20

<210> SEQ ID NO 408
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 408

Ala Ala Gly Gly Arg Ser Ala Arg Gly Gly Arg Leu Gln Gly Arg Arg
1               5                   10                  15

Glu Thr Ala Leu
            20

<210> SEQ ID NO 409
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 409

Ala Leu Val Leu Ile Ala Phe Cys Ile Ile Arg Arg Arg Pro Ser Ala
1               5                   10                  15

Tyr Gln Ala Leu
            20

<210> SEQ ID NO 410
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 410

Ala Arg His Arg Val Thr Ser Tyr Thr Ser Ser Ser Val Asn Val Ser
1               5                   10                  15
```

Ser Asn Leu

<210> SEQ ID NO 411
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 411

Ala Thr Asp Tyr Leu Val Gln Pro Phe Met Asp Gln Leu Ala Phe His
1               5                   10                  15

Gln Phe Tyr Ile
            20

<210> SEQ ID NO 412
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 412

Ala Val Gly Gly Arg Pro Ala Arg Gly Gly Arg Leu Gln Gly Arg Arg
1               5                   10                  15

Gln Thr Gln Val
            20

<210> SEQ ID NO 413
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 413

Asp Phe Arg Pro Ser Phe Lys His Ile Leu Phe Arg Arg Ala Arg Arg
1               5                   10                  15

Gly Phe Arg Gln
            20

<210> SEQ ID NO 414
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 414

Glu Leu Leu Gln Phe Cys Arg Thr Pro Asn Pro Ala Leu Lys Asn Gly
1               5                   10                  15

Gln Tyr Trp Val
            20

<210> SEQ ID NO 415
<211> LENGTH: 17
<212> TYPE: PRT
<213> ORGANISM: Artificial
<220> FEATURE:
<223> OTHER INFORMATION: PL sequence binding MAGI3 d1

<400> SEQUENCE: 415

Glu Asn Leu Ala Pro Val Thr Thr Phe Gly Lys Thr Asn Gly Tyr Ile
1               5                   10                  15

Ala

<210> SEQ ID NO 416
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 416

Glu Ser Ser Gly Thr Gln Ser Pro Lys Arg His Ser Gly Ser Tyr Leu
1               5                   10                  15

Val Thr Ser Val
            20

<210> SEQ ID NO 417
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 417

Phe Asn Gly Ser Ser Asn Gly His Val Tyr Glu Lys Leu Ser Ser Ile
1               5                   10                  15

Glu Ser Asp Val
            20

<210> SEQ ID NO 418
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 418

Gly Gly Asp Leu Gly Thr Arg Arg Gly Ser Ala His Phe Ser Ser Leu
1               5                   10                  15

Glu Ser Glu Val
            20

<210> SEQ ID NO 419
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 419

Gly Gly Glu Asp Phe Lys Thr Thr Asn Pro Ser Lys Gln Phe Asp Lys
1               5                   10                  15

Asn Ala Tyr Val
            20

<210> SEQ ID NO 420
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 420

Gly Gly Gly Gly Gly Ser Gly Gly Gly Gly Ser Gly Ile Glu Ser
1               5                   10                  15

```
Val Lys Ile

<210> SEQ ID NO 421
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 421

Gly Gly Gly Gly Gly Ser Gly Gly Gly Ser Gly Gly Gly His Ser
1               5                   10                  15

Thr Thr Arg Val
            20

<210> SEQ ID NO 422
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 422

Gly Gly Gly Gly Gly Ser Gly Gly Gly Ser Gly Leu Pro His Ser
1               5                   10                  15

Thr Thr Arg Val
            20

<210> SEQ ID NO 423
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 423

Gly Gly Gly Gly Gly Ser Gly Gly Gly Ser Gly Ser Arg Arg Pro
1               5                   10                  15

Lys Thr Arg Val
            20

<210> SEQ ID NO 424
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 424

Gly Arg Trp Ala Gly Arg Ser Ala Ala Ser Trp Arg Ser Arg Arg
1               5                   10                  15

Glu Thr Ala Leu
            20

<210> SEQ ID NO 425
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 425

Gly Arg Trp Thr Gly Arg Ala Met Ser Ala Trp Lys Pro Thr Arg Arg
1               5                   10                  15
```

-continued

Glu Thr Glu Val
        20

<210> SEQ ID NO 426
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 426

Gly Arg Trp Thr Gly Arg Cys Met Ser Cys Trp Lys Pro Thr Arg Arg
1               5                   10                  15

Glu Thr Glu Val
        20

<210> SEQ ID NO 427
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 427

Gly Arg Trp Thr Gly Arg Ser Ala Val Ser Trp Arg Pro Arg Arg Arg
1               5                   10                  15

Gln Thr Gln Val
        20

<210> SEQ ID NO 428
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 428

Gly Arg Trp Thr Gly Arg Ser Met Ser Ser Trp Lys Pro Thr Arg Arg
1               5                   10                  15

Glu Thr Glu Val
        20

<210> SEQ ID NO 429
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 429

His Ala Met Asn Ala Ala Pro Arg Ala Met Glu Asn Ala Pro Ala Leu
1               5                   10                  15

Arg Thr Ser His
        20

<210> SEQ ID NO 430
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 430

His His Leu Val Ala Gln Arg Asp Ile Arg Gln Phe Gln Leu Gln His
1               5                   10                  15

Trp Leu Ala Ile
            20

<210> SEQ ID NO 431
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 431

Ile Ser Gly Thr Pro Thr Ser Thr Met Val His Gly Met Thr Ser Ser
1               5                   10                  15

Ser Ser Val Val
            20

<210> SEQ ID NO 432
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 432

Ile Ser Lys Leu Gly Ile Ser Gly Asp Ile Asp Leu Thr Ser Ala Ser
1               5                   10                  15

Tyr Thr Met Ile
            20

<210> SEQ ID NO 433
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 433

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 434
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 434

Lys His Ser Arg Lys Ser Ser Ser Tyr Ser Ser Ser Ser Thr Thr Val
1               5                   10                  15

Lys Thr Ser Tyr
            20

<210> SEQ ID NO 435
<211> LENGTH: 23
<212> TYPE: PRT
<213> ORGANISM: Artificial
<220> FEATURE:
<223> OTHER INFORMATION: PL sequence binding MAGI3 d1

<400> SEQUENCE: 435

Lys Lys Lys Lys Gln Pro Gly Asn Ser Thr Lys Glu Ser Glu Ser Thr

```
                1               5                  10                 15

Asn Ser Val Arg Leu Met Leu
                20

<210> SEQ ID NO 436
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 436

Leu Ala Ser Lys Ser Ala Glu Glu Gly Lys Gln Ile Pro Asp Ser Leu
1               5                  10                 15

Ser Thr Asp Leu
                20

<210> SEQ ID NO 437
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 437

Leu Ala Val Leu Ala Tyr Ser Ile Thr Leu Val Met Leu Trp Ser Ile
1               5                  10                 15

Trp Gln Tyr Ala
                20

<210> SEQ ID NO 438
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 438

Leu His Asn Gln Ala Ser Val Pro Leu Glu Pro Arg Pro Leu Arg Arg
1               5                  10                 15

Glu Ser Glu Ile
                20

<210> SEQ ID NO 439
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 439

Leu Asn Ser Cys Ser Asn Arg Arg Val Tyr Lys Lys Met Pro Ser Ile
1               5                  10                 15

Glu Ser Asp Val
                20

<210> SEQ ID NO 440
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 440
```

-continued

Leu Asn Ser Ser Ser Asn Arg Arg Val Tyr Lys Lys Met Pro Ser Ile
1               5                   10                  15

Glu Ser Asp Val
            20

<210> SEQ ID NO 441
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 441

Leu Ser Glu Lys Lys Thr Ser Gln Ser Pro His Arg Phe Gln Lys Thr
1               5                   10                  15

Ser Ser Pro Ile
            20

<210> SEQ ID NO 442
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 442

Met Gly Arg Trp Thr Gly Arg Ser Ser Glu Ser Trp Arg Pro Arg Pro
1               5                   10                  15

Val Thr Gln Val
            20

<210> SEQ ID NO 443
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 443

Asn Thr Ser Ser Asp Gln Ala Arg Gln Glu Arg Leu Arg Arg Arg Arg
1               5                   10                  15

Glu Thr Gln Val
            20

<210> SEQ ID NO 444
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 444

Pro Gly Gln Pro Pro Lys Val Lys Ser Glu Phe Asn Ser Tyr Ser Leu
1               5                   10                  15

Thr Gly Tyr Val
            20

<210> SEQ ID NO 445
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 445

```
Pro Ile Pro Ala Gly Gly Cys Thr Phe Ser Gly Ile Phe Pro Thr Leu
1               5                   10                  15

Thr Ser Pro Leu
            20

<210> SEQ ID NO 446
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 446

Pro Tyr Ser Glu Leu Asn Tyr Glu Thr Ser His Tyr Pro Ala Ser Pro
1               5                   10                  15

Asp Ser Trp Val
            20

<210> SEQ ID NO 447
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 447

Gln Asp Phe Arg Arg Ala Phe Arg Arg Ile Leu Ala Arg Pro Trp Thr
1               5                   10                  15

Gln Thr Ala Trp
            20

<210> SEQ ID NO 448
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 448

Gln Ile Ser Pro Gly Gly Leu Glu Pro Pro Ser Glu Lys His Phe Arg
1               5                   10                  15

Glu Thr Glu Val
            20

<210> SEQ ID NO 449
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 449

Arg Glu Leu Val Asp Arg Gly Glu Val Arg Gln Phe Thr Leu Arg His
1               5                   10                  15

Trp Leu Lys Val
            20

<210> SEQ ID NO 450
<211> LENGTH: 20
<212> TYPE: PRT
<213> ORGANISM: Artificial
<220> FEATURE:
<223> OTHER INFORMATION: PL sequence binding MAGI3 d1
```

-continued

```
<400> SEQUENCE: 450

Arg Asn Ile Glu Glu Val Tyr Val Gly Gly Lys Gln Val Val Pro Phe
1               5                   10                  15

Ser Ser Ser Val
            20

<210> SEQ ID NO 451
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 451

Ser Phe Thr Ser Ile Leu Thr Cys His Gln Arg Arg Thr Gln Arg Lys
1               5                   10                  15

Glu Thr Val Ala
            20

<210> SEQ ID NO 452
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 452

Ser Gly Gly Asn Arg Ala Arg Gln Glu Arg Leu Gln Arg Arg Glu
1               5                   10                  15

Thr Gln Val

<210> SEQ ID NO 453
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 453

Ser Leu Ile Gly Pro Val Gln Lys Glu Tyr Gln Arg Glu Leu Gly Lys
1               5                   10                  15

Leu Ser Ser Pro
            20

<210> SEQ ID NO 454
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 454

Ser Leu Lys Pro Gly Thr Val Leu Pro Pro Pro Tyr Arg His Arg
1               5                   10                  15

Asn Thr Val Val
            20

<210> SEQ ID NO 455
<211> LENGTH: 18
<212> TYPE: PRT
<213> ORGANISM: Artificial
<220> FEATURE:
<223> OTHER INFORMATION: PL sequence binding MAGI3 d1
```

-continued

<400> SEQUENCE: 455

Ser Pro Gln Pro Asp Ser Thr Asp Asn Asp Asp Tyr Asp Asp Ile Ser
1               5                   10                  15

Ala Ala

<210> SEQ ID NO 456
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 456

Ser Ser Lys Ser Lys Ser Ser Glu Glu Ser Gln Thr Phe Phe Gly Leu
1               5                   10                  15

Tyr Lys Leu

<210> SEQ ID NO 457
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 457

Ser Ser Pro Asp Ser Ser Tyr Gln Gly Lys Gly Phe Val Met Ser Arg
1               5                   10                  15

Ala Met Tyr Val
            20

<210> SEQ ID NO 458
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 458

Ser Thr Asp Asn Leu Val Arg Pro Phe Met Asp Thr Leu Ala Ser His
1               5                   10                  15

Gln Leu Tyr Ile
            20

<210> SEQ ID NO 459
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 459

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 460
<211> LENGTH: 18
<212> TYPE: PRT
<213> ORGANISM: Artificial
<220> FEATURE:
<223> OTHER INFORMATION: PL sequence binding MAGI3 d1

<400> SEQUENCE: 460

Thr Phe Ala Ala Gly Phe Asn Ser Thr Gly Leu Pro His Ser Thr Thr
1               5                   10                  15

Arg Val

<210> SEQ ID NO 461
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 461

Thr Phe Lys Gly Thr Pro Thr Ala Glu Asn Pro Glu Tyr Leu Gly Leu
1               5                   10                  15

Asp Val Pro Val
            20

<210> SEQ ID NO 462
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 462

Thr Gly Arg Gly Met Ser Gly Gly Arg Ser Ser Arg Thr Arg Arg Glu
1               5                   10                  15

Thr Gln Leu

<210> SEQ ID NO 463
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 463

Thr Gly Ser Ala Leu Gln Ala Trp Arg His Thr Ser Arg Gln Ala Thr
1               5                   10                  15

Glu Ser Thr Val
            20

<210> SEQ ID NO 464
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 464

Thr Gln Gly Phe Pro Gly Pro Ala Thr Trp Arg Arg Ile Ser Ser Leu
1               5                   10                  15

Glu Ser Glu Val
            20

<210> SEQ ID NO 465
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 465

-continued

Thr Arg Glu Asp Ile Tyr Val Asn Tyr Pro Thr Phe Ser Arg Arg Pro
1               5                   10                  15

Lys Thr Arg Val
            20

<210> SEQ ID NO 466
<211> LENGTH: 19
<212> TYPE: PRT
<213> ORGANISM: Artificial
<220> FEATURE:
<223> OTHER INFORMATION: PL sequence binding MAGI3 d1

<400> SEQUENCE: 466

Thr Thr Asn Asn Pro Asn Ser Ala Val Asn Ile Lys Lys Ile Phe
1               5                   10                  15

Thr Asp Val

<210> SEQ ID NO 467
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 467

Val Asp Pro Asn Ser Pro Ala Ala Lys Lys Tyr Val Ser Tyr Asn
1               5                   10                  15

Asn Leu Val Ile
            20

<210> SEQ ID NO 468
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 468

Val Gly Thr Leu Leu Leu Glu Arg Val Ile Phe Pro Ser Val Lys Ile
1               5                   10                  15

Ala Thr Leu Val
            20

<210> SEQ ID NO 469
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 469

Val His Lys Val Arg Asn Lys Phe Lys Ala Lys Cys Ser Leu Cys Arg
1               5                   10                  15

Leu Tyr Ile Ile
            20

<210> SEQ ID NO 470
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 470

-continued

Trp Thr Gly Gln Ser Ala Asn Ser Arg Lys Pro Pro Arg Gln Arg Ser
1               5                   10                  15

Glu Thr Gln Val
            20

<210> SEQ ID NO 471
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 471

Tyr Gly Arg Lys Lys Arg Arg Gln Arg Arg Arg Lys Leu Ser Ser Ile
1               5                   10                  15

Glu Ser Asp Val
            20

<210> SEQ ID NO 472
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 472

Tyr Gly Arg Lys Lys Arg Arg Gln Arg Arg Arg Asn Asp Asn Ile Ala
1               5                   10                  15

Leu Leu Val Gln
            20

<210> SEQ ID NO 473
<211> LENGTH: 20
<212> TYPE: PRT
<213> ORGANISM: Artificial
<220> FEATURE:
<223> OTHER INFORMATION: PL sequence binding MAGI3 d1

<400> SEQUENCE: 473

Tyr Ser Ala Thr Tyr Ser Glu Leu Glu Asp Pro Gly Glu Met Ser Pro
1               5                   10                  15

Pro Ile Asp Leu
            20

<210> SEQ ID NO 474
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 474

Ala Thr Asp Tyr Leu Val Gln Pro Phe Met Asp Gln Leu Ala Phe His
1               5                   10                  15

Gln Phe Tyr Ile
            20

<210> SEQ ID NO 475
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 475

-continued

Ala Val Gly Gly Arg Pro Ala Arg Gly Gly Arg Leu Gln Gly Arg Arg
1               5                   10                  15

Gln Thr Gln Val
            20

<210> SEQ ID NO 476
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 476

Asp Phe Arg Pro Ser Phe Lys His Ile Leu Phe Arg Arg Ala Arg Arg
1               5                   10                  15

Gly Phe Arg Gln
            20

<210> SEQ ID NO 477
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 477

Asp Ser Asp Pro Glu Asn Glu Pro Phe Asp Glu Asp Gln His Thr Gln
1               5                   10                  15

Ile Thr Lys Val
            20

<210> SEQ ID NO 478
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 478

Asp Thr Leu Leu Leu Thr Glu Asn Glu Gly Asp Lys Thr Glu Glu Gln
1               5                   10                  15

Val Ser Tyr Val
            20

<210> SEQ ID NO 479
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 479

Glu Asp Pro Lys Asp Arg Pro Ser Ala Ala His Ile Val Glu Ala Leu
1               5                   10                  15

Glu Thr Asp Val
            20

<210> SEQ ID NO 480
<211> LENGTH: 20
<212> TYPE: PRT
<213> ORGANISM: Artificial
<220> FEATURE:
<223> OTHER INFORMATION: PL sequence binding MAGI3 d2

-continued

```
<400> SEQUENCE: 480

Glu Ser Ser Gly Thr Gln Ser Pro Lys Arg His Ser Gly Ser Tyr Leu
1               5                   10                  15

Val Thr Ser Val
            20

<210> SEQ ID NO 481
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 481

Gly Gly Gly Gly Gly Ser Gly Gly Gly Ser Gly Gly Gly His Ser
1               5                   10                  15

Thr Thr Arg Val
            20

<210> SEQ ID NO 482
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 482

Gly Gly Gly Gly Gly Ser Gly Gly Gly Ser Gly Leu Pro His Ser
1               5                   10                  15

Thr Thr Arg Val
            20

<210> SEQ ID NO 483
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 483

Gly Arg Trp Thr Gly Arg Ala Met Ser Ala Trp Lys Pro Thr Arg Arg
1               5                   10                  15

Glu Thr Glu Val
            20

<210> SEQ ID NO 484
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 484

Gly Arg Trp Thr Gly Arg Cys Met Ser Cys Trp Lys Pro Thr Arg Arg
1               5                   10                  15

Glu Thr Glu Val
            20

<210> SEQ ID NO 485
<211> LENGTH: 20
<212> TYPE: PRT
<213> ORGANISM: Artificial
<220> FEATURE:
<223> OTHER INFORMATION: PL sequence binding MAGI3 d2
```

-continued

```
<400> SEQUENCE: 485

His Asp Phe Arg Arg Ala Phe Lys Lys Ile Leu Ala Arg Gly Asp Arg
1               5                   10                  15

Lys Arg Ile Val
            20

<210> SEQ ID NO 486
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 486

His His Leu Val Ala Gln Arg Asp Ile Arg Gln Phe Gln Leu Gln His
1               5                   10                  15

Trp Leu Ala Ile
            20

<210> SEQ ID NO 487
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 487

His Pro Thr Asp Ile Thr Gly Leu Pro Asn Leu Ser Asp Pro Ser Val
1               5                   10                  15

Ser Thr Val Val
            20

<210> SEQ ID NO 488
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 488

Ile Leu Asn Ser Ile Gln Val Met Arg Ala Gln Met Asn Gln Ile Gln
1               5                   10                  15

Ser Val Glu Val
            20

<210> SEQ ID NO 489
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 489

Ile Ser Gly Thr Pro Thr Ser Thr Met Val His Gly Met Thr Ser Ser
1               5                   10                  15

Ser Ser Val Val
            20

<210> SEQ ID NO 490
<211> LENGTH: 20
<212> TYPE: PRT
<213> ORGANISM: Artificial
<220> FEATURE:
```

<223> OTHER INFORMATION: PL sequence binding MAGI3 d2

<400> SEQUENCE: 490

Ile Val Thr Val Val Thr Met Val Thr Asn Val Asp Phe Pro Pro Lys
1               5                   10                  15

Glu Ser Ser Leu
            20

<210> SEQ ID NO 491
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 491

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 492
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 492

Lys His Ser Arg Lys Ser Ser Tyr Ser Ser Ser Thr Thr Val
1               5                   10                  15

Lys Thr Ser Tyr
            20

<210> SEQ ID NO 493
<211> LENGTH: 23
<212> TYPE: PRT
<213> ORGANISM: Artificial
<220> FEATURE:
<223> OTHER INFORMATION: PL sequence binding MAGI3 d2

<400> SEQUENCE: 493

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 494
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 494

Leu Ala Ser Lys Ser Ala Glu Glu Gly Lys Gln Ile Pro Asp Ser Leu
1               5                   10                  15

Ser Thr Asp Leu
            20

<210> SEQ ID NO 495
<211> LENGTH: 20
<212> TYPE: PRT
<213> ORGANISM: Artificial

```
<220> FEATURE:
<223> OTHER INFORMATION: PL sequence binding MAGI3 d2

<400> SEQUENCE: 495

Leu Ala Val Leu Ala Tyr Ser Ile Thr Leu Val Met Leu Trp Ser Ile
1               5                   10                  15

Trp Gln Tyr Ala
            20

<210> SEQ ID NO 496
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 496

Leu Asn Ser Cys Ser Asn Arg Arg Val Tyr Lys Lys Met Pro Ser Ile
1               5                   10                  15

Glu Ser Asp Val
            20

<210> SEQ ID NO 497
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 497

Pro Gly Gln Pro Pro Lys Val Lys Ser Glu Phe Asn Ser Tyr Ser Leu
1               5                   10                  15

Thr Gly Tyr Val
            20

<210> SEQ ID NO 498
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 498

Pro Ile Pro Ala Gly Gly Cys Thr Phe Ser Gly Ile Phe Pro Thr Leu
1               5                   10                  15

Thr Ser Pro Leu
            20

<210> SEQ ID NO 499
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 499

Pro Tyr Gln Ser Gln Gly Phe Ser Thr Glu Glu Asp Glu Asp Glu Gln
1               5                   10                  15

Val Ser Ala Val
            20

<210> SEQ ID NO 500
<211> LENGTH: 20
<212> TYPE: PRT
```

```
<213> ORGANISM: Artificial
<220> FEATURE:
<223> OTHER INFORMATION: PL sequence binding MAGI3 d2

<400> SEQUENCE: 500

Gln Asp Phe Arg Arg Ala Phe Arg Arg Ile Leu Ala Arg Pro Trp Thr
1               5                   10                  15

Gln Thr Ala Trp
            20

<210> SEQ ID NO 501
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 501

Gln Ile Ser Pro Gly Gly Leu Glu Pro Pro Ser Glu Lys His Phe Arg
1               5                   10                  15

Glu Thr Glu Val
            20

<210> SEQ ID NO 502
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 502

Arg Glu Leu Val Asp Arg Gly Glu Val Arg Gln Phe Thr Leu Arg His
1               5                   10                  15

Trp Leu Lys Val
            20

<210> SEQ ID NO 503
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 503

Arg Ser Gly Ala Thr Ile Pro Leu Val Gly Gln Asp Ile Ile Asp Leu
1               5                   10                  15

Gln Thr Glu Val
            20

<210> SEQ ID NO 504
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 504

Ser Phe Thr Ser Ile Leu Thr Cys His Gln Arg Arg Thr Gln Arg Lys
1               5                   10                  15

Glu Thr Val Ala
            20

<210> SEQ ID NO 505
<211> LENGTH: 20
```

<212> TYPE: PRT
<213> ORGANISM: Artificial
<220> FEATURE:
<223> OTHER INFORMATION: PL sequence binding MAGI3 d2

<400> SEQUENCE: 505

Ser Leu Lys Pro Gly Thr Val Leu Pro Pro Pro Tyr Arg His Arg
1               5                   10                  15

Asn Thr Val Val
            20

<210> SEQ ID NO 506
<211> LENGTH: 18
<212> TYPE: PRT
<213> ORGANISM: Artificial
<220> FEATURE:
<223> OTHER INFORMATION: PL sequence binding MAGI3 d2

<400> SEQUENCE: 506

Ser Pro Gln Pro Asp Ser Thr Asp Asn Asp Tyr Asp Asp Ile Ser
1               5                   10                  15

Ala Ala

<210> SEQ ID NO 507
<211> LENGTH: 19
<212> TYPE: PRT
<213> ORGANISM: Artificial
<220> FEATURE:
<223> OTHER INFORMATION: PL sequence binding MAGI3 d2

<400> SEQUENCE: 507

Ser Ser Lys Ser Lys Ser Ser Glu Glu Ser Gln Thr Phe Phe Gly Leu
1               5                   10                  15

Tyr Lys Leu

<210> SEQ ID NO 508
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 508

Ser Ser Ser Arg Arg Asp Ser Ser Trp Ser Glu Thr Ser Glu Ala Ser
1               5                   10                  15

Tyr Ser Gly Leu
            20

<210> SEQ ID NO 509
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 509

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 510
<211> LENGTH: 18
<212> TYPE: PRT

-continued

```
<213> ORGANISM: Artificial
<220> FEATURE:
<223> OTHER INFORMATION: PL sequence binding MAGI3 d2

<400> SEQUENCE: 510

Thr Phe Ala Ala Gly Phe Asn Ser Thr Gly Leu Pro His Ser Thr Thr
1               5                   10                  15

Arg Val

<210> SEQ ID NO 511
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 511

Thr Gly Ser Ala Leu Gln Ala Trp Arg His Thr Ser Arg Gln Ala Thr
1               5                   10                  15

Glu Ser Thr Val
            20

<210> SEQ ID NO 512
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 512

Thr Gln Gly Phe Pro Gly Pro Ala Thr Trp Arg Arg Ile Ser Ser Leu
1               5                   10                  15

Glu Ser Glu Val
            20

<210> SEQ ID NO 513
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 513

Thr Arg Glu Asp Ile Tyr Val Asn Tyr Pro Thr Phe Ser Arg Arg Pro
1               5                   10                  15

Lys Thr Arg Val
            20

<210> SEQ ID NO 514
<211> LENGTH: 19
<212> TYPE: PRT
<213> ORGANISM: Artificial
<220> FEATURE:
<223> OTHER INFORMATION: PL sequence binding MAGI3 d2

<400> SEQUENCE: 514

Thr Thr Asn Asn Asn Pro Asn Ser Ala Val Asn Ile Lys Lys Ile Phe
1               5                   10                  15

Thr Asp Val

<210> SEQ ID NO 515
<211> LENGTH: 20
<212> TYPE: PRT
<213> ORGANISM: Artificial
```

-continued

```
<220> FEATURE:
<223> OTHER INFORMATION: PL sequence binding MAGI3 d2

<400> SEQUENCE: 515

Val Asp Pro Asn Ser Pro Ala Ala Lys Lys Tyr Val Ser Tyr Asn
1               5                   10                  15

Asn Leu Val Ile
            20

<210> SEQ ID NO 516
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 516

Val Gly Thr Leu Leu Leu Glu Arg Val Ile Phe Pro Ser Val Lys Ile
1               5                   10                  15

Ala Thr Leu Val
            20

<210> SEQ ID NO 517
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 517

Val His Lys Val Arg Asn Lys Phe Lys Ala Lys Cys Ser Leu Cys Arg
1               5                   10                  15

Leu Tyr Ile Ile
            20

<210> SEQ ID NO 518
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 518

Tyr Gly Arg Lys Lys Arg Arg Gln Arg Arg Ala Arg Gly Arg Arg
1               5                   10                  15

Glu Thr Trp Val
            20

<210> SEQ ID NO 519
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 519

Tyr Gly Arg Lys Lys Arg Arg Gln Arg Arg Lys Leu Ser Ser Ile
1               5                   10                  15

Glu Ser Asp Val
            20

<210> SEQ ID NO 520
<211> LENGTH: 20
<212> TYPE: PRT
```

```
<213> ORGANISM: Artificial
<220> FEATURE:
<223> OTHER INFORMATION: PL sequence binding MAGI3 d2

<400> SEQUENCE: 520

Tyr Gly Arg Lys Lys Arg Arg Gln Arg Arg Asn Asp Asn Ile Ala
1               5                   10                  15

Leu Leu Val Gln
            20

<210> SEQ ID NO 521
<211> LENGTH: 20
<212> TYPE: PRT
<213> ORGANISM: Artificial
<220> FEATURE:
<223> OTHER INFORMATION: PL sequence binding MAGI3 d2

<400> SEQUENCE: 521

Tyr Gly Arg Lys Lys Arg Arg Gln Arg Arg Ser Glu Gly Val Pro
1               5                   10                  15

Asp Leu Leu Val
            20

<210> SEQ ID NO 522
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 522

Ala Ala Gly Gly Arg Ser Ala Arg Gly Gly Arg Leu Gln Gly Arg Arg
1               5                   10                  15

Glu Thr Ala Leu
            20

<210> SEQ ID NO 523
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 523

Ala Gly Ala Val Arg Thr Pro Leu Ser Gln Val Asn Lys Val Trp Asp
1               5                   10                  15

Gln Ser Ser Val
            20

<210> SEQ ID NO 524
<211> LENGTH: 19
<212> TYPE: PRT
<213> ORGANISM: Artificial
<220> FEATURE:
<223> OTHER INFORMATION: PL sequence binding NeDLG d1

<400> SEQUENCE: 524

Ala Arg His Arg Val Thr Ser Tyr Thr Ser Ser Ser Val Asn Val Ser
1               5                   10                  15

Ser Asn Leu

<210> SEQ ID NO 525
<211> LENGTH: 20
<212> TYPE: PRT
```

```
<213> ORGANISM: Artificial
<220> FEATURE:
<223> OTHER INFORMATION: PL sequence binding NeDLG d1

<400> SEQUENCE: 525

Ala Val Gly Gly Arg Pro Ala Arg Gly Gly Arg Leu Gln Gly Arg Arg
1               5                   10                  15

Gln Thr Gln Val
            20

<210> SEQ ID NO 526
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 526

Asp Phe Arg Pro Ser Phe Lys His Ile Leu Phe Arg Arg Ala Arg Arg
1               5                   10                  15

Gly Phe Arg Gln
            20

<210> SEQ ID NO 527
<211> LENGTH: 19
<212> TYPE: PRT
<213> ORGANISM: Artificial
<220> FEATURE:
<223> OTHER INFORMATION: PL sequence binding NeDLG d1

<400> SEQUENCE: 527

Glu Val Ile Gly Tyr Ile Glu Lys Pro Gly Val Glu Thr Leu Glu Asp
1               5                   10                  15

Ser Val Phe

<210> SEQ ID NO 528
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 528

Gly Gly Glu Asp Phe Lys Thr Thr Asn Pro Ser Lys Gln Phe Asp Lys
1               5                   10                  15

Asn Ala Tyr Val
            20

<210> SEQ ID NO 529
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 529

Gly Arg Trp Thr Gly Arg Ala Met Ser Ala Trp Lys Pro Thr Arg Arg
1               5                   10                  15

Glu Thr Glu Val
            20

<210> SEQ ID NO 530
<211> LENGTH: 20
<212> TYPE: PRT
```

-continued

<213> ORGANISM: Artificial
<220> FEATURE:
<223> OTHER INFORMATION: PL sequence binding NeDLG d1

<400> SEQUENCE: 530

Gly Arg Trp Thr Gly Arg Cys Met Ser Cys Trp Lys Pro Thr Arg Arg
1               5                   10                  15

Glu Thr Glu Val
            20

<210> SEQ ID NO 531
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 531

His His Leu Val Ala Gln Arg Asp Ile Arg Gln Phe Gln Leu Gln His
1               5                   10                  15

Trp Leu Ala Ile
            20

<210> SEQ ID NO 532
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 532

His Ser Cys Cys Asn Arg Ala Arg Gln Glu Arg Leu Gln Arg Arg
1               5                   10                  15

Glu Thr Gln Val
            20

<210> SEQ ID NO 533
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 533

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 534
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 534

Lys His Ser Arg Lys Ser Ser Ser Tyr Ser Ser Ser Ser Thr Thr Val
1               5                   10                  15

Lys Thr Ser Tyr
            20

<210> SEQ ID NO 535
<211> LENGTH: 23

```
<212> TYPE: PRT
<213> ORGANISM: Artificial
<220> FEATURE:
<223> OTHER INFORMATION: PL sequence binding NeDLG d1

<400> SEQUENCE: 535

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 536
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 536

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 537
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 537

Leu Ala Val Leu Ala Tyr Ser Ile Thr Leu Val Met Leu Trp Ser Ile
1               5                   10                  15

Trp Gln Tyr Ala
            20

<210> SEQ ID NO 538
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 538

Leu Met Asp Gly Leu Pro Pro Gly Asp Ser Asn Gln Leu Ala Trp Phe
1               5                   10                  15

Asp Thr Asp Leu
            20

<210> SEQ ID NO 539
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 539

Leu Asn Ser Cys Ser Asn Arg Arg Val Tyr Lys Lys Met Pro Ser Ile
1               5                   10                  15

Glu Ser Asp Val
            20

<210> SEQ ID NO 540
```

-continued

```
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 540

Pro Gly Gln Pro Pro Lys Val Lys Ser Glu Phe Asn Ser Tyr Ser Leu
1               5                   10                  15

Thr Gly Tyr Val
            20

<210> SEQ ID NO 541
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 541

Pro Ile Pro Ala Gly Gly Cys Thr Phe Ser Gly Ile Phe Pro Thr Leu
1               5                   10                  15

Thr Ser Pro Leu
            20

<210> SEQ ID NO 542
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 542

Pro Tyr Ser Glu Leu Asn Tyr Glu Thr Ser His Tyr Pro Ala Ser Pro
1               5                   10                  15

Asp Ser Trp Val
            20

<210> SEQ ID NO 543
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 543

Gln Asp Phe Arg Arg Ala Phe Arg Arg Ile Leu Ala Arg Pro Trp Thr
1               5                   10                  15

Gln Thr Ala Trp
            20

<210> SEQ ID NO 544
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 544

Arg Glu Leu Val Asp Arg Gly Glu Val Arg Gln Phe Thr Leu Arg His
1               5                   10                  15

Trp Leu Lys Val
            20
```

```
<210> SEQ ID NO 545
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 545

Arg Glu Leu Val Asp Arg Gly Glu Val Arg Gln Phe Thr Leu Arg His
1               5                   10                  15

Trp Leu Lys Val
            20

<210> SEQ ID NO 546
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 546

Ser Leu Ile Gly Pro Val Gln Lys Glu Tyr Gln Arg Glu Leu Gly Lys
1               5                   10                  15

Leu Ser Ser Pro
            20

<210> SEQ ID NO 547
<211> LENGTH: 19
<212> TYPE: PRT
<213> ORGANISM: Artificial
<220> FEATURE:
<223> OTHER INFORMATION: PL sequence binding NeDLG d1

<400> SEQUENCE: 547

Ser Ser Lys Ser Lys Ser Ser Glu Glu Ser Gln Thr Phe Phe Gly Leu
1               5                   10                  15

Tyr Lys Leu

<210> SEQ ID NO 548
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 548

Ser Ser Pro Asp Ser Ser Tyr Gln Gly Lys Gly Phe Val Met Ser Arg
1               5                   10                  15

Ala Met Tyr Val
            20

<210> SEQ ID NO 549
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 549

Thr Ala Glu Asn Ala Glu Tyr Leu Arg Val Ala Pro Gln Ser Ser Glu
1               5                   10                  15

Phe Ile Gly Ala
            20
```

```
<210> SEQ ID NO 550
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 550

Thr Gly Ser Ala Leu Gln Ala Trp Arg His Thr Ser Arg Gln Ala Thr
1               5                   10                  15

Glu Ser Thr Val
            20

<210> SEQ ID NO 551
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 551

Thr Gln Gly Phe Pro Gly Pro Ala Thr Trp Arg Arg Ile Ser Ser Leu
1               5                   10                  15

Glu Ser Glu Val
            20

<210> SEQ ID NO 552
<211> LENGTH: 19
<212> TYPE: PRT
<213> ORGANISM: Artificial
<220> FEATURE:
<223> OTHER INFORMATION: PL sequence binding NeDLG d1

<400> SEQUENCE: 552

Thr Thr Asn Asn Asn Pro Asn Ser Ala Val Asn Ile Lys Lys Ile Phe
1               5                   10                  15

Thr Asp Val

<210> SEQ ID NO 553
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 553

Val Asp Pro Asn Ser Pro Ala Ala Lys Lys Tyr Val Ser Tyr Asn
1               5                   10                  15

Asn Leu Val Ile
            20

<210> SEQ ID NO 554
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 554

Val Asp Ser Glu Arg Arg Pro His Phe Pro Gln Phe Ser Tyr Ser Ala
1               5                   10                  15

Ser Gly Thr Ala
            20
```

-continued

```
<210> SEQ ID NO 555
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 555

Val Gly Thr Leu Leu Glu Arg Val Ile Phe Pro Ser Val Lys Ile
1               5                   10                  15

Ala Thr Leu Val
            20

<210> SEQ ID NO 556
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 556

Val His Lys Val Arg Asn Lys Phe Lys Ala Lys Cys Ser Leu Cys Arg
1               5                   10                  15

Leu Tyr Ile Ile
            20

<210> SEQ ID NO 557
<211> LENGTH: 20
<212> TYPE: PRT
<213> ORGANISM: Artificial
<220> FEATURE:
<223> OTHER INFORMATION: PL sequence binding NeDLG d1

<400> SEQUENCE: 557

Tyr Gly Arg Lys Lys Arg Arg Gln Arg Arg Arg Asn Asp Asn Ile Ala
1               5                   10                  15

Leu Leu Val Gln
            20

<210> SEQ ID NO 558
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 558

Ala Ala Gly Gly Arg Ser Ala Arg Gly Gly Arg Leu Gln Gly Arg Arg
1               5                   10                  15

Glu Thr Ala Leu
            20

<210> SEQ ID NO 559
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 559

Ala Gly Ala Val Arg Thr Pro Leu Ser Gln Val Asn Lys Val Trp Asp
1               5                   10                  15

Gln Ser Ser Val
            20
```

```
<210> SEQ ID NO 560
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 560

Ala Thr Asp Tyr Leu Val Gln Pro Phe Met Asp Gln Leu Ala Phe His
1               5                   10                  15

Gln Phe Tyr Ile
            20

<210> SEQ ID NO 561
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 561

Ala Val Gly Gly Arg Pro Ala Arg Gly Gly Arg Leu Gln Gly Arg Arg
1               5                   10                  15

Gln Thr Gln Val
            20

<210> SEQ ID NO 562
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 562

Asp Phe Arg Pro Ser Phe Lys His Ile Leu Phe Arg Arg Ala Arg Arg
1               5                   10                  15

Gly Phe Arg Gln
            20

<210> SEQ ID NO 563
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 563

Glu Asp Pro Lys Asp Arg Pro Ser Ala Ala His Ile Val Glu Ala Leu
1               5                   10                  15

Glu Thr Asp Val
            20

<210> SEQ ID NO 564
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 564

Glu Leu Leu Gln Phe Cys Arg Thr Pro Asn Pro Ala Leu Lys Asn Gly
1               5                   10                  15

Gln Tyr Trp Val
            20
```

```
<210> SEQ ID NO 565
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 565

Glu Ser Ser Gly Thr Gln Ser Pro Lys Arg His Ser Gly Ser Tyr Leu
1               5                   10                  15

Val Thr Ser Val
            20

<210> SEQ ID NO 566
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 566

Phe Asn Gly Ser Ser Asn Gly His Val Tyr Glu Lys Leu Ser Ser Ile
1               5                   10                  15

Glu Ser Asp Val
            20

<210> SEQ ID NO 567
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 567

Gly Gly Asp Leu Gly Thr Arg Arg Gly Ser Ala His Phe Ser Ser Leu
1               5                   10                  15

Glu Ser Glu Val
            20

<210> SEQ ID NO 568
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 568

Gly Arg Trp Thr Gly Arg Ala Met Ser Ala Trp Lys Pro Thr Arg Arg
1               5                   10                  15

Glu Thr Glu Val
            20

<210> SEQ ID NO 569
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 569

Gly Arg Trp Thr Gly Arg Cys Met Ser Cys Trp Lys Pro Thr Arg Arg
1               5                   10                  15

Glu Thr Glu Val
```

```
<210> SEQ ID NO 570
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 570

His His Leu Val Ala Gln Arg Asp Ile Arg Gln Phe Gln Leu Gln His
1               5                   10                  15

Trp Leu Ala Ile
            20

<210> SEQ ID NO 571
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 571

His Ser Cys Cys Asn Arg Ala Arg Gln Glu Arg Leu Gln Arg Arg Arg
1               5                   10                  15

Glu Thr Gln Val
            20

<210> SEQ ID NO 572
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 572

Ile Leu Asn Ser Ile Gln Val Met Arg Ala Gln Met Asn Gln Ile Gln
1               5                   10                  15

Ser Val Glu Val
            20

<210> SEQ ID NO 573
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 573

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 574
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 574

Lys His Ser Arg Lys Ser Ser Ser Tyr Ser Ser Ser Ser Thr Thr Val
1               5                   10                  15
```

-continued

Lys Thr Ser Tyr
         20

<210> SEQ ID NO 575
<211> LENGTH: 23
<212> TYPE: PRT
<213> ORGANISM: Artificial
<220> FEATURE:
<223> OTHER INFORMATION: PL sequence binding NeDLG d2

<400> SEQUENCE: 575

Lys Lys Lys Lys Gln Pro Gly Asn Ser Thr Lys Glu Ser Glu Ser Thr
1               5                   10                  15

Asn Ser Val Arg Leu Met Leu
         20

<210> SEQ ID NO 576
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 576

Lys Tyr Ser Ala Pro Arg Arg Pro Thr Ala Thr Gly Asp Tyr Asp Lys
1               5                   10                  15

Lys Asn Tyr Val
         20

<210> SEQ ID NO 577
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 577

Leu Ala Val Leu Ala Tyr Ser Ile Thr Leu Val Met Leu Trp Ser Ile
1               5                   10                  15

Trp Gln Tyr Ala
         20

<210> SEQ ID NO 578
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 578

Leu Gly Tyr Ser Ile Pro Ser Arg Ser Gly Ala Ser Gly Leu Asp Lys
1               5                   10                  15

Arg Asp Tyr Val
         20

<210> SEQ ID NO 579
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 579

Leu Met Asp Gly Leu Pro Pro Gly Asp Ser Asn Gln Leu Ala Trp Phe
1               5                   10                  15

Asp Thr Asp Leu
        20

<210> SEQ ID NO 580
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 580

Leu Asn Ser Cys Ser Asn Arg Arg Val Tyr Lys Lys Met Pro Ser Ile
1               5                   10                  15

Glu Ser Asp Val
        20

<210> SEQ ID NO 581
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 581

Leu Asn Ser Ser Ser Asn Arg Arg Val Tyr Lys Lys Met Pro Ser Ile
1               5                   10                  15

Glu Ser Asp Val
        20

<210> SEQ ID NO 582
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 582

Pro Gly Gln Pro Pro Lys Val Lys Ser Glu Phe Asn Ser Tyr Ser Leu
1               5                   10                  15

Thr Gly Tyr Val
        20

<210> SEQ ID NO 583
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 583

Pro Ile Pro Ala Gly Gly Cys Thr Phe Ser Gly Ile Phe Pro Thr Leu
1               5                   10                  15

Thr Ser Pro Leu
        20

<210> SEQ ID NO 584
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 584

Pro Tyr Ser Glu Leu Asn Tyr Glu Thr Ser His Tyr Pro Ala Ser Pro

-continued

```
1               5                   10                  15

Asp Ser Trp Val
            20

<210> SEQ ID NO 585
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 585

Gln Asp Phe Arg Arg Ala Phe Arg Arg Ile Leu Ala Arg Pro Trp Thr
1               5                   10                  15

Gln Thr Ala Trp
            20

<210> SEQ ID NO 586
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 586

Gln Ile Ser Pro Gly Gly Leu Glu Pro Pro Ser Glu Lys His Phe Arg
1               5                   10                  15

Glu Thr Glu Val
            20

<210> SEQ ID NO 587
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 587

Arg Glu Leu Val Asp Arg Gly Glu Val Arg Gln Phe Thr Leu Arg His
1               5                   10                  15

Trp Leu Lys Val
            20

<210> SEQ ID NO 588
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 588

Arg Glu Leu Val Asp Arg Gly Glu Val Arg Gln Phe Thr Leu Arg His
1               5                   10                  15

Trp Leu Lys Val
            20

<210> SEQ ID NO 589
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 589
```

-continued

Arg Asn Ile Glu Glu Val Tyr Val Gly Gly Lys Gln Val Val Pro Phe
1               5                  10                  15

Ser Ser Ser Val
            20

<210> SEQ ID NO 590
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 590

Ser Phe Thr Ser Ile Leu Thr Cys His Gln Arg Arg Thr Gln Arg Lys
1               5                  10                  15

Glu Thr Val Ala
            20

<210> SEQ ID NO 591
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 591

Ser Leu Lys Pro Gly Thr Val Leu Pro Pro Pro Tyr Arg His Arg
1               5                  10                  15

Asn Thr Val Val
            20

<210> SEQ ID NO 592
<211> LENGTH: 18
<212> TYPE: PRT
<213> ORGANISM: Artificial
<220> FEATURE:
<223> OTHER INFORMATION: PL sequence binding NeDLG d2

<400> SEQUENCE: 592

Ser Pro Gln Pro Asp Ser Thr Asp Asn Asp Asp Tyr Asp Asp Ile Ser
1               5                  10                  15

Ala Ala

<210> SEQ ID NO 593
<211> LENGTH: 19
<212> TYPE: PRT
<213> ORGANISM: Artificial
<220> FEATURE:
<223> OTHER INFORMATION: PL sequence binding NeDLG d2

<400> SEQUENCE: 593

Ser Ser Lys Ser Lys Ser Ser Glu Glu Ser Gln Thr Phe Phe Gly Leu
1               5                  10                  15

Tyr Lys Leu

<210> SEQ ID NO 594
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 594

Ser Ser Pro Asp Ser Ser Tyr Gln Gly Lys Gly Phe Val Met Ser Arg

```
1               5                  10                 15
Ala Met Tyr Val
            20

<210> SEQ ID NO 595
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 595

Thr Ala Glu Asn Ala Glu Tyr Leu Arg Val Ala Pro Gln Ser Ser Glu
1               5                  10                 15

Phe Ile Gly Ala
            20

<210> SEQ ID NO 596
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 596

Thr Phe Lys Gly Thr Pro Thr Ala Glu Asn Pro Glu Tyr Leu Gly Leu
1               5                  10                 15

Asp Val Pro Val
            20

<210> SEQ ID NO 597
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 597

Thr Gly Ser Ala Leu Gln Ala Trp Arg His Thr Ser Arg Gln Ala Thr
1               5                  10                 15

Glu Ser Thr Val
            20

<210> SEQ ID NO 598
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 598

Thr Gln Gly Phe Pro Gly Pro Ala Thr Trp Arg Arg Ile Ser Ser Leu
1               5                  10                 15

Glu Ser Glu Val
            20

<210> SEQ ID NO 599
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 599
```

```
Thr Arg Glu Asp Ile Tyr Val Asn Tyr Pro Thr Phe Ser Arg Arg Pro
1               5                   10                  15

Lys Thr Arg Val
            20

<210> SEQ ID NO 600
<211> LENGTH: 19
<212> TYPE: PRT
<213> ORGANISM: Artificial
<220> FEATURE:
<223> OTHER INFORMATION: PL sequence binding NeDLG d2

<400> SEQUENCE: 600

Thr Thr Asn Asn Pro Asn Ser Ala Val Asn Ile Lys Lys Ile Phe
1               5                   10                  15

Thr Asp Val

<210> SEQ ID NO 601
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 601

Val Asp Pro Asn Ser Pro Ala Ala Lys Lys Tyr Val Ser Tyr Asn
1               5                   10                  15

Asn Leu Val Ile
            20

<210> SEQ ID NO 602
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 602

Val Gly Thr Leu Leu Leu Glu Arg Val Ile Phe Pro Ser Val Lys Ile
1               5                   10                  15

Ala Thr Leu Val
            20

<210> SEQ ID NO 603
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 603

Val His Lys Val Arg Asn Lys Phe Lys Ala Lys Cys Ser Leu Cys Arg
1               5                   10                  15

Leu Tyr Ile Ile
            20

<210> SEQ ID NO 604
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 604
```

```
Tyr Gly Arg Lys Lys Arg Arg Gln Arg Arg Lys Leu Ser Ser Ile
1               5                   10                  15

Glu Ser Asp Val
            20
```

<210> SEQ ID NO 605
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 605

```
Tyr Gly Arg Lys Lys Arg Arg Gln Arg Arg Asn Asp Asn Ile Ala
1               5                   10                  15

Leu Leu Val Gln
            20
```

<210> SEQ ID NO 606
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 606

```
Tyr Gly Arg Lys Lys Arg Arg Gln Arg Arg Ser Glu Gly Val Pro
1               5                   10                  15

Asp Leu Leu Val
            20
```

<210> SEQ ID NO 607
<211> LENGTH: 20
<212> TYPE: PRT
<213> ORGANISM: Artificial
<220> FEATURE:
<223> OTHER INFORMATION: PL sequence binding NeDLG d2

<400> SEQUENCE: 607

```
Tyr Ser Ala Thr Tyr Ser Glu Leu Glu Asp Pro Gly Glu Met Ser Pro
1               5                   10                  15

Pro Ile Asp Leu
            20
```

<210> SEQ ID NO 608
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 608

```
Ala Ala Gly Gly Arg Ser Ala Arg Gly Gly Arg Leu Gln Gly Arg Arg
1               5                   10                  15

Glu Thr Ala Leu
            20
```

<210> SEQ ID NO 609
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 609

```
Ala Gly Ala Val Arg Thr Pro Leu Ser Gln Val Asn Lys Val Trp Asp
1               5                   10                  15

Gln Ser Ser Val
            20

<210> SEQ ID NO 610
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 610

Ala Val Gly Gly Arg Pro Ala Arg Gly Gly Arg Leu Gln Gly Arg Arg
1               5                   10                  15

Gln Thr Gln Val
            20

<210> SEQ ID NO 611
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 611

Asp Phe Arg Pro Ser Phe Lys His Ile Leu Phe Arg Arg Ala Arg Arg
1               5                   10                  15

Gly Phe Arg Gln
            20

<210> SEQ ID NO 612
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 612

Asp Gly Gly Ala Arg Thr Glu Asp Glu Val Gln Ser Tyr Pro Ser Lys
1               5                   10                  15

His Asp Tyr Val
            20

<210> SEQ ID NO 613
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 613

Glu Leu Leu Gln Phe Cys Arg Thr Pro Asn Pro Ala Leu Lys Asn Gly
1               5                   10                  15

Gln Tyr Trp Val
            20

<210> SEQ ID NO 614
<211> LENGTH: 20
<212> TYPE: PRT
<213> ORGANISM: Artificial
<220> FEATURE:
<223> OTHER INFORMATION: PL sequence binding Outer Membrane Protein
```

```
<400> SEQUENCE: 614

Glu Ser Ser Gly Thr Gln Ser Pro Lys Arg His Ser Gly Ser Tyr Leu
1               5                   10                  15

Val Thr Ser Val
            20

<210> SEQ ID NO 615
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 615

Phe Asn Gly Ser Ser Asn Gly His Val Tyr Glu Lys Leu Ser Ser Ile
1               5                   10                  15

Glu Ser Asp Val
            20

<210> SEQ ID NO 616
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 616

Gly Gly Asp Leu Gly Thr Arg Arg Gly Ser Ala His Phe Ser Ser Leu
1               5                   10                  15

Glu Ser Glu Val
            20

<210> SEQ ID NO 617
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 617

Gly Gly Glu Asp Phe Lys Thr Thr Asn Pro Ser Lys Gln Phe Asp Lys
1               5                   10                  15

Asn Ala Tyr Val
            20

<210> SEQ ID NO 618
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 618

Gly Arg Trp Thr Gly Arg Ala Met Ser Ala Trp Lys Pro Thr Arg Arg
1               5                   10                  15

Glu Thr Glu Val
            20

<210> SEQ ID NO 619
<211> LENGTH: 20
<212> TYPE: PRT
<213> ORGANISM: Artificial
<220> FEATURE:
<223> OTHER INFORMATION: PL sequence binding Outer Membrane Protein
```

```
<400> SEQUENCE: 619

His His Leu Val Ala Gln Arg Asp Ile Arg Gln Phe Gln Leu Gln His
1               5                   10                  15

Trp Leu Ala Ile
            20

<210> SEQ ID NO 620
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 620

His Ser Cys Cys Asn Arg Ala Arg Gln Glu Arg Leu Gln Arg Arg Arg
1               5                   10                  15

Glu Thr Gln Val
            20

<210> SEQ ID NO 621
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 621

Ile Ser Gly Thr Pro Thr Ser Thr Met Val His Gly Met Thr Ser Ser
1               5                   10                  15

Ser Ser Val Val
            20

<210> SEQ ID NO 622
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 622

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 623
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 623

Lys Glu Asn Asp Tyr Glu Ser Ile Ser Asp Leu Gln Gln Gly Arg Asp
1               5                   10                  15

Ile Thr Arg Leu
            20

<210> SEQ ID NO 624
<211> LENGTH: 20
<212> TYPE: PRT
<213> ORGANISM: Artificial
<220> FEATURE:
```

```
<223> OTHER INFORMATION: PL sequence binding Outer Membrane Protein

<400> SEQUENCE: 624

Lys His Ser Arg Lys Ser Ser Tyr Ser Ser Ser Thr Thr Val
1               5                   10                  15

Lys Thr Ser Tyr
            20

<210> SEQ ID NO 625
<211> LENGTH: 23
<212> TYPE: PRT
<213> ORGANISM: Artificial
<220> FEATURE:
<223> OTHER INFORMATION: PL sequence binding Outer Membrane Protein

<400> SEQUENCE: 625

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 626
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 626

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 627
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 627

Leu Ala Val Leu Ala Tyr Ser Ile Thr Leu Val Met Leu Trp Ser Ile
1               5                   10                  15

Trp Gln Tyr Ala
            20

<210> SEQ ID NO 628
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 628

Leu Gly Tyr Ser Ile Pro Ser Arg Ser Gly Ala Ser Gly Leu Asp Lys
1               5                   10                  15

Arg Asp Tyr Val
            20

<210> SEQ ID NO 629
<211> LENGTH: 20
<212> TYPE: PRT
<213> ORGANISM: Artificial
```

```
<220> FEATURE:
<223> OTHER INFORMATION: PL sequence binding Outer Membrane Protein

<400> SEQUENCE: 629

Leu His Asn Gln Ala Ser Val Pro Leu Glu Pro Arg Pro Leu Arg Arg
1               5                   10                  15

Glu Ser Glu Ile
            20

<210> SEQ ID NO 630
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 630

Leu Asn Ser Cys Ser Asn Arg Arg Val Tyr Lys Lys Met Pro Ser Ile
1               5                   10                  15

Glu Ser Asp Val
            20

<210> SEQ ID NO 631
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 631

Leu Asn Ser Ser Ser Asn Arg Arg Val Tyr Lys Lys Met Pro Ser Ile
1               5                   10                  15

Glu Ser Asp Val
            20

<210> SEQ ID NO 632
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 632

Pro Gly Gln Pro Pro Lys Val Lys Ser Glu Phe Asn Ser Tyr Ser Leu
1               5                   10                  15

Thr Gly Tyr Val
            20

<210> SEQ ID NO 633
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 633

Pro Ile Pro Ala Gly Gly Cys Thr Phe Ser Gly Ile Phe Pro Thr Leu
1               5                   10                  15

Thr Ser Pro Leu
            20

<210> SEQ ID NO 634
<211> LENGTH: 20
<212> TYPE: PRT
```

```
<213> ORGANISM: Artificial
<220> FEATURE:
<223> OTHER INFORMATION: PL sequence binding Outer Membrane Protein

<400> SEQUENCE: 634

Pro Tyr Ser Glu Leu Asn Tyr Glu Thr Ser His Tyr Pro Ala Ser Pro
1               5                   10                  15

Asp Ser Trp Val
            20

<210> SEQ ID NO 635
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 635

Gln Ala Thr Ser Arg Asn Gly His Ser Ala Arg Gln His Val Val Ala
1               5                   10                  15

Asp Thr Glu Leu
            20

<210> SEQ ID NO 636
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 636

Gln Asp Phe Arg Arg Ala Phe Arg Arg Ile Leu Ala Arg Pro Trp Thr
1               5                   10                  15

Gln Thr Ala Trp
            20

<210> SEQ ID NO 637
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 637

Gln Ile Ser Pro Gly Gly Leu Glu Pro Pro Ser Glu Lys His Phe Arg
1               5                   10                  15

Glu Thr Glu Val
            20

<210> SEQ ID NO 638
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 638

Gln Pro Thr Pro Thr Leu Gly Leu Asn Leu Gly Asn Asp Pro Asp Arg
1               5                   10                  15

Gly Thr Ser Ile
            20

<210> SEQ ID NO 639
<211> LENGTH: 20
```

```
<212> TYPE: PRT
<213> ORGANISM: Artificial
<220> FEATURE:
<223> OTHER INFORMATION: PL sequence binding Outer Membrane Protein

<400> SEQUENCE: 639

Arg Glu Leu Val Asp Arg Gly Glu Val Arg Gln Phe Thr Leu Arg His
1               5                   10                  15

Trp Leu Lys Val
        20

<210> SEQ ID NO 640
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 640

Arg Glu Leu Val Asp Arg Gly Glu Val Arg Gln Phe Thr Leu Arg His
1               5                   10                  15

Trp Leu Lys Val
        20

<210> SEQ ID NO 641
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 641

Arg Asn Ile Glu Glu Val Tyr Val Gly Gly Lys Gln Val Val Pro Phe
1               5                   10                  15

Ser Ser Ser Val
        20

<210> SEQ ID NO 642
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 642

Arg Ser Gly Ala Thr Ile Pro Leu Val Gly Gln Asp Ile Ile Asp Leu
1               5                   10                  15

Gln Thr Glu Val
        20

<210> SEQ ID NO 643
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 643

Ser Phe Thr Ser Ile Leu Thr Cys His Gln Arg Arg Thr Gln Arg Lys
1               5                   10                  15

Glu Thr Val Ala
        20

<210> SEQ ID NO 644
```

```
<211> LENGTH: 19
<212> TYPE: PRT
<213> ORGANISM: Artificial
<220> FEATURE:
<223> OTHER INFORMATION: PL sequence binding Outer Membrane Protein

<400> SEQUENCE: 644

Ser Gly Gly Asn Arg Ala Arg Gln Glu Arg Leu Gln Arg Arg Arg Glu
1               5                   10                  15

Thr Gln Val

<210> SEQ ID NO 645
<211> LENGTH: 18
<212> TYPE: PRT
<213> ORGANISM: Artificial
<220> FEATURE:
<223> OTHER INFORMATION: PL sequence binding Outer Membrane Protein

<400> SEQUENCE: 645

Ser Pro Gln Pro Asp Ser Thr Asp Asn Asp Asp Tyr Asp Asp Ile Ser
1               5                   10                  15

Ala Ala

<210> SEQ ID NO 646
<211> LENGTH: 19
<212> TYPE: PRT
<213> ORGANISM: Artificial
<220> FEATURE:
<223> OTHER INFORMATION: PL sequence binding Outer Membrane Protein

<400> SEQUENCE: 646

Ser Ser Lys Ser Lys Ser Ser Glu Glu Ser Gln Thr Phe Phe Gly Leu
1               5                   10                  15

Tyr Lys Leu

<210> SEQ ID NO 647
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 647

Ser Ser Pro Asp Ser Ser Tyr Gln Gly Lys Gly Phe Val Met Ser Arg
1               5                   10                  15

Ala Met Tyr Val
            20

<210> SEQ ID NO 648
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 648

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 649
<211> LENGTH: 18
<212> TYPE: PRT
```

-continued

```
<213> ORGANISM: Artificial
<220> FEATURE:
<223> OTHER INFORMATION: PL sequence binding Outer Membrane Protein

<400> SEQUENCE: 649

Thr Phe Ala Ala Gly Phe Asn Ser Thr Gly Leu Pro His Ser Thr Thr
1               5                   10                  15

Arg Val

<210> SEQ ID NO 650
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 650

Thr Phe Lys Gly Thr Pro Thr Ala Glu Asn Pro Glu Tyr Leu Gly Leu
1               5                   10                  15

Asp Val Pro Val
            20

<210> SEQ ID NO 651
<211> LENGTH: 19
<212> TYPE: PRT
<213> ORGANISM: Artificial
<220> FEATURE:
<223> OTHER INFORMATION: PL sequence binding Outer Membrane Protein

<400> SEQUENCE: 651

Thr Gly Arg Gly Met Ser Gly Gly Arg Ser Ser Arg Thr Arg Arg Glu
1               5                   10                  15

Thr Gln Leu

<210> SEQ ID NO 652
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 652

Thr Gly Ser Ala Leu Gln Ala Trp Arg His Thr Ser Arg Gln Ala Thr
1               5                   10                  15

Glu Ser Thr Val
            20

<210> SEQ ID NO 653
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 653

Thr Gln Gly Phe Pro Gly Pro Ala Thr Trp Arg Arg Ile Ser Ser Leu
1               5                   10                  15

Glu Ser Glu Val
            20

<210> SEQ ID NO 654
<211> LENGTH: 20
<212> TYPE: PRT
<213> ORGANISM: Artificial
```

```
<220> FEATURE:
<223> OTHER INFORMATION: PL sequence binding Outer Membrane Protein

<400> SEQUENCE: 654

Thr Arg Glu Asp Ile Tyr Val Asn Tyr Pro Thr Phe Ser Arg Arg Pro
1               5                   10                  15

Lys Thr Arg Val
            20

<210> SEQ ID NO 655
<211> LENGTH: 19
<212> TYPE: PRT
<213> ORGANISM: Artificial
<220> FEATURE:
<223> OTHER INFORMATION: PL sequence binding Outer Membrane Protein

<400> SEQUENCE: 655

Thr Thr Asn Asn Asn Pro Asn Ser Ala Val Asn Ile Lys Lys Ile Phe
1               5                   10                  15

Thr Asp Val

<210> SEQ ID NO 656
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 656

Val Asp Pro Asn Ser Pro Ala Ala Lys Lys Lys Tyr Val Ser Tyr Asn
1               5                   10                  15

Asn Leu Val Ile
            20

<210> SEQ ID NO 657
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 657

Val Gly Thr Leu Leu Leu Glu Arg Val Ile Phe Pro Ser Val Lys Ile
1               5                   10                  15

Ala Thr Leu Val
            20

<210> SEQ ID NO 658
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 658

Val His Asp Ala Glu Ser Ser Asp Glu Asp Gly Tyr Asp Trp Gly Pro
1               5                   10                  15

Ala Thr Asp Leu
            20

<210> SEQ ID NO 659
<211> LENGTH: 20
<212> TYPE: PRT
<213> ORGANISM: Artificial
```

```
<220> FEATURE:
<223> OTHER INFORMATION: PL sequence binding Outer Membrane Protein

<400> SEQUENCE: 659

Val His Lys Val Arg Asn Lys Phe Lys Ala Lys Cys Ser Leu Cys Arg
1               5                   10                  15

Leu Tyr Ile Ile
            20

<210> SEQ ID NO 660
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 660

Val Pro Gly Ala Leu Asp Tyr Ala Ala Phe Ser Ser Ala Leu Tyr Gly
1               5                   10                  15

Glu Ser Asp Leu
            20

<210> SEQ ID NO 661
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 661

Tyr Gly Arg Lys Lys Arg Arg Gln Arg Arg Lys Leu Ser Ser Ile
1               5                   10                  15

Glu Ser Asp Val
            20

<210> SEQ ID NO 662
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 662

Tyr Gly Arg Lys Lys Arg Arg Gln Arg Arg Asn Asp Asn Ile Ala
1               5                   10                  15

Leu Leu Val Gln
            20

<210> SEQ ID NO 663
<211> LENGTH: 20
<212> TYPE: PRT
<213> ORGANISM: Artificial
<220> FEATURE:
<223> OTHER INFORMATION: PL sequence binding Outer Membrane Protein

<400> SEQUENCE: 663

Tyr Gly Arg Lys Lys Arg Arg Gln Arg Arg Ser Glu Gly Val Pro
1               5                   10                  15

Asp Leu Leu Val
            20

<210> SEQ ID NO 664
<211> LENGTH: 20
<212> TYPE: PRT
```

```
<213> ORGANISM: Artificial
<220> FEATURE:
<223> OTHER INFORMATION: PL sequence binding PICK1 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 664

Tyr Gly Arg Lys Lys Arg Arg Gln Arg Arg Lys Leu Ser Ser Ile
1               5                   10                  15

Glu Ser Asp Xaa
            20

<210> SEQ ID NO 665
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 665

Ala Leu Val Leu Ile Ala Phe Cys Ile Ile Arg Arg Arg Pro Ser Ala
1               5                   10                  15

Tyr Gln Ala Leu
            20

<210> SEQ ID NO 666
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 666

Ala Thr Asp Tyr Leu Val Gln Pro Phe Met Asp Gln Leu Ala Phe His
1               5                   10                  15

Gln Phe Tyr Ile
            20

<210> SEQ ID NO 667
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 667

Asp Phe Arg Pro Ser Phe Lys His Ile Leu Phe Arg Arg Ala Arg Arg
1               5                   10                  15

Gly Phe Arg Gln
            20

<210> SEQ ID NO 668
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 668

Asp Gly Gly Ala Arg Thr Glu Asp Glu Val Gln Ser Tyr Pro Ser Lys
1               5                   10                  15

His Asp Tyr Val
            20
```

```
<210> SEQ ID NO 669
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 669

Glu Leu Leu Gln Phe Cys Arg Thr Pro Asn Pro Ala Leu Lys Asn Gly
1               5                   10                  15

Gln Tyr Trp Val
            20

<210> SEQ ID NO 670
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 670

Phe His Ser Lys Thr Ala Gly Ala Asn Thr Thr Asp Lys Glu Leu Glu
1               5                   10                  15

Val Leu Ser Leu
            20

<210> SEQ ID NO 671
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 671

Gly Arg Trp Thr Gly Arg Ala Met Ser Ala Trp Lys Pro Thr Arg Arg
1               5                   10                  15

Glu Thr Glu Val
            20

<210> SEQ ID NO 672
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 672

His Asp Phe Arg Arg Ala Phe Lys Lys Ile Leu Ala Arg Gly Asp Arg
1               5                   10                  15

Lys Arg Ile Val
            20

<210> SEQ ID NO 673
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 673

His His Leu Val Ala Gln Arg Asp Ile Arg Gln Phe Gln Leu Gln His
1               5                   10                  15

Trp Leu Ala Ile
```

-continued

```
            20

<210> SEQ ID NO 674
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 674

His Ser Cys Cys Asn Arg Ala Arg Gln Glu Arg Leu Gln Arg Arg Arg
1               5                   10                  15

Glu Thr Gln Val
            20

<210> SEQ ID NO 675
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 675

Ile Leu Asn Ser Ile Gln Val Met Arg Ala Gln Met Asn Gln Ile Gln
1               5                   10                  15

Ser Val Glu Val
            20

<210> SEQ ID NO 676
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 676

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 677
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 677

Lys His Ser Arg Lys Ser Ser Ser Tyr Ser Ser Ser Ser Thr Thr Val
1               5                   10                  15

Lys Thr Ser Tyr
            20

<210> SEQ ID NO 678
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 678

Lys Thr Met Pro Ala Ala Met Tyr Arg Leu Leu Thr Ala Gln Glu Gln
1               5                   10                  15
```

```
Pro Val Tyr Ile
            20

<210> SEQ ID NO 679
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 679

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 680
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 680

Leu Ala Val Leu Ala Tyr Ser Ile Thr Leu Val Met Leu Trp Ser Ile
1               5                   10                  15

Trp Gln Tyr Ala
            20

<210> SEQ ID NO 681
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 681

Leu Ser Glu Lys Lys Thr Ser Gln Ser Pro His Arg Phe Gln Lys Thr
1               5                   10                  15

Ser Ser Pro Ile
            20

<210> SEQ ID NO 682
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 682

Pro Gly Gln Pro Pro Lys Val Lys Ser Glu Phe Asn Ser Tyr Ser Leu
1               5                   10                  15

Thr Gly Tyr Val
            20

<210> SEQ ID NO 683
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 683

Pro Ile Pro Ala Gly Gly Cys Thr Phe Ser Gly Ile Phe Pro Thr Leu
1               5                   10                  15
```

Thr Ser Pro Leu
            20

<210> SEQ ID NO 684
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 684

Pro Tyr Ser Glu Leu Asn Tyr Glu Thr Ser His Tyr Pro Ala Ser Pro
1               5                   10                  15

Asp Ser Trp Val
            20

<210> SEQ ID NO 685
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 685

Gln Asp Phe Arg Arg Ala Phe Arg Arg Ile Leu Ala Arg Pro Trp Thr
1               5                   10                  15

Gln Thr Ala Trp
            20

<210> SEQ ID NO 686
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 686

Arg Glu Leu Val Asp Arg Gly Glu Val Arg Gln Phe Thr Leu Arg His
1               5                   10                  15

Trp Leu Lys Val
            20

<210> SEQ ID NO 687
<211> LENGTH: 18
<212> TYPE: PRT
<213> ORGANISM: Artificial
<220> FEATURE:
<223> OTHER INFORMATION: PL sequence binding PICK1 d1

<400> SEQUENCE: 687

Ser Pro Gln Pro Asp Ser Thr Asp Asn Asp Asp Tyr Asp Asp Ile Ser
1               5                   10                  15

Ala Ala

<210> SEQ ID NO 688
<211> LENGTH: 19
<212> TYPE: PRT
<213> ORGANISM: Artificial
<220> FEATURE:
<223> OTHER INFORMATION: PL sequence binding PICK1 d1

<400> SEQUENCE: 688

Ser Ser Lys Ser Lys Ser Ser Glu Glu Ser Gln Thr Phe Phe Gly Leu
1               5                   10                  15

Tyr Lys Leu

<210> SEQ ID NO 689
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 689

Ser Ser Pro Asp Ser Ser Tyr Gln Gly Lys Gly Phe Val Met Ser Arg
1               5                   10                  15

Ala Met Tyr Val
            20

<210> SEQ ID NO 690
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 690

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 691
<211> LENGTH: 19
<212> TYPE: PRT
<213> ORGANISM: Artificial
<220> FEATURE:
<223> OTHER INFORMATION: PL sequence binding PICK1 d1

<400> SEQUENCE: 691

Thr Thr Asn Asn Asn Pro Asn Ser Ala Val Asn Ile Lys Lys Ile Phe
1               5                   10                  15

Thr Asp Val

<210> SEQ ID NO 692
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 692

Val Asp Pro Asn Ser Pro Ala Ala Lys Lys Lys Tyr Val Ser Tyr Asn
1               5                   10                  15

Asn Leu Val Ile
            20

<210> SEQ ID NO 693
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 693

Val His Lys Val Arg Asn Lys Phe Lys Ala Lys Cys Ser Leu Cys Arg
1               5                   10                  15

Leu Tyr Ile Ile
            20

<210> SEQ ID NO 694
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 694

Tyr Gly Arg Lys Lys Arg Arg Gln Arg Arg Glu Met Gln Val Thr
1               5                   10                  15

Leu Gly Leu His
            20

<210> SEQ ID NO 695
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 695

Tyr Gly Arg Lys Lys Arg Arg Gln Arg Arg Glu Tyr Leu Gly Leu
1               5                   10                  15

Asp Val Pro Val
            20

<210> SEQ ID NO 696
<211> LENGTH: 20
<212> TYPE: PRT
<213> ORGANISM: Artificial
<220> FEATURE:
<223> OTHER INFORMATION: PL sequence binding PICK1 d1

<400> SEQUENCE: 696

Tyr Gly Arg Lys Lys Arg Arg Gln Arg Arg Ile Gly Glu Leu Gln
1               5                   10                  15

Leu Ser Ile Ala
            20

<210> SEQ ID NO 697
<211> LENGTH: 20
<212> TYPE: PRT
<213> ORGANISM: Artificial
<220> FEATURE:
<223> OTHER INFORMATION: PL sequence binding PICK1 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 697

Tyr Gly Arg Lys Lys Arg Arg Gln Arg Arg Lys Leu Ser Ser Ile
1               5                   10                  15

Glu Ser Asp Xaa
            20

<210> SEQ ID NO 698
<211> LENGTH: 20
<212> TYPE: PRT
<213> ORGANISM: Artificial
<220> FEATURE:
<223> OTHER INFORMATION: PL sequence binding PSD95 d1

-continued

```
<400> SEQUENCE: 698

Ala Ala Gly Gly Arg Ser Ala Arg Gly Gly Arg Leu Gln Gly Arg Arg
1               5                   10                  15

Glu Thr Ala Leu
            20

<210> SEQ ID NO 699
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 699

Ala Val Gly Gly Arg Pro Ala Arg Gly Gly Arg Leu Gln Gly Arg Arg
1               5                   10                  15

Gln Thr Gln Val
            20

<210> SEQ ID NO 700
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 700

Asp Phe Arg Pro Ser Phe Lys His Ile Leu Phe Arg Arg Ala Arg Arg
1               5                   10                  15

Gly Phe Arg Gln
            20

<210> SEQ ID NO 701
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 701

Asp Gly Gly Ala Arg Thr Glu Asp Glu Val Gln Ser Tyr Pro Ser Lys
1               5                   10                  15

His Asp Tyr Val
            20

<210> SEQ ID NO 702
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 702

Glu Leu Leu Gln Phe Cys Arg Thr Pro Asn Pro Ala Leu Lys Asn Gly
1               5                   10                  15

Gln Tyr Trp Val
            20

<210> SEQ ID NO 703
<211> LENGTH: 20
<212> TYPE: PRT
<213> ORGANISM: Artificial
<220> FEATURE:
<223> OTHER INFORMATION: PL sequence binding PSD95 d1
```

```
<400> SEQUENCE: 703

Phe Asn Gly Ser Ser Asn Gly His Val Tyr Glu Lys Leu Ser Ser Ile
1               5                   10                  15

Glu Ser Asp Val
            20

<210> SEQ ID NO 704
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 704

Gly Gly Asp Leu Gly Thr Arg Arg Gly Ser Ala His Phe Ser Ser Leu
1               5                   10                  15

Glu Ser Glu Val
            20

<210> SEQ ID NO 705
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 705

Gly Gly Glu Asp Phe Lys Thr Thr Asn Pro Ser Lys Gln Phe Asp Lys
1               5                   10                  15

Asn Ala Tyr Val
            20

<210> SEQ ID NO 706
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 706

Gly Arg Trp Ala Gly Arg Ser Ala Ala Ser Trp Arg Ser Arg Arg
1               5                   10                  15

Glu Thr Ala Leu
            20

<210> SEQ ID NO 707
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 707

Gly Arg Trp Thr Gly Arg Ala Met Ser Ala Trp Lys Pro Thr Arg Arg
1               5                   10                  15

Glu Thr Glu Val
            20

<210> SEQ ID NO 708
<211> LENGTH: 20
<212> TYPE: PRT
<213> ORGANISM: Artificial
<220> FEATURE:
```

```
<223> OTHER INFORMATION: PL sequence binding PSD95 d1

<400> SEQUENCE: 708

His His Leu Val Ala Gln Arg Asp Ile Arg Gln Phe Gln Leu Gln His
1               5                   10                  15

Trp Leu Ala Ile
            20

<210> SEQ ID NO 709
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 709

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 710
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 710

Lys His Ser Arg Lys Ser Ser Tyr Ser Ser Ser Ser Thr Thr Val
1               5                   10                  15

Lys Thr Ser Tyr
            20

<210> SEQ ID NO 711
<211> LENGTH: 23
<212> TYPE: PRT
<213> ORGANISM: Artificial
<220> FEATURE:
<223> OTHER INFORMATION: PL sequence binding PSD95 d1

<400> SEQUENCE: 711

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 712
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 712

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 713
<211> LENGTH: 20
<212> TYPE: PRT
<213> ORGANISM: Artificial
```

-continued

```
<220> FEATURE:
<223> OTHER INFORMATION: PL sequence binding PSD95 d1

<400> SEQUENCE: 713

Leu Ala Val Leu Ala Tyr Ser Ile Thr Leu Val Met Leu Trp Ser Ile
1               5                   10                  15

Trp Gln Tyr Ala
            20

<210> SEQ ID NO 714
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 714

Leu Gly Tyr Ser Ile Pro Ser Arg Ser Gly Ala Ser Gly Leu Asp Lys
1               5                   10                  15

Arg Asp Tyr Val
            20

<210> SEQ ID NO 715
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 715

Leu Asn Ser Cys Ser Asn Arg Arg Val Tyr Lys Lys Met Pro Ser Ile
1               5                   10                  15

Glu Ser Asp Val
            20

<210> SEQ ID NO 716
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 716

Leu Asn Ser Ser Ser Asn Arg Arg Val Tyr Lys Lys Met Pro Ser Ile
1               5                   10                  15

Glu Ser Asp Val
            20

<210> SEQ ID NO 717
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 717

Pro Gly Gln Pro Pro Lys Val Lys Ser Glu Phe Asn Ser Tyr Ser Leu
1               5                   10                  15

Thr Gly Tyr Val
            20

<210> SEQ ID NO 718
<211> LENGTH: 20
<212> TYPE: PRT
```

-continued

```
<213> ORGANISM: Artificial
<220> FEATURE:
<223> OTHER INFORMATION: PL sequence binding PSD95 d1

<400> SEQUENCE: 718

Pro Ile Pro Ala Gly Gly Cys Thr Phe Ser Gly Ile Phe Pro Thr Leu
1               5                   10                  15

Thr Ser Pro Leu
            20

<210> SEQ ID NO 719
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 719

Pro Tyr Ser Glu Leu Asn Tyr Glu Thr Ser His Tyr Pro Ala Ser Pro
1               5                   10                  15

Asp Ser Trp Val
            20

<210> SEQ ID NO 720
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 720

Gln Asp Phe Arg Arg Ala Phe Arg Arg Ile Leu Ala Arg Pro Trp Thr
1               5                   10                  15

Gln Thr Ala Trp
            20

<210> SEQ ID NO 721
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 721

Gln Ile Ser Pro Gly Gly Leu Glu Pro Pro Ser Glu Lys His Phe Arg
1               5                   10                  15

Glu Thr Glu Val
            20

<210> SEQ ID NO 722
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 722

Arg Glu Leu Val Asp Arg Gly Glu Val Arg Gln Phe Thr Leu Arg His
1               5                   10                  15

Trp Leu Lys Val
            20

<210> SEQ ID NO 723
<211> LENGTH: 20
```

<212> TYPE: PRT
<213> ORGANISM: Artificial
<220> FEATURE:
<223> OTHER INFORMATION: PL sequence binding PSD95 d1

<400> SEQUENCE: 723

Arg Asn Ile Glu Glu Val Tyr Val Gly Gly Lys Gln Val Val Pro Phe
1               5                   10                  15
Ser Ser Ser Val
            20

<210> SEQ ID NO 724
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 724

Ser Phe Thr Ser Ile Leu Thr Cys His Gln Arg Arg Thr Gln Arg Lys
1               5                   10                  15
Glu Thr Val Ala
            20

<210> SEQ ID NO 725
<211> LENGTH: 19
<212> TYPE: PRT
<213> ORGANISM: Artificial
<220> FEATURE:
<223> OTHER INFORMATION: PL sequence binding PSD95 d1

<400> SEQUENCE: 725

Ser Ser Lys Ser Lys Ser Ser Glu Glu Ser Gln Thr Phe Phe Gly Leu
1               5                   10                  15
Tyr Lys Leu

<210> SEQ ID NO 726
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 726

Ser Ser Pro Asp Ser Ser Tyr Gln Gly Lys Gly Phe Val Met Ser Arg
1               5                   10                  15
Ala Met Tyr Val
            20

<210> SEQ ID NO 727
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 727

Ser Tyr Pro Thr Pro Arg Pro Tyr Pro Lys Pro Ala Pro Ser Ser Gly
1               5                   10                  15
Lys Asp Tyr Val
            20

<210> SEQ ID NO 728
<211> LENGTH: 20

```
<212> TYPE: PRT
<213> ORGANISM: Artificial
<220> FEATURE:
<223> OTHER INFORMATION: PL sequence binding PSD95 d1

<400> SEQUENCE: 728

Thr Gly Ser Ala Leu Gln Ala Trp Arg His Thr Ser Arg Gln Ala Thr
1               5                   10                  15
Glu Ser Thr Val
            20

<210> SEQ ID NO 729
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 729

Thr Gln Gly Phe Pro Gly Pro Ala Thr Trp Arg Arg Ile Ser Ser Leu
1               5                   10                  15
Glu Ser Glu Val
            20

<210> SEQ ID NO 730
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 730

Thr Arg Glu Asp Ile Tyr Val Asn Tyr Pro Thr Phe Ser Arg Arg Pro
1               5                   10                  15
Lys Thr Arg Val
            20

<210> SEQ ID NO 731
<211> LENGTH: 19
<212> TYPE: PRT
<213> ORGANISM: Artificial
<220> FEATURE:
<223> OTHER INFORMATION: PL sequence binding PSD95 d1

<400> SEQUENCE: 731

Thr Thr Asn Asn Asn Pro Asn Ser Ala Val Asn Ile Lys Lys Ile Phe
1               5                   10                  15
Thr Asp Val

<210> SEQ ID NO 732
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 732

Val Asp Pro Asn Ser Pro Ala Ala Lys Lys Lys Tyr Val Ser Tyr Asn
1               5                   10                  15
Asn Leu Val Ile
            20

<210> SEQ ID NO 733
<211> LENGTH: 20
```

-continued

```
<212> TYPE: PRT
<213> ORGANISM: Artificial
<220> FEATURE:
<223> OTHER INFORMATION: PL sequence binding PSD95 d1

<400> SEQUENCE: 733

Val Gly Thr Leu Leu Leu Glu Arg Val Ile Phe Pro Ser Val Lys Ile
1               5                   10                  15

Ala Thr Leu Val
            20

<210> SEQ ID NO 734
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 734

Val His Lys Val Arg Asn Lys Phe Lys Ala Lys Cys Ser Leu Cys Arg
1               5                   10                  15

Leu Tyr Ile Ile
            20

<210> SEQ ID NO 735
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 735

Tyr Gly Arg Lys Lys Arg Arg Gln Arg Arg Ala Leu Lys Ser Ile
1               5                   10                  15

Glu Thr Glu Val
            20

<210> SEQ ID NO 736
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 736

Tyr Gly Arg Lys Lys Arg Arg Gln Arg Arg Ala Arg Gly Arg Arg
1               5                   10                  15

Glu Thr Trp Val
            20

<210> SEQ ID NO 737
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 737

Tyr Gly Arg Lys Lys Arg Arg Gln Arg Arg Glu Lys His Phe Arg
1               5                   10                  15

Glu Thr Glu Val
            20

<210> SEQ ID NO 738
```

```
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 738

Tyr Gly Arg Lys Lys Arg Arg Gln Arg Arg Gly Ala Ser Ala Asp
1               5                   10                  15

Ser Thr Gln Ala
            20

<210> SEQ ID NO 739
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 739

Tyr Gly Arg Lys Lys Arg Arg Gln Arg Arg Gly Met Thr Ser Ser
1               5                   10                  15

Ser Ser Val Val
            20

<210> SEQ ID NO 740
<211> LENGTH: 16
<212> TYPE: PRT
<213> ORGANISM: Artificial
<220> FEATURE:
<223> OTHER INFORMATION: PL sequence binding PSD95 d1

<400> SEQUENCE: 740

Tyr Gly Arg Lys Lys Arg Arg Gln Arg Arg Ile Glu Thr Glu Val
1               5                   10                  15

<210> SEQ ID NO 741
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 741

Tyr Gly Arg Lys Lys Arg Arg Gln Arg Arg Lys Leu Ser Ser Ile
1               5                   10                  15

Glu Ser Asp Val
            20

<210> SEQ ID NO 742
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 742

Tyr Gly Arg Lys Lys Arg Arg Gln Arg Arg Lys Leu Ser Ser Ile
1               5                   10                  15

Glu Ser Asp Val
            20

<210> SEQ ID NO 743
<211> LENGTH: 20
```

```
<212> TYPE: PRT
<213> ORGANISM: Artificial
<220> FEATURE:
<223> OTHER INFORMATION: PL sequence binding PSD95 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 743

Tyr Gly Arg Lys Lys Arg Arg Gln Arg Arg Lys Leu Ser Ser Ile
1               5                   10                  15

Glu Ser Asp Xaa
            20

<210> SEQ ID NO 744
<211> LENGTH: 20
<212> TYPE: PRT
<213> ORGANISM: Artificial
<220> FEATURE:
<223> OTHER INFORMATION: PL sequence binding PSD95 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 744

Tyr Gly Arg Lys Lys Arg Arg Gln Arg Arg Lys Leu Ser Ser Ile
1               5                   10                  15

Glu Ser Asp Xaa
            20

<210> SEQ ID NO 745
<211> LENGTH: 20
<212> TYPE: PRT
<213> ORGANISM: Artificial
<220> FEATURE:
<223> OTHER INFORMATION: PL sequence binding PSD95 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 745

Tyr Gly Arg Lys Lys Arg Arg Gln Arg Arg Lys Leu Ser Ser Ile
1               5                   10                  15

Glu Ser Asp Xaa
            20

<210> SEQ ID NO 746
<211> LENGTH: 20
<212> TYPE: PRT
<213> ORGANISM: Artificial
<220> FEATURE:
<223> OTHER INFORMATION: PL sequence binding PSD95 d1
<220> FEATURE:
<221> NAME/KEY: misc_feature
<222> LOCATION: (19)..(19)
<223> OTHER INFORMATION: Xaa can be any naturally occurring amino acid

<400> SEQUENCE: 746

Tyr Gly Arg Lys Lys Arg Arg Gln Arg Arg Lys Leu Ser Ser Ile
1               5                   10                  15

Glu Ser Xaa Val
            20

<210> SEQ ID NO 747
```

```
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 747

Tyr Gly Arg Lys Lys Arg Arg Gln Arg Arg Lys Leu Ser Ser Ile
1               5                   10                  15

Glu Ser Tyr Val
            20

<210> SEQ ID NO 748
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 748

Tyr Gly Arg Lys Lys Arg Arg Gln Arg Arg Lys Leu Ser Ser Ile
1               5                   10                  15

Glu Thr Asp Val
            20

<210> SEQ ID NO 749
<211> LENGTH: 20
<212> TYPE: PRT
<213> ORGANISM: Artificial
<220> FEATURE:
<223> OTHER INFORMATION: PL sequence binding PSD95 d1
<220> FEATURE:
<221> NAME/KEY: misc_feature
<222> LOCATION: (20)..(20)
<223> OTHER INFORMATION: Xaa can be any naturally occurring amino acid

<400> SEQUENCE: 749

Tyr Gly Arg Lys Lys Arg Arg Gln Arg Arg Lys Leu Ser Ser Ile
1               5                   10                  15

Glu Thr Asp Xaa
            20

<210> SEQ ID NO 750
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 750

Tyr Gly Arg Lys Lys Arg Arg Gln Arg Arg Lys Leu Ser Ser Ile
1               5                   10                  15

Glu Tyr Asp Val
            20

<210> SEQ ID NO 751
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 751

Tyr Gly Arg Lys Lys Arg Arg Gln Arg Arg Asn Asp Asn Ile Ala
1               5                   10                  15
```

-continued

Leu Leu Val Gln
            20

<210> SEQ ID NO 752
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 752

Tyr Gly Arg Lys Lys Arg Arg Gln Arg Arg Gln Asp Glu Arg Val
1               5                   10                  15

Glu Thr Arg Val
            20

<210> SEQ ID NO 753
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 753

Tyr Gly Arg Lys Lys Arg Arg Gln Arg Arg Gln Asp Ser Arg Glu
1               5                   10                  15

Glu Thr Gln Leu
            20

<210> SEQ ID NO 754
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 754

Tyr Gly Arg Lys Lys Arg Arg Gln Arg Arg Arg Ile Ser Ser Ile
1               5                   10                  15

Glu Thr Asp Val
            20

<210> SEQ ID NO 755
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 755

Tyr Gly Arg Lys Lys Arg Arg Gln Arg Arg Arg Ile Ser Ser Ile
1               5                   10                  15

Gln Thr Asp Val
            20

<210> SEQ ID NO 756
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 756

Tyr Gly Arg Lys Lys Arg Arg Gln Arg Arg Arg Ile Ser Ser Leu
1               5                   10                  15

Glu Ser Glu Val
        20

<210> SEQ ID NO 757
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 757

Tyr Gly Arg Lys Lys Arg Arg Gln Arg Arg Arg Ile Ser Ser Leu
1               5                   10                  15

Glu Thr Glu Val
        20

<210> SEQ ID NO 758
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 758

Tyr Gly Arg Lys Lys Arg Arg Gln Arg Arg Arg Ile Ser Ser Leu
1               5                   10                  15

Glu Thr Gln Val
        20

<210> SEQ ID NO 759
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 759

Tyr Gly Arg Lys Lys Arg Arg Gln Arg Arg Arg Ser Arg Arg
1               5                   10                  15

Glu Thr Ala Leu
        20

<210> SEQ ID NO 760
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 760

Tyr Gly Arg Lys Lys Arg Arg Gln Arg Arg Thr Lys Asn Tyr Lys
1               5                   10                  15

Gln Thr Ser Val
        20

<210> SEQ ID NO 761
<211> LENGTH: 20
<212> TYPE: PRT
<213> ORGANISM: Artificial
<220> FEATURE:
<223> OTHER INFORMATION: PL sequence binding PSD95 d1

<400> SEQUENCE: 761

Tyr Ser Ala Thr Tyr Ser Glu Leu Glu Asp Pro Gly Glu Met Ser Pro

-continued

```
1               5                  10                 15

Pro Ile Asp Leu
            20

<210> SEQ ID NO 762
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 762

Ala Ala Gly Gly Arg Ser Ala Arg Gly Gly Arg Leu Gln Gly Arg Arg
1               5                  10                 15

Glu Thr Ala Leu
            20

<210> SEQ ID NO 763
<211> LENGTH: 19
<212> TYPE: PRT
<213> ORGANISM: Artificial
<220> FEATURE:
<223> OTHER INFORMATION: PL sequence binding PSD95 d1, d2

<400> SEQUENCE: 763

Ala Arg His Arg Val Thr Ser Tyr Thr Ser Ser Ser Val Asn Val Ser
1               5                  10                 15

Ser Asn Leu

<210> SEQ ID NO 764
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 764

Ala Val Gly Gly Arg Pro Ala Arg Gly Gly Arg Leu Gln Gly Arg Arg
1               5                  10                 15

Gln Thr Gln Val
            20

<210> SEQ ID NO 765
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 765

Asp Phe Arg Pro Ser Phe Lys His Ile Leu Phe Arg Arg Ala Arg Arg
1               5                  10                 15

Gly Phe Arg Gln
            20

<210> SEQ ID NO 766
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 766

Glu Asp Pro Lys Asp Arg Pro Ser Ala Ala His Ile Val Glu Ala Leu
```

```
1               5                  10                 15

Glu Thr Asp Val
            20

<210> SEQ ID NO 767
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 767

Glu Leu Leu Gln Phe Cys Arg Thr Pro Asn Pro Ala Leu Lys Asn Gly
1               5                  10                 15

Gln Tyr Trp Val
            20

<210> SEQ ID NO 768
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 768

Glu Ser Ser Gly Thr Gln Ser Pro Lys Arg His Ser Gly Ser Tyr Leu
1               5                  10                 15

Val Thr Ser Val
            20

<210> SEQ ID NO 769
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 769

Phe Asn Gly Ser Ser Asn Gly His Val Tyr Glu Lys Leu Ser Ser Ile
1               5                  10                 15

Glu Ser Asp Val
            20

<210> SEQ ID NO 770
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 770

Gly Gly Asp Leu Gly Thr Arg Arg Gly Ser Ala His Phe Ser Ser Leu
1               5                  10                 15

Glu Ser Glu Val
            20

<210> SEQ ID NO 771
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 771
```

Gly Gly Glu Asp Phe Lys Thr Thr Asn Pro Ser Lys Gln Phe Asp Lys
1               5                   10                  15

Asn Ala Tyr Val
            20

<210> SEQ ID NO 772
<211> LENGTH: 19
<212> TYPE: PRT
<213> ORGANISM: Artificial
<220> FEATURE:
<223> OTHER INFORMATION: PL sequence binding PSD95 d1, d2

<400> SEQUENCE: 772

Gly Gly Gly Gly Gly Ser Gly Gly Gly Gly Ser Gly Ile Glu Ser
1               5                   10                  15

Val Lys Ile

<210> SEQ ID NO 773
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 773

Gly Arg Trp Ala Gly Arg Ser Ala Ala Ser Trp Arg Ser Arg Arg
1               5                   10                  15

Glu Thr Ala Leu
            20

<210> SEQ ID NO 774
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 774

Gly Arg Trp Thr Gly Arg Ala Met Ser Ala Trp Lys Pro Thr Arg Arg
1               5                   10                  15

Glu Thr Glu Val
            20

<210> SEQ ID NO 775
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 775

Gly Arg Trp Thr Gly Arg Ser Ala Val Ser Trp Arg Pro Arg Arg
1               5                   10                  15

Gln Thr Gln Val
            20

<210> SEQ ID NO 776
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 776

```
His His Leu Val Ala Gln Arg Asp Ile Arg Gln Phe Gln Leu Gln His
1               5                   10                  15

Trp Leu Ala Ile
            20

<210> SEQ ID NO 777
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 777

His Pro Thr Asp Ile Thr Gly Leu Pro Asn Leu Ser Asp Pro Ser Val
1               5                   10                  15

Ser Thr Val Val
            20

<210> SEQ ID NO 778
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 778

His Ser Cys Cys Asn Arg Ala Arg Gln Glu Arg Leu Gln Arg Arg Arg
1               5                   10                  15

Glu Thr Gln Val
            20

<210> SEQ ID NO 779
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 779

Ile Leu Asn Ser Ile Gln Val Met Arg Ala Gln Met Asn Gln Ile Gln
1               5                   10                  15

Ser Val Glu Val
            20

<210> SEQ ID NO 780
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 780

Ile Ser Gly Thr Pro Thr Ser Thr Met Val His Gly Met Thr Ser Ser
1               5                   10                  15

Ser Ser Val Val
            20

<210> SEQ ID NO 781
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 781
```

-continued

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 782
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 782

Lys Asp Ile Thr Ser Asp Ser Glu Asn Ser Asn Phe Arg Asn Glu Ile
1               5                   10                  15

Gln Ser Leu Val
            20

<210> SEQ ID NO 783
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 783

Lys Asp Ile Thr Ser Asp Ser Glu Asn Ser Asn Phe Arg Asn Glu Ile
1               5                   10                  15

Gln Ser Leu Val
            20

<210> SEQ ID NO 784
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 784

Lys His Ser Arg Lys Ser Ser Ser Tyr Ser Ser Ser Ser Thr Thr Val
1               5                   10                  15

Lys Thr Ser Tyr
            20

<210> SEQ ID NO 785
<211> LENGTH: 23
<212> TYPE: PRT
<213> ORGANISM: Artificial
<220> FEATURE:
<223> OTHER INFORMATION: PL sequence binding PSD95 d1, d2

<400> SEQUENCE: 785

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 786
<211> LENGTH: 20
<212> TYPE: PRT
<213> ORGANISM: Artificial
<220> FEATURE:
<223> OTHER INFORMATION: PL sequence binding PSD95 d1, d2

-continued

```
<400> SEQUENCE: 786

Leu Ala Val Leu Ala Tyr Ser Ile Thr Leu Val Met Leu Trp Ser Ile
1               5                   10                  15

Trp Gln Tyr Ala
            20

<210> SEQ ID NO 787
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 787

Leu His Asn Gln Ala Ser Val Pro Leu Glu Pro Arg Pro Leu Arg Arg
1               5                   10                  15

Glu Ser Glu Ile
            20

<210> SEQ ID NO 788
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 788

Leu Asn Ser Cys Ser Asn Arg Arg Val Tyr Lys Lys Met Pro Ser Ile
1               5                   10                  15

Glu Ser Asp Val
            20

<210> SEQ ID NO 789
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 789

Leu Asn Ser Ser Ser Asn Arg Arg Val Tyr Lys Lys Met Pro Ser Ile
1               5                   10                  15

Glu Ser Asp Val
            20

<210> SEQ ID NO 790
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 790

Met Gly Arg Trp Thr Gly Arg Ser Ser Glu Ser Trp Arg Pro Arg Pro
1               5                   10                  15

Val Thr Gln Val
            20

<210> SEQ ID NO 791
<211> LENGTH: 20
<212> TYPE: PRT
<213> ORGANISM: Artificial
<220> FEATURE:
<223> OTHER INFORMATION: PL sequence binding PSD95 d1, d2
```

```
<400> SEQUENCE: 791

Asn Thr Ser Ser Asp Gln Ala Arg Gln Glu Arg Leu Arg Arg Arg Arg
1               5                   10                  15

Glu Thr Gln Val
            20

<210> SEQ ID NO 792
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 792

Pro Ile Pro Ala Gly Gly Cys Thr Phe Ser Gly Ile Phe Pro Thr Leu
1               5                   10                  15

Thr Ser Pro Leu
            20

<210> SEQ ID NO 793
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 793

Pro Tyr Ser Glu Leu Asn Tyr Glu Thr Ser His Tyr Pro Ala Ser Pro
1               5                   10                  15

Asp Ser Trp Val
            20

<210> SEQ ID NO 794
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 794

Gln Asp Phe Arg Arg Ala Phe Arg Arg Ile Leu Ala Arg Pro Trp Thr
1               5                   10                  15

Gln Thr Ala Trp
            20

<210> SEQ ID NO 795
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 795

Gln Ile Ser Pro Gly Gly Leu Glu Pro Pro Ser Glu Lys His Phe Arg
1               5                   10                  15

Glu Thr Glu Val
            20

<210> SEQ ID NO 796
<211> LENGTH: 20
<212> TYPE: PRT
<213> ORGANISM: Artificial
<220> FEATURE:
```

-continued

<223> OTHER INFORMATION: PL sequence binding PSD95 d1, d2

<400> SEQUENCE: 796

Arg Glu Leu Val Asp Arg Gly Glu Val Arg Gln Phe Thr Leu Arg His
1               5                   10                  15

Trp Leu Lys Val
            20

<210> SEQ ID NO 797
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 797

Arg Asn Ile Glu Glu Val Tyr Val Gly Gly Lys Gln Val Val Pro Phe
1               5                   10                  15

Ser Ser Ser Val
            20

<210> SEQ ID NO 798
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 798

Arg Ser Gly Ala Thr Ile Pro Leu Val Gly Gln Asp Ile Ile Asp Leu
1               5                   10                  15

Gln Thr Glu Val
            20

<210> SEQ ID NO 799
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 799

Ser Phe Thr Ser Ile Leu Thr Cys His Gln Arg Arg Thr Gln Arg Lys
1               5                   10                  15

Glu Thr Val Ala
            20

<210> SEQ ID NO 800
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 800

Ser Leu Ile Gly Pro Val Gln Lys Glu Tyr Gln Arg Glu Leu Gly Lys
1               5                   10                  15

Leu Ser Ser Pro
            20

<210> SEQ ID NO 801
<211> LENGTH: 20
<212> TYPE: PRT
<213> ORGANISM: Artificial

```
<220> FEATURE:
<223> OTHER INFORMATION: PL sequence binding PSD95 d1, d2

<400> SEQUENCE: 801

Ser Leu Lys Pro Gly Thr Val Leu Pro Pro Pro Tyr Arg His Arg
1               5                   10                  15

Asn Thr Val Val
            20

<210> SEQ ID NO 802
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 802

Ser Leu Lys Pro Gly Thr Val Leu Pro Pro Pro Tyr Arg His Arg
1               5                   10                  15

Asn Thr Val Val
            20

<210> SEQ ID NO 803
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 803

Ser Tyr Pro Thr Pro Arg Pro Tyr Pro Lys Pro Ala Pro Ser Ser Gly
1               5                   10                  15

Lys Asp Tyr Val
            20

<210> SEQ ID NO 804
<211> LENGTH: 18
<212> TYPE: PRT
<213> ORGANISM: Artificial
<220> FEATURE:
<223> OTHER INFORMATION: PL sequence binding PSD95 d1, d2

<400> SEQUENCE: 804

Thr Phe Ala Ala Gly Phe Asn Ser Thr Gly Leu Pro His Ser Thr Thr
1               5                   10                  15

Arg Val

<210> SEQ ID NO 805
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 805

Thr Phe Lys Gly Thr Pro Thr Ala Glu Asn Pro Glu Tyr Leu Gly Leu
1               5                   10                  15

Asp Val Pro Val
            20

<210> SEQ ID NO 806
<211> LENGTH: 19
<212> TYPE: PRT
<213> ORGANISM: Artificial
```

-continued

```
<220> FEATURE:
<223> OTHER INFORMATION: PL sequence binding PSD95 d1, d2

<400> SEQUENCE: 806

Thr Gly Arg Gly Met Ser Gly Gly Arg Ser Ser Arg Thr Arg Glu
1               5                   10                  15

Thr Gln Leu

<210> SEQ ID NO 807
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 807

Thr Gly Ser Ala Leu Gln Ala Trp Arg His Thr Ser Arg Gln Ala Thr
1               5                   10                  15

Glu Ser Thr Val
            20

<210> SEQ ID NO 808
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 808

Thr Gln Gly Phe Pro Gly Pro Ala Thr Trp Arg Arg Ile Ser Ser Leu
1               5                   10                  15

Glu Ser Glu Val
            20

<210> SEQ ID NO 809
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 809

Thr Arg Glu Asp Ile Tyr Val Asn Tyr Pro Thr Phe Ser Arg Arg Pro
1               5                   10                  15

Lys Thr Arg Val
            20

<210> SEQ ID NO 810
<211> LENGTH: 19
<212> TYPE: PRT
<213> ORGANISM: Artificial
<220> FEATURE:
<223> OTHER INFORMATION: PL sequence binding PSD95 d1, d2

<400> SEQUENCE: 810

Thr Thr Asn Asn Asn Pro Asn Ser Ala Val Asn Ile Lys Lys Ile Phe
1               5                   10                  15

Thr Asp Val

<210> SEQ ID NO 811
<211> LENGTH: 20
<212> TYPE: PRT
<213> ORGANISM: Artificial
<220> FEATURE:
```

-continued

```
<223> OTHER INFORMATION: PL sequence binding PSD95 d1, d2

<400> SEQUENCE: 811

Val Asp Pro Asn Ser Pro Ala Ala Lys Lys Tyr Val Ser Tyr Asn
1               5                   10                  15

Asn Leu Val Ile
            20

<210> SEQ ID NO 812
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 812

Val Gly Thr Leu Leu Leu Glu Arg Val Ile Phe Pro Ser Val Lys Ile
1               5                   10                  15

Ala Thr Leu Val
            20

<210> SEQ ID NO 813
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 813

Val His Lys Val Arg Asn Lys Phe Lys Ala Lys Cys Ser Leu Cys Arg
1               5                   10                  15

Leu Tyr Ile Ile
            20

<210> SEQ ID NO 814
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 814

Trp Thr Gly Gln Ser Ala Asn Ser Arg Lys Pro Pro Arg Gln Arg Ser
1               5                   10                  15

Glu Thr Gln Val
            20

<210> SEQ ID NO 815
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 815

Tyr Gly Arg Lys Lys Arg Arg Gln Arg Arg Gly Ala Ser Ala Asp
1               5                   10                  15

Ser Thr Gln Ala
            20

<210> SEQ ID NO 816
<211> LENGTH: 20
<212> TYPE: PRT
<213> ORGANISM: Artificial
```

-continued

```
<220> FEATURE:
<223> OTHER INFORMATION: PL sequence binding PSD95 d1, d2

<400> SEQUENCE: 816

Tyr Gly Arg Lys Lys Arg Arg Gln Arg Arg Lys Leu Ser Ser Ile
1               5                   10                  15

Glu Ser Asp Val
            20

<210> SEQ ID NO 817
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 817

Tyr Gly Arg Lys Lys Arg Arg Gln Arg Arg Met Ala Gly Thr Ile
1               5                   10                  15

Arg Ser Glu Val
            20

<210> SEQ ID NO 818
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 818

Tyr Gly Arg Lys Lys Arg Arg Gln Arg Arg Met Ala Arg Thr Ile
1               5                   10                  15

Glu Ser Glu Ile
            20

<210> SEQ ID NO 819
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 819

Tyr Gly Arg Lys Lys Arg Arg Gln Arg Arg Met Ala Arg Thr Ile
1               5                   10                  15

Glu Ser Glu Val
            20

<210> SEQ ID NO 820
<211> LENGTH: 20
<212> TYPE: PRT
<213> ORGANISM: Artificial
<220> FEATURE:
<223> OTHER INFORMATION: PL sequence binding PSD95 d1, d2

<400> SEQUENCE: 820

Tyr Gly Arg Lys Lys Arg Arg Gln Arg Arg Met Glu Arg Thr Ile
1               5                   10                  15

Glu Pro Glu Val
            20

<210> SEQ ID NO 821
<211> LENGTH: 20
<212> TYPE: PRT
```

-continued

```
<213> ORGANISM: Artificial
<220> FEATURE:
<223> OTHER INFORMATION: PL sequence binding PSD95 d1, d2

<400> SEQUENCE: 821

Tyr Gly Arg Lys Lys Arg Arg Gln Arg Arg Asn Asp Asn Ile Ala
1               5                   10                  15

Leu Leu Val Gln
            20

<210> SEQ ID NO 822
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 822

Ala Ala Gly Gly Arg Ser Ala Arg Gly Gly Arg Leu Gln Gly Arg Arg
1               5                   10                  15

Glu Thr Ala Leu
            20

<210> SEQ ID NO 823
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 823

Ala Val Gly Gly Arg Pro Ala Arg Gly Gly Arg Leu Gln Gly Arg Arg
1               5                   10                  15

Gln Thr Gln Val
            20

<210> SEQ ID NO 824
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 824

Phe Asn Gly Ser Ser Asn Gly His Val Tyr Glu Lys Leu Ser Ser Ile
1               5                   10                  15

Glu Ser Asp Val
            20

<210> SEQ ID NO 825
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 825

Gly Gly Asp Leu Gly Thr Arg Arg Gly Ser Ala His Phe Ser Ser Leu
1               5                   10                  15

Glu Ser Glu Val
            20

<210> SEQ ID NO 826
<211> LENGTH: 20
```

```
<212> TYPE: PRT
<213> ORGANISM: Artificial
<220> FEATURE:
<223> OTHER INFORMATION: PL sequence binding PSD95 d2

<400> SEQUENCE: 826

Gly Arg Trp Ala Gly Arg Ser Ala Ala Ser Trp Arg Ser Arg Arg
1               5                   10                  15
Glu Thr Ala Leu
            20

<210> SEQ ID NO 827
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 827

Gly Arg Trp Thr Gly Arg Ala Met Ser Ala Trp Lys Pro Thr Arg Arg
1               5                   10                  15
Glu Thr Glu Val
            20

<210> SEQ ID NO 828
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 828

Gly Arg Trp Thr Gly Arg Ser Ala Val Ser Trp Arg Pro Arg Arg
1               5                   10                  15
Gln Thr Gln Val
            20

<210> SEQ ID NO 829
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 829

Lys Asp Ile Thr Ser Asp Ser Glu Asn Ser Asn Phe Arg Asn Glu Ile
1               5                   10                  15
Gln Ser Leu Val
            20

<210> SEQ ID NO 830
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 830

Lys His Ser Arg Lys Ser Ser Tyr Ser Ser Ser Thr Thr Val
1               5                   10                  15
Lys Thr Ser Tyr
            20

<210> SEQ ID NO 831
```

```
<211> LENGTH: 23
<212> TYPE: PRT
<213> ORGANISM: Artificial
<220> FEATURE:
<223> OTHER INFORMATION: PL sequence binding PSD95 d2

<400> SEQUENCE: 831

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 832
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 832

Leu Asn Ser Cys Ser Asn Arg Arg Val Tyr Lys Lys Met Pro Ser Ile
1               5                   10                  15

Glu Ser Asp Val
            20

<210> SEQ ID NO 833
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 833

Leu Asn Ser Ser Ser Asn Arg Arg Val Tyr Lys Lys Met Pro Ser Ile
1               5                   10                  15

Glu Ser Asp Val
            20

<210> SEQ ID NO 834
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 834

Asn Thr Ser Ser Asp Gln Ala Arg Gln Glu Arg Leu Arg Arg Arg
1               5                   10                  15

Glu Thr Gln Val
            20

<210> SEQ ID NO 835
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 835

Gln Ile Ser Pro Gly Gly Leu Glu Pro Pro Ser Glu Lys His Phe Arg
1               5                   10                  15

Glu Thr Glu Val
            20
```

```
<210> SEQ ID NO 836
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 836

Arg Glu Leu Val Asp Arg Gly Glu Val Arg Gln Phe Thr Leu Arg His
1               5                   10                  15

Trp Leu Lys Val
            20

<210> SEQ ID NO 837
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 837

Arg Ser Gly Ala Thr Ile Pro Leu Val Gly Gln Asp Ile Ile Asp Leu
1               5                   10                  15

Gln Thr Glu Val
            20

<210> SEQ ID NO 838
<211> LENGTH: 18
<212> TYPE: PRT
<213> ORGANISM: Artificial
<220> FEATURE:
<223> OTHER INFORMATION: PL sequence binding PSD95  d2

<400> SEQUENCE: 838

Ser Pro Gln Pro Asp Ser Thr Asp Asn Asp Asp Tyr Asp Asp Ile Ser
1               5                   10                  15

Ala Ala

<210> SEQ ID NO 839
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 839

Ser Ser Ser Arg Arg Asp Ser Ser Trp Ser Glu Thr Ser Glu Ala Ser
1               5                   10                  15

Tyr Ser Gly Leu
            20

<210> SEQ ID NO 840
<211> LENGTH: 19
<212> TYPE: PRT
<213> ORGANISM: Artificial
<220> FEATURE:
<223> OTHER INFORMATION: PL sequence binding PSD95  d2

<400> SEQUENCE: 840

Thr Gly Arg Gly Met Ser Gly Gly Arg Ser Ser Arg Thr Arg Arg Glu
1               5                   10                  15

Thr Gln Leu

<210> SEQ ID NO 841
```

```
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 841

Thr Gln Gly Phe Pro Gly Pro Ala Thr Trp Arg Arg Ile Ser Ser Leu
1               5                   10                  15

Glu Ser Glu Val
            20

<210> SEQ ID NO 842
<211> LENGTH: 19
<212> TYPE: PRT
<213> ORGANISM: Artificial
<220> FEATURE:
<223> OTHER INFORMATION: PL sequence binding PSD95 d2

<400> SEQUENCE: 842

Thr Thr Asn Asn Pro Asn Ser Ala Val Asn Ile Lys Lys Ile Phe
1               5                   10                  15

Thr Asp Val

<210> SEQ ID NO 843
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 843

Val His Lys Val Arg Asn Lys Phe Lys Ala Lys Cys Ser Leu Cys Arg
1               5                   10                  15

Leu Tyr Ile Ile
            20

<210> SEQ ID NO 844
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 844

Tyr Gly Arg Lys Lys Arg Arg Gln Arg Arg Ala Leu Lys Ser Ile
1               5                   10                  15

Glu Thr Glu Val
            20

<210> SEQ ID NO 845
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 845

Tyr Gly Arg Lys Lys Arg Arg Gln Arg Arg Ala Arg Gly Arg Arg
1               5                   10                  15

Glu Thr Trp Val
            20

<210> SEQ ID NO 846
```

-continued

```
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 846

Tyr Gly Arg Lys Lys Arg Arg Gln Arg Arg Asp Lys Glu Leu Glu
1               5                   10                  15

Val Leu Ser Leu
            20

<210> SEQ ID NO 847
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 847

Tyr Gly Arg Lys Lys Arg Arg Gln Arg Arg Glu Lys His Phe Arg
1               5                   10                  15

Glu Ala Glu Ala
            20

<210> SEQ ID NO 848
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 848

Tyr Gly Arg Lys Lys Arg Arg Gln Arg Arg Glu Lys His Phe Arg
1               5                   10                  15

Glu Thr Glu Val
            20

<210> SEQ ID NO 849
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 849

Tyr Gly Arg Lys Lys Arg Arg Gln Arg Arg Glu Tyr Leu Gly Leu
1               5                   10                  15

Asp Val Pro Val
            20

<210> SEQ ID NO 850
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 850

Tyr Gly Arg Lys Lys Arg Arg Gln Arg Arg Gly Met Thr Ser Ser
1               5                   10                  15

Ser Ser Val Val
            20
```

```
<210> SEQ ID NO 851
<211> LENGTH: 16
<212> TYPE: PRT
<213> ORGANISM: Artificial
<220> FEATURE:
<223> OTHER INFORMATION: PL sequence binding PSD95  d2

<400> SEQUENCE: 851

Tyr Gly Arg Lys Lys Arg Arg Gln Arg Arg Ile Glu Thr Glu Val
1               5                   10                  15

<210> SEQ ID NO 852
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 852

Tyr Gly Arg Lys Lys Arg Arg Gln Arg Arg Lys Leu Ser Ser Ile
1               5                   10                  15

Glu Ser Asp Leu
            20

<210> SEQ ID NO 853
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 853

Tyr Gly Arg Lys Lys Arg Arg Gln Arg Arg Lys Leu Ser Ser Ile
1               5                   10                  15

Glu Ser Asp Val
            20

<210> SEQ ID NO 854
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 854

Tyr Gly Arg Lys Lys Arg Arg Gln Arg Arg Lys Leu Ser Ser Ile
1               5                   10                  15

Glu Ser Asp Val
            20

<210> SEQ ID NO 855
<211> LENGTH: 20
<212> TYPE: PRT
<213> ORGANISM: Artificial
<220> FEATURE:
<223> OTHER INFORMATION: PL sequence binding PSD95  d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 855

Tyr Gly Arg Lys Lys Arg Arg Gln Arg Arg Lys Leu Ser Ser Ile
1               5                   10                  15

Glu Ser Asp Xaa
```

```
<210> SEQ ID NO 856
<211> LENGTH: 20
<212> TYPE: PRT
<213> ORGANISM: Artificial
<220> FEATURE:
<223> OTHER INFORMATION: PL sequence binding PSD95  d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 856

Tyr Gly Arg Lys Lys Arg Arg Gln Arg Arg Arg Lys Leu Ser Ser Ile
1               5                  10                  15

Glu Ser Asp Xaa
            20

<210> SEQ ID NO 857
<211> LENGTH: 20
<212> TYPE: PRT
<213> ORGANISM: Artificial
<220> FEATURE:
<223> OTHER INFORMATION: PL sequence binding PSD95  d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 857

Tyr Gly Arg Lys Lys Arg Arg Gln Arg Arg Arg Lys Leu Ser Ser Ile
1               5                  10                  15

Glu Ser Asp Xaa
            20

<210> SEQ ID NO 858
<211> LENGTH: 20
<212> TYPE: PRT
<213> ORGANISM: Artificial
<220> FEATURE:
<223> OTHER INFORMATION: PL sequence binding PSD95  d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 858

Tyr Gly Arg Lys Lys Arg Arg Gln Arg Arg Arg Lys Leu Ser Ser Ile
1               5                  10                  15

Glu Ser Asp Xaa
            20

<210> SEQ ID NO 859
<211> LENGTH: 20
<212> TYPE: PRT
<213> ORGANISM: Artificial
<220> FEATURE:
<223> OTHER INFORMATION: PL sequence binding PSD95  d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 859

Tyr Gly Arg Lys Lys Arg Arg Gln Arg Arg Arg Lys Leu Ser Ser Ile
1               5                  10                  15
```

Glu Ser Asp Xaa
            20

<210> SEQ ID NO 860
<211> LENGTH: 20
<212> TYPE: PRT
<213> ORGANISM: Artificial
<220> FEATURE:
<223> OTHER INFORMATION: PL sequence binding PSD95 d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 860

Tyr Gly Arg Lys Lys Arg Arg Gln Arg Arg Lys Leu Ser Ser Ile
1               5                   10                  15

Glu Ser Asp Xaa
            20

<210> SEQ ID NO 861
<211> LENGTH: 20
<212> TYPE: PRT
<213> ORGANISM: Artificial
<220> FEATURE:
<223> OTHER INFORMATION: PL sequence binding PSD95 d2
<220> FEATURE:
<221> NAME/KEY: misc_feature
<222> LOCATION: (19)..(19)
<223> OTHER INFORMATION: Xaa can be any naturally occurring amino acid

<400> SEQUENCE: 861

Tyr Gly Arg Lys Lys Arg Arg Gln Arg Arg Lys Leu Ser Ser Ile
1               5                   10                  15

Glu Ser Xaa Val
            20

<210> SEQ ID NO 862
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 862

Tyr Gly Arg Lys Lys Arg Arg Gln Arg Arg Lys Leu Ser Ser Ile
1               5                   10                  15

Glu Ser Tyr Val
            20

<210> SEQ ID NO 863
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 863

Tyr Gly Arg Lys Lys Arg Arg Gln Arg Arg Lys Leu Ser Ser Ile
1               5                   10                  15

Glu Thr Asp Val
            20

<210> SEQ ID NO 864
<211> LENGTH: 20
<212> TYPE: PRT

<213> ORGANISM: Artificial
<220> FEATURE:
<223> OTHER INFORMATION: PL sequence binding PSD95 d2
<220> FEATURE:
<221> NAME/KEY: misc_feature
<222> LOCATION: (20)..(20)
<223> OTHER INFORMATION: Xaa can be any naturally occurring amino acid

<400> SEQUENCE: 864

Tyr Gly Arg Lys Lys Arg Arg Gln Arg Arg Lys Leu Ser Ser Ile
1               5                   10                  15

Glu Thr Asp Xaa
            20

<210> SEQ ID NO 865
<211> LENGTH: 20
<212> TYPE: PRT
<213> ORGANISM: Artificial
<220> FEATURE:
<223> OTHER INFORMATION: PL sequence binding PSD95 d2
<220> FEATURE:
<221> NAME/KEY: misc_feature
<222> LOCATION: (18)..(18)
<223> OTHER INFORMATION: Xaa can be any naturally occurring amino acid

<400> SEQUENCE: 865

Tyr Gly Arg Lys Lys Arg Arg Gln Arg Arg Lys Leu Ser Ser Ile
1               5                   10                  15

Glu Xaa Asp Val
            20

<210> SEQ ID NO 866
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 866

Tyr Gly Arg Lys Lys Arg Arg Gln Arg Arg Lys Leu Ser Ser Ile
1               5                   10                  15

Glu Tyr Asp Val
            20

<210> SEQ ID NO 867
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 867

Tyr Gly Arg Lys Lys Arg Arg Gln Arg Arg Met Ala Arg Thr Ile
1               5                   10                  15

Glu Ser Glu Ile
            20

<210> SEQ ID NO 868
<211> LENGTH: 20
<212> TYPE: PRT
<213> ORGANISM: Artificial
<220> FEATURE:
<223> OTHER INFORMATION: PL sequence binding PSD95 d2

<400> SEQUENCE: 868

Tyr Gly Arg Lys Lys Arg Arg Gln Arg Arg Met Ala Arg Thr Ile

-continued

```
1               5                   10                  15

Glu Ser Glu Val
            20

<210> SEQ ID NO 869
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 869

Tyr Gly Arg Lys Lys Arg Arg Gln Arg Arg Met Glu Arg Thr Ile
1               5                   10                  15

Glu Pro Glu Val
            20

<210> SEQ ID NO 870
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 870

Tyr Gly Arg Lys Lys Arg Arg Gln Arg Arg Asn Asp Asn Ile Ala
1               5                   10                  15

Leu Leu Val Gln
            20

<210> SEQ ID NO 871
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 871

Tyr Gly Arg Lys Lys Arg Arg Gln Arg Arg Gln Asp Glu Arg Val
1               5                   10                  15

Glu Thr Arg Val
            20

<210> SEQ ID NO 872
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 872

Tyr Gly Arg Lys Lys Arg Arg Gln Arg Arg Gln Asp Ser Arg Glu
1               5                   10                  15

Glu Thr Gln Leu
            20

<210> SEQ ID NO 873
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 873
```

-continued

Tyr Gly Arg Lys Lys Arg Arg Gln Arg Arg Arg Ile Ser Ser Ile
1               5                   10                  15

Glu Thr Asp Val
            20

<210> SEQ ID NO 874
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 874

Tyr Gly Arg Lys Lys Arg Arg Gln Arg Arg Arg Ile Ser Ser Ile
1               5                   10                  15

Gln Thr Asp Val
            20

<210> SEQ ID NO 875
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 875

Tyr Gly Arg Lys Lys Arg Arg Gln Arg Arg Arg Ile Ser Ser Leu
1               5                   10                  15

Glu Ser Glu Val
            20

<210> SEQ ID NO 876
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 876

Tyr Gly Arg Lys Lys Arg Arg Gln Arg Arg Arg Ile Ser Ser Leu
1               5                   10                  15

Glu Thr Glu Val
            20

<210> SEQ ID NO 877
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 877

Tyr Gly Arg Lys Lys Arg Arg Gln Arg Arg Arg Ile Ser Ser Leu
1               5                   10                  15

Glu Thr Gln Val
            20

<210> SEQ ID NO 878
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 878

```
Tyr Gly Arg Lys Lys Arg Arg Gln Arg Arg Ser Arg Arg
1               5                   10                  15

Glu Thr Ala Leu
            20

<210> SEQ ID NO 879
<211> LENGTH: 20
<212> TYPE: PRT
<213> ORGANISM: Artificial
<220> FEATURE:
<223> OTHER INFORMATION: PL sequence binding PSD95  d2

<400> SEQUENCE: 879

Tyr Gly Arg Lys Lys Arg Arg Gln Arg Arg Thr Lys Asn Tyr Lys
1               5                   10                  15

Gln Thr Ser Val
            20

<210> SEQ ID NO 880
<211> LENGTH: 23
<212> TYPE: PRT
<213> ORGANISM: Artificial
<220> FEATURE:
<223> OTHER INFORMATION: PL sequence binding PTN-3

<400> SEQUENCE: 880

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 881
<211> LENGTH: 20
<212> TYPE: PRT
<213> ORGANISM: Artificial
<220> FEATURE:
<223> OTHER INFORMATION: PL sequence binding PTN-3

<400> SEQUENCE: 881

Leu Met Asp Gly Leu Pro Pro Gly Asp Ser Asn Gln Leu Ala Trp Phe
1               5                   10                  15

Asp Thr Asp Leu
            20

<210> SEQ ID NO 882
<211> LENGTH: 20
<212> TYPE: PRT
<213> ORGANISM: Artificial
<220> FEATURE:
<223> OTHER INFORMATION: PL sequence binding PTN-3

<400> SEQUENCE: 882

Tyr Gly Arg Lys Lys Arg Arg Gln Arg Arg Ala Val Ala Ala Thr
1               5                   10                  15

Ser Ala Asn Leu
            20

<210> SEQ ID NO 883
<211> LENGTH: 20
<212> TYPE: PRT
<213> ORGANISM: Artificial
<220> FEATURE:
<223> OTHER INFORMATION: PL sequence binding PTN-3
```

-continued

```
<400> SEQUENCE: 883

Tyr Gly Arg Lys Lys Arg Arg Gln Arg Arg Glu Tyr Leu Gly Leu
1               5                   10                  15

Asp Val Pro Val
            20

<210> SEQ ID NO 884
<211> LENGTH: 20
<212> TYPE: PRT
<213> ORGANISM: Artificial
<220> FEATURE:
<223> OTHER INFORMATION: PL sequence binding PTN-3

<400> SEQUENCE: 884

Tyr Gly Arg Lys Lys Arg Arg Gln Arg Arg Gly Ala Ser Ala Asp
1               5                   10                  15

Ser Thr Gln Ala
            20

<210> SEQ ID NO 885
<211> LENGTH: 20
<212> TYPE: PRT
<213> ORGANISM: Artificial
<220> FEATURE:
<223> OTHER INFORMATION: PL sequence binding PTN-3

<400> SEQUENCE: 885

Tyr Gly Arg Lys Lys Arg Arg Gln Arg Arg Asn Asp Asn Ile Ala
1               5                   10                  15

Leu Leu Val Gln
            20

<210> SEQ ID NO 886
<211> LENGTH: 20
<212> TYPE: PRT
<213> ORGANISM: Artificial
<220> FEATURE:
<223> OTHER INFORMATION: PL sequence binding PTN-3

<400> SEQUENCE: 886

Tyr Gly Arg Lys Lys Arg Arg Gln Arg Arg Ser Glu Gly Val Pro
1               5                   10                  15

Asp Leu Leu Val
            20

<210> SEQ ID NO 887
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 887

Ala Ala Gly Gly Arg Ser Ala Arg Gly Gly Arg Leu Gln Gly Arg
1               5                   10                  15

Glu Thr Ala Leu
            20

<210> SEQ ID NO 888
<211> LENGTH: 20
<212> TYPE: PRT
<213> ORGANISM: Artificial
<220> FEATURE:
<223> OTHER INFORMATION: PL sequence binding SHANK 1
```

```
<400> SEQUENCE: 888

Ala Leu Val Leu Ile Ala Phe Cys Ile Ile Arg Arg Arg Pro Ser Ala
1               5                   10                  15

Tyr Gln Ala Leu
            20

<210> SEQ ID NO 889
<211> LENGTH: 19
<212> TYPE: PRT
<213> ORGANISM: Artificial
<220> FEATURE:
<223> OTHER INFORMATION: PL sequence binding SHANK 1

<400> SEQUENCE: 889

Ala Trp Asp Asp Ser Ala Arg Ala Ala Gly Gly Gln Gly Leu His Val
1               5                   10                  15

Thr Ala Leu

<210> SEQ ID NO 890
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 890

Asp Ala Lys Leu Lys Ser Asp Gly Thr Ile Ala Ala Ile Thr Glu Lys
1               5                   10                  15

Glu Thr His Phe
            20

<210> SEQ ID NO 891
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 891

Asp Phe Arg Pro Ser Phe Lys His Ile Leu Phe Arg Arg Ala Arg Arg
1               5                   10                  15

Gly Phe Arg Gln
            20

<210> SEQ ID NO 892
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 892

Asp Gly Gly Ala Arg Thr Glu Asp Glu Val Gln Ser Tyr Pro Ser Lys
1               5                   10                  15

His Asp Tyr Val
            20

<210> SEQ ID NO 893
<211> LENGTH: 20
<212> TYPE: PRT
<213> ORGANISM: Artificial
<220> FEATURE:
<223> OTHER INFORMATION: PL sequence binding SHANK 1
```

-continued

```
<400> SEQUENCE: 893

Asp Ser Asp Pro Glu Asn Glu Pro Phe Asp Glu Asp Gln His Thr Gln
1               5                   10                  15

Ile Thr Lys Val
            20

<210> SEQ ID NO 894
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 894

Glu Ala Leu Gln Pro Glu Pro Gly Arg Lys Arg Ile Pro Leu Thr Arg
1               5                   10                  15

Thr Thr Thr Phe
            20

<210> SEQ ID NO 895
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 895

Glu Leu Leu Gln Phe Cys Arg Thr Pro Asn Pro Ala Leu Lys Asn Gly
1               5                   10                  15

Gln Tyr Trp Val
            20

<210> SEQ ID NO 896
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 896

Gly Gly Glu Asp Phe Lys Thr Thr Asn Pro Ser Lys Gln Phe Asp Lys
1               5                   10                  15

Asn Ala Tyr Val
            20

<210> SEQ ID NO 897
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 897

Gly Gly Gly Gly Gly Ser Gly Gly Gly Ser Gly Gly Gly His Ser
1               5                   10                  15

Thr Thr Arg Val
            20

<210> SEQ ID NO 898
<211> LENGTH: 20
<212> TYPE: PRT
<213> ORGANISM: Artificial
<220> FEATURE:
```

-continued

<223> OTHER INFORMATION: PL sequence binding SHANK 1

<400> SEQUENCE: 898

Gly Gly Gly Gly Gly Ser Gly Gly Gly Ser Gly Leu Pro His Ser
1               5                   10                  15

Thr Thr Arg Val
            20

<210> SEQ ID NO 899
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 899

Gly Gly Gly Gly Gly Ser Gly Gly Gly Ser Gly Ser Arg Arg Pro
1               5                   10                  15

Lys Thr Arg Val
            20

<210> SEQ ID NO 900
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 900

His His Leu Val Ala Gln Arg Asp Ile Arg Gln Phe Gln Leu Gln His
1               5                   10                  15

Trp Leu Ala Ile
            20

<210> SEQ ID NO 901
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 901

His Ser Cys Cys Asn Arg Ala Arg Gln Glu Arg Leu Gln Arg Arg
1               5                   10                  15

Glu Thr Gln Val
            20

<210> SEQ ID NO 902
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 902

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 903
<211> LENGTH: 19
<212> TYPE: PRT
<213> ORGANISM: Artificial

```
<220> FEATURE:
<223> OTHER INFORMATION: PL sequence binding SHANK 1

<400> SEQUENCE: 903

Lys Asp Ser Arg Pro Ser Phe Val Gly Ser Ser Ser Gly His Thr Ser
1               5                   10                  15

Thr Thr Leu

<210> SEQ ID NO 904
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 904

Lys Glu Asn Asp Tyr Glu Ser Ile Ser Asp Leu Gln Gln Gly Arg Asp
1               5                   10                  15

Ile Thr Arg Leu
            20

<210> SEQ ID NO 905
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 905

Lys His Ser Arg Lys Ser Ser Tyr Ser Ser Ser Ser Thr Thr Val
1               5                   10                  15

Lys Thr Ser Tyr
            20

<210> SEQ ID NO 906
<211> LENGTH: 23
<212> TYPE: PRT
<213> ORGANISM: Artificial
<220> FEATURE:
<223> OTHER INFORMATION: PL sequence binding SHANK 1

<400> SEQUENCE: 906

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 907
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 907

Lys Pro Gln Ile Ala Ala Leu Lys Glu Thr Glu Glu Glu Val Gln
1               5                   10                  15

Asp Thr Arg Leu
            20

<210> SEQ ID NO 908
<211> LENGTH: 20
<212> TYPE: PRT
<213> ORGANISM: Artificial
```

-continued

```
<220> FEATURE:
<223> OTHER INFORMATION: PL sequence binding SHANK 1

<400> SEQUENCE: 908

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 909
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 909

Leu Ala Ser Lys Ser Ala Glu Glu Gly Lys Gln Ile Pro Asp Ser Leu
1               5                   10                  15

Ser Thr Asp Leu
            20

<210> SEQ ID NO 910
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 910

Leu Ala Val Leu Ala Tyr Ser Ile Thr Leu Val Met Leu Trp Ser Ile
1               5                   10                  15

Trp Gln Tyr Ala
            20

<210> SEQ ID NO 911
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 911

Leu Gly Tyr Ser Ile Pro Ser Arg Ser Gly Ala Ser Gly Leu Asp Lys
1               5                   10                  15

Arg Asp Tyr Val
            20

<210> SEQ ID NO 912
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 912

Leu Met Asp Gly Leu Pro Pro Gly Asp Ser Asn Gln Leu Ala Trp Phe
1               5                   10                  15

Asp Thr Asp Leu
            20

<210> SEQ ID NO 913
<211> LENGTH: 20
<212> TYPE: PRT
```

<213> ORGANISM: Artificial
<220> FEATURE:
<223> OTHER INFORMATION: PL sequence binding SHANK 1

<400> SEQUENCE: 913

Leu Asn Glu Thr Thr Glu Thr Gln Arg Thr Leu Leu Asn Gly Asp Leu
1               5                   10                  15

Gln Thr Ser Ile
            20

<210> SEQ ID NO 914
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 914

Leu Asn Ser Cys Ser Asn Arg Arg Val Tyr Lys Lys Met Pro Ser Ile
1               5                   10                  15

Glu Ser Asp Val
            20

<210> SEQ ID NO 915
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 915

Leu Gln Phe His Arg Gly Ser Arg Ala Gln Ser Phe Leu Gln Thr Glu
1               5                   10                  15

Thr Ser Val Ile
            20

<210> SEQ ID NO 916
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 916

Pro Gly Gln Pro Pro Lys Val Lys Ser Glu Phe Asn Ser Tyr Ser Leu
1               5                   10                  15

Thr Gly Tyr Val
            20

<210> SEQ ID NO 917
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 917

Pro Ile Pro Ala Gly Gly Cys Thr Phe Ser Gly Ile Phe Pro Thr Leu
1               5                   10                  15

Thr Ser Pro Leu
            20

<210> SEQ ID NO 918
<211> LENGTH: 20

-continued

```
<212> TYPE: PRT
<213> ORGANISM: Artificial
<220> FEATURE:
<223> OTHER INFORMATION: PL sequence binding SHANK 1

<400> SEQUENCE: 918

Pro Pro Ala Thr Pro Ser Pro Arg Leu Ala Leu Pro Ala His His Asn
1               5                   10                  15

Ala Thr Arg Leu
            20

<210> SEQ ID NO 919
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 919

Pro Ser Trp Arg Arg Ser Ser Leu Ser Glu Ser Glu Asn Ala Thr Ser
1               5                   10                  15

Leu Thr Thr Phe
            20

<210> SEQ ID NO 920
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 920

Pro Tyr Ser Glu Leu Asn Tyr Glu Thr Ser His Tyr Pro Ala Ser Pro
1               5                   10                  15

Asp Ser Trp Val
            20

<210> SEQ ID NO 921
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 921

Gln Asp Phe Arg Arg Ala Phe Arg Arg Ile Leu Ala Arg Pro Trp Thr
1               5                   10                  15

Gln Thr Ala Trp
            20

<210> SEQ ID NO 922
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 922

Arg Glu Leu Val Asp Arg Gly Glu Val Arg Gln Phe Thr Leu Arg His
1               5                   10                  15

Trp Leu Lys Val
            20

<210> SEQ ID NO 923
```

```
<211> LENGTH: 11
<212> TYPE: PRT
<213> ORGANISM: Artificial
<220> FEATURE:
<223> OTHER INFORMATION: PL sequence binding SHANK 1

<400> SEQUENCE: 923

Arg Arg Ala Ser Thr Ser Arg Glu Thr Trp Val
1               5                   10

<210> SEQ ID NO 924
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 924

Arg Ser Gly Ala Thr Ile Pro Leu Val Gly Gln Asp Ile Ile Asp Leu
1               5                   10                  15

Gln Thr Glu Val
            20

<210> SEQ ID NO 925
<211> LENGTH: 19
<212> TYPE: PRT
<213> ORGANISM: Artificial
<220> FEATURE:
<223> OTHER INFORMATION: PL sequence binding SHANK 1

<400> SEQUENCE: 925

Ser Ser Lys Ser Lys Ser Ser Glu Glu Ser Gln Thr Phe Phe Gly Leu
1               5                   10                  15

Tyr Lys Leu

<210> SEQ ID NO 926
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 926

Ser Ser Pro Asp Ser Ser Tyr Gln Gly Lys Gly Phe Val Met Ser Arg
1               5                   10                  15

Ala Met Tyr Val
            20

<210> SEQ ID NO 927
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 927

Ser Ser Ser Arg Arg Asp Ser Ser Trp Ser Glu Thr Ser Glu Ala Ser
1               5                   10                  15

Tyr Ser Gly Leu
            20

<210> SEQ ID NO 928
<211> LENGTH: 18
<212> TYPE: PRT
<213> ORGANISM: Artificial
```

-continued

```
<220> FEATURE:
<223> OTHER INFORMATION: PL sequence binding SHANK 1

<400> SEQUENCE: 928

Thr Phe Ala Ala Gly Phe Asn Ser Thr Gly Leu Pro His Ser Thr Thr
1               5                   10                  15

Arg Val

<210> SEQ ID NO 929
<211> LENGTH: 19
<212> TYPE: PRT
<213> ORGANISM: Artificial
<220> FEATURE:
<223> OTHER INFORMATION: PL sequence binding SHANK 1

<400> SEQUENCE: 929

Thr Gly Arg Gly Met Ser Gly Gly Arg Ser Ser Arg Thr Arg Glu
1               5                   10                  15

Thr Gln Leu

<210> SEQ ID NO 930
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 930

Thr Arg Glu Asp Ile Tyr Val Asn Tyr Pro Thr Phe Ser Arg Arg Pro
1               5                   10                  15

Lys Thr Arg Val
            20

<210> SEQ ID NO 931
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 931

Val Asp Pro Asn Ser Pro Ala Ala Lys Lys Lys Tyr Val Ser Tyr Asn
1               5                   10                  15

Asn Leu Val Ile
            20

<210> SEQ ID NO 932
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 932

Val His Lys Val Arg Asn Lys Phe Lys Ala Lys Cys Ser Leu Cys Arg
1               5                   10                  15

Leu Tyr Ile Ile
            20

<210> SEQ ID NO 933
<211> LENGTH: 20
<212> TYPE: PRT
<213> ORGANISM: Artificial
<220> FEATURE:
```

```
<223> OTHER INFORMATION: PL sequence binding SHANK 1

<400> SEQUENCE: 933

Val Pro Gly Ala Leu Asp Tyr Ala Ala Phe Ser Ser Ala Leu Tyr Gly
1               5                   10                  15

Glu Ser Asp Leu
            20

<210> SEQ ID NO 934
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 934

Tyr Gly Arg Lys Lys Arg Arg Gln Arg Arg Asp Lys Glu Leu Glu
1               5                   10                  15

Val Leu Ser Leu
            20

<210> SEQ ID NO 935
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 935

Tyr Gly Arg Lys Lys Arg Arg Gln Arg Arg Leu Leu Lys Glu Arg
1               5                   10                  15

Ser Thr Glu Leu
            20

<210> SEQ ID NO 936
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 936

Tyr Gly Arg Lys Lys Arg Arg Gln Arg Arg Asn Asp Asn Ile Ala
1               5                   10                  15

Leu Leu Val Gln
            20

<210> SEQ ID NO 937
<211> LENGTH: 20
<212> TYPE: PRT
<213> ORGANISM: Artificial
<220> FEATURE:
<223> OTHER INFORMATION: PL sequence binding SHANK 1

<400> SEQUENCE: 937

Tyr Gly Arg Lys Lys Arg Arg Gln Arg Arg Pro Ser Arg Lys Leu
1               5                   10                  15

Asn Thr Glu Ile
            20

<210> SEQ ID NO 938
<211> LENGTH: 20
<212> TYPE: PRT
<213> ORGANISM: Artificial
```

```
-continued

<220> FEATURE:
<223> OTHER INFORMATION: PL sequence binding SHANK 1

<400> SEQUENCE: 938

Tyr Gly Arg Lys Lys Arg Arg Gln Arg Arg Tyr Ile Pro Glu Ala
1               5                   10                  15

Gln Thr Arg Leu
            20

<210> SEQ ID NO 939
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 939

Ala Ala Gly Gly Arg Ser Ala Arg Gly Gly Arg Leu Gln Gly Arg Arg
1               5                   10                  15

Glu Thr Ala Leu
            20

<210> SEQ ID NO 940
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 940

Phe His Ser Lys Thr Ala Gly Ala Asn Thr Thr Asp Lys Glu Leu Glu
1               5                   10                  15

Val Leu Ser Leu
            20

<210> SEQ ID NO 941
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 941

Phe Asn Gly Ser Ser Asn Gly His Val Tyr Glu Lys Leu Ser Ser Ile
1               5                   10                  15

Glu Ser Asp Val
            20

<210> SEQ ID NO 942
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 942

Gly Gly Asp Leu Gly Thr Arg Arg Gly Ser Ala His Phe Ser Ser Leu
1               5                   10                  15

Glu Ser Glu Val
            20

<210> SEQ ID NO 943
<211> LENGTH: 20
<212> TYPE: PRT
```

-continued

```
<213> ORGANISM: Artificial
<220> FEATURE:
<223> OTHER INFORMATION: PL sequence binding TIP43 d1

<400> SEQUENCE: 943

Gly Arg Trp Thr Gly Arg Ala Met Ser Ala Trp Lys Pro Thr Arg Arg
1               5                   10                  15

Glu Thr Glu Val
            20

<210> SEQ ID NO 944
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 944

Lys His Ser Arg Lys Ser Ser Tyr Ser Ser Ser Ser Thr Thr Val
1               5                   10                  15

Lys Thr Ser Tyr
            20

<210> SEQ ID NO 945
<211> LENGTH: 23
<212> TYPE: PRT
<213> ORGANISM: Artificial
<220> FEATURE:
<223> OTHER INFORMATION: PL sequence binding TIP43 d1

<400> SEQUENCE: 945

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 946
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 946

Leu Ala Ser Lys Ser Ala Glu Glu Gly Lys Gln Ile Pro Asp Ser Leu
1               5                   10                  15

Ser Thr Asp Leu
            20

<210> SEQ ID NO 947
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 947

Leu Asn Ser Ser Ser Asn Arg Arg Val Tyr Lys Lys Met Pro Ser Ile
1               5                   10                  15

Glu Ser Asp Val
            20

<210> SEQ ID NO 948
<211> LENGTH: 20
```

-continued

```
<212> TYPE: PRT
<213> ORGANISM: Artificial
<220> FEATURE:
<223> OTHER INFORMATION: PL sequence binding TIP43 d1

<400> SEQUENCE: 948

Arg Ser Gly Ala Thr Ile Pro Leu Val Gly Gln Asp Ile Ile Asp Leu
1               5                   10                  15

Gln Thr Glu Val
            20

<210> SEQ ID NO 949
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 949

Ser Phe Thr Ser Ile Leu Thr Cys His Gln Arg Arg Thr Gln Arg Lys
1               5                   10                  15

Glu Thr Val Ala
            20

<210> SEQ ID NO 950
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 950

Ser Ser Ser Arg Arg Asp Ser Ser Trp Ser Glu Thr Ser Glu Ala Ser
1               5                   10                  15

Tyr Ser Gly Leu
            20

<210> SEQ ID NO 951
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 951

Thr Gln Gly Phe Pro Gly Pro Ala Thr Trp Arg Arg Ile Ser Ser Leu
1               5                   10                  15

Glu Ser Glu Val
            20

<210> SEQ ID NO 952
<211> LENGTH: 19
<212> TYPE: PRT
<213> ORGANISM: Artificial
<220> FEATURE:
<223> OTHER INFORMATION: PL sequence binding TIP43 d1

<400> SEQUENCE: 952

Thr Thr Asn Asn Asn Pro Asn Ser Ala Val Asn Ile Lys Lys Ile Phe
1               5                   10                  15

Thr Asp Val

<210> SEQ ID NO 953
<211> LENGTH: 20
```

```
<212> TYPE: PRT
<213> ORGANISM: Artificial
<220> FEATURE:
<223> OTHER INFORMATION: PL sequence binding TIP43 d1

<400> SEQUENCE: 953

Val His Lys Val Arg Asn Lys Phe Lys Ala Lys Cys Ser Leu Cys Arg
1               5                   10                  15

Leu Tyr Ile Ile
            20

<210> SEQ ID NO 954
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 954

Tyr Gly Arg Lys Lys Arg Arg Gln Arg Arg Glu Tyr Leu Gly Leu
1               5                   10                  15

Asp Val Pro Val
            20

<210> SEQ ID NO 955
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 955

Tyr Gly Arg Lys Lys Arg Arg Gln Arg Arg Gly Ala Ser Ala Asp
1               5                   10                  15

Ser Thr Gln Ala
            20

<210> SEQ ID NO 956
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 956

Tyr Gly Arg Lys Lys Arg Arg Gln Arg Arg Lys Leu Ser Ser Ile
1               5                   10                  15

Glu Ser Asp Val
            20

<210> SEQ ID NO 957
<211> LENGTH: 20
<212> TYPE: PRT
<213> ORGANISM: Artificial
<220> FEATURE:
<223> OTHER INFORMATION: PL sequence binding TIP43 d1

<400> SEQUENCE: 957

Tyr Gly Arg Lys Lys Arg Arg Gln Arg Arg Asn Asp Asn Ile Ala
1               5                   10                  15

Leu Leu Val Gln
            20

<210> SEQ ID NO 958
```

-continued

```
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 958

Ala Ala Gly Gly Arg Ser Ala Arg Gly Gly Arg Leu Gln Gly Arg Arg
1               5                   10                  15

Glu Thr Ala Leu
            20

<210> SEQ ID NO 959
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 959

Ala Gly Ala Val Arg Thr Pro Leu Ser Gln Val Asn Lys Val Trp Asp
1               5                   10                  15

Gln Ser Ser Val
            20

<210> SEQ ID NO 960
<211> LENGTH: 19
<212> TYPE: PRT
<213> ORGANISM: Artificial
<220> FEATURE:
<223> OTHER INFORMATION: PL sequence binding Vartul d2

<400> SEQUENCE: 960

Ala Arg His Arg Val Thr Ser Tyr Thr Ser Ser Ser Val Asn Val Ser
1               5                   10                  15

Ser Asn Leu

<210> SEQ ID NO 961
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 961

Ala Thr Asp Tyr Leu Val Gln Pro Phe Met Asp Gln Leu Ala Phe His
1               5                   10                  15

Gln Phe Tyr Ile
            20

<210> SEQ ID NO 962
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 962

Asp Phe Arg Pro Ser Phe Lys His Ile Leu Phe Arg Arg Ala Arg Arg
1               5                   10                  15

Gly Phe Arg Gln
            20

<210> SEQ ID NO 963
```

```
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 963

Glu Leu Leu Gln Phe Cys Arg Thr Pro Asn Pro Ala Leu Lys Asn Gly
1               5                   10                  15

Gln Tyr Trp Val
            20

<210> SEQ ID NO 964
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 964

Glu Ser Ser Gly Thr Gln Ser Pro Lys Arg His Ser Gly Ser Tyr Leu
1               5                   10                  15

Val Thr Ser Val
            20

<210> SEQ ID NO 965
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 965

Gly Arg Trp Thr Gly Arg Ala Met Ser Ala Trp Lys Pro Thr Arg Arg
1               5                   10                  15

Glu Thr Glu Val
            20

<210> SEQ ID NO 966
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 966

His His Leu Val Ala Gln Arg Asp Ile Arg Gln Phe Gln Leu Gln His
1               5                   10                  15

Trp Leu Ala Ile
            20

<210> SEQ ID NO 967
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 967

Lys His Ser Arg Lys Ser Ser Tyr Ser Ser Ser Ser Thr Thr Val
1               5                   10                  15

Lys Thr Ser Tyr
            20
```

<210> SEQ ID NO 968
<211> LENGTH: 23
<212> TYPE: PRT
<213> ORGANISM: Artificial
<220> FEATURE:
<223> OTHER INFORMATION: PL sequence binding Vartul d2

<400> SEQUENCE: 968

Lys Lys Lys Lys Gln Pro Gly Asn Ser Thr Lys Glu Ser Glu Ser Thr
1 5 10 15

Asn Ser Val Arg Leu Met Leu
20

<210> SEQ ID NO 969
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 969

Leu Ala Val Leu Ala Tyr Ser Ile Thr Leu Val Met Leu Trp Ser Ile
1 5 10 15

Trp Gln Tyr Ala
20

<210> SEQ ID NO 970
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 970

Leu Asn Ser Cys Ser Asn Arg Arg Val Tyr Lys Lys Met Pro Ser Ile
1 5 10 15

Glu Ser Asp Val
20

<210> SEQ ID NO 971
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 971

Pro Ile Pro Ala Gly Gly Cys Thr Phe Ser Gly Ile Phe Pro Thr Leu
1 5 10 15

Thr Ser Pro Leu
20

<210> SEQ ID NO 972
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 972

Pro Val Tyr Ile Val Gln Glu Met Pro Pro Gln Ser Pro Ala Asn Ile
1 5 10 15

Tyr Tyr Lys Val
20

-continued

```
<210> SEQ ID NO 973
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 973

Pro Tyr Ser Glu Leu Asn Tyr Glu Thr Ser His Tyr Pro Ala Ser Pro
1               5                   10                  15

Asp Ser Trp Val
            20

<210> SEQ ID NO 974
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 974

Gln Asp Phe Arg Arg Ala Phe Arg Arg Ile Leu Ala Arg Pro Trp Thr
1               5                   10                  15

Gln Thr Ala Trp
            20

<210> SEQ ID NO 975
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 975

Gln Ile Ser Pro Gly Gly Leu Glu Pro Pro Ser Glu Lys His Phe Arg
1               5                   10                  15

Glu Thr Glu Val
            20

<210> SEQ ID NO 976
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 976

Arg Glu Leu Val Asp Arg Gly Glu Val Arg Gln Phe Thr Leu Arg His
1               5                   10                  15

Trp Leu Lys Val
            20

<210> SEQ ID NO 977
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 977

Ser Leu Ile Gly Pro Val Gln Lys Glu Tyr Gln Arg Glu Leu Gly Lys
1               5                   10                  15

Leu Ser Ser Pro
            20
```

```
<210> SEQ ID NO 978
<211> LENGTH: 19
<212> TYPE: PRT
<213> ORGANISM: Artificial
<220> FEATURE:
<223> OTHER INFORMATION: PL sequence binding Vartul d2

<400> SEQUENCE: 978

Ser Ser Lys Ser Lys Ser Ser Glu Glu Ser Gln Thr Phe Phe Gly Leu
1               5                   10                  15
Tyr Lys Leu

<210> SEQ ID NO 979
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 979

Ser Tyr Pro Thr Pro Arg Pro Tyr Pro Lys Pro Ala Pro Ser Ser Gly
1               5                   10                  15
Lys Asp Tyr Val
            20

<210> SEQ ID NO 980
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 980

Thr Gln Gly Phe Pro Gly Pro Ala Thr Trp Arg Arg Ile Ser Ser Leu
1               5                   10                  15
Glu Ser Glu Val
            20

<210> SEQ ID NO 981
<211> LENGTH: 19
<212> TYPE: PRT
<213> ORGANISM: Artificial
<220> FEATURE:
<223> OTHER INFORMATION: PL sequence binding Vartul d2

<400> SEQUENCE: 981

Thr Thr Asn Asn Asn Pro Asn Ser Ala Val Asn Ile Lys Lys Ile Phe
1               5                   10                  15
Thr Asp Val

<210> SEQ ID NO 982
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 982

Val Asp Pro Asn Ser Pro Ala Ala Lys Lys Tyr Val Ser Tyr Asn
1               5                   10                  15
Asn Leu Val Ile
            20
```

-continued

```
<210> SEQ ID NO 983
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 983

Val His Lys Val Arg Asn Lys Phe Lys Ala Lys Cys Ser Leu Cys Arg
1               5                   10                  15

Leu Tyr Ile Ile
            20

<210> SEQ ID NO 984
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 984

Tyr Gly Arg Lys Lys Arg Arg Gln Arg Arg Gly Ala Ser Ala Asp
1               5                   10                  15

Ser Thr Gln Ala
            20

<210> SEQ ID NO 985
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 985

Tyr Gly Arg Lys Lys Arg Arg Gln Arg Arg Lys Leu Ser Ser Ile
1               5                   10                  15

Glu Ser Asp Val
            20

<210> SEQ ID NO 986
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 986

Tyr Gly Arg Lys Lys Arg Arg Gln Arg Arg Asn Asp Asn Ile Ala
1               5                   10                  15

Leu Leu Val Gln
            20

<210> SEQ ID NO 987
<211> LENGTH: 20
<212> TYPE: PRT
<213> ORGANISM: Artificial
<220> FEATURE:
<223> OTHER INFORMATION: PL sequence binding Vartul d2

<400> SEQUENCE: 987

Tyr Ser Ala Thr Tyr Ser Glu Leu Glu Asp Pro Gly Glu Met Ser Pro
1               5                   10                  15

Pro Ile Asp Leu
            20
```

<210> SEQ ID NO 988
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 988
attgagtcag aagtttgaag a                                           21

<210> SEQ ID NO 989
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 989
attgagccag aagtttgaag a                                           21

<210> SEQ ID NO 990
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 990
attgagtcaa aagtttgaag a                                           21

<210> SEQ ID NO 991
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 991
gctaggtcaa aagtttgaag a                                           21

<210> SEQ ID NO 992
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 992
attaagtcag aagtttgaag a 21

<210> SEQ ID NO 993
<211> LENGTH: 21
<212> TYPE: DNA
<213> ORGANISM: Artificial
<220> FEATURE:
<223> OTHER INFORMATION: NS1 C-Term Coding Region

<400> SEQUENCE: 993
attaggtcag aagtttgaag a 21

<210> SEQ ID NO 994
<211> LENGTH: 7
<212> TYPE: PRT
<213> ORGANISM: Artificial
<220> FEATURE:

```
<223> OTHER INFORMATION: NS2 Region

<400> SEQUENCE: 994

Gln Leu Ser Gln Lys Phe Glu
1               5

<210> SEQ ID NO 995
<211> LENGTH: 7
<212> TYPE: PRT
<213> ORGANISM: Artificial
<220> FEATURE:
<223> OTHER INFORMATION: NS2 Region

<400> SEQUENCE: 995

Gln Leu Gly Gln Lys Phe Glu
1               5

<210> SEQ ID NO 996
<211> LENGTH: 4
<212> TYPE: PRT
<213> ORGANISM: Artificial
<220> FEATURE:
<223> OTHER INFORMATION: Preferred C-terminal sequence

<400> SEQUENCE: 996

Asp Ser Asp Val
1

<210> SEQ ID NO 997
<211> LENGTH: 4
<212> TYPE: PRT
<213> ORGANISM: Artificial
<220> FEATURE:
<223> OTHER INFORMATION: Preferred C-terminal sequence

<400> SEQUENCE: 997

Asp Ser Glu Val
1
```

METHODS AND COMPOSITIONS FOR DIAGNOSIS AND TREATMENT OF INFLUENZA

RELATED APPLICATIONS

This application claims priority of U.S. Provisional Application 60/696,221, filed Jul. 1, 2005, 60/726,377, filed Oct. 13, 2005, 60/765,292, filed Feb. 2, 2006, and 60/792,274, filed Apr. 14, 2006, each of which is herein incorporated by reference in its entirety.

BACKGROUND OF THE INVENTION

Epidemic viral infections are responsible for significant worldwide loss of life and income in human illnesses ranging from the common cold to life-threatening influenza, West Nile and HIV infections. Timely detection, diagnosis and treatment are key in limiting spread of disease in epidemic, pandemic and epizootic settings. Rapid screening and diagnostic methods are particularly useful in reducing patient suffering and population risk. Similarly, therapeutic agents that rapidly inhibit viral assembly and propagation are particularly useful in treatment regimens.

Influenza A has emerged recently as a potential significant risk to human populations. Avian strains have crossed into humans and there is growing evidence that human to human spread may soon occur[1]. Examples of the impact of avian influenza strains on human populations is provided by the recent emergence of highly virulent strains of avian influenza H5N1 (bird flu) where approximately 50% of infected individuals (42 people) succumbed and food shortages resulted from slaughter of millions of birds in China, Indonesia and Vietnam. Tracking the potential for epidemic, the World Health Organization considered raising the global threat level to 4 or 5 (on a scale of six) in July of 2005. One opinion leader recently expressed in press that with avian influenza—"detection, surveillance, prevention and therapy" . . . (is) . . . "a race against time"[1]. Since avian strains have rarely been isolated from humans and mortality rates in humans are high, it seems likely that immunity in the worldwide population is virtually non-existent. Thus, the opportunity exists for a worldwide pandemic. For comparison, in 1918 a global influenza epidemic resulted in an estimated 20-40 million deaths. With increased population density today, higher mortality is likely.

Virology test methods for detection and confirmation of influenza A infection in a virus-secure reference laboratory, e.g., satisfying requirements for Containment Group 4 pathogens, are time consuming, high-risk and laborious, i.e., involving 4-7 days isolation of the virus in embryonated eggs; harvesting allantoic fluids from dead or dying embryos; testing the fluid in hemagglutination and hemagglutination inhibition tests, immunodiffusion; and, eventual subtyping of the virus in the fluid by hemagglutinin and neuraminidase in overnight immunodiffusion assays using specially prepared monospecific antisera. Present subtyping involves identifying each of 16 different possible viral hemagglutinin proteins in combination with 9 different possible viral neuraminidase proteins. Unfortunately, since only a few pathogenic strains of influenza A are of economic and health concern at any point in time, much of this time-consuming effort may be unnecessary and wasted.

Current rapid immunodiagnostic tests for influenza antigens like "Binax NOW FluA and FluB™" (Binax, Inc., Portland, Me.), "Directigen Flu A+B™" (Becton Dickinson, Franklin Lakes, N.J.), "Flu OIA™" (Biostar Inc., Boulder, Colo.), "Quick Vue™" (Quidel, Sand Diego, Calif.), "Influ AB Quick™" (Denka Sieken Co., Ltd., Japan) and "Xpect Flu A & B" (Remel Inc., Lenexa, Kans.), can reportedly either detect influenza A or distinguish between Influenza A and B, but importantly, not between different influenza A subtypes or between pathogenic and non-pathogenic strains of influenza A. The complexity of the test formats may require special training. In addition, significant amounts of virion particles are commonly required to obtain a positive test result, limiting their use to a short window of time when virus shedding is at its highest levels. Assay sensitivity is also variable with up to 20% false negative test results in certain assays being of significant current concern (e.g., see "WHO recommendations on the use of rapid testing for influenza diagnosis", July 2005). Recent introduction of reverse-transcriptase PCR-based diagnostics (RT-PCR) for confirming influenza A virus have resulted in important advances in capabilities[36], but are laborious and require highly trained personnel making on-site or field-testing difficult. Because of the relative inefficiency of the reverse transcriptase enzyme, significant amounts of virus (e.g., $10^4$ virion particles) and as many as 20 primers may be required to effectively detect viral RNA. Despite these significant obstacles, in reference laboratory RT-PCR influenza A testing high levels of proficiency have recently been recorded between 12 different participating test laboratories in the US, Canada and Hong Kong[36]. Using RT-PCR and HA primers, Lee et al.[37] described quantitative discrimination between H5 and H7 subtypes of virus. Munch et al.[38] report similar possible differential specificity in RT-PCR using NP primers. Unfortunately, RT-PCR is not easily adapted to high throughput screening of subjects in an epidemic setting or to field uses in an agricultural or point-of-care setting.

Additionally, the complexity, diversity and rapid emergence of new influenza strains has made diagnosis of high risk strains difficult, and therefore rapid response is at present nearly impossible. For epidemiologists, diversity resulting from high mutation rates and genetic reassortment make it difficult to anticipate where new strains may originate and respond with the timely introduction of new diagnostic primers for PCR. As a result, (at present) the diversity of influenza dictates the necessity of multiplex PCR approaches.

Avian influenza virus (H5N1) is believed to be evolving by both mutation and segmental reassortment with influenza viruses in aquatic wildfowl[2,3]. Highly pathogenic disease in "sick" birds may vary from sudden death with few overt signs of disease to a more characteristic disease with respiratory signs, excessive lacrimation, sinusitis, edema of the head, cyanosis of the unfeathered skin and diarrhea, i.e., the diagnostic signs of "sick" employed by OIE in their health guidelines (*Manual of Diagnostic Tests and Vaccines for Terrestrial Animals,* 5$^{th}$ edition, 2004, World Organization for Animal Health). In infected birds influenza A virus is shed in just 2-3 days[4,5]. Given the high mortality rates in humans, rapid detection is essential to isolate infected avian and human subjects and protect human populations. In the field, human cases of bird flu have historically originated in regions of South East Asia that lacks easy access to sophisticated diagnostic test equipment, virus-secure reference BL4 laboratories and methods. Thus, assessing population risk at an individual patient level is presently highly problematic. In other objects, the invention offers solutions to these problems.

Rapid diagnostic testing, needed to support agriculture and the public health, is proving to be challenging—i.e., for either serological detection of anti-viral host responses (antibody) or identification of viral proteins (antigens) in samples. Testing for influenza A subtypes is also complicated by: (i) the scope of epidemiological and the public health needs, i.e., potential needs for viral detection in environmental samples and in infected livestock, (e.g. swine flu), poultry (e.g. avian flu) and humans (e.g. bird flu); and, (ii) the wide range of possible test samples which may include serum, nasopharyngeal, throat gargle, nasal or laryngeal samples (human); and, cloacal, feces and tracheal samples (bird). Since high risk viruses tend to spread rapidly, speed is of the essence. High affinity specific binding reagents are clearly key and required. In other objects, the invention solves these key needs.

Classical influenza serological testing (for antibody) by hemagglutination-inhibition (HI) is relatively simple, but in agricultural practice these tests are relatively insensitive for detecting avian antibody responses following either vaccination or natural infection as serum antibody tends to fall rapidly after infection. Under optimal conditions Xu et al.[39] e.g. recently described a latex agglutination test, i.e., using complete heat inactivated vaccine virus and serum from vaccinated birds. The latter HI-test reportedly had 88% sensitivity (12% false negatives) and 98% specificity, in this case, false negative rates too high for agricultural or public health detection of such dangerous viral pathogens. Similarly, using avian field samples in China, Jin et al.[4] recently described potential uses of a recombinant influenza NP antigen in ELISA assays. These investigators observed that virus shedding began at days 2, but titers of anti-viral antibodies were most significant at 2 weeks. Unfortunately, the latter "lag" before detection of infected animals is unacceptable in the current worldwide crisis. Demonstrating a further possible complication, data in the latter studies showed that low doses of virus generated only very low titers of antibody, i.e., suggesting that subclinical infections might go undetected.

Present limitations in routine diagnostic methods for flu, i.e., Influenza B, were noted in data published by Steininger et al.[41]. In the latter studies, different test methods were employed to detect a standard influenza A stock virus preparation; and, with the following findings: namely, rapid enzyme-based assays were about 1000-fold less sensitive than detection by conventional virus isolation methods; which were, in turn, about 1000-fold less sensitive than RT-PCR. Despite the latter gross quantitative limitations in sensitivity, the ELISA still correctly identified 62% of positive samples and 88% for samples obtained from patients younger than 5 yrs. of age with Influenza B (flu). As an example of the impact that poor samples can have on assay performance, commercially viable flu tests were assayed for their sensitivity in detecting viral antigen in nasopharyngeal samples of experimentally infected volunteers. The reported results suggest that assay sensitivity was about 60% for the Directigen flu test[43] (Becton Dickinson); and, in the range of 48-100% for the flu optical immunoassay (FLU OIA; ThermoBioStar/Biota)[44]. Importantly, (despite the obvious limitations of the latter tests), Sharma et al.[45] reported that rapid confirmation of influenza virus type A infection: (i) decreased irrelevant laboratory testing, e.g. urinalysis and wbc testing, as well as, (ii) inappropriate antibiotic use in febrile infants and toddlers. Thus, a relatively poor sensitivity in these screening assays was still useful in clinical practice because the assay correctly identified those patients who needed additional follow-up. Clearly, for non-reference lab uses, improvements in user friendliness, speed, discrimination and absolute quantitative sensitivity are needed, i.e., even for routine flu testing. Similarly, routine flu testing is not particularly helpful in suggesting how one may achieve a method with the requisite assay performance needed to test for high risk strains of influenza A in patient samples.

Emergent virulence factors in H5N1 and H7 avian influenza A viruses and the panzooic spread of H9N2 influenza virus and their known interactions with mammalian host factors have been reviewed[5]. Among the proteins encoded by virulent avian strains of influenza, NS1 (non-structural protein-1) is expressed early in infected cells, but unlike HA and NA, it is not virion associated and is expressed only as an intracellular protein. NS1 is encoded by genome segment 8 and is a viral regulatory factor enhancing translation of viral mRNA; interfering with maturation and transport of host cell mRNA[6]; binding poly(A) tails of host mRNA; altering intrinsic small interfering RNA (siRNA) control of host cell gene expression[7]; preventing ds-RNA induction of antiviral protein kinase R; inhibiting induction[8] of, and antagonizing[9,10] anti-viral action of interferon α/β (IFN-α/β); and, stimulating production of pro-inflammatory cytokines by macrophages[11] and dendritic cells[12]. The roles of INF-α/β signaling in innate and adaptive immune responses and pathogenesis has recently been reviewed.[13]

Distribution of NS1 protein in infected cells suggest preferential nuclear localization, i.e., but with lesser amounts in cytoplasmic, ribosomal and polysomal fractions[22-24]. NS1 protein of the highly virulent avian H5N1 strain apparently suppresses interferon responses of human cells in vitro[25]. Certain mechanistic studies suggest that carboxyl terminal deletions in NS1, may attenuate in vivo virulence of wild-type A/Swine/Texas/4199-2/98 (TX/98) virus[26], as well as, equine influenza virus[27]. Interestingly, Influenza A lacking the NS1 gene seems to replicates best in interferon-deficient cell lines[28], suggesting to the authors that NS1 inhibition of INF-α/β may be necessary for efficient viral propagation. In addition, reassortment of the high-virulence H5N1-NS1 gene into the lower virulence H1N1-A strain reportedly reduced lung clearance rates of the hybrid virus, and also resulted in increased levels of inflammatory cytokines[29]. Tumpey et al.[40] reported that detecting anti-NS1 antibodies may be useful in distinguishing vaccinated from infected poultry, i.e., because NS1 is only expressed in infected cells not in inactivated gradient purified vaccine virus. Unfortunately, the latter antibody-based serological test methods suffer from the same general problems identified above in regard to HI tests: namely, low sensitivity and inability to detect virus prior to virus shedding and potential spread of infection.

Using the H7N3 strain, Cattoli et al.[42] reportedly evaluated the timing, specificity and sensitivity of detection of virus in tracheal samples from experimentally and naturally infected turkeys, i.e., in antigen-capture ELISA, RT-PCR and a real-time RT-PCR, (i.e., the later two tests targeting the M gene). Under the latter relatively controlled laboratory conditions, virus was detectable with good specificity and sensitivity as early as 3-5 days post-infection. They concluded that it should be theoretically possible to detect, at least this particular avian virus and perhaps other more highly virulent avian strains at day 3 to 5 of infection provided there were sufficient assay sensitivity.

Thus, there remains a significant need in the medical arts for improved, inexpensive, rapid, accurate and discriminatory methods capable of detecting the particular strains of pathogenic viruses most often involved in generating medically important diseases. There is also a special need for simple assay methodologies that can be routinely used by relatively untrained individuals in underdeveloped nations, markets, clinics, doctor's and veterinary offices, schools and food processing plants where resources may be limited and sophisticated lab equipment not widely available. In view of the worldwide threat posed by the spread of new Influenza A variants, there is a need in the clinical arts for new and improved anti-viral medicinal agents. This invention meets these needs.

BRIEF SUMMARY OF THE INVENTION

In one aspect, the invention provides methods for identifying whether a patient is infected with influenza virus type A, by determining whether NS1 protein of influenza virus type A is present in a patient sample, presence indicating the patient is infected with influenza virus type A. The determining step can involve contacting a patient sample with an agent that specifically binds to influenza virus type A protein NS1; and detecting specific binding between the agent and the NS1 protein, specific binding indicating presence of the influenza virus type A. Alternatively or in addition, the determining can include determining the presence of mRNA encoding the PDZ ligand motif (PL) of the NS1 protein and inferring presence of the NS1 protein from the presence of the mRNA. Preferably the PL has the motif: S/T-X-V/I/L where the S is serine, T is threonine, V is valine, I is isoleucine, L is leucine and X is any amino acid. Preferably, the agent is at least one PDZ polypeptide. Alternatively, the agent can be at least one antibody. For pan-specific antibodies, the antibody can be specific to a conserved region of the NS1 protein. Preferably, the contacting step involves contacting the patient sample with first and second agents that specifically bind to different epitopes of influenza virus type A protein NS1, and the first agent is immobilized on a support, and the detecting step detects a sandwich in which the first and second agents are specifically bound to the NS1 protein to indicate presence of the virus. The first and second agents can be first and second antibodies, but preferably, the first agent is one or more PDZ polypeptides and the second agent is one or more antibodies. The first agent can be a mixture of one or more PDZ polypeptides and one or more antibodies. The antibody can be an antibody specific for all subtypes of Influenza virus type A NS1.

The one or more PDZ polypeptides can be one or more of the following: Outer Membrane, PSD95 (PDZ # 2), PSD95 (PDZ #1,2,3), DLG1 (PDZ #1), DLG1 (PDZ #1,2), DLG1 (PDZ #2), DLG2 (PDZ #1), DLG2 (PDZ #2), Magi3 (PDZ #1), PTN3 (PDZ #1), MAST2 (PDZ #1), NeDLG (PDZ #1,2), Shank1 d1, Shank2 d1, Shank3 d1, Syntrophin1 alpha, Syntrophin gamma 1, Magi1 (PDZ #1), Magi1 (PDZ #4), Tip1; PTPL1 (PDZ #1), Mint3 (PDZ #1), Lym Mystique (PDZ #1), DLG2 (PDZ #3), MUPP1 (PDZ #8), NeDLG (PDZ #1), DLG5 (PDZ #1), PSD95 (PDZ #1), NumBP (PDZ #3), LIMK1 (PDZ #1), KIAA0313, DLG1 (PDZ #2), Syntenin (PDZ #2), Pick1, MAST2, PTN3 (PDZ #1), NOS1 (PDZ # 1, 2, 3), MINT1 (PDZ # 2), ZO-1 (PDZ #2), NSP and RIM212.

The patient sample can be any of the following: blood, tissue, a nasal secretion, a lung exudate, a cloacal sample, a fecal sample, a throat swab and saliva. Preferably, the patient is a human, a bird, a swine, a horse, or a mammal. The PDZ polypeptide preferably includes the PL binding region (80-100 amino acid region), for example the PL binding region for PSD95 d2 is provided in SEQ ID NO:1. For subtype specific assays, the PDZ polypeptide is preferably PSD95 d1, PSD95 d2, PSD95 d3, INADL8d1, Magi1 d1, DLG1d2, DLG1d3, NeDLG1d1, or NeDLG1d2

In a further aspect, the invention provides methods for the diagnosis and typing of Influenza type A infections, by identifying the presence of subtype specific Influenza type A virus protein NS1 PDZ ligand motif (PL) regions. Preferably, the PL regions have the motif: S/T-X-V/I/L where the S is serine, T is threonine, V is valine, I is isoleucine, L is leucine and X is any amino acid.

In one aspect, the invention provides methods for detecting the presence and amount of Influenza virus type A protein containing a PL region in a test sample, by admixing an aliquot of a test sample with at least one PDZ peptide and at least one PDZ ligand (PL) detect reagent under conditions suitable for binding; and measuring the binding between the PDZ peptide and the PL detect reagent, a decrease in binding indicates the presence of Influenza virus type A protein in the test sample. Preferably, the Influenza virus type A protein is NP, HA, M1 or NS1. Preferably, the PL detect reagent includes the PL motif from the C-terminus of an Influenza virus type A protein selected from the group consisting of: NP, HA, M1 and NS1. Preferably the PL motif is: S/T-X-V/ I/L where the S is serine, T is threonine, V is valine, I is isoleucine, L is leucine and X is any amino acid.

In a further aspect, the invention provides methods for identifying whether a patient is infected with influenza virus type A, by determining whether NS1 protein of influenza virus type A is present in a nasal secretion, a sputum sample or a throat swab from the patient, presence indicating the patient is infected with influenza virus type A.

In one aspect, the invention provides methods for detecting the presence and amount of Influenza virus type A protein containing a PL region in a test sample, by admixing an aliquot of a test sample with at least one PDZ peptide; and measuring the binding between the PDZ peptide and the PL Influenza virus type A protein, binding indicates the presence of Influenza virus type A protein in the test sample.

In a further aspect, the invention provides methods of determining whether a patient is infected with a pathogenic strain of influenza A, by determining whether a patient is infected with influenza A, and if the patient is infected, determining presence of a nonstructural protein with a PL motif in a patient sample, presence indicating that the patient is infected with a pathogenic strain of influenza virus type A.

In one aspect, the invention provides methods for identifying the presence of a specific subtype of an Influenza type A virus in a patient sample, by contacting a patient sample with at least one PDZ polypeptide or at least one capture antibody that specifically binds to a PL motif of an NS1 protein specific to a subtype of an influenza virus A; and detecting whether the PDZ polypeptide or capture antibody specifically binds to the PL motif in the sample, specific binding indicating presence of the subtype. Preferably, the contacting step involves contacting the patient sample with a plurality of PDZ polypeptides that specifically bind to a plurality of PL motifs in a plurality of NS1 proteins specific to a plurality of subtypes of influenza virus A; and the detecting involves determining which of the PDZ polypeptides specifically binds to its PL motif, the binding at one or more PDZ polypeptides thereby indicating presence of the subtype. Preferably, the capture antibody recognizes the carboxy terminus of NS1. Preferably, the capture antibody or PDZ polypeptide recognizes one or more of PDZ ligand motifs (PLs): ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV, and SKI. Preferably, the PDZ polypeptide is at least one of the following: Outer Membrane, PSD95 (PDZ # 2), PSD95 (PDZ #1,2, 3), DLG1 (PDZ #1), DLG1 (PDZ #1,2), DLG1 (PDZ #2), DLG2 (PDZ #1), DLG2 (PDZ #2), Magi3 (PDZ #1), PTN3 (PDZ #1), MAST2 (PDZ #1), NeDLG (PDZ #1,2), Shank1 d1, Shank2 d1, Shank3 d1, Syntrophin1 alpha, Syntrophin gamma 1, Magi1 (PDZ #1), Magi1 (PDZ #4), Tip1; PTPL1 (PDZ #1), Mint3 (PDZ #1), Lym Mystique (PDZ #1), DLG2 (PDZ #3), MUPP1 (PDZ #8), NeDLG (PDZ #1), DLG5 (PDZ #1), PSD95 (PDZ #1), NumBP (PDZ #3), LIMK1 (PDZ #1), KIAA0313, DLG1 (PDZ #2), Syntenin (PDZ #2), Pick1, MAST2, PTN3 (PDZ #1), NOS1 (PDZ # 1, 2, 3), MINT1 (PDZ # 2), ZO-1 (PDZ #2), NSP and RIM2. The patient sample can be a nasal secretion, a sputum sample, a throat swab, a cloacal sample, a fecal sample, a lung exudates, or saliva. If the method is used to identify a subtype, the subtype is preferably avian influenza A and the PL is the PL motif ESEV/I/A (SEQ ID NO:19). Alternatively the subtype is H3N2 and the PL is the PL motif RSKV (SEQ ID NO:8). Alternatively, the PL is the PL motif ESKV (SEQ ID NO:4). Alternatively, the subtype is H1N1 and the PL is the PL motif RSEV (SEQ ID NO:7). The method can also include contacting the sample with a detection antibody. Preferably, the detection antibody includes a signal generating compound and does not inhibit the binding of PL to the PDZ or the capture antibody to the NS1.

The PDZ polypeptide or antibody can be immobilized on a solid support. If the solid support is a capillary flow assay device the contacting step involves dipping the stick in the patient sample. Preferably, the capillary flow assay is an immunoassay. Preferably, the solid support is a lateral flow assay.

In one aspect, the invention provides kits for the identification and subtyping of Influenza A virus in a patient sample, having an agent that specifically binds to the Influenza A virus NS1 immobilized on a solid support. Preferably, the agent is an antibody, a PDZ polypeptide, an oligonucleotide aptamer, or a mixture.

In a further aspect, the invention provides kits for the identification and or subtyping of influenza A virus in a patient sample, including an agent that specifically binds to a Influenza A virally encoded protein; and an agent that specifically binds to an NS1 protein. Preferably, the agent that specifically binds to an NS1 protein, binds to the PL region on the protein. Preferably, the agent is an antibody, a PDZ polypeptide, an oligonucleotide aptamer, or a mixture. Preferably, the Influenza A virally encoded protein is NS1.

In one aspect, the invention provides kits for the identification and or subtyping of influenza A virus in a patient sample, including an agent that specifically binds to NS1 other than at a PL motif and an agent that specifically binds to NS1 at a PL motif.

In one aspect, the invention provides kits having a plurality of PDZ polypeptides specific for a plurality of PL motifs in a plurality of NS1 proteins of a plurality of influenza A viruses.

In one aspect, the invention provides methods for identifying a PDZ polypeptide capable of specifically binding to an influenza virus PDZ ligand (PL), by bringing the influenza virus non-structural protein PL into contact with a candidate polypeptide having a PDZ domain under conditions suitable for binding; detecting specific binding of the PL to the candidate polypeptide; and confirming that the PL is binding to the PDZ binding site.

In one aspect, the invention provides isolated antibodies that specifically bind to a carboxy-terminal motif in an NS1 protein of influenza virus type A. Preferably, the carboxy-terminal motif having a PL motif is ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV, or SKI. Preferably, the antibody is a monoclonal antibody or an antibody fragment. Preferably, the PL motif is ESEV/I/A (SEQ ID NO:19).

In one aspect, the invention provides methods for the treatment or prophylaxis of a patient having or at risk of an Influenza virus type A infection, by administering to the patient an effective regime of an agent that that inhibits interaction of an NS1 protein of the virus with a PDZ protein of the cell and thereby effecting treatment or prophylaxis of the infection. Preferably, the agent is an antibody that specifically binds to the PL motif of an NS1 protein of Influenza virus type A. Preferably, the agent is an antisense oligonucleotide, a small molecule, an siRNA or a zinc finger protein, and the agent inhibits expression of either the influenza A NS1 protein or a PDZ protein. Preferably, the PL motif of the NS1 is ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV, or SKI. Preferably, the agent is a PDZ polypeptide and it includes at least the binding region that interacts with a PL, SEQ ID NO:1. Preferably, the PDZ polypeptide is at least one of: Outer membrane, PSD95 (PDZ # 2), PSD95 (PDZ #1,2,3), DLG1 (PDZ #1), DLG1 (PDZ #1,2), DLG1 (PDZ #2), DLG2 (PDZ #1), DLG2 (PDZ #2), Magi3 (PDZ #1), PTN3 (PDZ #1), MAST2 (PDZ #1), NeDLG (PDZ #1,2), Shank1 d1, Shank2 d1, Shank3 d1, Syntrophin 1 alpha, Syntrophin gamma 1, Magi1 (PDZ #1), Magi1 (PDZ #4), Tip1; PTPL1 (PDZ #1), Mint3 (PDZ #1), Lym Mystique (PDZ #1), DLG2 (PDZ #3), MUPP1 (PDZ #8), NeDLG (PDZ #1), DLG5 (PDZ #1), PSD95 (PDZ #1), NumBP (PDZ #3), LIMK1 (PDZ #1), KIAA0313, DLG1 (PDZ #2), Syntenin (PDZ #2), Pick1, MAST2, PTN3 (PDZ #1), NOS1 (PDZ # 1, 2, 3), MINT1 (PDZ # 2), ZO-1 (PDZ #2), NSP and RIM2.

In a further aspect, the invention provides methods for screening for anti-viral agents, by contacting a PDZ polypeptide and an influenza viral PDZ ligand (PL) in the presence and absence of a test compound; and comparing the amount of PDZ/PL binding in the presence of the test compound as compared to the absence, preferably the anti-viral agent reduces PDZ/PL binding and may also include testing the agent in vivo or intracellularly to identify whether it interferes with Interferon production.

In one aspect, the invention provides non-natural PDZ ligand (PL) peptide diagnostic reagents, having a linear array of amino acids selected from within the C-terminal amino acid sequence of an Influenza A protein, such that the PL is capable of binding to a mammalian PDZ polypeptide. Preferably, the PL has the motif: S/T-X-V/I/L where the S is serine, T is threonine, V is valine, I is isoleucine, L is leucine and X is any amino acid. Preferably, the array of Influenza A NS1 proteins includes at least one of ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV or SKI. A diagnostic reagent such as a positive control, a negative control, an assay standard, an assay calibrator, a competition assay ligand, a labeled peptide detect agent or a solid-phase capture agent can also be included. A synthetic peptide, a recombinant polypeptide, a substantially purified natural PL polypeptide, a substantially purified fragment of a natural PL polypeptide, a peptide mimetic PL, an oligonucleotide aptamer PL or a polypeptide aptamer PL can also be included. Preferably, the PL peptide is from the Influenza A NS1 protein.

In one aspect, the invention provides a non-natural PDZ polypeptide diagnostic reagent for detecting an Influenza A PL in a biological sample having a non-natural PDZ polypeptide capable of binding to an Influenza A NS1 protein, preferably the PDZ domain protein diagnostic reagent is selected from the group of diagnostic reagents consisting of a positive control, a negative control, an assay standard, an assay calibrator, a competition ligand, a labeled protein detect binding partner and a capture agent, preferably Outer Membrane, PSD95 (PDZ # 2), PSD95 (PDZ #1,2,3), DLG1 (PDZ #1), DLG1 (PDZ #1,2), DLG1 (PDZ #2), DLG2 (PDZ #1), DLG2 (PDZ #2), Magi3 (PDZ #1), PTN3 (PDZ #1), MAST2 (PDZ #1), NeDLG (PDZ #1,2), Shank1 d1, Shank2 d1, Shank3 d1, Syntrophin1 alpha, Syntrophin gamma 1, Magi1 (PDZ #1), Magi1 (PDZ #4), Tip1; PTPL1 (PDZ #1), Mint3 (PDZ #1), Lym Mystique (PDZ #1), DLG2 (PDZ #3), MUPP1 (PDZ #8), NeDLG (PDZ #1), DLG5 (PDZ #1), PSD95 (PDZ #1), NumBP (PDZ #3), LIMK1 (PDZ #1), KIAA0313, DLG1 (PDZ #2), Syntenin (PDZ #2), Pick1, MAST2, PTN3 (PDZ #1), NOS1 (PDZ # 1, 2, 3), MINT1 (PDZ # 2), ZO-1 (PDZ #2), NSP or RIM2.

In a further aspect, the invention provides signal generating conjugate agents for detecting an Influenza A protein in a test sample having a non-natural PL or a non-natural PDZ either of which PL or PDZ is a peptide or a polypeptide covalently linked with a signal generating compound.

In one aspect, the invention provides methods for identifying whether a patient is infected with a pathogenic influenza A, by determining whether NS2 protein of influenza virus type A is present in a patient sample, the protein having a Serine at position 70, presence indicating the patient is infected with a pathogenic strain of Influenza A. Preferably the determining step is contacting a patient sample with an agent that specifically binds to a sequence having the Serine 70. Preferably the agent is an antibody or a nucleic acid.

In one aspect, methods for identifying whether a patient is infected with a pathogenic avian influenza virus type A are provides that involve, contacting a patient sample with a PSD-95 PDZ protein; and detecting specific binding between the PSD-95 PDZ protein and the sample, specific binding indicating presence of the influenza virus type A, presence indicating the patient is infected with a pathogenic avian influenza virus type A. Preferably, the pathogenic influenza virus type A is H5N1. Preferably, the PSD-95 PDZ protein is domain 2 of PSD-95. Preferably, the influenza NS1 protein PL has a motif of ESKV, ESEI (SEQ ID NO:3), or ESEV (SEQ ID NO:2). In one aspect, the contacting step involves contacting the patient sample with the PSD-95 PDZ protein and an antibody that specifically binds to a different epitope of influenza virus type A protein NS1 than the PSD-95 PDZ protein, and the PSD-95 is immobilized on a support, and the detecting step detects the NS1 protein specifically bound to the antibody. In a further aspect, the method includes another step of contacting the patient sample with a second PDZ protein, INADL d8 as a control and determining specific binding, a greater specific binding of the first PDZ-95 protein relative to the second PDZ protein, indicating that the patient is infected with a pathogenic avian influenza virus type A.

BRIEF DESCRIPTION OF THE DRAWINGS

FIG. 7 shows that INADL d8 interacts with H3N2 NS1 in cells.

DEFINITIONS

Figure 1:
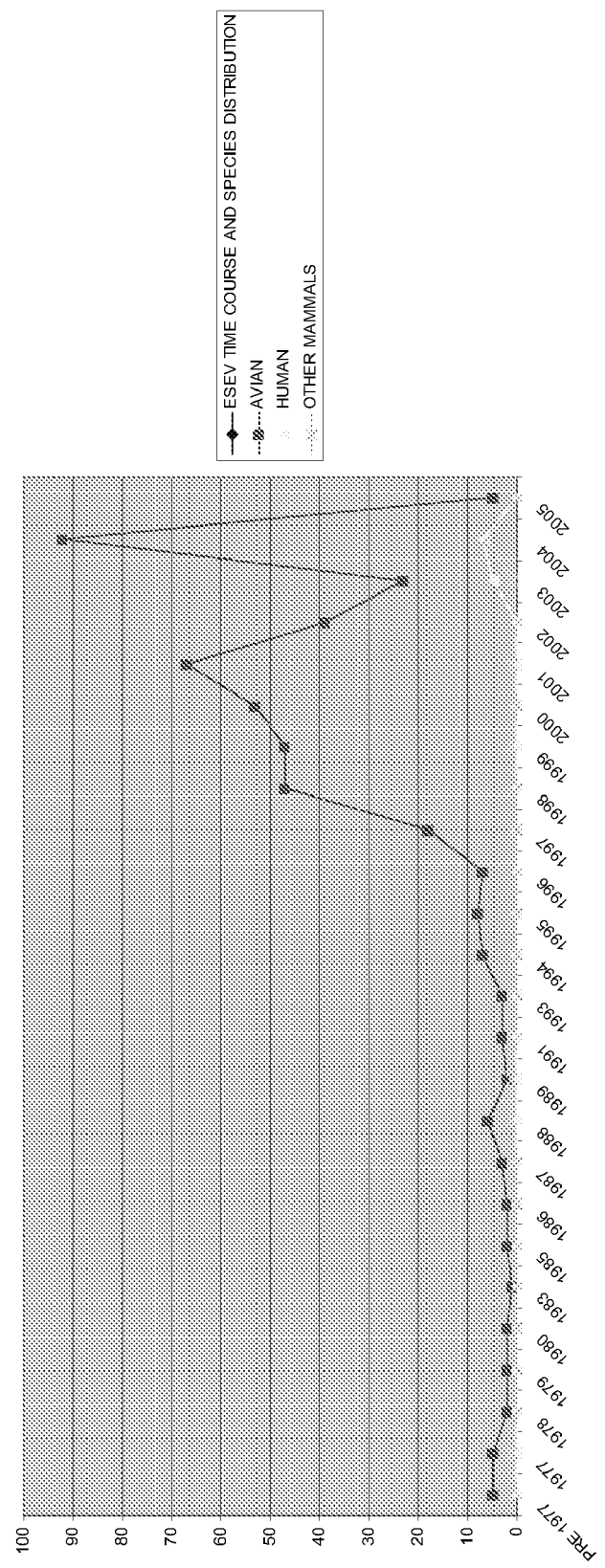
FIG. 1 is a graph showing the timecourse for the appearance of the NS1 PL sequence ESEV (SEQ ID NO:2) in avian, human and other mammals.

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the presently preferred methods and materials are described. Definitions are provided in a logical (rather than alphabetical) order to assist the reader in the practice of the invention, i.e., as follows: namely, "Agent" includes any substance, molecule, element, compound, entity, or a combination thereof including but not limited to, e.g., proteins, polypeptides, small organic molecules, polysaccharide-peptide chimeric molecules, nucleotide-peptide chimeric molecules and the like. Representative examples of agents include natural products in a non-natural state, synthetic peptide compounds, chemical compounds, as well as, combinations of two or more natural or unnatural compounds. Unless otherwise specified, the terms "agent", "substance", and "compound" are used interchangeably.

"Avian influenza A" means an influenza A subtype that infects an avian subject and is transmissible between avian subjects. Representative examples of avian influenza hemmagglutinin subtypes include H5, H6, H7, H9 and H10 and representative strains include H5N1, H6N2, H7N3, H7N7, H9N2, H10N4 and H10N5.

"Avian subject" means a subject suitable for testing or treatment including all species of birds, including both wild birds (such as wildfowl) and domesticated species (such as poultry). Preferably, the avian subject to be tested or treated is selected from the group consisting of chickens, turkeys, ducks, geese, quail, ostrich, emus and exotic birds such as parrots, cockatoos and cockatiels. More preferably, the avian subject to be tested is a chicken, turkey, goose or quail.

"Non-natural" is used to mean a composition not occurring in nature. Representative examples of non-natural compositions include substantially purified compositions, as well as, those containing compounds which do not appear in the same chemical form in nature, e.g., chemically and genetically modified proteins, nucleic acids and the like.

"Modulation" as used herein refers to both up-regulation, (i.e., activation or stimulation) for example by agonizing, and down-regulation (i.e. inhibition or suppression) for example by antagonizing a binding activity. As used herein, the term "PDZ ligand binding modulator" refers to an agent that is able to alter binding of a PDZ domain-containing polypeptide to a PDZ-ligand (i.e., "PL"). Modulators include, but are not limited to, both activators e.g. agonists and inhibitors e.g. antagonists. An inhibitor may cause partial or complete inhibition of binding.

"Pathogenic strain of influenza A" when used in the context of distinguishing between different strains of influenza virus means a "notifiable avian influenza" (NAI) virus according to the guidelines set forth by the OIE World Organization for Animal Health, World Health Organization or their designated representatives e.g., as set forth in the OIE "Manual of Diagnostic Tests and Vaccines for Terrestrial Animals, 5th edition, 2004 (www.oie.int). Further, the subject pathogenic strain has "high pathogenicity" in a representative test for virulence or an H5 or H7 virus with an influenza A hemmagglutinin (HA) precursor protein HA0 cleavage site amino acid sequence that is similar to any of those that have been observed in virulent viruses, i.e., as defined by the OIE or a representative similar national or international organization or trade association. Representative examples of HA0 cleavage site amino acid sequences in virulent H5 and H7 strains of influenza A comprise multiple basic amino acids (arginine or lysine) at the cleavage site of the viral precursor hemagglutinin protein, e.g., where low virulence strains of H7 viruses have -PEIPKGR*GLF-(SEQ ID NO:20) or -PENPKGR*GLF-(SEQ ID NO:21) highly pathogenic strains have -PEIPKKKKR*GLF-(SEQ ID NO:22), -PETPKRKRKR*GLSF-(SEQ ID NO:23), -PEIPKKREKR*GLF-(SEQ ID NO:24) or -PETPKRRRR*GLF-(SEQ ID NO:25). Current representative tests for virulence include inoculation of 4-8 week old chickens with infectious virus wherein strains are considered to be highly pathogenic if they cause more than 75% mortality within 10 days; and/or, any virus that has an intravenous pathogenicity index (IVPI) greater than 1.2, wherein intravenously inoculated birds are examined at 24-hour intervals over a 10-day period; scored for "0", normal; "1" sick; "2" severely sick"; "3" dead; and, the mean score calculated as the IVPI. The latter highly pathogenic strains are referred to by the OIE as a "highly pathogenic NAI virus" (HPNIA). Current representative examples of NAI include the H5 and H7 strains of influenza A. Current representative examples of HPNIA include H5N1.

"Less Pathogenic strain of influenza A" means an avian influenza A that is notifiable, i.e., an NAI isolate (supra), but which is not pathogenic for chickens and does not have an HA0 cleavage site amino acid sequence similar to any of those that have been observed in virulent viruses, i.e., a strain referred to by the OIE as a "low pathogenicity avian influenza (LPAI).

"PDZ domain" means an amino acid sequence homologous over about 90 contiguous amino acids; preferably about 80-90; more preferably, about 70-80, more preferably about 50-70 amino acids with the brain synaptic protein PSD-95, the *Drosophila* septate junction protein Discs-Large (DLG) and/or the epithelial tight junction protein ZO1 (ZO1). Representative examples of PDZ domains are also known in the art as Discs-Large homology repeats ("DHRs") and "GLGF" repeats (SEQ ID NO:26). Examples of PDZ domains are found in diverse membrane-associated proteins including members of the MAGUK family of guanylate kinase homologs, several protein phosphatases and kinases, neuronal nitric oxide synthase, tumor suppressor proteins, and several dystrophin-associated proteins, collectively known as syntrophins. The instant PDZ domains encompass both natural and non-natural amino acid sequences. Representative examples of PDZ domains include polymorphic variants of PDZ proteins, as well as, chimeric PDZ domains containing portions of two different PDZ proteins and the like. Preferably, the instant PDZ domains contain amino acid sequences which are substantially identical to those disclosed in U.S. patent application Ser. No. 10/485,788 (filed Feb. 3, 2004), International patent application PCT/US03/285/28508 (filed Sep. 9, 2003), International patent application PCT/US01/44138 (filed Nov. 9, 2001), incorporated herein by reference in their entirety. Representative non-natural PDZ domains include those in which the corresponding genetic code for the amino acid sequence has been mutated, e.g., to produce amino acid changes that alter (strengthen or weaken) either binding or specificity of binding to PL. Optionally a PDZ domain or a variant thereof has at least 50, 60, 70, 80 or 90% sequence identity with a PDZ domain from at least one of brain synaptic protein PSD-95, the *Drosophila* septate junction protein Discs-Large (DLG) and/or the epithelial tight junction protein ZO1 (ZO1), and animal homologs. Optionally a variant of a natural PDZ domain has at least 90% sequence identity with the natural PDZ domain. Sequence identities of PDZ domains are determined over at least 70 amino acids within the PDZ domain, preferably 80 amino acids, and more preferably 80-90 or 80-100 amino acids. Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. The term "allelic variant" is used to refer to variations between genes of different individuals in the same species and corresponding variations in proteins encoded by the genes. An exemplary PDZ domain for PSD-95 d2 is provided as SEQ ID NO:1.

"PDZ protein", used interchangeably with "PDZ-domain containing polypeptides" and "PDZ polypeptides", means a naturally occurring or non-naturally occurring protein having a PDZ domain (supra). Representative examples of PDZ proteins have been disclosed previously (supra) and include CASK, MPP1, DLG1, DLG2, PSD95, NeDLG, TIP-33, TIP-43, LDP, LIM, LIMK1, LIMK2, MPP2, AF6, GORASP1, INADL, KIAA0316, KIAA1284, MAGI1, MAST2, MINT1, NSP, NOS1, PAR3, PAR3L, PAR6 beta, PICK1, Shank 1, Shank 2, Shank 3, SITAC-18, TIP1, and ZO-1. The instant non-natural PDZ domain polypeptides useful in screening assays may contain e.g. a PDZ domain that is smaller than a natural PDZ domain. For example a non-natural PDZ domain may optionally contain a "GLGF" motif, i.e., a motif having the GLGF amino acid sequence (SEQ ID NO:26), which typically resides proximal, e.g. usually within about 10-20 amino acids N-terminal, to an PDZ domain. The latter GLGF motif (SEQ ID NO:26), and the 3 amino acids immediately N-terminal to the GLGF motif (SEQ ID NO:26) are often required for PDZ binding activity. Similarly, non-natural PDZ domains may be constructed that lack the β-sheet at the C-terminus of a PDZ domain, i.e., this region may often be deleted from the natural PDZ domain without affecting the binding of a PL. Some exemplary PDZ proteins are provided and the GI or accession numbers are provided in parenthesis: PSMD9 (9184389), af6 (430993), AIPC (12751451), ALP (2773059), APXL-1 (13651263), MAGI2 (2947231), CARDI1 (1282772), CARD14 (13129123), CASK (3087815), CNK1 (3930780), CBP (3192908), Densin 180 (16755892), DLG1 (475816), DLG2 (12736552), DLG5 (3650451), DLG6 splice var 1 (14647140), DLG6 splice var 2 (AB053303), DVL1 (2291005), DVL2 (2291007), DVL3 (6806886), ELFIN 1 (2957144), ENIGMA (561636), ERBIN (8923908), EZRIN binding protein 50 (3220018), FLJ00011 (10440342), FLJ11215 (11436365), FLJ12428 (BC012040), FLJ12615 (10434209), FLJ20075 Semcap2 (7019938), FLJ21687 (10437836), FLJ31349 (AK055911), FLJ32798 (AK057360), GoRASP1 (NM031899), GoRASP2 (13994253), GRIP1 (4539083), GTPase Activating Enzyme (2389008), Guanine Exchange Factor (6650765), HEMBA 1000505 (10436367), HEMBA 1003117 (7022001), HSPC227 (7106843), HTRA3 (AY040094), HTRA4 (AL576444), INADL (2370148), KIAA0147 Vartul (1469875), KIAA0303 MAST4 (2224546), KIAA0313 (7657260), KIAA0316 (6683123), KIAA0340 (2224620), KIAA0380 (2224700), KIAA0382 (7662087), KIAA0440 (2662160), KIAA0545 (14762850), KIAA0559 (3043641), KIAA0561 MAST3 (3043645), KIAA0613 (3327039), KIAA0751 RIM2 (12734165), KIAA0807 MAST2 (3882334), KIAA0858 (4240204), KIAA0902 (4240292), KIAA0967 (4589577), KIAA0973 SEMCAP3 (5889526), KIAA1202 (6330421), KIAA1222 (6330610), KIAA1284 (6331369), KIAA1389 (7243158), KIAA1415 (7243210), KIAA1526 (5817166), KIAA1620 (10047316), KIAA1634 MAGI3 (10047344), KIAA1719 (1267982), LIM Mystique (12734250), LIM (3108092), LIMK1 (4587498), LIMK2 (1805593), LIM-RIL (1085021), LU-1 (U52111), MAGI1 (3370997), MGC5395 (BC012477), MINT1 (2625024), MINT3 (3169808) MPP1 (189785), MPP2 (939884), MPP3 (1022812), MUPP1 (2104784), NeDLG (10853920), Neurabin II (AJ401189), NOS1 (642525), novel PDZ gene (7228177), Novel Serine Protease (1621243), Numb Binding Protein (AK056823), Outer Membrane Protein (7023825), p55T (12733367), PAR3 (8037914), PAR3-like (AF428250), PAR6 (2613011), PAR6BETA (13537116), PAR6GAMMA (13537118), PDZ-73 (5031978), PDZK1 (2944188), PICK1 (4678411), PIST (98394330), prIL16 (1478492), PSAP (6409315), PSD95 (3318652), PTN-3 (179912), PTN-4 (190747), PTPL1 (515030), RGS12 (3290015), RGS3 (18644735), Rho-GAP10 (NM020824), Rhophilin-like (14279408), Serine Protease (2738914), Shank 2 (6049185), Shank 3 (AC000036), Shroom (18652858), Similar to GRASP65 (14286261), Similar to Ligand of Numb px2 (BC036755), Similar to PTP Homolog (21595065), SIP1 (2047327), SITAC-18 (8886071), SNPCIIA (20809633), Shank 1 (7025450), Syntenin (2795862), Syntrophin 1 alpha (1145727), Syntrophin beta 2 (476700), Syntrophin gamma 1 (9507162), Syntrophin gamma 2 (9507164), TAX2-like protein (3253116), TIAM 1 (4507500), TIAM 2 (6912703), TIP 1 (2613001), TIP2 (2613003), TIP33 (2613007), TIP43 (2613011), X-11 beta (3005559), ZO-1 (292937), ZO-2 (12734763), ZO-3 (10092690).

"PDZ ligand", abbreviated "PL", means a naturally occurring protein that has an amino acid sequence which binds to and forms a molecular interaction complex with a PDZ-domain. Representative examples of PL have been provided previously in prior US and International patent applications (supra). Additional examples of influenza A PL are provided in the Examples section, below.

"PDZ agent" is used to mean a compound that interferes with the binding interaction occurring between a PDZ ligand polypeptide and a PDZ domain-containing polypeptide in a test assay by at least 20%, e.g., at least 30%, at least 40%, at least 50%, at least 60%, at least 70%, at least 80%, at least 90%, at least 95%, up to about 99% or 100%, as compared to controls that do not include the PDZ agent. While not wishing to be limited to any particular mechanism of action, the instant PDZ agent may interfere e.g. by binding to a PDZ domain that would otherwise bind to an influenza NS1 ligand; or alternatively, it may bind directly to the NS1 ligand to prevent its binding to the PDZ protein. In general, the latter PDZ agents are those which exhibit $IC_{50}$s in a particular assay in the range of about 1 mM or lower. Compounds which exhibit lower $IC_{50}$s, for example, commonly have $IC_{50}$s of about 100 μM, 10 μM, 1 μM, 100 nM, 10 nM, 1 nM, or even lower. The latter PDZ agents are useful in therapeutic and prophylactic medicinal compositions administered to alleviate, treat or prevent one or more symptoms of disease resulting from infection with an influenza A virus. "PL modulator" is used in the context of a PDZ agent (supra) to mean a compound that binds to an influenza A NS1 protein and modulates its binding to a PDZ domain.

"PDZ modulator" is used in the context of a PDZ agent (supra) to mean a compound that binds to a PDZ domain and modulates the binding of an influenza NS1 protein at the subject PDZ domain site.

The instant PDZ modulators and PL modulators may be peptides, peptidomimetics or small molecule mimetics designed to bind a PDZ domain or PL, respectively. Assays for determining whether a PDZ modulator binds to a PDZ domain are described in great detail in the Examples section, below. Similarly, assays for determining whether a PL modulator binds to a PDZ domain are set forth, e.g., recombinant PDZ domain fusion proteins binding to recombinant NS1 fusion proteins.

"PDZ-mediated disorder" means one or more symptoms in an Influenza A infected subject that result from binding of an influenza A viral protein PL at a host cell PDZ domain. The latter symptoms caused by viral infection, include, but are not limited to fever, cough, sore throat, muscle aches, conjunctivitis, breathing problems, excessive mucus production in the airways, increased susceptibility to secondary bacterial infection, pneumonia, neural infection and the like.

"Sick" when used herein to refer to an avian subject, includes signs and symptoms which may vary from sudden death with few overt signs of disease to a more characteristic disease with respiratory signs, excessive lacrimation, sinusitis, edema of the head, cyanosis of the unfeathered skin and diarrhea. Representative diagnostic signs, specimens and tests of "sick" disclosed by OIE in their health guidelines "Manual of Diagnostic Tests and Vaccines for Terrestrial Animals, 5th edition, 2004, World Organization for Animal Health" are incorporated herein by reference in their entirety.

"Analog" is used herein to refer to a molecule that structurally resembles a natural PDZ or PL molecule of interest but which has been modified e.g. by replacing or chemically modifying one or more selected amino acid substituents.

Compared to the starting molecule, an analog may exhibit the same, similar or improved utility. Synthesis and screening of analogs to identify variants of known compounds having improved traits is well known in the medicinal arts, e.g., increasing binding affinity, altering selectivity of binding to a target, lowering binding to non-target molecules, improving stability in vitro and in vivo and improving pharmacologic properties.

"Contacting" has its normal meaning and refers to combining two or more agents so that constituents are thereby brought together, e.g., a PL in a test sample is brought together with a PDZ. Contacting can occur in vitro, e.g., a PDZ protein is brought together with a cell lysate in a test tube or other container; or, in situ, e.g., a natural host cell PDZ protein and a natural viral PL are brought together in an influenza infected cell by virtue of the natural biosynthetic activities of the cell. Alternatively, a recombinant PDZ is brought together with a viral PL by e.g. transfecting a PDZ domain coding sequence into an influenza A infected cell.

"Polymer" is used to refer to a serial array of one or more types of repeating units, regardless of the source. Polymers may be found in biological systems and particularly include polypeptides and polynucleotides, as well as, compounds containing amino acids, nucleotides, or analogs thereof. The term "polynucleotide" refers to a polymer of nucleotides, or analogs thereof, of any length, including oligonucleotides that range from 10-100 nucleotides in length and polynucleotides of greater than 100 nucleotides in length. The term "polypeptide" refers to a polymer having a serial array of amino acids of any length, preferably in the range of about 12 to about 50 amino acids in serial array; and, most preferably greater than about 50 amino acids.

"Polypeptide" and "protein" are used interchangeably to include polymeric serial arrays of amino acids in which the natural peptide-bond backbone has been replaced with non-natural synthetic backbones, and polypeptides in which one or more of the natural amino acids have been replaced with one or more non-naturally occurring or synthetic mimetic amino acids.

"Fusion protein" means a polypeptide composed of amino acid sequences derived from two or more natural proteins which are expressed as a single recombinant protein, i.e., two or more amino acid sequences that while not attached in their native state are joined together in the recombinant protein e.g. by their respective amino and carboxyl termini through a peptide linkage to form a single continuous amino acid sequence. Fusion proteins may be a combination of two, three or even four or more different natural or non-natural proteins. Representative fusion proteins include those with two or more heterologous, i.e., unrelated, amino acid sequences; those with both heterologous and homologous, i.e., related, sequences. Fusion proteins also consist of amino acid sequences with or without N-terminal methionine residues, those tagged for identification with antigenic epitopes, as well as, those having a signal generating compound as a fusion partner, e.g., fusion proteins with a fluorescent partner; an enzyme partner such as β-galactosidase; a chemilluminescent partner such as luciferase; and the like.

"Capture agent", when used in the context of a diagnostic assay reagent or method, refers to an agent that is capable of binding to an influenza viral analyte in a binding interaction that is of sufficient strength, e.g. measured as a binding affinity, and specificity that it enables concentration of the viral analyte from within a mixture of different viral analytes; and, in a time period suitable for use in an a diagnostic assay format, i.e., typically about 5 minutes to about 90 minutes; preferably about 5 minutes to about 60 minutes; and, most preferably about 5 minutes to about 30 minutes. According to alternative embodiments of the invention, the instant capture agents are contain either a PDZ domain or a PL. Representative capture agents are illustrated in the Examples section below. Capture agents usually "specifically bind" one or more viral analytes, e.g., PL containing proteins, to the exclusion of other analytes, e.g., proteins that do not contain a PL. Preferably, the instant capture agents bind the subject viral analyte with a dissociation constant ($K_D$) that is less than about $10^{-6}$ M; preferably, less than about $10^{-7}$M; and, most preferably, less than about $10^{-8}$ M.

"Specific binding", when used in regard to the binding interaction between the instant natural and non-natural PDZ domain and PL reagents, is used to refer to the ability of a capture- or detect-agent to preferentially bind to a particular viral analyte that is present in a mixture of different viral analytes. In certain embodiments, the subject specific binding interaction is capable of discriminating between proteins having or lacking a PL, i.e., in some embodiments the discriminatory capacity is greater than about 10- to about 100-fold; and, preferably greater than about 1000- to about 10,000-fold.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

"Binding interference", is used in regard to the first binding interaction of a PDZ domain with a PL to form a complex in a diagnostic assay format; wherein, the subject complex is subsequently detected in a requisite second binding interaction, i.e., interference results when the first binding interaction inhibits the second binding interaction resulting in a decrease in the strength of the signal produced by a signal generating compound. The signal generated by the instant compositions in the methods of the invention are subject to less than 15% binding interference; preferably, less than 10%; and, most preferably less than about 5%.

"Capture agent/analyte complex" is a complex that results from the specific binding of a capture agent, e.g. a PDZ domain fusion protein, with an analyte, e.g. an influenza viral protein having a PL. A capture agent and an analyte specifically bind, i.e., the one to the other, under "conditions suitable for specific binding", wherein such physicochemical conditions are conveniently expressed e.g. in terms of salt concentration, pH, detergent concentration, protein concentration, temperature and time. The subject conditions are suitable to allow binding to occur e.g. in a solution; or alternatively, where one of the binding members is immobilized on a solid phase. Representative conditions so-suitable are well known in the diagnostic arts e.g. see, Harlow and Lane, "Antibodies: A Laboratory Manual", Cold Spring Harbor Laboratory, Cold Spring Harbor, N.Y. (1989). Suitable conditions preferably result in binding interactions having dissociation constants ($K_D$) that are less than about $10^{-6}$M; preferably, less than about $10^{-7}$M; and, most preferably less than about $10^{-8}$M.

"Surface-bound capture agent" is used interchangeably with "solid-phase capture agent" to refer to a PDZ domain or PL capture agent that is immobilized on a surface of a solid substrate, e.g., a sheet, bead, or other structure, such as a plate with wells and the like as set forth in greater detail below. In certain embodiments, the collections of capture agents employed herein are present on a surface of the same support, e.g., in the form of an array wherein a particular location on a surface is correspond to the presence of a particular surface-bound capture agent.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

"Assessing", when used in the context of the instant assay, refers to evaluating a test result and/or conducting a test measurement to determine whether an influenza A viral analyte is present in a test sample. Representative evaluations include "determining", "measuring", "evaluating", "assessing" and "assaying", as they may be used interchangeably to include quantitative and/or qualitative determinations. Assessing may be relative or absolute. "Assessing binding" includes determining the amount or extent of a binding interaction, as well as, determining whether particular binding interaction has occurred, i.e., whether binding is present or absent.

"Treatment", "treating", "treat", and the like, refer to administering a compound according the invention to a subject in need thereof with the aim of achieving a desired pharmacologic and/or physiologic effect, e.g., preventing or alleviating one or more symptoms of disease (supra). The treatment may be administered in a prophylactic manner, i.e., to prevent development of one or more symptoms of disease; and/or, therapeutically, to reduce or eliminate a disease symptom. Subjects in need thereof include mankind and domesticated animals.

"Subject", is used herein to refer to a man and domesticated animals, e.g. mammals, fishes, birds, reptiles, amphibians and the like.

"Signal generating compound", abbreviated "SGC", means a molecule that can be linked to a PL or a PDZ (e.g. using a chemical linking method as disclosed further below and is capable of reacting to form a chemical or physical entity (i.e., a reaction product) detectable in an assay according to the instant disclosure. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds, radioisotopes (e.g., $^{131}$I, $^{125}$I, $^{14}$C, $^{3}$H, $^{35}$S, $^{32}$P and the like), enzymes (e.g., below), binding proteins (e.g., biotin, avidin, streptavidin and the like), magnetic particles, chemically reactive compounds (e.g., colored stains), labeled-oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative SGC's useful in a signal generating conjugate include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); IUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); IUB Class 4 (e.g., lyases); IUB Class 5 especially 5.3 and 5.4 (e.g., phosphoglucose isomerase, trios phosphatase isomerase, phosphoglucose mutase and the like.) Signal generating compounds also include SGC whose products are detectable by fluorescent and chemilluminescent wavelengths, e.g., luciferase, fluorescence emitting metals such as $^{152}$Eu, or others of the lanthanide series; compounds such as luminol, isoluminol, acridinium salts, and the like; bioluminescent compounds such as luciferin; fluorescent proteins; and the like. Fluorescent proteins include, but are not limited to the following: namely, (i) green fluorescent protein (GFP), i.e., including, but not limited to, a "humanized" versions of GFP wherein codons of the naturally-occurring nucleotide sequence are exchanged to more closely match human codon bias; (ii) GFP derived from *Aequoria victoria* and derivatives thereof, e.g., a "humanized" derivative such as Enhanced GFP, which are available commercially, e.g., from Clontech, Inc.; (iii) GFP from other species such as *Renilla reniformis, Renilla mulleri*, or *Ptilosarcus guernyi*, as described in, e.g., WO 99/49019 and Peelle et al. (2001) *J. Protein Chem.* 20:507-519; (iv) "humanized" recombinant GFP (hrGFP) (Stratagene); and, (v) other fluorescent and colored proteins from Anthozoan species, such as those described in Matz et al. (1999)*Nature Biotechnol.* 17:969-973; and the like. The subject signal generating compounds may be coupled to a PL or PDZ domain polypeptide. Attaching certain SGC to proteins can be accomplished through metal chelating groups such as EDTA. The subject SGC share the common property of allowing detection and/or quantification of an influenza PL analyte in a test sample. The subject SGC are detectable using a visual method; preferably, an a method amenable to automation such as a spectrophotometric method, a fluorescence method, a chemilluminescent method, a electrical nanometric method involving e.g., a change in conductance, impedance, resistance and the like and a magnetic field method.

"Solid phase", as used herein, means a surface to which one or more reactants may be attached electrostatically, hydrophobically, or covalently. Representative solid phases include e.g.: nylon 6; nylon 66; polystyrene; latex beads; magnetic beads; glass beads; polyethylene; polypropylene; polybutylene; butadiene-styrene copolymers; silastic rubber; polyesters; polyamides; cellulose and derivatives; acrylates; methacrylates; polyvinyl; vinyl chloride; polyvinyl chloride; polyvinyl fluoride; copolymers of polystyrene; silica gel; silica wafers glass; agarose; dextrans; liposomes; insoluble protein metals; and, nitrocellulose. Representative solid phases include those formed as beads, tubes, strips, disks, filter papers, plates and the like. Filters may serve to capture analyte e.g. as a filtrate, or act by entrapment, or act by covalently-binding PL or PDZ onto the filter (e.g., see the Examples section below). According to certain embodiments of the invention, a solid phase capture reagent for distribution to a user may consist of a solid phase (supra) coated with a "capture reagent" (below), and packaged (e.g., under a nitrogen atmosphere) to preserve and/or maximize binding of the capture reagent to an influenza PL analyte in a biological sample.

"Capture reagent" means an immobilized PDZ polypeptide (or peptide) capable of binding an influenza PL. The subject capture reagent may consist of a solution of a PDZ; or a PDZ modified so as to promote its binding to a solid phase; or a PDZ already immobilized onto the surface of a solid phase, e.g., immobilized by attaching the PDZ to a solid phase (supra) through electrostatic forces, van Der Waals forces, hydrophobic forces, covalent chemical bonds, and the like (as disclosed further below.) Representative examples of PDZ capture reagents are disclosed in the Examples section, below, and include mobile solid phase PDZ capture reagents such as PDZ immobilized on movable latex beads e.g. in a latex bead dipstick assay.

"Detect reagent" means a conjugate containing an SGC linked to a PL or P)DZ polypeptide or peptide; or alternatively, an SGC linked to an antibody capable of binding specifically to a PL or a PDZ. Representative examples of the instant detect reagents include complexes of one or more PL or PDZ with one or more SGC compounds, i.e., macromolecular complexes. The subject detect reagents include mobile solid-phase detect reagents such as movable latex beads in latex bead dipstick assays.

"Biological sample" means a sample obtained from a living (or dead) organism, e.g., a mammal, fish, bird, reptile, marsupial and the like. Biological samples include tissue fluids, tissue sections, biological materials carried in the air or in water and collected there from e.g. by filtration, centrifugation and the like, e.g., for assessing bioterror threats and the like. Alternative biological samples can be taken from fetus or egg, egg yolk, and amniotic fluids. Representative biological fluids include, e.g. urine, blood, plasma, serum, cerebrospinal fluid, semen, lung lavage fluid, feces, sputum, mucus, water carrying biological materials and the like. Alternatively, biological samples include nasopharyngeal or oropharyngeal swabs, nasal lavage fluid, tissue from trachea, lungs, air sacs, intestine, spleen, kidney, brain, liver and heart, sputum, mucus, water carrying biological materials, cloacal swabs, sputum, nasal and oral mucus, and the like. Representative biological samples also include foodstuffs, e.g., samples of meats, processed foods, poultry, swine and the like. Biological samples also include contaminated solutions (e.g., food processing solutions and the like), swab samples from outpatient sites, hospitals, clinics, food preparation facilities (e.g., restaurants, slaughter-houses, cold storage facilities, supermarket packaging and the like). Biological samples may also include in-situ tissues and bodily fluids (i.e., samples not collected for testing), e.g., the instant methods may be useful in detecting the presence or severity or viral infection in the eye e.g., using eye drops, test strips applied directly to the conjunctiva; or, the presence or extent of lung infection by e.g. placing an indicator capsule in the mouth or nasopharynx of the test subject. Alternatively, a swab or test strip can be placed in the mouth. The biological sample may be derived from any tissue, organ or group of cells of the subject. In some embodiments a scrape, biopsy, or lavage is obtained from a subject. Biological samples may include bodily fluids such as blood, urine, sputum, and oral fluid; and samples such as nasal washes, swabs or aspirates, tracheal aspirates, chancre swabs, and stool samples. Methods are known to those of skill in the art for the collection of biological specimens suitable for the detection of individual pathogens of interest, for example, nasopharyngeal specimens such as nasal swabs, washes or aspirates, or tracheal aspirates in the case of high risk influenza A viruses involved in respiratory disease, oral swabs and the like. Thus, embodiments of the invention provide methods useful in testing a variety of different types of biological samples for the presence or amount of a influenza A contamination or infection. Optionally, the biological sample may be suspended in an isotonic solution containing antibiotics such as penicillin, streptomycin, gentamycin, and mycostatin.

"Ligand" as used herein refers to a PL compound capable of binding to an PDZ binding site. Representative examples of ligands include PL-containing complex viral particles (supra) as found in a variety of different strains of influenza A. The subject ligand is capable of filling a three-dimensional space in binding site of a PDZ domain binding site so that electrostatic repulsive forces are minimized, electrostatic attractive forces are maximized, and hydrophobic and hydrogen bonding forces are maximized. Ligands bind to PDZ polypeptides in a specific and saturable manner, and binding affinities may be measured according to ligand binding assays known to those skilled in the art, e.g. as disclosed further below.

"Specificity", when used in the context of an assay according to an embodiment of the invention, means that the subject assay, as performed according to the steps of the invention, is capable of properly identifying an "indicated" percentage of samples from within a panel of biological samples (e.g., a panel of 100 samples). The subject panel of samples all contain one or more murein analytes (e.g., positive control samples contaminated with bacteria or fungi.) Preferably the subject "indicated" specificity is greater than 85%, (e.g., the assay is capable of indicating that more than 85 of the 100 samples contain one or more murein analyte), and most preferably, the subject assay has an indicated specificity that is greater than 90%. Optionally, the subject assay is capable of identifying "true non-influenza A cases", i.e., detecting an "indicated" percentage of negative samples from within a panel of biological samples (e.g., a panel of 100 samples). Preferably, the instant steps of the invention are capable of properly identifying "true non-avian influenza A cases"; and most preferably, the instant steps of the invention are capable of properly identifying "true low-pathogenic avian influenza A cases". In different embodiments, the subject negative control panel of samples either do not contain influenza A PL analytes; or, contain non-avian influenza A PL analytes; or, contain non-pathogenic influenza A PL. Preferably the subject specificity is greater than 85%, (e.g., the assay is capable of indicating that more than 85 of the 100 samples and most preferably, the subject assay has specificity that is greater than 90%.

"Sensitivity", when used in the context of an assay according to an embodiment of the invention, means that the subject assay, as performed according to the steps of the invention, is capable of identifying at an "indicated" percentage those samples which contain an influenza PL analyte from within a panel of samples containing both positive controls (supra) and negative controls (i.e., lacking PL analyte.) Preferably the subject "indicated" sensitivity is greater than 85% and most preferably greater than 90%. Optionally, the subject assay is capable of identifying "true influenza A cases" at an "indicated" percentage of those samples which contain an influenza PL analyte from within a panel of samples. Preferably, the instant steps of the invention are capable of properly identifying "true avian influenza A cases"; and, most preferably, the instant steps of the invention are capable of properly identifying "true pathogenic avian influenza A cases". In different embodiments, the subject positive control panel of samples either contain influenza A PL analytes; or, contain avian influenza A PL analytes; or, contain highly pathogenic influenza A PL. Preferably the subject "indicated" sensitivity is greater than about 70% and more preferably greater than about 80%. Even more preferably, the sensitivity is greater than about 85% and most preferably greater than about 90% of that of the control. Alternatively, the sensitivity can be measured with respect to the sensitivity of a PCR reaction that identifies the same protein With respect to Specificity and Sensitivity, optionally, the following definitions can be applied:

"Positive predictive value", abbreviated PPV, means the percentage of samples that test positive in the instant method and are true avian influenza A cases. Preferably, the instant method has a PPV greater than about 65% and most preferably greater than about 80%.

"Negative predictive value", abbreviated NPV, means the percentage of samples the percentage of samples that test negative and are true negative influenza A cases. Preferably, the instant method has an NPV greater than about 85% and most preferably greater than about 90%.

"True positive influenza A" when used in reference to a biological sample means a sample containing influenza A virion particles as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype, RT-PCR detection of viral RNA or immunofluorescence detection of influenza A antigen in cells in respiratory specimens.

"True positive avian influenza A" when used in reference to a biological sample means a sample containing avian influenza A virion particles as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype, RT-PCR detection of viral RNA or immunofluorescence detection of influenza A antigen in cells in respiratory specimens.

"True positive highly pathogenic avian influenza A" when used in reference to a biological sample means a sample containing highly pathogenic avian influenza A virion particles as defined supra and as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype RT-PCR detection of viral RNA or immunofluorescence detection of influenza A antigen in cells in respiratory specimens.

"True negative influenza A" when used in reference to a biological sample means a sample that does not contain influenza A virion particles as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype RT-PCR detection of viral RNA or immunofluorescence detection of influenza A antigen in cells in respiratory specimens.

"True negative avian influenza A" when used in reference to a biological sample means a sample that does not contain avian influenza A virion particles as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype, RT-PCR detection of viral RNA or immunofluorescence detection of influenza A antigen in cells in respiratory specimens. In this case, the biological sample may contain influenza A virion particles other than avian influenza A virion particles, i.e., as defined supra.

"True negative highly pathogenic avian influenza A" when used in reference to a biological sample means a sample does not contain highly pathogenic avian influenza A virion particles as defined supra and as confirmed in two or more independent tests, e.g., isolation and cultivation in embryonated chicken eggs, identification of viral antigen in a commercial immunoassay test, immunodiffusion, hemagglutination and/or hemagglutination inhibition testing to identify the HA and/or NA subtype, RT-PCR detection of viral RNA or immunofluorescence detection of influenza A antigen in cells in respiratory specimens. The subject sample may however contain influenza A virion particles or lower pathogenicity avian influenza A virion particles as defined supra.

"Background", when used in the context of an assay according to an embodiment of the invention, means the uncertainty in a test result, (sometime expressed as a percentage of false-positive or false-negative test results or by a measurement of a degree of confidence in a test result), occasioned by substances which may interfere with the proper performance of the assay when they are present in the assay. Representative examples of substances which may so interfere, i.e., interfering substances, confounding substances, and the like, include endogenous PDZ binding polypeptides, inhibitors or substrates for signal generating compounds, e.g., enzyme inhibitors, free radical reactive compounds, endogenous peroxides and the like.

"Substantially purified" is used herein to refer to a preparation that contains a natural PDZ or PL polypeptide or peptide in a non-natural state e.g. a higher level of purity than in nature. Representative higher levels of purity than recorded in natural samples include PDZ and PL polypeptides and fragments thereof that are enriched greater than about 10-fold to about 25-fold, preferably greater than about 26-fold to about 50-fold and most preferably greater than about 100-fold from the levels present in a natural source material. The subject preparation also preferably contains less than about 10% impurities, and most preferably less than about 5% impurities detectable e.g. by either SDS-PAGE or reverse-phase HPLC.

Nucleic acid and protein sequences that have been previously determined and electronically deposited into NCBI's Genbank database are referenced herein by Genbank accession number (GI). The sequences set forth in those Genbank entries are incorporated by reference herein in their entirety for all purposes. The Applicants expressly reserve the right to later amend the specification to specifically recite one or more of these sequences, or any indicated portion thereof.

Various biochemical and molecular biology methods referred to herein are well known in the art, and are described in, for example, Sambrook et al., Molecular Cloning: A Laboratory Manual, Cold Spring Harbor Press, N.Y. Second (1989) and Third (2000) Editions, and Current Protocols in Molecular Biology, (Ausubel, F. M. et al., eds.) John Wiley & Sons, Inc., New York (1987-1999).

A nucleic acid can be DNA or RNA, and single- or double-stranded. Oligonucleotides can be naturally occurring or synthetic, but are typically prepared by synthetic means. Preferred nucleic acids of the invention include segments of DNA, or their complements including any one of the NS2 sequences comprising Ser 70 shown in Table 12. The segments are usually between 5 and 100 contiguous bases, and often range from 5, 10, 12, 15, 20, or 25 nucleotides to 10, 15, 30, 25, 20, 50 or 100 nucleotides. Nucleic acids between 5-10, 5-20, 10-20, 12-30, 15-30, 10-50, 20-50 or 20-100 bases are common. The polymorphic site can occur within any position of the segment. The segments can be from any of the allelic forms of NS2 shown in Table 12. For brevity in the table, the symbol T is used to represent both thymidine in DNA and uracil in RNA. Thus, in RNA oligonucleotides, the symbol T should be construed to indicate a uracil residue.

Hybridization probes are capable of binding in a base-specific manner to a complementary strand of nucleic acid. Such probes include nucleic acids, peptide nucleic acids, as described in Nielsen et al., Science 254, 1497-1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 40 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

Polymorphism refers to the occurrence of two or more genetically determined alternative sequences or alleles in a population of viruses. The first identified allelic form is arbitrarily designated as the reference form and other allelic forms are designated as alternative or variant alleles. In this case, the polymorphism comprises the position 70 in which Glycine is replaced with Serine.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A set of polymorphisms means at least 2, and sometimes 5, or more of the polymorphisms shown in Tables 12 or 13 and/or Tables 3a-e.

Hybridizations are usually performed under stringent conditions that allow for specific binding between an oligonucleotide and a target DNA containing one of the polymorphic sites shown in Tables 12 or 13 and/or Tables 3a-e. A stringent condition is defined as any suitable buffer concentrations and temperatures that allow specific hybridization of the oligonucleotide to highly homologous sequence spanning at least one of the polymorphic sites shown in Table 12 or 13 and any washing conditions that remove non-specific binding of the oligonucleotide. For example, conditions of 5×SSPE (750 mM NaCl, 50 mM Na Phosphate, 5 mM EDTA, pH 7.4) and a temperature of 25-30° C. are suitable for allele-specific probe hybridizations.

The washing conditions usually range from room temperature to 60° C.

The term "primer" refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides, although shorter or longer primers can also be used. Short primer molecules generally require cooler temperatures to form sufficiently stable hybrid complexes with the template. A primer need not reflect the exact sequence of the template but must be sufficiently complementary to hybridize with a template. The term "primer site" refers to the area of the target DNA to which a primer hybridizes. The term "primer pair" means a set of primers including a 5' upstream primer that hybridizes with the 5' end of the DNA sequence to be amplified and a 3', downstream primer that hybridizes with the complement of the 3' end of the sequence to be amplified.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Methods recited herein may be carried out in any order of the recited events, i.e., to the extent that such order is logically possible. Furthermore, where a range of values is provided, it is understood that every intervening value, between the upper and lower limit of the recited range, as well as, any other stated or intervening value falling within the subject range is encompassed within the invention. Also, it is contemplated that any optional feature of the inventive variations described may be set forth and claimed independently, or in combination with any one or more of the features described herein.

Reference to a singular item includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

DETAILED DESCRIPTION OF THE INVENTION

The invention is premised in part on the insight that the influenza NS1 proteins possess a PL region that interacts with mammalian PDZ proteins and that different PL motifs interact specifically with different PDZ proteins. The invention is further premised in part on the result that detectable levels of the NS1 PL protein can be found in body secretions, such as nasal secretions. Influenza A usurps normal host cell functions and triggers changes that result in pathogenicity. It has been discovered that certain pathogenic strains of influenza have nonstructural NS1 proteins with ligand motifs that bind to mammalian PDZ proteins. As emergent virulence factors, NS1 proteins likely interfere with, or divert, PDZ proteins assembly of host cell macromolecular protein complexes.

Since PDZ proteins are also normally involved in chaperone, endocytic and secretory processes, evidence disclosed herein is highly supportive of the notion that virulent influenza strains disrupt cellular PDZ-based regulatory mechanisms. The invention provides novel diagnostic compositions and methods, as well as, therapeutic anti-viral targets and candidate compounds.

The present results show that specific PDZ proteins bind influenza NS1 with high affinity and specificity. PDZ proteins bind C-terminal tri- and tetra-peptide NS1 motifs in virulent, but not in non-virulent, strains of influenza A. As an illustration of the methods, utilizing recombinant PDZ proteins and cross-reactive anti-NS1 monoclonal antibodies, chimeric assays were constructed to distinguish between pathogenic and non-pathogenic strains of influenza A (also called virulent and non-virulent). The assay methods involved contacting a test sample from a subject with a PDZ-domain containing polypeptide and detecting whether a pathogenic influenza A NS1 PDZ ligand in the sample bound to the PDZ ligand polypeptide. Binding between the PDZ-containing polypeptide and the viral PDZ ligand indicated that the NS1 was from a virulent strain of influenza A. This result when using the assay for a patient sample indicates that the subject is infected with a pathogenic strain of influenza A virus. The assay is particularly suitable to identify the pathogenic strains H5 and/or H7. More preferably the assay identifies at least one pathogenic strain including H5N1, H7N2, H7N7, H10N7, and most preferably the assay identifies the strain H5N1. More preferably, the assay identifies a pathogenic strain that is an avian strain, such as that currently causal for avian influenza, H5N1 having the NS1 PL motif ESEV (SEQ ID NO:2).

The various strains of influenza A encode proteins that have different PDZ ligands (PL). The various strains of influenza A can, therefore, be distinguished on the basis of their PL. Thus, the invention also provides methods for determining the sub-type of an influenza virus by the correlation with a specific NS1 PL class. Methods are also provided for determining whether a human subject is infected with an avian H5N1 strain of influenza virus. Assays for identifying anti-viral agents are also provided. Because the instant methods detect viral NS1 antigens that are produced only inside infected cells, the instant methods are useful in screening to detect subjects that are currently infected. The method is particularly advantageous because, unlike other methods, it can distinguish between vaccinated and infected subjects. Infected subjects have viral NS1 antigens, whereas vaccinated do not. Most preferably, the instant method is capable of distinguishing between the different subtypes of avian influenza A virus to identify, i.e., with a positive test result, one or more highly pathogenic strains of avian influenza A if they are present in a biological sample. Preferably, the instant test methods comprise steps for monitoring avian subjects for infection with a highly pathogenic strain of avian influenza A such as H5N1 or H7, e.g., in a commercial slaughter house facility, farm or breeding facility. In other embodiments, the invention provides methods for preventing the spread of an influenza A virus epidemic in a plurality of subjects by identifying infected animals and removing and/or destroying and/or treating them to prevent transmission to other subjects. Preferably, the instant methods comprise distinguishing avian and human subjects that are infected with a highly pathogenic influenza A strain, e.g., an avian subtype such as H5N1, from those who are infected with a lower pathogenicity strain.

The invention additionally provides a method for determining if a subject is infected with an influenza virus; and/or, whether the subject is infected with a high risk avian strain of influenza A virus. The method involves contacting a test sample from the subject with a PDZ-domain polypeptide, antibody, and/or aptamer and/or other agent, that specifically recognizes an NS1 PL, and determining whether a binding interaction occurs between an analyte in the test sample and the PDZ domain polypeptide, antibody, and/or aptamer. Assessing and detecting the subject binding interaction serves to determine that the test sample contains an influenza virus PL; thereby identifying that the subject is infected. The instant methods can also distinguish between the strains of influenza A virus, e.g., assessing whether a subject is infected with a high risk strain (pathogenic) of avian influenza virus such as H5N1, or alternatively, with a lower risk H1N1 strain (not pathogenic). Screening assays useful for identifying medicinal anti-viral compounds, e.g. in pharmaceutical development, are also provided. Thus, the invention finds uses in a variety of diagnostic and therapeutic applications.

I. Influenza Virus

The influenza viruses belong to the Orthomyxoviridae family, and are classified into groups A, B, and C based upon antigenic differences in their nucleoprotein (NP) and matrix protein (M1). Further subtyping into strains is commonly based upon assessing the type of antigen present in two virion glycoproteins, namely, hemagglutinin (HA; H) and neuraminidase (NA; N). HA and NP are virulence factors mediating attachment of the virion to the surface of host cells. M1 protein is thought to function in virus assembly and budding, while NP functions in RNA replication and transcription. In addition to these virion proteins, two other non-structural, i.e., non-virion, proteins are expressed in virus infected cells which are referred to as non-structural proteins 1 and 2 (NS1; NS2). The non-structural viral protein NS1 has multiple functions including the regulation of splicing and nuclear export of cellular mRNAs and stimulation of translation, as well as the counteracting of host interferon ability. The NS1 protein has been identified and sequenced in influenza viruses and the sequence can be found in the NCBI database. The NS1 protein in other influenza viruses, means a protein having the greatest sequence similarity to one of the proteins identified as NS1 proteins in known influenza subtypes, using as sequence for example, genbank accession numbers, CY003340, CY003324, DQ266101, etc.

All avian influenza viruses are classified as type A. Type A viruses have been isolated from humans, pigs, horses and sea mammals as well as both domestic and wild birds. Avian influenza viruses are key contributors to the emergence of human influenza pandemics, as both the Asian flu of 1957 and the Hong Kong flu of 1968 were caused by viruses believed to have been derived from avian sources. In recent years pure avian influenza viruses, of subtypes H5N1 and H7N7, have directly caused fatal human illnesses in Hong Kong and in Holland (Horimoto, T. and Kawaoka, Y. (2001) Clin. Microbiol. Rev. 14: 129-149; Guan, Y. et al. (2004) Proc. Natl. Acad. Sci. USA 101: 8156-8161).

II. PL Regions

Figure 2:
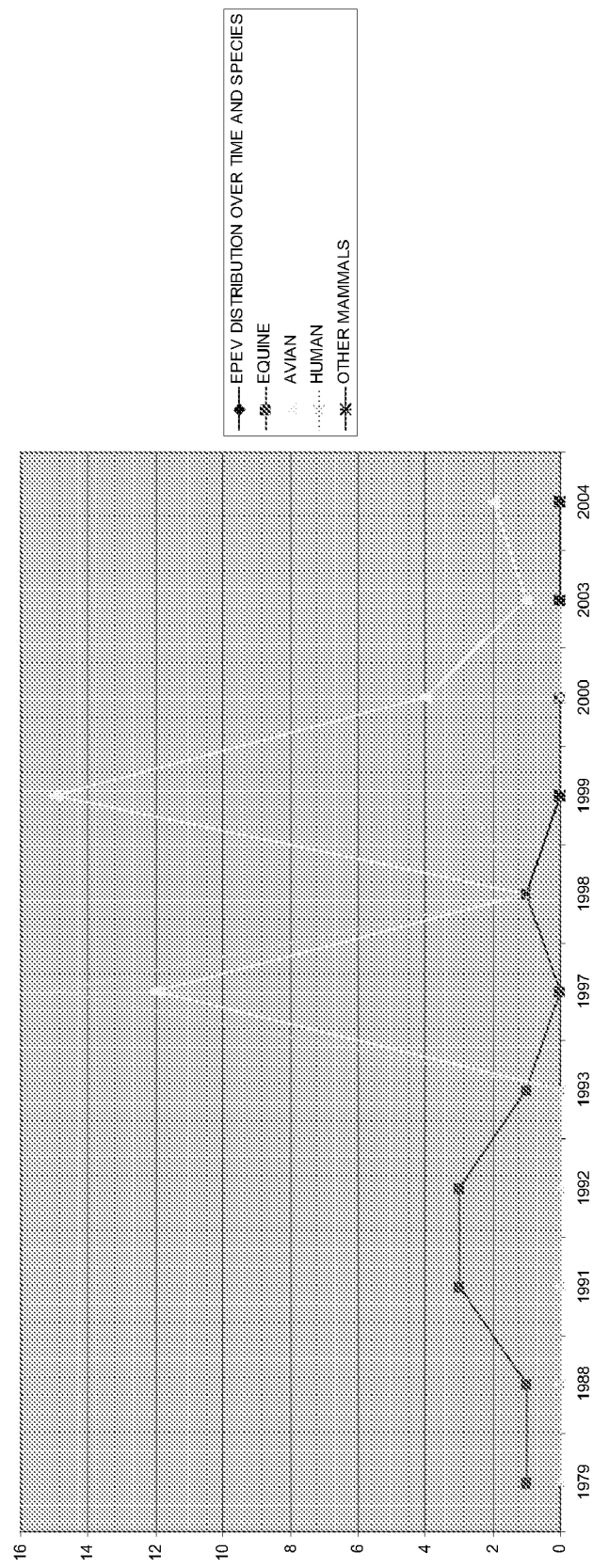
FIG. 2 is a graph showing the timecourse for the appearance of the NS1 PL sequence EPEV (SEQ ID NO:27) in avian, human and other mammals.
Figure 3:
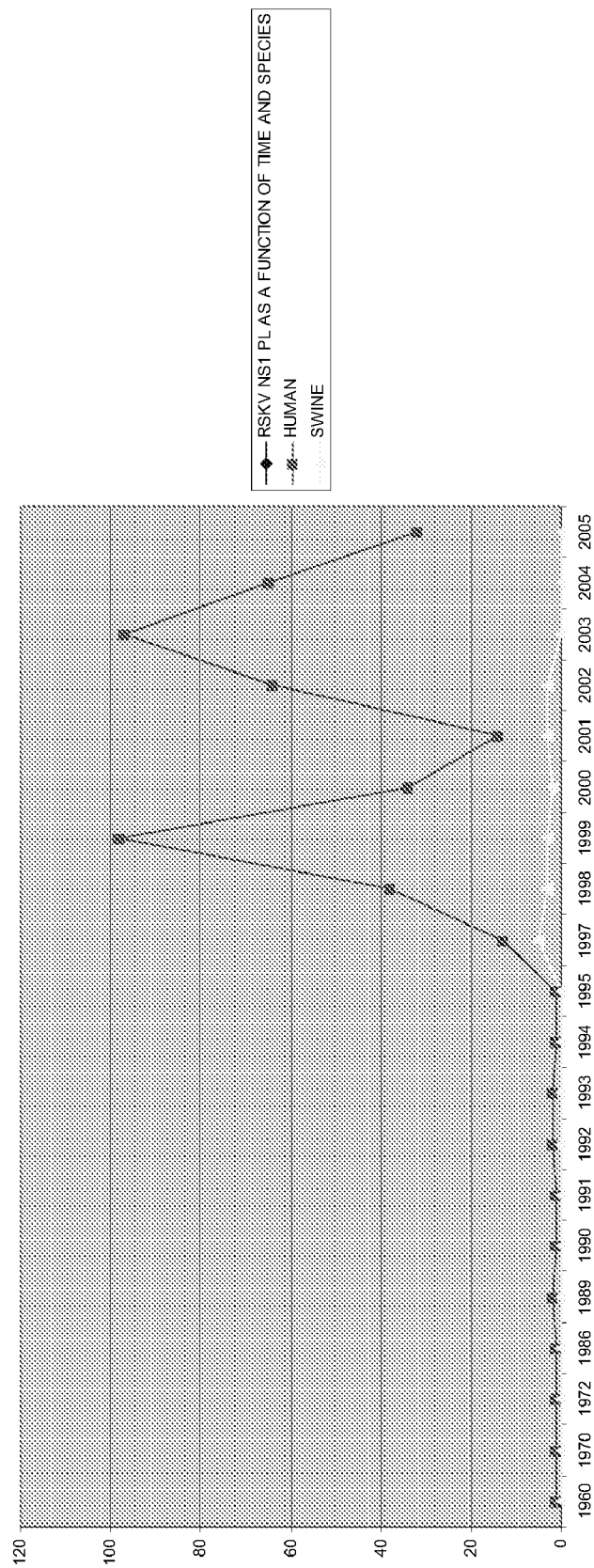
FIG. 3 is a graph showing the timecourse for the appearance of the NS1 PL sequence RSKV (SEQ ID NO:8) in avian, human and other mammals.

The examples below show that the Influenza viral pathogens contain viral proteins having motifs for PDZ ligands that bind to PDZ proteins. The viral proteins having PL motifs, include the hemagglutinin (HA), nucleoprotein (NP), matrix 1 (M1) and non-structural protein 1 (NS1) proteins. However, the class II PL motifs (in all but the NS1 proteins) show a weaker binding for PDZ proteins. The PL motifs can typically be found in the last three or four C-terminal amino acids of the protein. An identifiable motif found in the majority of influenza NS1 proteins is S/T-X-V/I/L, where the S is serine, T is threonine, V is valine, I is isoleucine, L is leucine and X is any amino acid. The frequency of each specific motif is shown in Example 1, and Tables 3a-e). Although EPEV (SEQ ID NO:27) and KMAD (SEQ ID NO:28) do not correspond to typical PL motifs, they bind to PDZs at some level and can also be used for identification. The results in Table 3a-e and FIGS. 1-3 show a nonrandom correlation between subtypes as identified by H and N antigens and the corresponding NS1 PL motif. The specific NS1 PL motifs are referred to herein as NS1 PL classes.

III. PDZ Proteins

PDZ domains have recently emerged as central organizers of protein complexes at the plasma membrane. PDZ domains were originally identified as conserved sequence elements within the postsynaptic density protein PSD95/SAP90, the *Drosophila* tumor suppressor d1g-A, and the tight junction protein ZO-1. Although originally referred to as GLGF (SEQ ID NO:26) or DHR motifs, they are now known by an acronym representing these first three PDZ-containing proteins (PDZ: PSD95/DLG/ZO-1). These 80-90 amino acids sequences have now been identified in well over 75 proteins and are characteristically expressed in multiple copies within a single protein. PDZ domains are recognized as families by the National Center for Biotechnology Information (www.ncbi.gov) for example in Pfam. They are also found throughout phylogeny in organisms as diverse as metazoans, plants, and bacteria. Such a broad species distribution appears to be unique to this domain, but perhaps the most distinguishing feature of PDZ domains is the observation that the overwhelming majority of proteins containing them are associated with the plasma membrane. Although PDZ domains are found in many different structures, each PDZ protein is generally restricted to specific subcellular domains, such as synapses; cell-cell contacts; or the apical, basal, or lateral cell surface. This leads to the speculation that PDZ domains evolved early to provide a central role in the organization of plasma membrane domains. The most general function of PDZ domains may be to localize their ligands to the appropriate plasma membrane domain. In polarized epithelial cells, PDZ proteins clearly localize at distinct apical, basal-lateral, and junctional membrane domains and, in most cases, colocalize with their transmembrane and cytosolic binding partners. PDZ proteins also clearly have a fundamental role spatially clustering and anchoring transmembrane proteins within specific subcellular domains.

PDZ domains contain ~80-90 residues that fold into a structure with a beta-sandwich of 5-6 beta-strands and two alpha-helices. The peptide ligand binds in a hydrophobic cleft composed of a beta-strand (bB), an alpha-helix and a loop that binds the peptide carboxylate group. The peptide binds in an anti-parallel fashion to the bB strand, with the C-terminal residue occupying a hydrophobic pocket. PDZ heterodimers form a linear head-to-tail arrangement that involves recognition of an internal on one of the partner proteins. PDZ domain proteins are known in the art and new proteins can be identified as having PDZ domains by sequencing the protein and identifying the presence of a PDZ domain. PDZ proteins are explained in detail and a large number of examples are given in U.S. patent application Ser. No. 10/485,788, filed Aug. 2, 2004. Alternatively, a protein suspected of being a PDZ protein can be tested for binding to a variety of PL proteins or NS1 PL classes.

IV. PDZ/PL Interactions

NS1 proteins from influenza containing the PL motif bound to PDZ proteins as shown in the Examples. Methods used to identify binding are shown in Example 2. Two complementary assays (the A and G assays) to detect binding between a PDZ-domain polypeptide and candidate PDZ ligand polypeptide are set out in detail in U.S. patent application Ser. No. 10/485,788, filed Aug. 2, 2004 and Ser. No. 10/714,537, filed Nov. 14, 2003. In each of the two different assays, binding is detected between a peptide having a sequence corresponding to the C-terminus of a protein anticipated to bind to one or more PDZ domains (i.e. a candidate PL peptide) and a PDZ-domain polypeptide (typically a fusion protein containing a PDZ domain).

A. Assays for Detection of Interactions Between PDZ-Domain Polypeptides and NMDA Receptor PL Proteins Two complementary assays, termed "A" and "G," were developed to detect binding between a PDZ-domain polypeptide and candidate PDZ ligand. In each of the two different assays, binding is detected between a peptide having a sequence corresponding to the C-terminus of a protein anticipated to bind to one or more PDZ domains (i.e. a candidate PL peptide) and a PDZ-domain polypeptide (typically a fusion protein containing a PDZ domain). In the "A" assay, the candidate PL peptide is immobilized and binding of a soluble PDZ-domain polypeptide to the immobilized peptide is detected (the "A"' assay is named for the fact that in one embodiment an avidin surface is used to immobilize the peptide). In the "G" assay, the PDZ-domain polypeptide is immobilized and binding of a soluble PL peptide is detected (The "G" assay is so-named because a GST-binding surface is used to immobilize the PDZ-domain polypeptide). Exemplary assays are described below.

1. "A Assay" Detection of PDZ-Ligand Binding Using Immobilized PL Peptide.

The assay involves the following:

(1) Biotinylated candidate PL peptides are immobilized on an avidin coated surface. The binding of PDZ-domain fusion protein to this surface is then measured.

(2) Avidin is bound to a surface, e.g. a protein binding surface. Optionally, avidin is bound to a polystyrene 96 well plate (e.g., Nunc Polysorb (cat #475094) by addition of 100 μL per well of 20 μg/mL of avidin (Pierce) in phosphate buffered saline without calcium and magnesium, pH 7.4 ("PBS", GibcoBRL) at 4° C. for 12 hours. The plate is then treated to block nonspecific interactions by addition of 200 μL per well of PBS containing 2 g per 100 mL protease-free bovine serum albumin ("PBS/BSA") for 2 hours at 4° C. The plate is then washed 3 times with PBS by repeatedly adding 200 μL per well of PBS to each well of the, plate and then dumping the contents of the plate into a waste container and tapping the plate gently on a dry surface.

(3) Biotinylated PL peptides (or candidate PL peptides) are immobilized on the surface of wells of the plate by addition of 50 μL per well of 0.4 μM peptide in PBS/BSA for 30 minutes at 4° C. Usually, each different peptide is added to at least eight different wells so that multiple measurements (e.g. duplicates and also measurements using different (GST/PDZ-domain fusion proteins and a GST alone negative control) can be made, and also additional negative control wells are prepared in which no peptide is immobilized. Following immobilization of the PL peptide on the surface, the plate is washed 3 times with PBS.

(4) GST/PDZ-domain fusion protein is allowed to react with the surface by addition of 50 μL per well of a solution containing 5 μg/mL GST/PDZ-domain fusion protein in PBS/BSA for 2 hours at 4° C. As a negative control, GST alone (i.e. not a fusion protein) is added to specified wells, generally at least 2 wells (i.e. duplicate measurements) for each immobilized peptide. After the 2 hour reaction, the plate is washed 3 times with PBS to remove unbound fusion protein.

(5) The binding of the GST/PDZ-domain fusion protein to the avidin-biotinylated peptide surface can be detected using a variety of methods, and detectors known in the art. In one embodiment, 50 µL per well of an anti-GST antibody in PBS/BSA (e.g. 2.5 µg/mL of polyclonal goat-anti-GST antibody, Pierce) is added to the plate and allowed to react for 20 minutes at 4° C. The plate is washed 3 times with PBS and a second, detectably labeled antibody is added. In one embodiment, 50 µL per well of 2.5 µg/mL of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 µL per well of HRP-substrate solution (TMB, Dako) for 20 minutes at room temperature (RT). The reaction of the HRP and its substrate is terminated by the addition of 100 µL per well of 1M sulfuric acid and the optical density (O.D.) of each well of the plate is read at 450 nm.

(6) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction involves multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value<0.05, more typically a p-value<0.01, and most typically a p-value<0.001 or less. As noted, in an embodiment of the "A" assay, the signal from binding of a GST/PDZ-domain fusion protein to an avidin surface not exposed to (i.e. not covered with) the PL peptide is one suitable negative control (sometimes referred to as "B"). The signal from binding of GST polypeptide alone (i.e. not a fusion protein) to an avidin-coated surface that has been exposed to (i.e. covered with) the PL peptide is a second suitable negative control (sometimes referred to as "B2"). Because all measurements are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2.

II. "G Assay"-Detection of PDZ-Ligand Binding Using Immobilized PDZ-Domain Fusion Polypeptide In one aspect, the invention provides an assay in which a GST/PDZ fusion protein is immobilized on a surface ("G" assay). The binding of labeled PL peptide (for example one of those listed in FIGS. 3a-e) to this surface is then measured. In a preferred embodiment, the assay is carried out as follows:

(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:

a. 100 µL per well of 5 µg/mL goat anti-GST polyclonal antibody (Pierce) in PBS is added to a polystyrene 96-well plate (e.g., Nunc Polysorb) at 4° C. for 12 hours.

b. The plate is blocked by addition of 200 µL per well of PBS/BSA for 2 hours at 4° C.

c. The plate is washed 3 times with PBS.

d. 50 µL per well of 5 µg/mL GST/PDZ fusion protein) or, as a negative control, GST polypeptide alone (i.e. not a fusion protein) in PBS/BSA is added to the plate for 2 hours at 4° C.

e. the plate is again washed 3 times with PBS.

(2) Biotinylated PL peptides are allowed to react with the surface by addition of 50 µL per well of 20 µM solution of the biotinylated peptide in PBS/BSA for 10 minutes at 4° C., followed by an additional 20 minute incubation at 25° C. The plate is washed 3 times with ice cold PBS.

(3) The binding of the biotinylated peptide to the GST/PDZ fusion protein surface can be detected using a variety of methods and detectors known to one of skill in the art. In an exemplary procedure, 100 µL per well of 0.5 µg/mL streptavidin-horse radish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 µL per well of HRP-substrate solution (TMB, Dako) for 20 minutes at room temperature (RT). The reaction of the HRP and its substrate is terminated by addition of 100 µL per well of 1 M sulfuric acid, and the optical density (O.D.) of each well of the plate is read at 450 um.

(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control(s). Typically a specific or selective reaction is at least twice background signal, more typically more than 5 times background, and most typically 10 or more times the background signal. In addition, a statistically significant reaction involves multiple measurements of the reaction with the signal and the background differing by at least two standard errors, more typically four standard errors, and most typically six or more standard errors. Correspondingly, a statistical test (e.g. a T-test) comparing repeated measurements of the signal with—repeated measurements of the background will result in a p-value<0.05, more typically a p-value<0.01, and most typically a p-value<0.001 or less. As noted, in an embodiment of the "G" assay, the signal from binding of a given PL peptide to immobilized (surface bound) GST polypeptide alone is one suitable negative control (sometimes referred to as "B 1"). Because all measurement are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1.

i) "G' Assay" and "G" Assay"

Two specific modifications of the specific conditions described supra for the "G assay" are particularly useful. The modified assays use lesser quantities of labeled PL peptide and have slightly different biochemical requirements for detection of PDZ-ligand binding compared to the specific assay conditions described supra.

For convenience, the assay conditions described in this section are referred to as the "G' assay" and the "G" assay," with the specific conditions described in the preceding section on G assays being referred to as the "$G^0$ assay." The "G' assay" is identical to the "$G^0$ assay" except at step (2) the peptide concentration is 10 uM instead of 20 uM. This results in slightly lower sensitivity for detection of interactions with low affinity and/or rapid dissociation rate. Correspondingly, it slightly increases the certainty that detected interactions are of sufficient affinity and half-life to be of biological importance and useful therapeutic targets.

The "G" assay" is identical to the "$G^0$ assay" except that at step (2) the peptide concentration is 1 μM instead of 20 μM and the incubation is performed for 60 minutes at 25° C. (rather than, e.g., 10 minutes at 4° C. followed by 20 minutes at 25° C.). This results in lower sensitivity for interactions of low affinity, rapid dissociation rate, and/or affinity that is less at 25° C. than at 4° C. Interactions will have lower affinity at 25° C. than at 4° C. if (as we have found to be generally true for PDZ-ligand binding) the reaction entropy is negative (i.e. the entropy of the products is less than the entropy of the reactants). In contrast, the PDZ-PL binding signal may be similar in the "G" assay" and the "$G^0$ assay" for interactions of slow association and dissociation rate, as the PDZ-PL complex will accumulate during the longer incubation of the "G" assay." Thus comparison of results of the "G" assay" and the "$G^0$ assay" can be used to estimate the relative entropies, enthalpies, and kinetics of different PDZ-PL interactions. (Entropies and enthalpies are related to binding affinity by the equations delta G=RT ln (Kd)=delta H−T delta S where delta G, H, and S are the reaction free energy, enthalpy, and entropy respectively, T is the temperature in degrees Kelvin, R is the gas constant, and Kd is the equilibrium dissociation constant). In particular, interactions that are detected only or much more strongly in the "$G^0$ assay" generally have a rapid dissociation rate at 25° C. (t1/2<10 minutes) and a negative reaction entropy, while interactions that are detected similarly strongly in the "G" assay" generally have a slower dissociation rate at 25° C. (t1/2>10 minutes). Rough estimation of the thermodynamics and kinetics of PDZ-PL interactions (as can be achieved via comparison of results of the "$G^0$ assay" versus the "G" assay" as outlined supra) can be used in the design of efficient inhibitors of the interactions. For example, a small molecule inhibitor based on the chemical structure of a PL that dissociates slowly from a given PDZ domain (as evidenced by similar binding in the "G" assay" as in the "$G^0$ assay") may itself dissociate slowly and thus be of high affinity.

In this manner, variation of the temperature and duration of step (2) of the "G assay" can be used to provide insight into the kinetics and thermodynamics of the PDZ-ligand binding reaction and into design of inhibitors of the reaction.

The detectable labels of the invention can be any detectable compound or composition which is conjugated directly or indirectly with a molecule (such as described above). The label can be detectable by itself (e.g., radioisotope labels or fluorescent labels) or, in the case of an enzymatic label, can catalyze a chemical alteration of a substrate compound or composition which is detectable. The preferred label is an enzymatic one which catalyzes a color change of a non-radioactive color reagent.

Sometimes, the label is indirectly conjugated with the antibody. One of skill is aware of various techniques for indirect conjugation. For example, the antibody can be conjugated with biotin and any of the categories of labels mentioned above can be conjugated with avidin, or vice versa (see also "A" and "G" assay above). Biotin binds selectively to avidin and thus, the label can be conjugated with the antibody in this indirect manner. See, Ausubel, supra, for a review of techniques involving biotin-avidin conjugation and similar assays. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

Assay variations can include different washing steps. By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or HRP antibody) is removed therefrom. To reduce background noise, it is convenient to include a detergent (e.g., Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) can be required.

Various buffers can also be used in PDZ-PL detection assays. For example, various blocking buffers can be used to reduce assay background. The term "blocking buffer" refers to an aqueous, pH buffered solution containing at least one blocking compound which is able to bind to exposed surfaces of the substrate which are not coated with a PL or PDZ-containing protein. The blocking compound is normally a protein such as bovine serum albumin (BSA), gelatin, casein or milk powder and does not cross-react with any of the reagents in the assay. The block buffer is generally provided at a pH between about 7 to 7.5 and suitable buffering agents include phosphate and TRIS.

Various enzyme-substrate combinations can also be utilized in detecting PDZ-PL interactions. Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3', 5,5'-tetramethyl benzidine hydrochloride [TMB]) (as described above).

(ii) alkaline phosphatase (AP) with para-Nitrophenyl phosphate as chromogenic substrate.

(iii) β-D-galactosidase (β D-Gal) with a chromogenic substrate (e.g. p-nitrophenyl-β-D-galactosidase) or fluorogenic substrate 4-methylumbelliferyl-β-D-galactosidase. Numerous other enzyme-substrate combinations are available. For a general review of these, see U.S. Pat. Nos. 4,275,149 and 4,318,980, both of which are herein incorporated by reference.

TABLES 1 and 2, on the following page, list PDZ domain-containing proteins ("PDZ proteins") and PDZ ligands ("PL") which have been identified as herein as binding to one another. Each of the PL proteins has binding affinity for at least one PDZ protein. The second column of TABLE 1 lists the influenza A protein from which the PL protein is derived (for example, hemagglutinin (HA), nucleoprotein (NP), matrix (M1) and non-structural protein 1 (NS1); the third column lists the PL motif amino acid sequence; and the fourth column provides the GenBank identification number (GI number) for the PDZ domain proteins binding to the PL (which database entries are incorporated by reference herein, including any annotation described therein).

TABLE 1

| | | | PDZ-PL Interactions* |
|---|---|---|---|
| Pathogen | Protein | C-terminus | PDZ Partners |
| influenza A | NS1 | ESEV (SEQ ID NO: 2) | Outer Membrane; PSD95 (PDZ #2); PSD95 (PDZ #1, 2, 3); DLG1 (PDZ #1); DLG1 (PDZ #1, 2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1, 2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 |
| | NS1 | EPEV (SEQ ID NO: 27) | PSD95 (PDZ #2)<br>PSD95 (PDZ #1, 2, 3) |
| | NS1 | ESEI (SEQ ID NO: 3) | Outer Membrane; PSD95 (PDZ #2); PSD95 (PDZ #1, 2, 3); NeDLG (PDZ #1, 2); DLG2 (PDZ #2); MAST2; PTN3 (PDZ #1) |
| | NS1 | ESKV (SEQ ID NO: 4) | PSD95 (PDZ #2); PSD95 (PDZ #1, 2, 3); MAST2; Magi3 (PDZ #1); NeDLG (PDZ #1, 2); NumBP(PDZ #4) |

*Interactions verified experimentally.

TABLE 2

| | | | PDZ-PL Interactions | |
|---|---|---|---|---|
| influenza A | HA | 8486126 | RICI (SEQ ID NO: 13), NICI (SEQ ID NO: 11), TICI (SEQ ID NO: 12) | NOS1 (PDZ #1, 2, 3); MINT1 (PDZ #2); ZO-1 (PDZ #2); NSP; RIM2 |
| | NS1 | 8486133 | ESEV (SEQ ID NO: 2), RSEV (SEQ ID NO: 7), RSKV (SEQ ID NO: 8) | NeDLG (PDZ #1, 2); LIM-RIL; Vartul (PDZ #1, 2); MAGI2; DLG2 (PDZ #1, 2); MAST2; DLG1 (PDZ #1, 2); PSD95 (PDZ #1, 2, 3); MAGI1; TIP1; MAGI 3; Outer membrane protein; MAST2; Syntrophin gamma 1; MUPP1 (PDZ #13); PTPL1 (PDZ #2); Syntrophin 1 alpha; ERBIN; KIAA 1526; AIPC; LIM mystique; TIP43; TIP2 |
| influenza B | HA | 8486153 | SICL (SEQ ID NO: 18) | NOS1 (PDZ #1, 2, 3); MINT1 (PDZ #2); ZO-1 (PDZ #2); NSP; RIM2; Novel serine protease; PICK1 |
| | NA | 8486155 | DMAL (SEQ ID NO: 14), DMTL (SEQ ID NO: 15), DIAL (SEQ ID NO: 16) | ZO-1 (PDZ #2); RIM2; Novel serine protease; MINT1 |
| | M1 | 8486158 | RKYL (SEQ ID NO: 29), KKYL (SEQ ID NO: 30) | ZO-1 (PDZ #2)<br>RIM2 d1 |
| | Nucleo-protein | 8486160 | DLDY (SEQ ID NO: 17) | ZO-1 (PDZ #2)<br>RIM2 d1; syntenin |

PDZ proteins can be produced as fusion proteins, as long as they contain an active PDZ domain. For example, PDZ domains cloned into a vector (PGEX-3× vector) for production of GST-PDZ fusion proteins (Pharmacia) have been produced and taught in prior US and International patent applications, e.g., U.S. patent application Ser. No. 10/485,788 (filed Feb. 3, 2004), International patent application PCT/US03/285/28508 (filed Sep. 9, 2003), International patent application PCT/US01/44138 (filed Nov. 9, 2001), incorporated herein by reference in their entirety.

V. Screening for PDZ Proteins

Methods of screening can include the use of sequence analysis to identify PDZ domains using any computer program known for the use of sequence analysis and/or domain analysis. Once a PDZ protein is identified, it can be screened for the ability to interact with influenza PL proteins.

A PDZ protein or PDZ domain polypeptide is any protein that contains a PDZ domain. Any protein containing a PDZ domain, whether natural, recombinant, chimeric or a fragment can be screened for its ability to bind to an influenza PL domain. Methods of identification of PDZ domains are given in U.S. patent application Ser. No. 10/485,788 (filed Feb. 3, 2004), International patent application PCT/US03/285/28508 (filed Sep. 9, 2003), International patent application PCT/US01/44138 (filed Nov. 9, 2001), incorporated herein by reference in their entirety.

VI. Screening for Other PL-Binding Agents

PL binding agents suitable for use in a diagnostic assay include any agent that specifically binds to one or more PL motifs. Such agents can be identified using the same methods as disclosed in methods of screening for anti-viral agents. For example, agents can be identified using a protein containing a PL motif. Test compounds can be identified using any type of library, including expression libraries and small molecule libraries for example. A preferred source of test compounds for use in screening for therapeutics or therapeutic leads is a phage display library. See, e.g., Devlin, WO 91/18980; Key, B. K., et al., eds., Phage Display of Peptides and Proteins, A Laboratory Manual, Academic Press, San Diego, Calif., 1996. Phage display is a powerful technology that allows one to use phage genetics to select and amplify peptides or proteins of desired characteristics from libraries containing $10^8$-$10^9$ different sequences. Libraries can be designed for selected variegation of an amino acid sequence at desired positions, allowing bias of the library toward desired characteristics. Libraries are designed so that peptides are expressed fused to proteins that are displayed on the surface of the bacteriophage. The phage displaying peptides of the desired characteristics are selected and can be regrown for expansion. Since the peptides are amplified by propagation of the phage, the DNA from the selected phage can be readily sequenced facilitating rapid analyses of the selected peptides.

Phage encoding peptide inhibitors can be selected by selecting for phage that bind specifically to a PDZ domain protein and/or to an NS1 PL. Libraries are generated fused to proteins such as gene II that are expressed on the surface of the phage. The libraries can be composed of peptides of various lengths, linear or constrained by the inclusion of two Cys amino acids, fused to the phage protein or can also be fused to additional proteins as a scaffold. One can also design libraries biased toward the PL regions disclosed herein or biased toward peptide sequences obtained from the selection of binding phage from the initial libraries provide additional test inhibitor compound.

VII. Antibodies for Diagnostic and Therapeutic Uses

The NS1, NS1 PL, PDZ and PDZ PL binding domain polypeptides of the invention are useful for generating antibodies for use in diagnostics and therapeutics. The antibodies can be polyclonal antibodies, distinct monoclonal antibodies or pooled monoclonal antibodies with different epitopic specificities. Monoclonal antibodies are made from antigen-containing fragments of the protein by standard procedures according to the type of antibody (see, e.g., Kohler, et al., Nature, 256:495, (1975); and Harlow & Lane, Antibodies, A Laboratory Manual (C.S.H.P., NY, 1988) Queen et al., Proc. Natl. Acad. Sci. USA 86:10029-10033 (1989) and WO 90/07861; Dower et al., WO 91/17271 and McCafferty et al., WO 92/01047 (each of which is incorporated by reference for all purposes). Phage display technology can also be used to mutagenize CDR regions of antibodies previously shown to have affinity for the peptides of the present invention. Some antibodies bind to an epitope present in one form of NS1 or PDZ protein but not others. For example, some antibodies bind to an epitope within the C-terminus PL site of NS1. Those antibodies that bind to specific NS1 PL motifs can be classified as NS1 PL class-specific antibodies. Further, some antibodies bind to an epitope within the PDZ domain of a PDZ protein. Some antibodies specifically bind to a PDZ polypeptide such as that shown in Table 1 without binding to others. The antibodies can be purified, for example, by binding to and elution from a support to which the polypeptide or a peptide to which the antibodies were raised is bound.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The antibodies may be utilized as reagents (e.g., in pre-packaged kits) for prognosis and diagnosis of influenza A infection and subtypes thereof, and in particular Avian influenza A infection. A variety of methods may be used to prognosticate and diagnose influenza A infection.

A. Pan-Reactive Antibodies

Pan-reactive or pan-specific antibodies are monoclonal or polyclonal antibodies that bind to any and all influenza A virus NS1 proteins or alternatively, that bind to more than 3 influenza NS1 proteins, or more preferably more than 5. Preferably, the pan-reactive or Pan-specific antibodies recognize at least the following three influenza A strains: H5N1, H3N2, and H1N1. Pan-reactive antibodies can be used to identify the presence of an influenza A virus without identifying what subtype it is. Thus, pan-reactive monoclonal antibodies can specifically recognize conserved regions of the NS1 protein or can recognize two or more PL regions of the NS1 proteins or specific NS1 PL classes. Preferred conserved regions of the NS1 protein can be found for example in the RNA binding domain and are shown on the National Center for Biotechnology Information website as NCBI IVNS1ABP. While, the PL region has been shown to differ between virus subtypes, it is possible to identify monoclonal antibodies that bind to more than one PL in the NS1 region.

However, other embodiments of pan-reactive antibodies include polyclonal antibodies and/or mixtures of monoclonal antibodies that, as a whole, identify all or many influenza A viruses. These antibodies can recognize conserved or non-conserved regions of the NS1 protein. If the antibodies recognize the NS1 PL region, the mixture of antibodies preferably recognize the NS1 that also contain PL regions: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. If more than one antibody and/or PDZ protein is used, the PDZ protein is preferably at least one of those selected from Tables 1 or 2 and the antibody preferably mimics at least one of the PDZ proteins.

B. Monoclonal Antibody Surrogates of PDZ Proteins

As shown above and in the examples, there are a wide variety of PDZ proteins that recognize and bind to the PL motif on NS1 proteins. Antibodies that recognize the same motif can also be used as surrogates of these PDZ proteins. Preferably, the PDZ proteins are one of the following: Outer membrane proteins, PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin 1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment. More preferably the antibodies mimic any PDZ protein that specifically recognizes the PL ESEV (SEQ ID NO:2). The antibodies surrogates that recognize specific NS1 PL motifs can be designated NS1 PL class-specific.

C. Mixture of Antibodies and Other Binding Agents

A mixture of antibodies and PDZ proteins (and/or aptamers) can be used in any of the assays. The PDZ proteins and antibodies can be used for identification of different subtypes of NS1, identification of influenza A virus, and identification of pathogenic forms as compared to those that are less pathogenic. In some assays, the antibody(s) and PDZ protein(s) are mixed and administered together to a sample. In other assays, the antibody(s) and PDZ protein(s) are separated and allowed to bind to different samples for identification of two different subtypes or for confirmation of the identification of a subtype.

VIII. Aptamers

Aptamers are RNA or DNA molecules selected in vitro from vast populations of random sequence that recognize specific ligands by forming binding pockets. Allosteric ribozymes are RNA enzymes whose activity is modulated by the binding of an effector molecule to an aptamer domain, which is located apart from the active site. These RNAs act as precision molecular switches that are controlled by the presence or absence of a specific effector. Aptamers can bind to nucleic acids, proteins, and even entire organisms. Aptamers are different from antibodies, yet they mimic properties of antibodies in a variety of diagnostic formats. Thus, aptamers can be used instead of or in combination with antibodies and/or PDZ proteins to identify the presence of general and specific NS1 PL regions.

IX. Correlation Between NS2 Sequence and Pathogenicity

The nonstructural proteins NS1 and NS2 of Influenza A are both produced from the same gene using differential splicing. The type of splicing that occurs results in differences at the carboxy terminus of the NS1 and NS2 proteins. In the case of NS1 this results in the distinctive PL at the carboxy terminus, whereas NS2 does not possess a PL at the C-terminus. Because the specific sequence of the PL region in NS1 can be correlated with pathogenicity, changes in the NS2 protein were analyzed for any type of correlation. The NS2 sequences resulting from the splice were analyzed in pathogenic strains as compared to those that were not pathogenic. The sequence was analyzed both at the protein level and at the nucleotide level in Tables 12 and 13. The tables show that a Glycine to Serine substitution in position 70 is highly correlative with the pathogenicity and/or virulence of the virus, particularly with reference to the H1N1 strain that of 1918. An exemplary NS2 sequence is described by the H5N1 strain as described by the National Center for Biotechnology Information (www.ncbi.gov) for example AF144307, and the amino acid and codons encoding the amino acids are numbered for other NS2 proteins correspondingly when the sequences are maximally aligned. Because of this correlation, a method was identified that uses the NS2 polymorphism at Ser 70 as a separate test to analyze whether a given influenza A strain is pathogenic. The method may also be used to identify specific Influenza strains. Alternatively, the NS2 polymorphism can be used in conjunction with the NS1 tests disclosed herein to identify pathogenicity or to confirm pathogenicity identified by a different method.

Methods of screening for the Ser 70 sequence change in the NS2 protein include methods of identifying the change at the protein level or at the nucleotide level.

1. Protein-Based Diagnostic Tests

The invention provides protein-based diagnostic tests to identify the presence of an NS2 protein comprising Ser 70 for identifying Influenza A viruses, Influenza A virus strains, and pathogenic Influenza A virus strains. The diagnostic tests using the Ser 70 polymorphic sequence in NS2 can use the same formats as those for use in NS1 analysis (see section VIII and other related sections). The assay identifies the presence of a serine at position 70 and if the serine is present, the influenza strain is identified as pathogenic. If the serine is not present, the influenza strain is identified as not pathogenic.

Monoclonal or polyclonal antibodies that recognize the Serine 70 change in the NS2 protein can be used to identify an influenza strain as Influenza A, can identify a specific Influenza A strain, and can identify whether a virus is pathogenic. NS2 antibodies can be produced to recognize the presence of a Serine 70 and can be used to identify pathogenic strains. For example, antibodies can be produced using the peptides provided in Tables 12 or 13 for the NS2 region having a serine at the 70 position. Ser-70 antibodies can then be screened to ascertain whether they cross-react with a peptide having a Glycine or other amino acid at position 70. Alternatively, the antibodies can be produced to recognize the specific sequence comprising the Serine 70 for each strain, producing strain-specific antibodies (see also section VIII as applied to NS1 antibodies). In some assays, the antibody is used to identify a strain as pathogenic. In some assays the NS2 antibody is used as an alternative to an NS1 antibody. In some assays the NS2 antibody is used in combination with an NS1 antibody in any of the assays employing the NS1 protein. The NS2 antibody can be used to identify a specific Influenza A virus, to identify a virus as an Influenza A virus, or to identify a virus as pathogenic.

Alternatively, other binding agents can be used in lieu of antibodies, such as peptides selected by phage display library techniques.

2. Nucleic Acid Diagnostic Tests

The invention also provides nucleic acid-based diagnostic tests to identify the presence of an NS2 nucleic acid coding for a protein comprising Ser 70. These can be used for identifying Influenza A viruses, Influenza A virus strains, and pathogenic Influenza A virus strains. The diagnostic tests use a sequence comprising a codon encoding the Ser 70 in NS2 in a variety of formats. For example, the diagnostic tests can use probes or primers complementary to a sequence encoding the Ser 70. Preferably, the sequences encoding the peptides identified in Table 12 are used. If the Ser 70 is identified as present, the influenza virus is identified as pathogenic.

Methods of detection of polymorphisms in NS2. The identity of bases occupying the sequence comprising Ser-70 shown in Table 12 of the NS2 nucleic acid can be determined in a sample by several methods, which are described in turn.

A. Single Base Extension Methods

Single base extension methods are described by e.g., U.S. Pat. Nos. 5,846,710, 6,004,744, 5,888,819 and 5,856,092. In brief, the methods work by hybridizing a primer that is complementary to a target sequence such that the 3' end of the primer is immediately adjacent to but does not span a site of potential variation in the target sequence. That is, the primer comprises a subsequence from the complement of a target polynucleotide terminating at the base that is immediately adjacent and 5' to the polymorphic site. The hybridization is performed in the presence of one or more labeled nucleotides complementary to base(s) that may occupy the site of potential variation. For example, for the sequence encoding the NS2 Ser 70 polymorphisms, one or more labeled nucleotides primers can be used. The primers for each polymorphism can include different labels to differentiate the polymorphism. Preferably, the primer overlaps or partially codes for the splicing site. This means that some part of the splicing site or polymorphic region is contained in the primer, preferably the Ser 70 site. In some methods, particularly methods employing multiple differentially labeled nucleotides, the nucleotides are dideoxynucleotides. Hybridization is performed under conditions permitting primer extension if a nucleotide complementary to a base occupying the site of variation in the target sequence is present. Extension incorporates a labeled nucleotide thereby generating a labeled extended primer. If multiple differentially labeled nucleotides are used and the target is heterozygous then multiple differentially labeled extended primers can be obtained. Extended primers are detected providing an indication of which bas(es) occupy the site of variation in the target polynucleotide.

B. Allele-Specific Probes

The design and use of probes for analyzing polymorphisms is described by e.g., Saiki et al., Nature 324, 163-166 (1986); Dattagupta, EP 235,726, Saiki, WO 89/11548. Using this disclosure, probes can be designed that recognize specific sequences comprising the Ser 70 polymorphism that hybridizes to a segment of target DNA from one type of virus or viral strain but do not hybridize to the corresponding segment from another type of virus or viral strain due to the presence of different polymorphic forms in the respective segments from the two viruses. Hybridization conditions should be sufficiently stringent that there is a significant difference in hybridization intensity between alleles of the Ser 70 region, and preferably an essentially binary response, whereby a probe hybridizes to only one of the alleles. Some probes are designed to hybridize to a segment of target DNA such that the polymorphic site at Ser 70 aligns with a central position (e.g., in a 15 mer at the 7 position; in a 16 mer, at either the 8 or 9 position) of the probe. This design of the probe achieves good discrimination in hybridization between different nucleic acids encoding NS2 proteins from different viruses and/or strains.

These probes are often used in pairs, one member of a pair showing a perfect match to one reference form of a target sequence and the other member showing a perfect match to a variant form or a different reference form. Several pairs of probes can then be immobilized on the same support for simultaneous analysis of multiple polymorphisms within the same target sequence. The polymorphisms can also be identified by hybridization to nucleic acid arrays, some example of which are described by WO 95/11995 (incorporated by reference in its entirety for all purposes).

C. Allele-Specific Amplification Methods

An allele-specific primer hybridizes to a site on target DNA overlapping a polymorphism and only primes amplification of an allelic form to which the primer exhibits perfect complementarily. See Gibbs, Nucleic Acid Res. 17, 2427-2448 (1989). This primer is used in conjunction with a second primer that hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. In some methods, the mismatch is included in the 3'-most position of the oligonucleotide aligned with the polymorphism because this position is most destabilizing to elongation from the primer. See, e.g., WO 93/22456. In this case, the allele specific primer can be designed to overlap the splice site of NS2, comprising the Ser 70 position.

D. Direct-Sequencing

The direct analysis of the sequence of the NS2 polymorphisms of the present invention can be accomplished using either the dideoxy-chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

E. Denaturing Gradient Gel Electrophoresis

Amplification products generated using the polymerase chain reaction can be analyzed by the use of denaturing gradient gel electrophoresis. Different alleles of the NS2 Ser 70 polymorphism can be identified based on the different sequence-dependent melting properties and electrophoretic migration of DNA in solution. Erlich, ed., PCR Technology, Principles and Applications for DNA Amplification, (W.H. Freeman and Co, New York, 1992), Chapter 7.

F. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770 (1989). Amplified PCR products can be generated as described above, and heated or otherwise denatured, to form single stranded amplification products. Single-stranded nucleic acids may refold or form secondary structures that are partially dependent on the base sequence. The different electrophoretic mobilities of single-stranded amplification products can be related to base-sequence difference between alleles of target sequences.

3. NS2 therapeutics—the anti-viral therapeutics and methods for screening for anti-viral therapeutics as disclosed herein for NS1 and PDZ proteins can similarly be used for identifying binding partners for NS2, identifying therapeutic agents that block an interaction between NS2 and a binding partner, and treating a patient with a virulent Influenza A infection. (see section XI Pharmaceutical compositions). Targets for identification of therapeutics with respect to NS2 include agents that block the interaction between a binding partner and NS2 at the overlap region, including the Ser 70, agents that block an interaction between an NS2 PL (internal site) and a PDZ binding partner, and serine kinases that phosphorylate the Ser 70, resulting in inhibition of an interaction.

X. Diagnostic Tests

Embodiments of the invention provide diagnostic capture and detect reagents useful in assay methods for identifying influenza A viruses and their products in a variety of different types of biological samples. Representative assay formats useful for detecting influenza viruses include enzyme-linked solid-phase absorbent assays, radiolabeled binding assays, fluorescence PDZ- and PL-binding assays, time-resolved PDZ and PL fluorescence assays, as well as, sandwich- and enzyme-cascade assay formats. Illustrative methods, as may be adaptable from the immunoassay art for use in the subject assays include homogeneous and heterogeneous assay formats; competitive and non-competitive assay formats; enzyme-linked solid phase assay formats, fluorescence assay formats, time resolved fluorescence assay formats, bioluminescent assay formats, cascade enzyme assays and the like.

In certain embodiments of the invention, one or more PDZ proteins are used as capture agents to isolate one or more PL analyte from a biological sample. In other alternative embodiments, one or more PDZ proteins are conjugated with one or more signal generating compounds and used as detect reagents for identifying the presence or amount of one or more PL analytes in a biological sample. In yet other embodiments, PL proteins and PL peptides are conjugated with signal generating compounds (PL-SGC) and used in competitive ligand inhibition assays, i.e., where the presence of a viral PL competes the binding of one or more PL-SGC to a PDZ. Preferably, the PDZ proteins are at least one of: Outer membrane protein, PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip 1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment. For tests that generally identify influenza A, a mixture of PDZ proteins and antibodies can be used. For these tests, the PDZ protein may include one of the above in admixture with others that recognize other pathogen-specific or influenza A specific PL motifs.

The present invention provides methods of detecting pathogen PL proteins in a sample and finds utility in diagnosing viral infection in a subject. In many embodiments, a biological sample is obtained from a subject, and, the presence of a pathogen PL protein in the sample is determined. The presence of a detectable amount of pathogen PL protein in a sample indicates that the individual is infected with a particular virus. In other embodiments, the level of pathogen PL protein in a biological sample is determined, and compared to the amount of a control in the sample. The relative amount of pathogen PL protein in a sample indicates the severity of the infection by the pathogen.

The methods generally involve two binding partners specific for an influenza A PL protein, one of which is a PDZ domain polypeptide, as described above. In general, the methods involve a) isolating the pathogen PL from a sample using one of the binding partners, and b) detecting the pathogen PL protein with the other binding partner.

For sub-type specific tests or NS1 PL class-specific tests, the PL to be identified is preferably one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. For the sub-type specific test, the PDZ protein used is preferably at least one of: PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment. The NS1 PL can be strongly predictive of the H and A antigens and sub-type of the virus.

For the pathogen-specific test, the NS1 PL to be identified is preferably at least one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. For the pathogen-specific test, the PDZ protein used is preferably at least one of those selected from Tables 1 or 2 or an analog or fragment.

For the influenza A specific test, the NS1 PL to be identified is preferably at least one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. For the pathogen-specific test, the PDZ protein used is preferably at least one of those selected from Tables 1 or 2 or an analog or fragment.

A. ELISA Sandwich Heterogeneous Assay Format

Using the instant PDZ capture and monoclonal anti-NS1, as illustrated in the Examples section, below, a sandwich assay format was constructed to detect high risk influenza A strains in biological samples. The instant assays had a sensitivity in the range of 1-1,000 ng/ml, i.e., sufficiently sensitive for commercial use in detecting the type or amount of an Influenza A virus in a biological sample, with the following caveats: namely, a) Immunoassays are capable of distinguishing between the NS1 proteins in the H5N1, H1N1 and H3N2 strains of Influenza A;
b) The cross-reactivity profiles of different assay formats vary and also depend upon the particular Influenza A strains being detected, as well as, the absolute sensitivity in biological samples that contain cell lysates; and,
c) It is now relatively routine in the art of diagnostic devices to determine the detection limits for different assay formats.

While a variety of competitive and non-competitive assay formats are identifiable for possible use in the instant methods, a sandwich assay format is presently preferred because these assays have proven performance characteristics and a variety of well established signal amplification strategies. In a presently preferred sandwich immunoassay embodiment, a specific high affinity non-natural PDZ protein is employed to capture a natural viral NS1 antigen from within a biological sample; an anti-NS1 mouse monoclonal antibody is used to detect the bound NS1 antigen; and, the presence of the bound anti-NS1 antibody is detected using a signal generating compound, e.g. with either an enzyme-conjugated second antibody (e.g., horse radish peroxidase-conjugated antibody;

HRP) or a biotinylated second antibody and streptavidin-enzyme conjugate (e.g., HRP).

In general, methods of the invention involve the steps of (i) separating (i.e., isolating) native viral PL protein analyte from within a complex biological sample using a first binding agent, i.e., a capture agent; and, (ii) detecting the isolated PL analyte using a second binding agent, i.e., a detect agent. The separating and detecting steps may be achieved using binding partners that have different levels of specificity for the PL analyte, e.g., if the capture agent is highly specific then lesser specificity may be required in the detect reagent and vice versa. In certain embodiments, the capture agent is preferably a PDZ domain polypeptide. More preferably, the capture agent is one of those listed in Table 1 and/or Table 2. In alternative embodiments, the first binding partner is an anti-pathogen PL protein antibody or mixture of antibodies, with the proviso that in these embodiments at least one component of the detect reagent is a PDZ polypeptide, e.g., a PDZ protein detect agent that binds to the captured/isolated PL analyte and whose presence in the complex is then detected using an anti-PDZ antibody conjugated with a signal generating compound. In certain presently preferred embodiments, a PDZ capture agent is bound, directly or via a linker, to a solid phase. For example, in one non-limiting example the PDZ domain polypeptide is bound to a magnetic bead. In the latter example, when brought into contact with a biological sample the PDZ capture agent immobilized on the magnetic bead is effective in forming a PDZ-PL interaction complex with an influenza viral PL protein in the sample. Next, a magnetic field is applied and the interaction complex, with the bound influenza virus PL, is isolated from the sample. In another non-limiting example, a PDZ domain polypeptide capture agent is immobilized on the surface of a microtiter plate; a biological sample containing an influenza PL is brought into contact with the immobilized capture reagent resulting in binding of the PL to the surface of the plate; the plate is washed with buffer removing non-PL viral analytes from the plate; and, the immobilized PL analyte is, thus, isolated from the biological sample. Different separation/isolation means are known, e.g., applying a magnetic field, washing and the like. The particular means employed is dependent upon the particular assay format. For example, separation may be accomplished by a number of different methods including but not limited to washing; magnetic means; centrifugation; filtration; chromatography including molecular sieve, ion exchange and affinity; separation in an electrical field; capillary action as e.g. in lateral flow test strips; immunoprecipitation; and, the like as disclosed further below.

In certain embodiments, influenza PL protein is separated from other viral and cellular proteins in a biological sample by bringing an aliquot of the biological sample into contact with one end of a test strip, and then allowing the proteins to migrate on the test strip, e.g., by capillary action such as lateral flow. The instant methods are distinguished from prior immunoassay methods by the presence in the assay of one or more PDZ polypeptide agents, antibodies, and/or aptamers, e.g., as capture and/or detect reagents, conferring upon the assay the ability to specifically identify the presence or amount of a high risk influenza A strain of virus. The instant methods are distinguished from prior immunoassay methods by the fact that they identify a viral protein that is present in the patient sample, rather than an antibody. Methods and devices for lateral flow separation, detection, and quantification are known in the art, e.g., U.S. Pat. Nos. 6,942,981; 5,569,608; 6,297,020; and 6,403,383 incorporated herein by reference in their entirety. In one non-limiting example, a test strip comprises a proximal region for loading the sample (the sample-loading region) and a distal test region containing a PDZ polypeptide capture agent and buffer reagents and additives suitable for establishing binding interactions between the PDZ polypeptide and any influenza PL protein in the migrating biological sample. In alternative embodiments, the test strip comprises two test regions that contain different PDZ domain polypeptides, i.e., each capable of specifically interacting with a different influenza PL protein analyte.

According to the methods disclosed above, influenza PL protein analytes are separated from other proteins in a biological sample, i.e., in such a manner that the analyte in the sample is suitable for detection and/or quantification. Embodiments of the invention provide novel methods for detection of isolated influenza PL proteins using PDZ polypeptides, PDZ polypeptides conjugated with signal generating compounds, antibodies, aptamers and the like. According to alternative embodiments, influenza PL analyte bound to a PDZ capture agent, antibody and/or aptamer is detected using an antibody or antibodies specific for the pathogen PL protein, e.g., an antibody conjugated with a signal generating compound. A variety of detection methods are, of course, known in the diagnostic arts and it is not the intention of the present (non-limiting) disclosure to set forth all alternative well-known methods. Rather, the instant disclosure is intended to satisfy the requirement for setting forth the best mode of practicing the invention and to act as a general reference guide to alternative methods.

In certain embodiments, a PDZ domain conjugated with an SGC (signal generating compound) is used to detect the presence of a pathogen PL protein analyte in a sample in a homogeneous assay format, i.e., without need for a separation step. In this assay method the binding of a PL to the PDZ domain induces a change in the signal produced by the SGC, e.g., a change in fluorescent anisotropy.

In other embodiments, heterogeneous solid phase assay formats (disclosed supra) are useful for detecting influenza PL analytes in biological samples. As noted in the Background section above, PDZ proteins bind cellular proteins containing PL. Similarly, in infected cells influenza viral proteins containing PL bind host cell PDZ proteins. While these interactions would normally be expected to compete with binding in a diagnostic assay format, further guidance is provided hereby that, unexpectedly, the affinities and mass balance of these latter natural interactions are sufficiently weak, or are sufficiently disrupted in detergent extracted cell lysates, that influenza PL analytes are detectable in the instant diagnostic assay formats. Accordingly, lysates may be prepared and assays may be conducted in the presence of less than about 0.5% of a detergent such as Tween-20 or Triton X100; preferably, less than about 0.2%; and, most preferably, less than about 0.1%.

In certain embodiments, the level of viral PL protein in a sample may be quantified and/or compared to controls. Suitable negative control samples are e.g. obtained from individuals known to be healthy, e.g., individuals known not to have a influenza viral infection. Specificity controls may be collected from individuals having known influenza B infection, or individuals infected with lower virulence influenza strains, e.g., H1N1, H3N2 and the like. Control samples can be from individuals genetically related to the subject being tested, but can also be from genetically unrelated individuals. A suitable negative control sample may also be a sample collected from an individual at an earlier stage of infection, i.e., a time point earlier than the time point at which the test sample is taken. Embodiments of the invention also include non-infectious positive controls, i.e., recombinant proteins having amino acid sequences of high-risk influenza A vi Initial Western blots, (see the Examples section, below), show that NS1 levels in biological samples are sufficient to allow detection of these antigens in a variety of different possible immunoassay formats. However, should the levels of NS1 in a particular biological sample prove to be limiting for detection in a particular immunoassay format, then, as one other alternative embodiment, the live virus in a biological sample can be amplified by infecting cells in vitro, i.e., the NS1 protein in the virus-amplified sample should be detectable in about 6 hrs to about 12 hrs. In other alternative embodiments, methods for improving the yield of NS1 antigen in biological samples and virus-amplified samples include uses of protease inhibitors and proteasome inhibitors, e.g. MG 132.

B. Preparation of Reagents

PL peptides, PDZ domain polypeptides, and aptamers may be made synthetically (i.e., using a machine) or using recombinant means, as is known in the art. For example, methods and conditions for expression of recombinant proteins are well known in the art, e.g., see Sambrook, supra, and Ausubel, supra. The use of mammalian tissue cell culture to express polypeptides is discussed generally in Winnacker, "From Genes to Clones, VCH Publishers, N.Y., N.Y., 1987; and, in Ausubel, supra.

Details of the binding assays are also disclosed in U.S. patent application Ser. No. 10/630,590, filed Jul. 29, 2003 and published as US20040018487 and in U.S. Pat. No. 6,942,981.

Cell-based assays generally involve co-producing (i.e., producing in the same cell, regardless of the time at which they are produced), the subject PDZ domain polypeptides and influenza PL using recombinant expression systems. Suitable cells for producing the subject polypeptides in eukaryotic cells are disclosed in the Examples section, below. Cell types that are potentially suitable for expression of subject PDZ domain polypeptide and influenza PL include the following: e.g., monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); HEK-293T cells; baby hamster kidney cells (BHK, ATCC CCL 10); Chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); and mouse L cells (ATCC CCL-1). Additional cell lines will be apparent. A wide variety of cell lines are available from the American Type Culture Collection, 10801 University Boulevard, Manassas, Va. 20110-2209.

C. Sample Preparation

Any sample can be used that contains a detectable concentration of influenza proteins and preferably of NS1. Examples of samples that can be used are lung exudates, cell extracts (respiratory, epithelial lining nose), blood, mucous, and nasal swabs, for example. It was shown herein that a very high concentration of NS1 can be found in nasal swabs from swine and humans. This was surprising in that NS1 was thought to be an intracellular protein. Thus, a preferred sample for identification of NS1 is nasal secretion.

Binding of the PL protein to the PDZ protein and/or to an antibody was shown in the Examples to occur in the presence of up to 0.05% SDS, including 0.03% and 0.01%. Therefore, when the nasal or other bodily secretion is not likely to easily be used in a lateral flow format, it can be treated with SDS. Preferably, the amount of SDS added is up to a final concentration of 0.01%, more preferably 0.03% and even more preferably, 0.05%. Other detergents and the like can be used that do not interfere with binding of the PDZ protein, antibody, or aptamer or other agent to the PL protein. Other methods of sample treatment that do not interfere with protein/protein interactions can be used, including dilution with a buffer or water.

D. General Influenza A Test Alone or in Combination

This test identifies the presence of influenza A in a sample. Therefore, the test can use the method of identifying the presence of an NS1 conserved region using antibodies or aptamers or the like. Preferably, a single monoclonal antibody or a single aptamer identifies all of the variants of NS1. This is most likely when using an antibody that recognizes a conserved region of the NS1 protein. Alternatively, more than one antibody and/or aptamer and/or PDZ protein or other binding agent can be uses to identify all Influenza A subtypes. The method can also use a mixture of antibodies and PDZ proteins to identify all influenza A by the presence of the NS1 protein. The general Influenza A test can be used in combination with a more specific test to subtype the virus, the tests can be performed sequentially or at the same time. See also the description of a pan-specific antibody above for preferred PL regions and PDZ proteins if used in the test.

E. Pathogenic Influenza A Test

This test identifies all forms of the virus having an NS1 protein PL motif. It was identified herein that the nonpathogenic strains of Influenza A have NS1 proteins that are devoid of the avian PL motifs. Thus, methods to specifically identify the presence of a pathogenic influenza A virus can identify the presence of NS1 containing an avian PL region. One or more PDZ proteins and/or antibodies can be used to identify all of the varieties of PL regions. For example, if only PDZ proteins were used, at least two PDZ proteins would be necessary to identify all of the NS1 PL proteins. Alternatively, a single antibody that is capable of recognizing NS1 proteins having a PL region is used. Preferably, the PL region of NS1 to be identified is at least one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. Preferably, the PL region to be identified is that having an avian PL region. Preferably, the one or more PDZ proteins is at least one of those selected from Tables 1 or 2 or analogs or active fragments.

F. Pathogenic Avian Influenza Virus Type A Test

The NS1 protein from H5N1 avian influenza has a C-terminal sequence that binds to a diversity of PDZ domains that fail to bind to NS1 from typical human influenza, such as H3N2. NS1 protein from 77% of avian flu H5N1 isolates terminates in ESEV (SEQ ID NO:2), moreover, the two most common C-terminal NS1 sequences after ESEV (SEQ ID NO:2), ESKV (SEQ ID NO:4) and ESEI (SEQ ID NO:3), account for another 17% of avian influenza isolates also bind PSD-95 with high affinity (i.e.: 45 nM and 200 nM respectively). H3N2 NS1 terminates in RSKV (SEQ ID NO:8) which binds PSD-95 with very low affinity if at all. Therefore PSD-95 can be used as a detection reagent for avian flu and distinguish avian flu from other strains such as H3N2.

Although any part of PSD-95 protein can be used as long as it has a PDZ domain, PSD-95 domains-1, -2 and -3 have different binding specificities and affinities. As part of the identification of which PDZ protein binds with highest affinity to the avian flu H5N1 PLs (see Example 2 and Tables 4a-e), it was found that the PSD-95 domain 2 PDZ binds with highest affinity. Therefore, the PSD-95 PDZ protein used in the assay need only comprise one PDZ domain from the protein, and preferably comprises at least the PDZ from domain 2 or a fragment thereof sufficient for specific binding. The PSD-95 PDZ protein is contacted with a sample. If the sample contains a pathogenic influenza virus A, the PSD-95 PDZ specifically binds to the PL of the NS1 protein of the pathogenic influenza virus.

Figure 8:
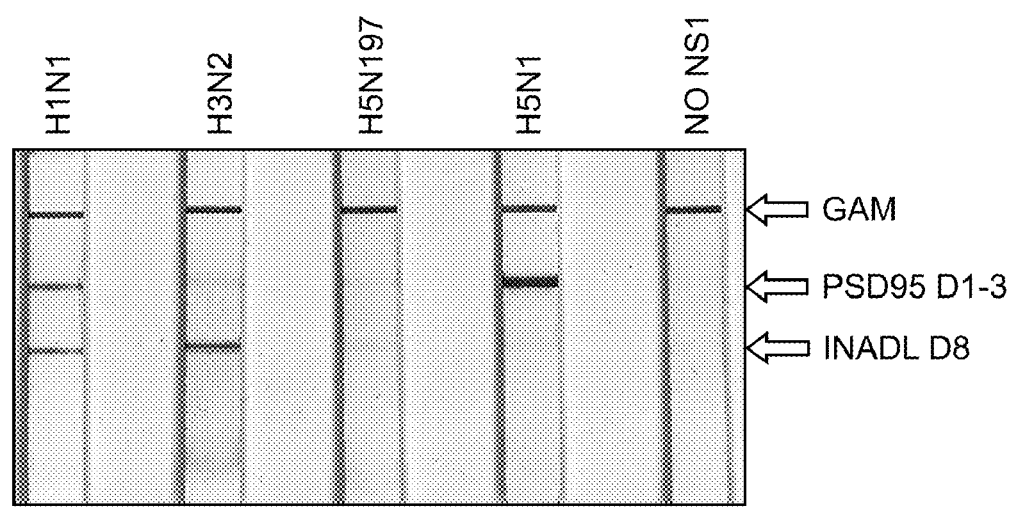
FIG. 8 shows a lateral flow format for an NS1 diagnostic using a PDZ capture agent and monoclonal antibody detect agent AU-4B2.

A lateral flow format such as that set out in FIGS. 8 and 11 and Example 6 can be used for detection of avian NS1 PL proteins using PDZ capture followed by monoclonal antibody detection. Alternatively, the lateral flow format could use monoclonal antibody capture and PDZ detection. The lateral flow can be produced using one or more recombinant PDZ proteins as capture agents deposited on a membrane at specific locations along the membrane (see also Example 6). Analysis of the results of the lateral flow can be qualitative or quantitative. Preferably, a patient sample from a nasal secretion is used. The sample can be pretreated to more easily flow onto a membrane as used in a lateral flow format. The patient sample can be initially contacted with a pan-reactive anti-NS1 monoclonal antibody conjugated with a signal molecule. The monoclonal antibody used for detection preferably does not bind to the same epitope as the PDZ protein that is used, but, instead binds to a separate epitope common to all NS1 proteins. If an NS1 protein in the sample, binds to the capture agent (the PDZ protein deposited on the membrane), a band appears at the site where the PDZ protein was deposited on the membrane. The C-terminal NS1 motifs that are specific to avian influenza strains can be detected with this lateral flow format. These include ESEV (SEQ ID NO:2), ESEI (SEQ ID NO:3) and ESKV (SEQ ID NO:4). In some cases EPEV (SEQ ID NO:27) can be used. Alternative capture agents can be used, including antibodies that specifically bind to only one PL motif on the NS1 proteins.

For qualitative or quantitative analysis and for quality control, any one or all of the following controls can be included. A control band composed of goat anti-mouse antibody (GAM). A lane that identifies whether any influenza A is present, by depositing an antibody that binds to all forms of the NS1 protein on the membrane. A negative control including a PSD-95 protein having all of the domains except the PDZ domains can be included. Other controls can include controls for quantitating the signal, such as purified forms of PL proteins that are known to bind weakly, moderately, strongly or not at all to the capture agent on the membrane, preferably the capture agent is either a PDZ protein or an antibody specific for one or more PLs.

Controls for quantitating the signal can be included to allow for analysis of the strength of binding to differentiate PLs that bind weakly or moderately to PSD-95. For example, Example 6 states the binding strength is quantified by using the following symbols: (−) for no binding, (+) for weak binding, (++) for moderate binding and (+++) for strong binding. The strength of binding to a specific PDZ protein can be used to differentiate H1N1 which has an NS1 that terminates in RSEV which binds PSD-95 with moderate affinity. A positive control for strong binding can be purified NS1 from H5N1, a control for weak binding can be purified NS1 from H3N2, a control for moderate binding can be purified NS1 from H1N1.

Alternatively, other PDZ proteins can be used to further differentiate between strains that bind to PSD-95. For example, as shown in Example 6, both H5N1 and H1N1 bind to PSD-95. So, INADL D8 is used to identify whether the strain is H1N1 or H5N1, since only H1N1 binds. The binding to INADL D8 allows one to unequivocally identify the PL binding to PSD-95 as H5N1. Other PDZ proteins that bind to H1N1 and do not bind to H5N1 can be found in Tables 4a-e and Example 2.

G. Specific NS1 PL Test

This test allows for the identification of a specific class of NS1 PL class by the specific NS1 PL. It may also allow for identifying a subtype by the specific NS1 PL class. Although generally, the type of HA and NP antigens correlate with the NS1 PL region, this is not always the case. It is possible that, for example, due to re-assortment or other genetic processes the virus can undergo, the NS1 PL region from, for example an H1N1 virus can be transferred to an H2N1 virus. However, without being bound to a specific theory, the presence of the NS1 PL region is likely to be more indicative of the pathogenicity of the virus in the patient sample. This may be because of the biological role that NS1 plays in the infection. A preferred test identifies the human PLs ESEV (SEQ ID NO:2). A preferred test identifies the Avian influenza A NS1 PLs having the motifs ESEV (SEQ ID NO:2), ESEI (SEQ ID NO:3), and ESKV (SEQ ID NO:4). This identifies a very pathogenic strain of the virus and appropriate measures can be taken to treat and to contain the disease. Other preferred tests include, for example, an array that allows one to specifically identify the NS1 PL subtype. This type of array can also include a general test for Influenza A. This type of test can also include a test to determine the type of HA and NP protein. Preferably, the PL to be identified is one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. More preferably, the NS1 PL to be identified is ESEV (SEQ ID NO:2). Preferably, the at least one PDZ protein used is at least one of those selected from Tables 1 or 2, fragments or analogs. More preferably, the at least one PDZ protein is at least one of: Outer membrane protein, PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment and/or antibodies (or aptamers) that mimic any PDZ protein.

H. Test for Serum Antibodies

Tests to identify the presence of serum antibodies that bind to specific NS1 PL motifs and/or to NS2 proteins that have a serine at position 70 can be used in any of the diagnostic methods for formats. The specific NS1 PL peptide and/or peptides that include the overlap region containing the Ser 70 can be used as capture reagents in lateral flow or other formats.

I. Use of the Assay in an Epidemic Setting

Assay sensitivity and specificity can be changed to achieve different absolute levels of detection of influenza A NS1 in a biological sample, e.g., by decreasing the levels of a competitive ligand in a competition assay format, changing the amounts of capture and detect reagent in sandwich assays and the like. Thus, the instant test methods encompass a variety of assays having different performance attributes to meet different needs encountered in different uses as illustrated in the Examples section, below. For instance, in an avian epidemic setting the highest PPV is commonly recorded and positive test results are more likely to be true, i.e., with the lowest NPV and false negative results tending to be more likely. Also in monitoring epidemics of influenza A in avian subjects, it is presently common practice to submit all samples to reference laboratories for testing. By identifying the true positive samples in the instant screening assay, e.g., in the field or at the point of care, the instant test assays find uses in reducing the number of samples that must ultimately be submitted to a reference laboratory for testing, i.e., a particular value when the burden of testing is high during an epidemic. Because it is current practice to slaughter all animals, irrespective of whether they are infected, a relatively high false positive rate may be acceptable, but it must also be accompanied by a relatively low false negative rate. In certain embodiments, the invention provides test kits having different specificity, sensitivity, PPV and NPV for use during epidemics, referred to herein as "epidemic test methods". Preferably to suit current needs, the instant epidemic test methods have assay performance as follows: namely, specificity greater than about 65%; sensitivity greater than about 90%; PPV greater than about 85%; NPV greater than about 65%; false positive values of less than about 25% and false negative values of less than about 5%.

In contrast, in times of low influenza A incidence in avian subjects, the lowest PPV is commonly recorded with false positive test results more likely and with the highest NPV and negative tests results tending to be more likely and true. During these times of low incidence the aim in screening may be to rapidly identify potentially infected animals and isolate them until confirmatory testing is completed e.g. in a reference laboratory. Thus, in certain embodiments the invention provides test methods having increased sensitivity and NPV for use during times of low influenza A incidence where monitoring is essential, i.e., referred to herein as "monitoring test methods". Preferably, the instant monitoring test methods have assay performance as follows: namely, specificity greater than about 65%; sensitivity greater than about 90%; PPV greater than about 85%; NPV greater than about 65%; false positive values of less than about 20% and false negative values of less than about 5%. When the instant monitoring test methods are used to screen more than 100 members of a flock, the PPV for the flock as a whole is significantly higher than the predictive values achieved in any one particular assay. Thus, when a positive test result is obtained in a monitoring test method it may prove beneficial to retest the members of the flock using an epidemic test assay, supra.

In human, rather than avian, testing the aims are of course different. Timely evidence of an influenza A infection can have important case management implications, e.g., prompting early administration of anti-viral agents in children or aged subjects. Generally with human diagnostic products a high degree of specificity and sensitivity are needed, e.g., greater than 90% specificity and sensitivity with greater than 90% PPV. However, in a defined epidemic setting, e.g., a cruise ship infection, where PPV is high; the likelihood of false positives is low and likelihood of false negatives is high; and, when samples are submitted for confirmatory testing, it may prove desirable to have a lesser specificity such as 65% in order to yet further lower the number of false negative test results e.g. to a value less than about 5%.

J. Diagnostic and Therapeutic Kits

Kits are provided for carrying out the instant methods. The instant kit is distinguished from immunoassay kits by at least the presence of one or more of: (i) a PDZ domain polypeptide and (ii) printed instructions for conducting an assay to identify a high risk influenza A avian virus strain in a biological sample using the PDZ domain polypeptide. The kit allows for the identification of a viral protein in the patient sample rather than an antibody, making it more specific to an infected individual. The instant kit optionally contains one or more of the reagents, buffers or additive compositions or reagents disclosed supra; and, in certain embodiments the kit can also contain antibodies specific for influenza A viral PL, preferably NS1. In yet other embodiments, the instant kit can further comprise a means, such as a device or a system, for removing the influenza viral PL from other potential interfering substances in the biological sample. The instant kit can further include, if desired, one or more of various components useful in conducting an assay: e.g., one or more assay containers; one or more control or calibration reagents; one or more solid phase surfaces on which to conduct the assay; or, one or more buffers, additives or detection reagents or antibodies; one or more printed instructions, e.g. as package inserts and/or container labels, for indicating the quantities of the respective components that are to be used in performing the assay, as well as, guidelines for assessing the results of the assay. The instant kit can contain components useful for conducting a variety of different types of assay formats, including e.g. test strips, sandwich ELISA, Western blot assays, latex agglutination and the like. The subject reference, control and calibrators within the instant kits can contain e.g. one or more natural and non-natural influenza PL proteins, recombinant PL polypeptides, synthetic PL peptides, PDZ domain polypeptides, PDZ domain peptides and/or appropriate calorimetric and enzyme standards for assessing the performance and accuracy of the instant methods.

The instructions for practicing the subject methods are commonly recorded on a suitable recording medium and included with the kit, e.g., as a package insert. For example, the instructions can be printed on a substrate such as paper or plastic. In other embodiments, the instructions can be digitally recorded on an electronic computer-readable storage medium, e.g. CD-ROM, diskette and the like. In yet other embodiments, instructions for conducting the instant methods can be obtained by a user from a remote digital source, e.g. at an internet website in the form of a downloadable document file.

Optionally, the kits can include reagents for performing a general test for Influenza A as well as specific tests. For example a lateral flow test can have a lane for identifying the presence of a general influenza A virus and a lane for identifying whether that virus is Avian Influenza A. The general test can be any test that identified the presence of an influenza A virus, including the test for the presence of NS1. Other types of general influenza A that can be included can identify any Influenza A protein. Alternatively the presence of influenza A can be identified by the presence of antibodies in the blood of the patient. Finally, PCR tests can be used to generally identify the presence of influenza A.

K. Arrays

In yet other embodiments, the invention provides PDZ, antibody, and/or aptamer arrays consisting of different PDZ polypeptides, antibodies, and/or aptamers or comparable binding agents immobilized at identifiable selected locations on a solid phase. Each of the immobilized PDZ polypeptides, antibodies and/or aptamers in the array has a defined binding affinity and specificity for PL ligands, i.e., including identified binding interactions with PL in influenza viral proteins. The discriminatory activity of the array is contributed by (i) the binding affinity of the respective different PDZ polypeptides, antibodies, and/or aptamers; (ii) the binding specificities of the respective different PDZ polypeptides, antibodies, and/or aptamers for PL; and, (iii) the assay conditions, e.g., ionic strength, time, pH and the like. PDZ domains are highly specific, e.g., the PDZ domain in MAST205 is capable of distinguishing between C-terminal PL sequences containing TDV and SDV. Similarly, within the same PDZ protein the different respective domains can have different binding specificities and affinities, i.e., PSD-95 domains-1, -2 and -3 have different binding specificities and affinities. Applicants have cloned, expressed and disclosed in prior US patent applications, the sequences of more than 255 different human PDZ domains comprising greater than 90% of all the PDZ domains in the human genome. Mapped interactions of the PDZ domain fusion proteins with different PL peptides constitute the basis for selecting particular members of the instant influenza array. Unexpectedly, the selectivity of the array is based in the findings of: (i) distinguishingly different NS-1 PL amino acid sequence motifs in different strains of influenza A, as illustrated in the Examples section below; and, combined with (ii) the different PL sequence motifs in different influenza viral proteins, i.e., HA, NP, MA1, NS1 and the like.

Embodiments of the invention provide methods for distinguishing between the different strains of an Influenza A virus, or Influenza B, in a test sample based on the constituent binding properties of the PL in the influenza viral proteins, e.g., HA, NP, MA-1, NS 1 and the like, in which the different strains and/or subtypes of influenza A and B produce a distinctive pattern of binding on the array. The methods involve the steps of: (a) bringing into contact aliquots of a test sample at different predefined positions in the array; (b) detecting the presence or absence of binding at a particular position in the array; (c) determining from the pattern of binding in the array that (i) influenza PL are present in test sample and (ii) that the pattern of PL binding in the array constitutes a distinguishing signature for a particular strain of influenza A or B virus. Representative examples of the influenza A viruses that are distinguishable based in arrays include e.g. H1N1, H2N2, H2N3, H2N5, H3N2, H3N8, H4N6, H5N1, H6N1, H6N2, H7N2, H7N3 and H7N7. Preferably, the array is at least partly based on the binding to NS1 PL. More preferably, the PDZ, antibody, and/or aptamer arrays specifically identify the presence of at least one NS1 PL, including: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. More preferably, the NS1 PL is ESEV (SEQ ID NO:2). Preferably, the PDZ protein is at least one of those selected from Tables 1 or 2, fragments or analogs. More preferably, the array includes at least one PDZ protein, antibody or aptamer mimic of any PDZ protein listed in Tables 1 and 2, analogs and active fragments. More preferably, the array includes a PDZ protein, antibody mimic and/or aptamer, including Outer membrane protein, PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment and/or antibodies (or aptamers) that mimic any PDZ protein.

L. Lateral Flow Designs

Similar to a home pregnancy test, lateral flow devices work by applying fluid to a test strip that has been treated with specific biologicals. Carried by the liquid sample, phosphors labeled with corresponding biologicals flow through the strip and can be captured as they pass into specific zones. The amount of phosphor signal found on the strip is proportional to the amount of the target analyte.

A sample suspected of containing influenza A is added to a lateral flow device by some means, the sample is allowed to move by diffusion and a line or colored zone indicates the presence of Influenza A. The lateral flow typically contains a solid support (for example nitrocellulose membrane) that contains three specific areas: a sample addition area, a capture area containing one or more PDZ proteins and antibodies immobilized, and a read-out area that contains one or more zones, each zone containing one or more labels. The lateral flow can also include positive and negative controls. Thus, for example a lateral flow device in certain embodiments would perform as follows: an influenza PL protein is separated from other viral and cellular proteins in a biological sample by bringing an aliquot of the biological sample into contact with one end of a test strip, and then allowing the proteins to migrate on the test strip, e.g., by capillary action such as lateral flow. One or more PL binding agents such as PDZ polypeptide agents, antibodies, and/or aptamers are included as capture and/or detect reagents. Methods and devices for lateral flow separation, detection, and quantification are known in the art, e.g., U.S. Pat. Nos. 5,569,608; 6,297,020; and 6,403,383 incorporated herein by reference in their entirety. In one non-limiting example, a test strip comprises a proximal region for loading the sample (the sample-loading region) and a distal test region containing a PDZ polypeptide capture agent and buffer reagents and additives suitable for establishing binding interactions between the PDZ polypeptide and any influenza PL protein in the migrating biological sample. In alternative embodiments, the test strip comprises two test regions that contain different PDZ domain polypeptides, i.e., each capable of specifically interacting with a different influenza PL protein analyte.

XI. Pharmaceutical Compositions

The above screening processes can identify one or more types of compounds that can be incorporated into pharmaceutical compositions. These compounds include agents that are inhibitors of transcription, translation and post-translational processing of either at least one NS1 protein, at least one PDZ protein. The agents also may also inhibit or block binding of an NS1 and a PDZ protein, or mixtures thereof. These compounds also include agents that are inhibitors of either one or more NS1 proteins, one or more PDZ proteins or the interaction between an NS1 and a PDZ protein and have an inherent respiratory and/or digestive or epithelial cell-specific activity or imaging activity. The compounds also include conjugates in which a pharmaceutical agent or imaging component is linked to an inhibitor of either an NS1, a PDZ protein or the interaction between NS1 proteins and PDZ proteins. Conjugates comprising an agent with a pharmacological activity and a conjugate moiety having decreased substrate capacity for a PDZ protein relative to the agent alone are also provided for the purpose of reducing transport of the agent into non-infected cells, where the agent would confer undesired side effects. Preferably, the compound or agent inhibits or blocks the binding of at least one of the following PLs to a PDZ protein: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. More preferably, the NS1 PL that is blocked or inhibited is ESEV. Preferably, the compound or agent inhibits the binding to at least one of the PDZ proteins from Tables 1 or 2. More preferably, the PDZ protein or interaction that is inhibited is at least one of: PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment and/or antibodies (or aptamers) that mimic any PDZ protein.

One or more of the above entities can be combined with pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

Pharmaceutical compositions for oral administration can be in the form of e.g., tablets, pills, powders, lozenges, sachets, cachets, elixirs, suspensions, emulsions, solutions, or syrups. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. Preserving agents such as methyl- and propylhydroxy-benzoates; sweetening agents; and flavoring agents can also be included. Depending on the formulation, compositions can provide quick, sustained or delayed release of the active ingredient after administration to the patient. Polymeric materials can be used for oral sustained release delivery (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J. Macromol. Sci. Rev. Macromol Chem. 23:61; see also Levy et al., 1985, Science 228: 190; During et al., 1989, Ann. Neurol. 25:351; Howard et al., 1989, J. Neurosurg. 71:105). Sustained release can be achieved by encapsulating conjugates within a capsule, or within slow-dissolving polymers. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, Int. J. Pharm. Tech. & Prod. Mfr., 1984, 5(3) 1-9). Factors affecting drug release have been described in the art (Bamba et al., Int. J. Pharm., 1979, 2, 307). For administration by inhalation, the compounds for use according to the disclosures herein are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Effective dosage amounts and regimes (amount and frequency of administration) of the pharmaceutical compositions are readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

A compound can be administered to a patient for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, a compound is administered to a patient susceptible to or otherwise at risk of a particular disease or infection. Hence, a "prophylactically effective" amount is an amount sufficient to prevent, hinder or retard a disease state or its symptoms. In either instance, the precise amount of compound contained in the composition depends on the patient's state of health and weight.

An appropriate dosage of the pharmaceutical composition is determined, for example, using animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The components of pharmaceutical compositions are preferably of high purity and are substantially free of potentially harmful contaminants (e.g., at least National Food (NF) grade, generally at least analytical grade, and more typically at least pharmaceutical grade).

To the extent that a given compound must be synthesized prior to use, the resulting product is typically substantially free of any potentially toxic agents, particularly any endotoxins, which may be present during the synthesis or purification process. Compositions are usually made under GMP conditions. Compositions for parenteral administration are usually sterile and substantially isotonic.

A. Antiviral Agents

Pharmaceutical compositions suitable for use in the present invention include compositions wherein the active agents are contained in an effective dosage. Anti-viral agents include inhibitors of NS1, PDZ, and/or NS1/PDZ interactions that preferably show at least 30, 50, 75, 95, or 99% inhibition of levels of NS1 or PDZ mRNA or protein. Protein expression can be quantified by forming immunological analyses using an antibody that specifically binds to the protein followed by detection of complex formed between the antibody and protein. mRNA levels can be quantified by, for example, dot blot analysis, in-situ hybridization, RT-PCR, quantitative reverse-transcription PCR (i.e., the so-called "TaqMan" methods), Northern blots and nucleic acid probe array methods. Preferably, the NS1 PL used to identify inhibitors is one of: ESEV (SEQ ID NO:2), ESEI (SEQ ID NO:3), ESKV (SEQ ID NO:4), TSEV (SEQ ID NO:5), GSEV (SEQ ID NO:6), RSEV (SEQ ID NO:7), RSKV (SEQ ID NO:8), GSEI (SEQ ID NO:9), GSKV (SEQ ID NO:10), NICI (SEQ ID NO:11), TICI (SEQ ID NO:12), RICI (SEQ ID NO:13), DMAL (SEQ ID NO:14), DMTL (SEQ ID NO:15), DIAL (SEQ ID NO:16), DLDY (SEQ ID NO:17), SICL (SEQ ID NO:18), SEV, SEI, SKV and SKI. More preferably, the NS1 PL used to identify inhibitors is ESEV (SEQ ID NO:2). Preferably, the PDZ protein used to identify inhibitors is at least one of those selected from Tables 1 or 2, fragments or analogs. More preferably, the PDZ protein used to identify inhibitors is at least one of: Outer membrane protein, PSD95 (PDZ # 2); PSD95 (PDZ #1,2,3); DLG1 (PDZ #1); DLG1 (PDZ #1,2); DLG1 (PDZ #2); DLG2 (PDZ #1); DLG2 (PDZ #2); Magi3 (PDZ #1); PTN3 (PDZ #1); MAST2 (PDZ #1); NeDLG (PDZ #1,2); Shank1 d1; Shank2 d1; Shank3 d1; Syntrophin1 alpha; Syntrophin gamma 1; Magi1 (PDZ #1); Magi1 (PDZ #4); Tip1; PTPL1 (PDZ #1); Mint3 (PDZ #1); Lym Mystique (PDZ #1); DLG2 (PDZ #3); MUPP1 (PDZ #8); NeDLG (PDZ #1); DLG5 (PDZ #1); PSD95 (PDZ #1); NumBP (PDZ #3); LIMK1 (PDZ #1); KIAA0313; DLG1 (PDZ #2); Syntenin (PDZ #2); Pick1 or an analog or fragment and/or antibodies (or aptamers) that mimic any PDZ protein.

Anti-viral agents can include PL peptide therapeutics identified as binding to a PDZ protein that interacts with an influenza NS1 or other PL protein. Anti-viral agents include peptides including on based PL motifs or PDZ domains. Some exemplary peptides for inhibiting interactions between influenza virus PL and PDZ domains binding to the PLs are shown in table 11 (SEQ ID NOS:89-987). Other useful peptides are SEQ ID NOS: 2, 48, 53, 996 and 997, as described in the Examples. Therapeutic agents of the invention include the peptides themselves, truncations thereof including at least 5, 10, 15 or 20 contiguous residues starting at the C-terminus, and conservatively substituted variants and mimetics of all of these peptides, optionally incorporated into pharmaceutical compositions. Conservative substitutions, if any, preferably occur outside the C-terminal 3-4 amino acids of the peptides. Peptides that block binding of a pathogenic influenza PL to the PDZ are useful for treating pathogenic influenza. Preferably, the peptides shown in Table 11, truncations, conservatively substituted variants or mimetics thereof are linked to a transporter peptide (protein transduction domain) at the N-terminus of the peptide sequence. Several transporter peptide sequences can be used, including Tat and antennapedia (see also Example 7). Anti-viral therapeutics also include small molecules that inhibit the interaction between a viral PL and a PDZ, as well as Cox2 inhibitors (as identified in Table 8 herein). Some small molecule inhibitors have been identified in Tables 9 and 10 herein.

B. Methods of Screening for Anti-Viral Agents

Methods of screening for agents that bind to NS1 PL proteins and/or PDZ proteins are disclosed herein. The agents are initially screened for binding to the NS1 PL or the PDZ domain of the PDZ protein. Then they are tested for the ability to inhibit the PDZ/PL interaction. These methods are also provided below in "B. assay for anti-viral agents." The binding assay can be performed in vitro using natural or synthetic PL proteins. Alternatively, natural or synthetic PDZ domain containing proteins can be used to identify agents capable of binding to a particular PDZ protein.

Methods of screening for anti-viral agents disclosed herein identify agents that block or inhibit the interaction between the viral PL and any PDZ protein that it interacts with. Inhibitors and DNA encoding them are screened for capacity to inhibit expression of NS1 and/or PDZ. An initial screen can be performed to select a subset of agents capable of inhibiting or stopping the PDZ/PL interaction. Such an assay can be performed in vitro using an isolated PDZ protein and PL protein or fragments thereof capable of binding to each other. Agents identified by such a screen can then be assayed functionally. Agents can also be screened in cells expressing PL proteins and either expressing the PDZ protein naturally or transformed to express the PDZ protein.

In addition to the diagnostic assays disclosed and illustrated above, embodiments provide assays for identifying candidate anti-viral agents capable of modulating one or more binding interactions occurring between an influenza viral PL and a host cell PDZ polypeptide in an influenza A infected cell. The instant methods involve testing the binding of a control PL, e.g., a synthetic PL peptide, to a PDZ domain polypeptide, e.g., a recombinant PDZ fusion protein, in the presence of an anti-viral test agent. A candidate anti-viral agent modulates the binding between the control PL and the PDZ domain polypeptide. Applicant has previously disclosed assays for measuring binding interactions between control PL and PDZ domain polypeptides in US and International patent applications, e.g., U.S. Pat. Nos. 5,569,608; 6,297,020; and 6,403,383 incorporated herein by reference in their entirety.

Particularly useful screening assays employ cells which express both one or more influenza NS1 PLs and one or more PDZ domain proteins. Such cells can be made recombinantly by co-transfection of the cells with polynucleotides encoding the proteins, or can be made by transfecting a cell which naturally contains one of the proteins with the second protein. In a particular embodiment, such cells are grown up in multi-well culture dishes and are exposed to varying concentrations of a test compound or compounds for a pre-determined period of time, which can be determined empirically. Whole cell lysates, cultured media or cell membranes are assayed for inhibition of the PL/PDZ interaction. Test compounds that significantly inhibit activity compared to control (as discussed below) are considered therapeutic candidates.

Isolated PDZ domain proteins or PL-binding fragments thereof, can be used for screening therapeutic compounds in any of a variety of drug screening techniques. Alternatively, isolated NS1 PL proteins or fragments containing the PL motif can be used The protein employed in such a test can be membrane-bound, free in solution, affixed to a solid support, borne on a cell surface, or located intracellularly. The formation of binding complexes between the PDZ domain or NS1 PL and the agent being tested can be measured. More specifically, a test compound is considered as an inhibitor of the PDZ/PL interaction if the interaction is significantly lower than the interaction measured in the absence of test compound. In this context, the term "significantly lower" means that in the presence of the test compound the PDZ/PL interaction, when compared to that measured in the absence of test compound, is measurably lower, within the confidence limits of the assay method.

Random libraries of peptides or other compounds can also be screened for suitability as inhibitors of the PDZ/PL binding, or for simply binding to either the PDZ domain protein or the NS1 PL protein. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes).

A preferred source of test compounds for use in screening for therapeutics or therapeutic leads is a phage display library. See, e.g., Devlin, WO 91/18980; Key, B. K., et al., eds., Phage Display of Peptides and Proteins, A Laboratory Manual, Academic Press, San Diego, Calif., 1996. Phage display is a powerful technology that allows one to use phage genetics to select and amplify peptides or proteins of desired characteristics from libraries containing $10^8$-$10^9$ different sequences. Libraries can be designed for selected variegation of an amino acid sequence at desired positions, allowing bias of the library toward desired characteristics. Libraries are designed so that peptides are expressed fused to proteins that are displayed on the surface of the bacteriophage. The phage displaying peptides of the desired characteristics are selected and can be regrown for expansion. Since the peptides are amplified by propagation of the phage, the DNA from the selected phage can be readily sequenced facilitating rapid analyses of the selected peptides.

Phage encoding peptide inhibitors can be selected by selecting for phage that bind specifically to a PDZ domain protein and/or to an NS1 PL. Libraries are generated fused to proteins such as gene II that are expressed on the surface of the phage. The libraries can be composed of peptides of various lengths, linear or constrained by the inclusion of two Cys amino acids, fused to the phage protein or can also be fused to additional proteins as a scaffold. One can also design libraries biased toward the PL regions disclosed herein or biased toward peptide sequences obtained from the selection of binding phage from the initial libraries provide additional test inhibitor compound.

C. Types of Anti-Viral Agents

Any of the agents set out below can be used as pharmaceuticals as well as those identified in screening methods. Inhibitors can be identified from any type of library, including RNA expression libraries, bacteriophage expression libraries, small molecule libraries, peptide libraries. Inhibitors can also be produced using the known sequence of the nucleic acid and/or polypeptide. The compounds also include several categories of molecules known to regulate gene expression, such as zinc finger proteins, ribozymes, siRNAs and antisense RNAs.

(a) siRNA Inhibitors siRNAs are relatively short, at least partly double stranded, RNA molecules that serve to inhibit expression of a complementary mRNA transcript. Although an understanding of mechanism is not required for practice of the invention, it is believed that siRNAs act by inducing degradation of a complementary mRNA transcript. Principles for design and use of siRNAs generally are described by WO 99/32619, Elbashir, EMBO J. 20, 6877-6888 (2001) and Nykanen et al., Cell 107, 309-321 (2001); WO 01/29058.

siRNAs of the invention are formed from two strands of at least partly complementary RNA, each strand preferably of 10-30, 15-25, or 17-23 or 19-21 nucleotides long. The strands can be perfectly complementary to each other throughout their length or can have single stranded 3'-overhangs at one or both ends of an otherwise double stranded molecule. Single stranded overhangs, if present, are usually of 1-6 bases with 1 or 2 bases being preferred. The antisense strand of an siRNA is selected to be substantially complementary (e.g., at least 80, 90, 95% and preferably 100%) complementary to a segment of a NS1 or PDZ transcript. Any mismatched based preferably occur at or near the ends of the strands of the siRNA. Mismatched bases at the ends can be deoxyribonucleotides. The sense strand of an siRNA shows an analogous relationship with the complement of the segment of the NS1 or PDZ transcript. siRNAs having two strands, each having 19 bases of perfect complementarity, and having two unmatched bases at the 3' end of the sense strand and one at the 3' end of the antisense strand are particularly suitable.

If an siRNA is to be administered as such, as distinct from the form of DNA encoding the siRNA, then the strands of an siRNA can contain one or more nucleotide analogs. The nucleotide analogs are located at positions at which inhibitor activity is not substantially effected, e.g. in a region at the 5'-end and/or the 3'-end, particularly single stranded overhang regions. Preferred nucleotide analogues are sugar- or backbone-modified ribonucleotides. Nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8 position, e.g. 8-bromo guanosine; deaza nucleotides, e.g. 7-deaza-adenosine; O- and N-alkylated nucleotides, e.g. N6-methyl adenosine are also suitable. In preferred sugar-modified ribonucleotides, the 2' OH-group is replaced by a group selected from H, OR, R, halo, SH, SR, NH2, NHR, NR2 or CN, wherein R is C1-C6 alkyl, alkenyl or alkynyl and halo is F, CI, Br or I. In preferred backbone-modified ribonucleotides the phosphoester group connecting to adjacent ribonucleotides is replaced by a modified group, e.g. of phosphothioate group. A further preferred modification is to introduce a phosphate group on the 5' hydroxide residue of an siRNA. Such a group can be introduced by treatment of an siRNA with ATP and T4 kinase. The phosphodiester linkages of natural RNA can also be modified to include at least one of a nitrogen or sulfur heteroatom. Modifications in RNA structure can be tailored to allow specific genetic inhibition while avoiding a general panic response in some organisms which is generated by dsRNA. Likewise, bases can be modified to block the activity of adenosine deaminase.

A number of segments within the NS1 or PDZ transcript are suitable targets for design of siRNAs. When a selected segment of NS1 PL is used to selectively target a subtype, the segment preferably shows a lack of perfect sequence identity with other NS1 PL regions of the transcript. Preferably, the selected segment of an NS1 or PDZ protein shows at least at least 1, 2, 3, 4 or more nucleotide differences from a corresponding segment (if any) of a NS1 PL. Target sites can be chosen from the coding region, 5'UTR and 3'UTR of NS1 or PDZ, in some cases, the PL site of NS1 is preferred. A preferred target site is that of the siRNA termed NS1 PL (see Examples). This site is at the C-terminus and is specific for subtypes of the Influenza A virus. Other preferred sites include the PL binding site of the PDZ protein.

siRNA can be synthesized recombinantly by inserting a segment of DNA encoding the siRNA between a pair of promoters that are oriented to drive transcription of the inserted segment in opposite orientations. Transcription from such promoters produces two complementary RNA strands that can subsequently anneal to form the desired dsRNA. Exemplary plasmids for use in such systems include the plasmid (PCR 4.0 TOPO) (available from Invitrogen). Another example is the vector pGEM-T (Promega, Madison, Wis.) in which the oppositely oriented promoters are T7 and SP6; the T3 promoter can also be used. Alternatively, DNA segments encoding the strands of the siRNA are inserted downstream of a single promoter. In this system, the sense and antisense strands of the siRNA are co-transcribed to generate a single RNA strand that is self-complementary and thus can form dsRNA. Vectors encoding siRNAs can be transcribed in vitro, or in cell culture or can be introduced into transgenic animals or patients for expression in situ. Suitable vectors are described below. The selection of promoters and optionally other regulatory sequences for recombinant expression can determine the tissue specificity of expression. For example, PDGF, prion, neural enolase, or thy-1 promoters are suitable for expression in the central nervous system.

The strands of an siRNAs can also be synthesized by organic chemical synthesis and annealed in vitro. If synthesized chemically or by in vitro enzymatic synthesis, the RNA can be purified prior to introduction into the cell. For example, RNA can be purified from a mixture by extraction with a solvent or resin precipitation, electrophoresis, chromatography; or a combination thereof. The RNA can be dried for storage or dissolve in an aqueous solution. The solution can contain buffers or salts to promote annealing, and/or stabilization of the duplex stands. siRNAs can be introduced into cells or organisms either as RNA or in the form of DNA encoding the RNA by a variety of approaches, as described below.

(b) Antisense Polynucleotides

Antisense polynucleotides can cause suppression by binding to, and interfering with, the translation of sense mRNA, interfering with transcription, interfering with processing or localization of RNA precursors, repressing transcription of mRNA or acting through some other mechanism. The particular mechanism by which the antisense molecule reduces expression is not critical.

Typically antisense polynucleotides comprise a single-stranded antisense sequence of at least 7 to 10 to typically 20 or more nucleotides that specifically hybridize to a sequence from mRNA of a gene. Some antisense polynucleotides are from about 10 to about 50 nucleotides in length or from about 14 to about 35 nucleotides in length. Some antisense polynucleotides are polynucleotides of less than about 100 nucleotides or less than about 200 nucleotides. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

To ensure specific hybridization, the antisense sequence is at least substantially complementary to a segment of target mRNA or gene encoding the same. Some antisense sequences are exactly complementary to their intended target sequence. The antisense polynucleotides can also include, however, nucleotide substitutions, additions, deletions, transitions, transpositions, or modifications, or other nucleic acid sequences or non-nucleic acid moieties so long as specific binding to the relevant target sequence corresponding to RNA or its gene is retained as a functional property of the polynucleotide. Antisense polynucleotides intended to inhibit NS1 or PDZ protein expression are designed to show perfect or a substantial degree of sequence identity to a specific NS1 or PDZ gene or transcript and imperfect and a lower degree of sequence identity to different PDZ gene.

Some antisense sequences are complementary to relatively accessible sequences of mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., 1997, Nature Biotechnology 15:537).

Antisense nucleic acids (DNA, RNA, modified, analogues, and the like) can be made using any suitable method for producing a nucleic acid, such as the chemical synthesis and recombinant methods disclosed herein. Antisense RNA can be delivered as is or in the form of DNA encoding the antisense RNA. DNA encoding antisense RNA can be delivered as a component of a vector, or in nonreplicable form, such as described below.

(c) Zinc Finger Proteins

Zinc finger proteins can also be used to suppress expression of the NS1 or PDZ protein or nucleic acid or a specific NS1 subtype. Zinc finger proteins can be engineered or selected to bind to any desired target site within a target gene. In some methods, the target site is within a promoter or enhancer. In other methods, the target site is within the structural gene. In some methods, the zinc finger protein is linked to a transcriptional repressor, such as the KRAB repression domain from the human KOX-1 protein (Thiesen et al., *New Biologist* 2, 363-374 (1990); Margolin et al., *Proc. Natl. Acad. Sci. USA* 91, 4509-4513 (1994); Pengue et al., *Nucl. Acids Res.* 22:2908-2914 (1994); Witzgall et al., *Proc. Natl. Acad. Sci. USA* 91, 4514-4518 (1994). Methods for selecting target sites suitable for targeting by zinc finger proteins, and methods for design zinc finger proteins to bind to selected target sites are described in WO 00/00388. Methods for selecting zinc finger proteins to bind to a target using phage display are described by EP.95908614.1. The target site used for design of a zinc finger protein is typically of the order of 9-19 nucleotides. For inhibition of NS1 or PDZ protein or polynucleotide, a target site is chosen within the NS1 or PDZ protein or polynucleotide that shows imperfect or lack of substantial sequence identity to a different PDZ gene or transcript as discussed above. Methods for using zinc finger proteins to regulate endogenous genes are described in WO 00/00409. Zinc finger proteins can be administered either as proteins or in the form of nucleic acids encoding zinc fingers. In the latter situation, the nucleic acids can be delivered using vectors or in nonreplicable form as described below.

(d) Ribozymes

Ribozymes are RNA molecules that act as enzymes and can be engineered to cleave other RNA molecules at specific sites. The ribozyme itself is not consumed in this process, and can act catalytically to cleave multiple copies of mRNA target molecules. General rules for the design of ribozymes that cleave target RNA in trans are described in Haseloff &

Gerlach, (1988) Nature 334:585-591 and Uhlenbeck, (1987) Nature 328:596-603 and U.S. Pat. No. 5,496,698.

Ribozymes typically include two flanking segments that show complementarity to and bind to two sites on a transcript (target subsites) and a catalytic region between the flanking segments. The flanking segments are typically 5-9 nucleotides long and optimally 6 to 8 nucleotides long. The catalytic region of the ribozyme is generally about 22 nucleotides in length. The mRNA target contains a consensus cleavage site between the target subsites having the general formula NUN, and preferably GUC. (Kashani-Sabet and Scanlon, (1995) Cancer Gene Therapy 2:213-223; Perriman, et al., (1992) Gene (Amst.) 113:157-163; Ruffner, et al., (1990) Biochemistry 29: 10695-10702); Birikh, et al., (1997) Eur. J. Biochem. 245:1-16; Perrealt, et al., (1991) Biochemistry 30:4020-4025).

The specificity of a ribozyme can be controlled by selection of the target subsites and thus the flanking segments of the ribozyme that are complementary to such subsites. For an inhibitor of NS1 or PDZ proteins, the target subsites are preferably chosen so that there are no exact corresponding subsites in other PDZ proteins and preferably no corresponding subsites with substantial sequence identity. Ribozymes can be delivered either as RNA molecules or in the form of DNA encoding the ribozyme as a component of a replicable vector or in nonreplicable form as described below.

(e) Antibodies

The compounds include antibodies, both intact and binding fragments thereof, such as Fabs, Fvs, which specifically bind to a protein encoded by a gene of the invention. Usually the antibody is a monoclonal antibody although polyclonal antibodies can also be expressed recombinantly (see, e.g., U.S. Pat. No. 6,555,310). Examples of antibodies that can be expressed include mouse antibodies, chimeric antibodies, humanized antibodies, veneered antibodies and human antibodies. Chimeric antibodies are antibodies whose light and heavy chain genes have been constructed, typically by genetic engineering, from immunoglobulin gene segments belonging to different species (see, e.g., Boyce et al., Annals of Oncology 14:520-535 (2003)). For example, the variable (V) segments of the genes from a mouse monoclonal antibody can be joined to human constant (C) segments. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions substantially from a mouse-antibody, (referred to as the donor immunoglobulin). See Queen et al., Proc. Natl. Acad. Sci. USA 86:10029-10033 (1989) and WO 90/07861, U.S. Pat. Nos. 5,693,762 , 5,693, 761, 5,585,089 5,530,101 and Winter, U.S. Pat. No. 5,225, 539. The constant region(s), if present, are also substantially or entirely from a human immunoglobulin. Antibodies can be obtained by conventional hybridoma approaches, phage display (see, e.g., Dower et al., WO 91/17271 and McCafferty et al., WO 92/01047), use of transgenic mice with human immune systems (Lonberg et al., WO93/12227 (1993)), among other sources. Nucleic acids encoding immunoglobulin chains can be obtained from hybridomas or cell lines producing antibodies, or based on immunoglobulin nucleic acid or amino acid sequences in the published literature.

(f) Mimetic Compounds

In particular embodiments, the subject candidate anti-viral compound identified in the instant screening methods compound is a peptidomimetic of the subject PDZ domain polypeptide or PL, i.e., a synthetic chemical compound that has substantially the same structural and/or functional characteristics as a subject PDZ domain or PL. The subject mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation determines whether a mimetic is within the scope of the invention, i.e., that its structure and/or function is not substantially altered. Thus, a mimetic composition is within the scope of the invention if it is capable of inhibiting binding between the subject polypeptides.

Mimetics can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=-dicyclohexylcarbodiimide (DCC) or N,N=-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, NY).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R—N═C═N—R—) such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines, to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

An amino acid of a subject polypeptide can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S- form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110:1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114: 10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777. Secondary structures of polypeptides can be analyzed by, e.g., high-field 1H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

D. Improving Anti-Viral Agents

To improve acceptance and introduction of the anti-viral agent into a cell of choice, there are a number of known methods. For example, PEGylation of proteins can be used to make them more resistant to the immune system. Alternatively, intracellular signals or moieties can be added to proteins and vectors to allow them to more easily enter the cell of choice. Moieties that make the protein or vector specifically acceptable to uptake by infected cells can be added, in this case a ligand that is specific for a receptor expressed by respiratory cells. The moiety may be specific for an influenza receptor or cell-type specific receptor.

The instant therapeutic compounds may be further modified to make the compound more soluble or to facilitate its entry into a cell. For example, the compound may be PEGylated at any position, or the compound may be conjugated to a membrane translocating peptide such as a tat, Antennapedia or signal sequence membrane translocation peptide such as described by U. Langel, "Cell Penetrating Peptides", CRC Press, Boca Rotan, 2002, i.e., incorporated herein by reference in its entirety.

A number of peptide sequences have been described in the art as capable of facilitating the entry of a peptide linked to these sequences into a cell through the plasma membrane (Derossi et al., 1998, Trends in Cell Biol. 8:84). For the purpose of this invention, such peptides are collectively referred to as "transmembrane transporter peptides", which is used interchangeably with "cell penetrating peptides". Examples of the latter cell penetrating peptides include, but are not limited to the following: namely, tat derived from HIV (Vives et al., 1997, *J. Biol. Chem.* 272:16010; Nagahara et al., 1998, *Nat. Med.* 4:1449), antennapedia from *Drosophila* (Derossi et al., 1994, *J. Biol. Chem.* 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, *Proc. Natl Acad. Sci. U.S.A.*, 95:5601-5606), 70 KDa heat shock protein (Fujihara, 1999, *EMBO J.* 18:411-419) and transportan (Pooga et al., 1998, *FASEB J.* 12:67-77). In certain embodiments, a truncated HIV tat peptide may be employed.

E. Interferon Production

Interferon-α and -β (IFN-α/β) play key roles in innate cellular mechanisms of anti-viral resistance, e.g., inhibiting transcription and translation of viral sequences. Assembly of IFN-α/β receptor signaling complexes requires recruitment of factors including transcription factors, e.g. NF-κB, STAT and INF-induced transcription factor-3; and protein kinases to the receptor complex. It is believed RACK1 may serve as the scaffolding protein recruiting and/or binding PKC and STAT to the complex; possibly in association with Plectin, i.e., a hemidesmasome organizer. Recent data from other laboratories suggests that mumps and measles viruses may disrupt the INF-α/β signaling complex, i.e., the mumps V-protein reportedly associates with RACK1 and induces dissociation of STAT from the receptor complexes; and, in measles virus infected cells the viral C and/or V proteins reportedly inhibit phosphorylation of signaling kinases by associating with and "freezing" the INF-α/β receptor complex.

Interferon-α/β signaling inhibits pro-apoptotic responses promoting cell survival through nuclear mobilization of STAT and NFκB[14]. Interferon receptor signaling triggers activation of PKC-δ[15] which, in turn, can down-regulate caspase 3[16], as well as, proinflammatory signaling through STAT[17] and, in the airway, through NFκB[18,19]. PKC-δ activation also reportedly suppresses TNFα-induced apoptosis[20,21]. In this respect, avian influenza NS1 inhibition of IFN-α/β signaling seems destined to promote cell death and determine the severity of disease. Thus, candidate medicinal agents and novel molecular targets for drug development are those that interfere with and/or interrupt NS1 effects on IFN-α/β signaling. These agents promote a desired therapeutic effect of ameliorating one or more symptoms of disease in a subject infected with influenza A.

High-risk (see also pathogenic) avian strains of influenza A establish fulminant infections in humans, i.e., spreading rapidly beyond mucosal pulmonary tissues into circulation and the CNS. Without being bound to a particular theory, it is highly likely that certain of the latter effects result from inhibition of INF-α/β signaling mediated by non-structural influenza A viral proteins. Further, it is highly likely that viral proteins such as NS1 and NS2 inhibit intracellular PDZ domain-PL interactions requisite for effective IFN-α/β signaling and induction of cellular anti-viral resistance mechanisms.

Possible PDZ-ligand (PL) sequences were identified herein in INF-α/β receptor-1 (Accession No. 16166194), the C-terminal sequence "QDFV" (SEQ ID NO: 31), i.e., a possible class-1 PL sequence. Similarly, other potential members of the INF-α/β-receptor-1 signaling complex also contain putative C-terminal PL sequence motifs as follows: namely, MAP-1A (Accession No. 2119250) contains "KSRV" (SEQ ID NO: 32); MAP-1B (Accession No. 14165456/5174525) contains "KIEL" (SEQ ID NO: 33); MAP-1A/1B light chain-3 (Accession No. 12383056/18551443) contains C-terminal "KLSV" (SEQ ID NO: 34); Plectin-1 (Accession No. 4505877) contains C-terminal PL sequence motif "SAVA" (SEQ ID NO: 35); PKC-6 (Accession No. 509050) contains "KVLL" (SEQ ID NO: 36); INF-inducible protein kinase (Accession Nos. 13637584 and 4506103—elf2 alpha) contain C-terminal sequence motifs "RHTC" (SEQ ID NO: 37); interferon alpha responsive transcription factor-3 (Accession No. 5174475) has C-terminal motif "LSLV" (SEQ ID NO: 38); and, interferon regulatory factor-2 (Accession No. 20141499/4504723) contains "VKSC" (SEQ ID NO: 39).

Thus, it is highly likely that PDZ domain-PL interactions play significant roles in viral pathogenesis and thus constitute targets for development of medicinal compounds.

Medicinal compounds capable of inhibiting the interaction of NS1 with the intracellular PDZ-domains of the IFN-α/β receptor complex include PL peptides, and mimetics thereof, peptide inhibitors of NS1 PL/IFN interactions, inhibitors of NS1 expression, cell permeable non-natural PDZ domain polypeptides, and mimetics thereof, and small molecule inhibitors capable of inhibiting the binding of NS1 PL to human the specific PDZ domains involved in the IFN-α/β response.

F. Methods of Treatment

Pharmaceutical compositions disclosed herein are used in methods of treatment of prophylaxis of Influenza A diseases.

As can be appreciated from the disclosure above, the present invention has a wide variety of applications. For example, the inhibitors of either NS1 protein, PDZ protein or the interaction between an NS1 and PDZ protein, can be used to identify an agent or conjugate that interacts with the transporter and that can cross into the infected cell. The inhibitors of either NS1 protein, PDZ protein or the interaction between NS1 protein and PDZ protein also can be used to increase the capacity of an agent to bind to an infected cell by identifying a conjugate moiety that binds to the infected cell and linking the conjugate moiety to the agent.

In prophylactic application, pharmaceutical compositions or medicants are administered to a patient susceptible to, or otherwise at risk for developing Influenza A infections in an amount sufficient to prevent, reduce, or arrest the development of influenza A infections. In therapeutic applications, compositions or medicants are administered to a patient suspected to develop, or already suffering from influenza in an amount sufficient to reverse, arrest, or at least partially arrest, the symptoms of influenza A infections. In both prophylactic and therapeutic regimes, active agents in the form of inhibitors of NS1, PDZ, and/or the NS1-PDZ interaction, of the present invention are usually administered in several dosages until a sufficient response has been achieved. However, in both prophylactic and therapeutic regimes, the active agents can be administered in a single dosages until a sufficient response has been achieved. Typically, the treatment is monitored and repeated dosages can be given. Furthermore, the treatment regimes can employ similar dosages; routes of administration and frequency of administration to those used in treating Influenza A infection or progression of an influenza A infection.

The amount of the inhibitors of NS1 protein, PDZ protein and/or the NS1/PDZ interaction and other active agents that can be combined with a carrier material to produce a single dosage form vary depending upon the disease treated, the mammalian species, and the particular mode of administration. The "effective dosage", "pharmacologically acceptable dose" or "pharmacologically acceptable amount" for any particular patient can depend on a variety of factors including the activity of the specific compound employed, the species, age, body weight, general health, sex and diet of the patient being treated; the time and route of administration; the rate of metabolism or excretion; other drugs which are concurrently or have previously been administered; the type and severity of the disease; severity of side-effects, whether the patient is animal or human, and the like. Usually the patient is human, but nonhuman mammals, including transgenic mammals, can also be treated. Full length or active fragments of the active agents may be administered in effective dosages.

For any inhibitors of NS1 protein, PDZ protein and/or the NS1/PDZ interaction and other active agents used in the methods of the present invention, an effective dose for humans can be estimated initially from non-human animal models. An effective dose can be determined by a clinician using parameters known in the art. Generally, dosing begins with an amount somewhat less than the optimal effective dose. Dosing is then increased by small increments thereafter until an effective dosage is achieved. (See *The Merck Manual of Diagnosis and Therapy*, $16^{th}$ Edition, § 22, 1992, Berkow, Merck Research Laboratories, Rahway, N.J., which is incorporated herein by reference).

Dosages need to be titrated to optimize safety and efficacy. Toxicity and therapeutic efficacy of the compounds described herein can be determined by standard pharmaceutical procedures in experimental animals, e.g., by determining the $LD_{50}$, (the dose lethal to 50% of the population tested) and the $ED_{50}$ (the dose therapeutically effective in 50% of the population tested). The dose ratio between toxic and therapeutic effect is the therapeutic index and can be expressed as the ratio between $LD_{50}$ and $ED_{50}$. Compounds that exhibit high therapeutic indices are preferred. The data obtained from these nonhuman animal studies can be used in formulating a dosage range that is not toxic for use in humans. The dosage of such compounds lies preferably within a range of circulating concentrations that include the $ED_{50}$ with little or no toxicity. The exact formulation, route of administration and dosage can be chosen by the individual physician in view of the patient's condition. (See, e.g., Fingl et al. (1975) In: *The Pharmacological Basis of Therapeutics*, Chapter 1, which is incorporated herein by reference).

G. Methods of Administration

Inhibitors of NS1 protein, PDZ protein and/or the NS1/PDZ interaction and other active agents can be delivered or administered to a mammal, e.g., a human patient or subject, alone, in the form of a pharmaceutically acceptable salt or hydrolyzable precursor thereof, or in the form of a pharmaceutical composition wherein the compound is mixed with suitable carriers or excipient(s) in an effective dosage. An effective regime means that a drug or combination of drugs is administered in sufficient amount and frequency and by an appropriate route to at least detectably prevent, delay, inhibit or reverse development of at least one symptom of influenza A infection. An "effective dosage", "pharmacologically acceptable dose", "pharmacologically acceptable amount" means that a sufficient amount of an inhibitors of NS1 proteins or expression, PDZ proteins or expression and/or the NS1/PDZ protein interaction, an active agent or inhibitors of NS1, PDZ protein and/or the NS1/PDZ protein interaction in combination with other active agents is present to achieve a desired result, e.g., preventing, delaying, inhibiting or reversing a symptom of influenza A infections or the progression of influenza A infections when administered in an appropriate regime.

Inhibitors of NS1 from influenza A, one or more PDZ proteins and/or the NS1/PDZ protein interaction and other active agents that are used in the methods of the present invention can be administered as pharmaceutical compositions comprising the inhibitors of NS1, PDZ protein and/or the NS1/PDZ protein interaction or active agent, together with a variety of other pharmaceutically acceptable components. Pharmaceutical compositions can be in the form of solids (such as powders, granules, dragees, tablets or pills), semi-solids (such as gels, slurries, or ointments), liquids, or gases (such as aerosols or inhalants).

Suitable formulations for use in the present invention are found in *Remington's Pharmaceutical Sciences* (Mack Publishing Company 1985) Philadelphia, Pa., $17^{th}$ edition) and Langer, *Science* (1990) 249:1527-1533, which are incorporated herein by reference. The pharmaceutical compositions described herein can be manufactured in a conventional manner, i.e., mixing, dissolving, granulating, dragee-making, levigating, emulsifying, encapsulating, entrapping or lyophilizing processes.

Inhibitors of NS1, PDZ protein and/or the NS1/PDZ protein interaction and other active agents can be formulated with common excipients, diluents or carriers, and compressed into tablets, or formulated as elixirs or solutions for convenient oral administration. Inhibitors of NS1, PDZ protein and/or NS1/PDZ protein interaction and other active agents can also be formulated as sustained release dosage forms and the like.

Administration of the compounds can be achieved in various ways, including oral, buccal, rectal, parenteral, intraperitoneal, intradermal, transdermal, intratracheal, intravenous, and intramuscular administration. The compound can be administered in a local rather than systemic manner, in a depot or sustained release formulation. In addition, the compounds can be administered in a liposome. Moreover, the compound can be administered by gene therapy.

For buccal administration, the compositions can take the form of tablets or lozenges formulated in a conventional manner.

For administration by inhalation, the compounds for use according to the present invention are conveniently delivered in the form of an aerosol spray preparation from pressurized packs, a nebulizer or a syringe sprayer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oil-based or aqueous vehicles, and can contain formulator agents such as suspending, stabilizing and/or dispersing agents. The compositions are formulated as sterile, substantially isotonic and in full compliance with all Good Manufacturing Practice (GMP) regulations of the U.S. Food and Drug Administration.

Inhibitors of NS1, PDZ protein and/or the NS1/PDZ protein interaction and other active agents can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, for example, as a sparingly soluble salt. (See, e.g., Urquhart et al., (1984), *Ann Rev. Pharmacol. Toxicol.* 24:199; Lewis, ed., 1981, *Controlled Release of Pesticides and Pharmaceuticals*, Plenum Press, New York, N.Y., U.S. Pat. Nos. 3,773,919, and 3,270,960, which are incorporated herein by reference).

Alternatively, other delivery systems for hydrophobic pharmaceutical compounds can be employed. Liposomes and emulsions are well known examples of delivery vehicles or carriers for hydrophobic drugs. In some methods, long-circulating, i.e., stealth, liposomes can be employed. Such liposomes are generally described in Woodle, et al., U.S. Pat. No. 5,013,556, the teaching of which is hereby incorporated by reference. The compounds of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

For administration by gene therapy, genetic material (e.g., DNA or RNA) of interest is transferred into a host to treat or prevent Influenza A infection. In the present invention, the genetic material of interest encodes an inhibitor of NS1, PDZ and/or the NS1/PDZ interaction, an active agent or a fragment thereof. According to one aspect of the invention, the genetic material should be therapeutically effective. Many such proteins, vectors, DNA are known per se. (See Culver, K. W., "Gene Therapy", 1994, p. xii, Mary Ann Liebert, Inc., Publishers, New York, N.Y., incorporated herein by reference in its entirety). For the purposes of example only, vectors can be selected from the group consisting of Moloney murine leukemia virus vectors, adenovirus vectors with tissue specific promoters, herpes simplex vectors, vaccinia vectors, artificial chromosomes, receptor mediated gene delivery, and mixtures of the above vectors. Gene therapy vectors are commercially available from different laboratories such as Chiron, Inc., Emeryville, Calif.; Genetic Therapy, Inc., Gaithersburg, Md.; Genzyme, Cambridge, Mass.; Somtax, Alameda, Calif.; Targeted Genetics, Seattle, Wash.; Viagene and Vical, San Diego, Calif.

Adenoviruses are promising gene therapy vectors for genetic material encoding inhibitors of NS1, PDZ and/or NS1/PDZ interaction, active agent or a fragment thereof. Adenovirus can be manipulated such that it encodes and expresses the desired gene product (e.g., inhibitors of NS1, PDZ and/or NS1/PDZ interaction or a fragment thereof) and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233-238). Finally, adenovirus mediated gene transfer has been demonstrated in a number of instances including transfer of alpha-1-antitrypsin and CFTR to the lungs of cotton rats (Rosenfeld, M. A. et al. (1991)*Science* 252:431-434; Rosenfeld et al., (1992)*Cell* 68:143-155). Furthermore, extensive studies to attempt to establish adenovirus as a causative agent in human cancer were uniformly negative (Green, M. et al. (1979) *PNAS USA* 76:6606).

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

EXAMPLES

Example 1

Influenza A NS1 Proteins have a PDZ Domain Ligand (PL) Motif

Examination of the influenza resource database of the NCBI revealed that NS1 protein sequences possess features consistent with the ability to bind to PDZ domains. Such sequences are designated PDZ domain ligand or PL. The PL motif in these Influenza NS1 proteins was identified to be S/T-X-V/I/L where the S is serine, T is threonine, V is valine, I is isoleucine, L is leucine and X is any amino acid. Of the 747 full-length human NS1 sequences in the NCBI database, 572 had this motif. Of the 345 full-length chicken NS1 sequences in the NCBI database, 237 had this motif. The data is summarized in Tables 3a-3e, and FIGS. 1-3. This data provides a statistical representation of the appearance of specific NS1 PL motifs in different animals and humans. The statistical analysis can be used to analyze which PL motifs are found in each animal, how they may have traveled between species and, in some cases, which PL is usually found with a specific H or N protein.

Human PL fell into five sequence groups (see Table 3a): RSKI (SEQ ID NO:40), ESEV (SEQ ID NO:2), KSEV (SEQ ID NO: 41), RSEV (SEQ ID NO: 7), and RSKV (SEQ ID NO: 8). There was a strong association of subtypes with a particular PL motif; RSKI (SEQ ID NO: 40) with H3N2 (93%), ESEV (SEQ ID NO:2) with H5N1 (100%), KSEV (SEQ ID NO: 41) with H1N1 (100%, though numbers are small), RSEV (SEQ ID NO: 7) with H3N2 (98%), and RSKV (SEQ ID NO: 8) with H3N2 (95%).

Chicken PL fell into five sequence groups (see Table 3b): ESEI (SEQ ID NO:3), ESEV (SEQ ID NO:2), GSEV (SEQ ID NO: 6), ESKV (SEQ ID NO:4) and GSKV (SEQ ID NO: 10). There was a strong association of subtypes or groups of subtypes with a particular PL motif; ESEI (SEQ ID NO:3) with H7N2 (90%), ESEV (SEQ ID NO:2) with H5N1 (64%), ESKV (SEQ ID NO:4) with H5N2 (84%) and GSKV (SEQ ID NO: 10) with H5N2 (100%—but the numbers were somewhat small). If the notifiable avian influenza or H5 and H7 were combined, ESEI (SEQ ID NO:3) was 100% associated with NAI and ESEV (SEQ ID NO:2) was 83% associated with NAI.

Duck PL fell into three sequence groups (seeTable 3c). Swine PL fell into seven sequence groups (seeTable 3d). Equine PL fell into one sequence group (seeTable 3e).

The non-random assortment of NS1 PL sequences with HN subtyping suggests a method of identifying HN subtypes by NS1 PL typing. PDZ binding profiles can be used to differentiate between the different PL sequences and act as the foundation for influenza subtyping.

Table 3a-e

TABLE 3a

| HUMAN NS1 PL 572 PL/747 isolates | | | |
|---|---|---|---|
| PL motif | N (NUMBER) | | SUBTYPE % |
| RSKI | 1 | H1N2 | 7% |
|  | 13 (TOTAL 14) | H3N2 | 93% |
| ESEV | 11 (TOTAL 11) | H5N1 | 100% |
| KSEV | 1 (TOTAL 1) | H1N1 (1918) | 100% |
| RSEV | 65 | H1N1 | 98% |
|  | 1 (TOTAL 66) | H3N2 | 2% |

TABLE 3a-continued

HUMAN NS1 PL 572 PL/747 isolates

| PL motif | N (NUMBER) | | SUBTYPE | % |
|---|---|---|---|---|
| RSKV | 24 | | H1N2 | 5% |
| | 1 | | H2N2 | 0% |
| | 455 | (TOTAL 480) | H3N2 | 95% |

TABLE 3b

CHICKEN NS1 PL 237 PL/345 isolates

| | | | | |
|---|---|---|---|---|
| ESEI | 3 | | H5N1 | 10% |
| | 26 | (TOTAL 29) | H7N2 | 9% (H5/H7 100%) |
| ESEV | 1 | | H10N7 | 1% |
| | 96 | | H5N1 | 64% |
| | 4 | | H5N2 | 3% |
| | 1 | | H5N2 | 1% |
| | 2 | | H6N1 | 1% |
| | 15 | | H6N2 | 10% |
| | 9 | | H7N2 | 6% |
| | 14 | | H7N3 | 9% |
| | 2 | | H7N7 | 1% |
| | 6 | | H9N2 | 4% |
| | 125 | (TOTAL 150) | H5/H7 | 83% |
| GSEV | 1 | | H6N2 | 50% |
| | 1 | (TOTAL 2) | H6N8 | 50% |
| ESKV | 9 | | H5N1 | 16% |
| | 46 | (TOTAL 55) | H5N2 | 84% |
| GSKV | 1 | (TOTAL 1) | H5N2 | 100% |
| TOTAL 237 | | | | |

TABLE 3c

DUCK NS1 PL 72 PL/110 isolates

| | | | | |
|---|---|---|---|---|
| ESEI | 1 | | H6N1 | 50% |
| | 1 | (TOTAL 2) | H9N2 | 50% |
| ESEV | 2 | | H11N8 | 3% |
| | 2 | | H11N9 | 3% |
| | 1 | | H2N2 | 1% |
| | 3 | | H2N3 | 4% |
| | 2 | | H3N8 | 3% |
| | 1 | | H4N8 | 1% |
| | 31 | | H5N1 | 46% |
| | 8 | | H5N2 | 12% |
| | 1 | | H5N8 | 1% |
| | 1 | | H6N1 | 1% |
| | 2 | | H6N2 | 3% |
| | 2 | | H6N8 | 3% |
| | 1 | | H7N7 | 1% |
| | 1 | | N7N8 | 1% |
| | 2 | | H9N1 | 3% |
| | 7 | | H9N2 | 10% |
| | 1 | (TOTAL 68) | H9N8 | 1% |
| ESKV | 2 | (TOTAL 2) | H5N1 | 100% |

TABLE 3d

SWINE NS1 PL 31 PL/109 isolates

| | | | | |
|---|---|---|---|---|
| RSEA | 1 | (TOTAL 1) | H1N1 | 100% |
| ESEI | 1 | | H3N2 | 25% |
| | 3 | (TOTAL 4) | H9N2 | 75% |
| ESEV | 1 | | H4N6 | 33% |
| | 2 | (TOTAL 3) | H5N1 | 67% |
| GSEV | 1 | | H1N1 | 50% |
| | 1 | (TOTAL 2) | H3N2 | 50% |
| RSEV | 1 | (TOTAL 1) | H9N2 | 100% |
| TSEV | 1 | (TOTAL 1) | H1N1 | 100% |
| RSKV | 19 | (TOTAL 19) | H3N2 | 100% |
| TOTAL 31 | | | | |

TABLE 3e

EQUINE NS1 PL 3 PL/21 isolates

| | | | | |
|---|---|---|---|---|
| ESEV | 2 | | H3N8 | 67% |
| | 1 | (TOTAL 3) | H7N7 | 33% |

Examination of three representative PL sequence groups, ESEV (SEQ ID NO:2), EPEV (SEQ ID NO: 27) and RSKV (SEQ ID NO: 8) revealed a possible origin of the PL. ESEV (SEQ ID NO:2) first appeared in avian isolates and did not enter into the human and mammalian host until 2003 (see FIG. 1). EPEV (SEQ ID NO:27) first appeared in equine isolates and entered into the human, avian and other mammalian hosts in 1997 (see FIG. 2). RSKV (SEQ ID NO: 8) first appeared in human isolates and did not enter into other species, specifically swine, until 1997 (see FIG. 3). This type of analysis can be important in assessing the species origin of the epidemic influenza.

The above analysis demonstrated a new method for testing for the presence of influenza virus NS1 polypeptides using PL motifs specific to Influenza A and to specific subtypes. Identification of a specific PL is a means for identifying which strain of influenza virus is present in a sample.

Example 2

PDZ Analysis

This example describes the binding of PDZ proteins to various influenza A PL motifs. The PDZ proteins were assessed using a modified ELISA. Briefly, a GST-PDZ fusion was produced that contained the entire PDZ domain of the PDZ proteins. In addition, biotinylated peptides corresponding to the C-terminal 20 amino acids of various influenza A strain NS1 proteins were synthesized and purified by HPLC. Binding between these entities was detected through the "G" Assay, a colorimetric assay using avidin-HRP to bind the biotin and a peroxidase substrate. The sequences of the NS1 proteins from the specific influenza strains are shown as SEQ ID NOS: 42-47.

Binding of NS1 PL (or C terminus in the case of H5N1A) to human PDZ proteins was determined using both (i) biotinylated synthetic 20-mer peptides selected to mimic certain of the NS1 PL (or C terminus) sequences in the H5N1, H1N1, and H3N2 strains of Influenza A; and, (ii) recombinant NS1 proteins encoded by synthetic genes in recombinant systems, i.e., NS1 DNA snythesized and fused to sequences encoding a MBP immunochemical tag in an expression system (maltose binding protein; NEB; produced according to manufacturer's instructions).

Matrix graphPeptides and proteins were tested in an array format constituting a near complete set (255) of all the different PDZ domains in the human genome. Each PDZ domain polypeptide was expressed as a recombinant GST-PDZ polypeptide in a commercial glutathione S-transferase tagged expression system. Specific binding of biotinylated-PL peptides to PDZ domain polypeptides was detected using streptavidin-HRP and TMB substrate. Similarly, specific binding of NS1-MBP fusion proteins to PDZ domain polypeptides was visualized using biotinylated anti-MBP, streptavidin-HRP and TMB substrate. The relative strength of binding was analyzed and the strong and weak binders are shown for each PL. A PDZ protein that binds more strongly is preferable when used for capturing or identifying PL proteins. However for tests that use differential binding of the PDZ protein to various PL proteins, weak binding PDZ proteins may still be useful. The results were as follows: MBP.NS1 H1N1 (RSEV) PL (SEQ ID NO:42) from strain A/Taiwan/1996 Ac.# AAC14269 was tested for binding to a variety of PDZ proteins. The following PDZ proteins were found to bind strongly: Rho-Gap 10, Syntrophin 1 alpha, outer Membrane, Magi2 d3, Magi1 d4, Tip43 d1, Magi1 d1, Tip 1, PSD95 d1,2,3, PTPL1 d2, PSD95 d2, INADL d8, DLG1 d1,2, Vartul d2, PSD95 d1, magi13 d1, DLG1 d2, Mast2 d1, NeDLG d1,2, SNPC 11a, DLG2 d2. The following PDZ proteins were found to bind weakly: Magi3 d2, PTN3 d1, DLG2 d1. In a titration study using a direct binding sandwich assay, PSD95 d1,2,3 was found to bind with an EC50 of 1.29 µg/ml and Outer Membrane protein was found to bind with an EC50 of 1.25 µg/ml. Other measurement are shown in Table 4a.

TABLE 4a titration EC50's: MBP.NS1 H1N1 (RSEV-SEQ ID NO: 7)

| MBP-H1N1 Rec. ID | (in µg/ml) G Assay | Direct Binding assay |
|---|---|---|
| DLG1 d1, 2 | 1 | 2.6 |
| Outer membrane | 1.2 | 6 |
| PSD95 d1, 2, 3 | 1.3 | 1.3 |
| INADL d8 | 3.2 | |
| Magi3 d1 | 3.1 | |
| MAST2 d1 | 2 | |
| NeDLG d1, 2 | 1.1 | |

MBP.NS1 H3N2 (RSKV) PL (SEQ ID NO:43) from strain A/New York/31/2004 Ac.# AAX56415 was tested for binding to a variety of PDZ proteins. The following PDZ proteins were found to bind strongly: Outer Membrane, PSD95 d1,2,3, INADL d8, DLG1 d1,2, Grip 1 d4, Shank 1, GoRasp1 d1, Sim GoRasp65, Syntenin d2, NeDLG d3, FLJ12615, KIAA0967, PTN3 d1, DLG2 d1, NeDLG1, d1,2, DLG2 d2, mast1 d1, Kiaa1719d4, Kiaa1415 d1, and PICK1 FL. The following were found to bind weakly: Shank 2, NumbBP d3, psd95 d1,2,3, and Mast2d1. In a titration study using a direct binding sandwich assay, PSD95 d1,2,3 was found to bind with an EC50 of 25.3 µg/ml and INADL d8 was found to bind with an EC50 of 0.869 µg/ml. Other measurement are shown in Table 4b.

TABLE 4b titration EC50's: MBP.NS1 H3N2 (RSKV-SEQ ID NO: 8)

| MBP-h3n2 Rec. ID | (in µg/ml) G Assay | Direct Binding assay |
|---|---|---|
| DLG1 d1, 2 | 20.8 | 7.7 |
| Outer membrane | 13 | 3 |
| PSD95 d1, 2, 3 | 25 | 1.6 |
| JNADL d8 | 0.9 | |
| Magi3 d1 | 3 | |
| MAST2 d1 | 50< | |
| NeDLG d1, 2 | 50< | |

MBP.NS1 H5N1A (EPEV) PL (SEQ ID NO:44) from strain A/Hong Kong/97/1998 Ac.# AAK49317 was tested for binding to a variety of PDZ proteins. The following PDZ proteins were found to bind strongly: ALP, PSD95 d1, and PICK FL. The following were found to bind weakly: INADL d8, NeDLG d1,2, and KIAA1719 d4. In a titration study using a direct binding sandwich assay, Outer membrane protein was found to bind with an EC50 of 12.55 µg/ml and PSD95 d1,2,3 was found to bind with an EC50 of 15.76 µg/ml. Other measurement are shown in Table 4c.

TABLE 4c titration EC50's: MBP.NS1 H5N1A (EPEV-SEQ ID NO: 27)

| MBP-H5N1A Rec. ID | (in µg/ml) G Assay | Direct Binding assay |
|---|---|---|
| DLG1 d1, 2 | 23 | 100< |
| Outer membrane | 27 | 12.5 |
| PSD95 d1, 2, 3 | 100< | 15.7 |

MBP.NS1 H5N1B (ESEV) PL (SEQ ID NO:45) from strain A/Viet nam/1194/2004 Ac.# AAT73394 was tested for binding to a variety of PDZ proteins. The following PDZ proteins were found to bind strongly: DLG1 d1,2, LIM mystique d1, DLG2 d3, Vartul d2, PSD95 d1, Magi3 d1, DLG1 d2, PTN-3 d1, DLG2 d1, NeDLG1 d1,2, Magi2 d5, DLG2 d2, and PSD95 d3 CS Bound, Magi2 d1, DLG1 d1, RhoGap10, Outer membrane, Magi1 d4, Tip 43, Tip1 d1, PSD95 d1,2,3, Tip33 d1, PSD95 d2. The following were found to bind weakly: SIP1 d2, Lim RiL, mint3 d2, ALP1, PSD95 d3, SEMCAP 3 d1, LIMK 1, Kiaa0613, Syntrophin Gamma 1, Magi2 d6, Mast2d1, Magi1 d5, INADL d3, Magi3 d2, syntrophin 1 Alpha, magi2 d3, par3L d2, Magi1 d1, Kiaa1719 d5, Vartul d1, and PTPL1 d1. In a titration study using a direct binding sandwich assay, PSD95 d1,2,3 was found to bind with an EC50 of 0.29 µg/ml and Outer Membrane protein was found to bind with an EC50 of 0.18 µg/ml. Other measurement are shown in Table 4d (ND means not done).

TABLE 4d titration EC50's: MBP.NS1 H5N1B (ESEV-SEQ ID NO: 2)

| MBP-H5N1B Rec. ID | (in µg/ml) G Assay | Direct Binding assay |
|---|---|---|
| DLG1 d1, 2 | 0.2 | 0.4 |
| Outer membrane | 0.2 | 0.8 |
| PSD95 d1, 2, 3 | 0.3 | 0.3 |
| INADL d8 | 1.8 | 6.1 |
| Magi3 d1 | 0.9 | 5 |
| MAST2 d1 | 0.9 | ND |
| NeDLG d1, 2 | 0.2 | 0.8 |

Peptide 1958 H5N1A (EPEV) PL (SEQ ID NO:46) from strain A/duck/ST/4003/2003 Ac.# AAF02349/6048830 was tested for binding to a variety of PDZ proteins. The following PDZ proteins were found to bind weakly: MAST2 d1, PSD95 d 1,2,3, and PSD95 d2. In a titration study using a direct binding sandwich assay, PSD95 d2 was found to bind with an EC50 of 3.8 µg/ml and PSD95 d1,2,3 was found to bind with an EC50 of 4.1 µg/ml. Other measurement are shown in Table 4e.

TABLE 4e titration EC50's: Peptide 1958 H5N1A (EPEV-SEQ ID NO: 27)

| Peptide 1958 Rec. ID | (in µg/ml) G Assay |
|---|---|
| MAST 2 d1 | 5.5 |
| PSD95 d1, 2, 3 | 4.1 |
| PSD95 d2 | 3.8 |

Peptide 1959 H5N1B (ESEV) PL (SEQ ID NO:47) from strain A/chicken/Hong Kong/915/1997 Ac.# AAT73457/50296374 was tested for binding to a variety of PDZ proteins.

The PDZs that met specific criteria for hit classification are summarized in the Matrix Hits List tables 4a-e, showing the relative strength of the interaction. To be classified as a hit the OD of the NS1-PDZ interaction had to be greater than twice the average background, and it had to qualify as a hit in at least two samples. Hits classified as "weak" had an OD of less than 0.5, and hits classified as "strong" had an OD of greater than 0.5.

Peptide and fusion protein titrations were performed using the same detection system as described above for the Matrix assays. The Matrix Hits Lists were used to determine which PDZs would be titrated with NS1 to measure the strengths of the interactions. The results of the titrations are shown above with respect to each specific PL tested. The EC50s calculated for the titrated NS1-PDZ interactions are listed. The specific assays and methods that were used are provided below.

A. Peptide Purification

Peptides representing the C-terminal 20 amino acids of various Influenza A NS1 proteins, were synthesized by standard FMOC chemistry and biotinylated if not used as an unlabeled competitor. The peptides were purified by reverse phase high performance liquid chromatography (HPLC) using a Vydac 218TP C18 Reversed Phase column having the dimensions of 10*25 mm, 5 um. Approximately 40 mg of peptide was dissolved in 2.0 ml of aqueous solution of 49.9% acetonitrile and 0.1% Tri-Fluoro acetic acid (TFA). This solution was then injected into the HPLC machine through a 25 micron syringe filter (Millipore). Buffers used to get a good separation were (A) distilled water with 0.1% TFA and (B) 0.1% TFA with Acetonitrile. The separation occured based on the nature of the peptides. A peptide of overall hydrophobic nature eluted off later than a peptide of a hydrophilic nature. Fractions containing the "pure" peptide were collected and checked by Mass Spectrometer (MS). Purified peptides were lyophilized for stability and later use.

B. "G" Assay for Identification of Interactions Between Peptides and Fusion Proteins Reagents and Materials:

Nunc Polysorp 96 well Immuno-plate (Nunc cat#62409-005) (Maxisorp plates have been shown to have higher background signal)

PBS pH 7.4 (Gibco BRL cat#16777-148) or (AVC phosphate buffered saline, 8 gm NaCl, 0.29 gm KCl, 1.44 gm $Na_2HPO_4$, 0.24 gm $KH_2PO_4$, add $H_2O$ to 1 L and pH 7.4; 0.2 μm filter 2% BSA/PBS (10 gm of bovine serum albumin, fraction V (ICN Biomedicals cat#IC15142983) into 500 ml PBS Goat anti-GST mAb stock @ 5 mg/ml, store at 4° C., (Amersham Pharmacia cat#27-4577-01), dilute 1:1000 in PBS, final concentration 5 μg/ml HRP-Streptavidin, 2.5 mg/2 ml stock stored at 4° C. (Zymed cat#43-4323), dilute 1:2000 into 2% BSA, final concentration at 0.5 μg/ml Wash Buffer, 0.2% Tween 20 in 50 mM Tris pH 8.0

TMB ready to use (Dako cat#S1600)

1M $H_2SO_4$ 12 w multichannel pipettor, 50 ml reagent reservoirs, 15 ml polypropylene conical tubes Protocol 1) Coat plate with 100 μl of 5 μg/ml goat anti GST, O/N @ 4° C.
2) Dump coating antibodies out and tap dry
3) Blocking—Add 200 μl per well 2% BSA, 2 hrs at 4° C.
4) Prepare proteins in 2% BSA
   (2 ml per row or per two columns)
5) 3 washes with cold PBS (must be cold through entire experiment)
   (at last wash leave PBS in wells until immediately adding next step)
6) Add proteins at 50 μl per well on ice (1 to 2 hrs at 4° C.)
7) Prepare Peptides in 2% BSA (2 ml/row or /columns)
8) 3× wash with cold PBS
9) Add peptides at 50 μl per well on ice (time on/time off)
   a. keep on ice after last peptide has been added for 10 minutes exactly
   b. place at room temp for 20 minutes exactly
10) Prepare 12 ml/plate of HRP-Streptavidin (1:2000 dilution in 2% BSA)
11) 3× wash with cold PBS
12) Add HRP-Streptavidin at 100 ul per well on ice, 20 minutes at 4° C.
13) Turn on plate reader and prepare files
14) 5× washes, avoid bubbles
15) Using gloves, add TMB substrate at 100 μl per well
    a. incubate in dark at room temp
    b. check plate periodically (5, 10, & 20 minutes)
    c. take early readings, if necessary, at 650 nm (blue)
    d. at 20 minutes, stop reaction with 100 ul of 1M $H_2SO_4$
    e. take last reading at 450 nm (yellow)

Example 3

NS1 Protein is Expressed in Human Clinical Specimens

Figure 4:
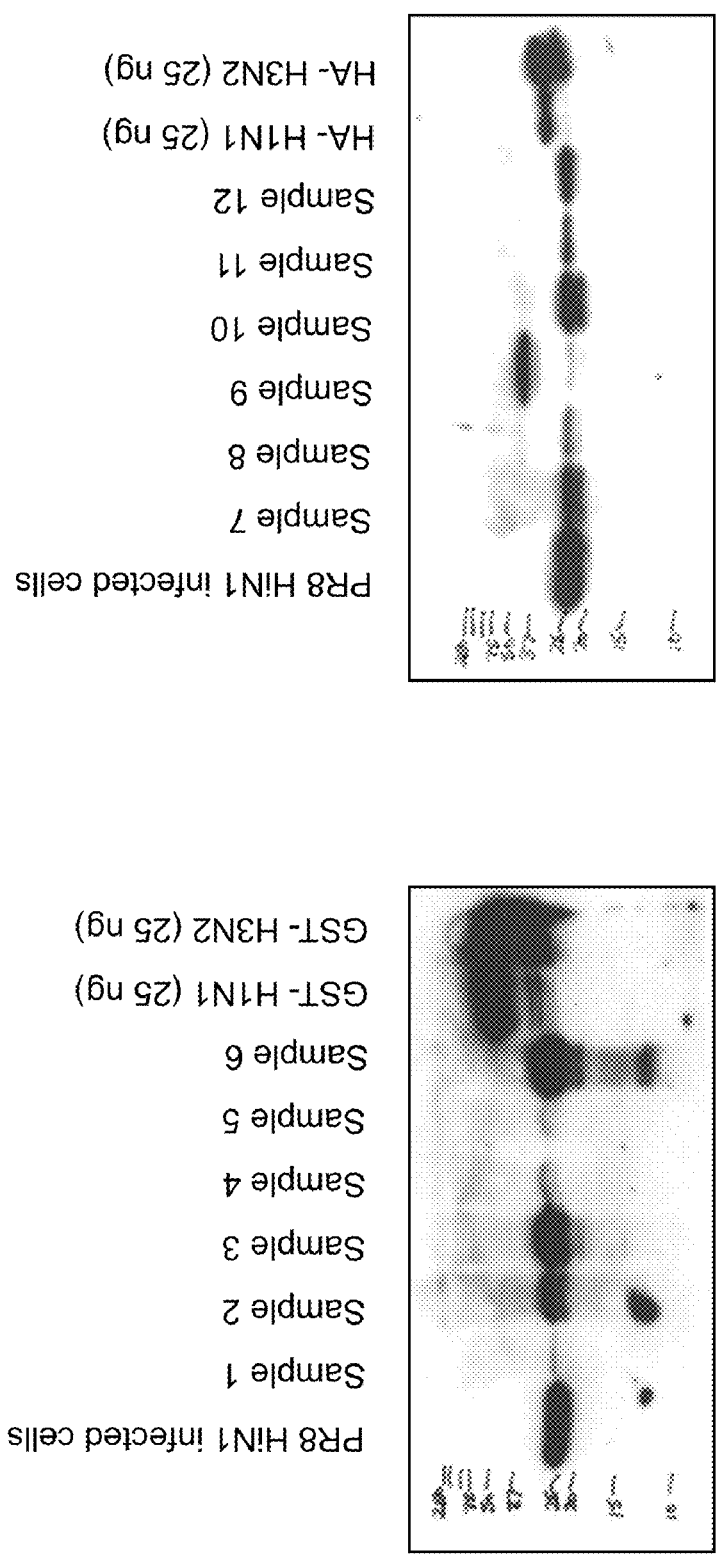
FIG. 4 shows the results of testing nasal secretions from six human Flu A positive samples.

Human nasal secretions were examined for the presence and amount of NS1 from Influenza A. Human nasal aspirates were collected and stored in M4 viral transport media (Remel, Inc, Lenexa, Kans.) at −80° C. Stored material was thawed and run on 10% SDS-PAGE. Western blot analysis was performed with monoclonal antibodies to NS1, 3H3 and 1A10 (Arbor Vita Corporation, Sunnyvale, Calif.). The results for six samples are shown in FIG. 4. The results show that NS1 is present in large amounts in nasal secretions.

Figure 5:
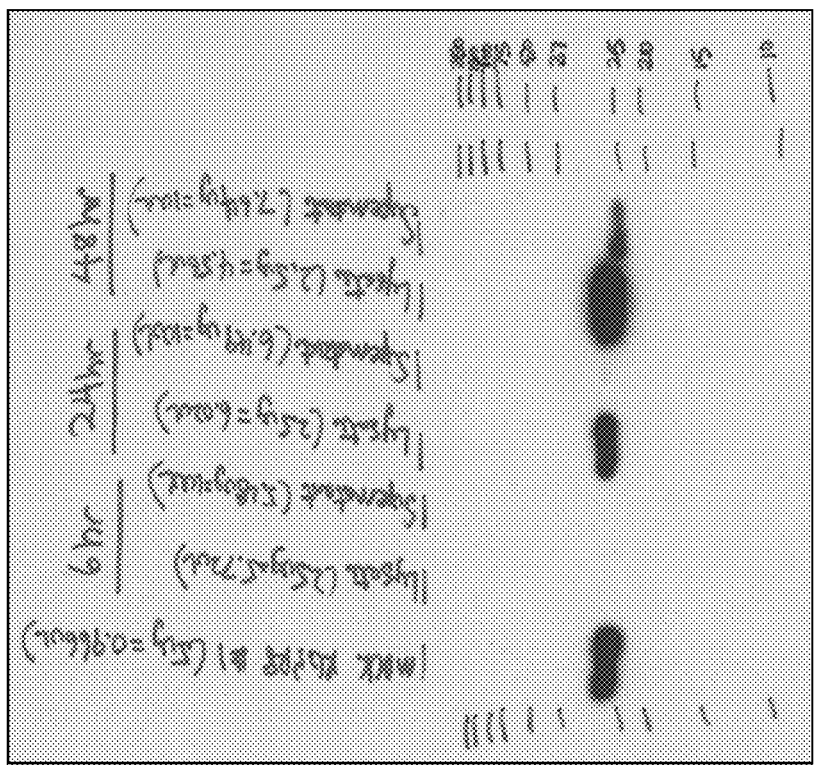
FIG. 5 shows NS1 expression in MDCK cells infected with A/PR/8/34. The left panel was developed with ECL reagent for 1 second; the right panel was developed with the ECL reagent for 3 minutes.
Figure 5:
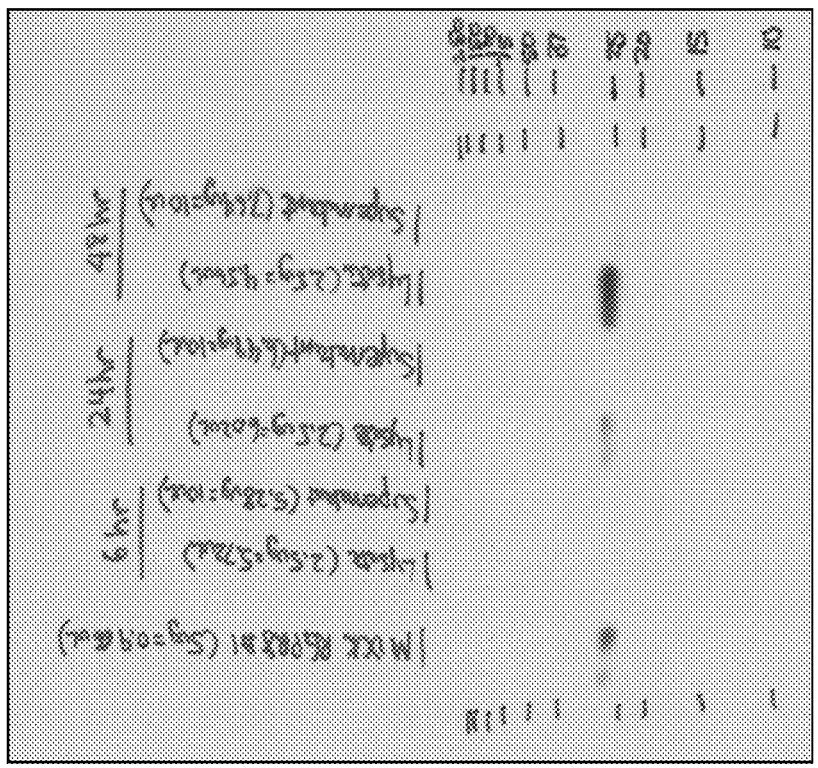

To investigate the timeline of when NS1 was produced and secreted by cells infected with influenza A virus, MDCK cells were infected with human influenza A/PR/8 at a MOI of 0.1. Supernatant as well as cells were collected and lysed in 1% Triton X-100 and subjected to SDS-PAGE and western analysis with monoclonal antibody 3H3 which is pan-reactive to NS1. NS1 was detected in infected cells within 24 hours after infection and detected in the supernatant of infected cells within 48 hours (see FIG. 5). This suggests that a NS1 based diagnostic may be able to detect infection by influenza A within 48 hours and possibly within 24 hours.

Example 4

NS1 Interacts with PDZ in Cells

Figure 6:
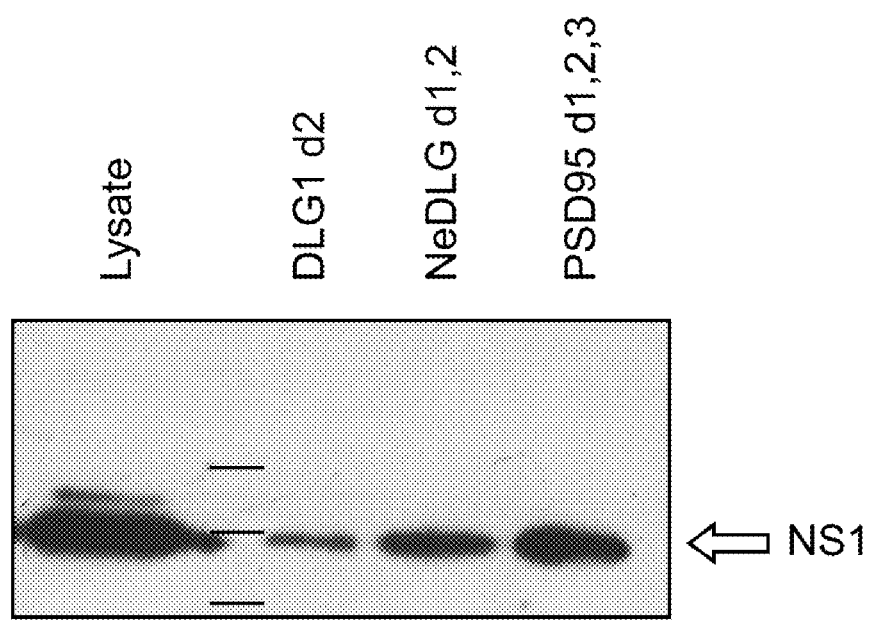
FIG. 6 shows that PDZ interacts with NS1 in cells.
Figure 7:
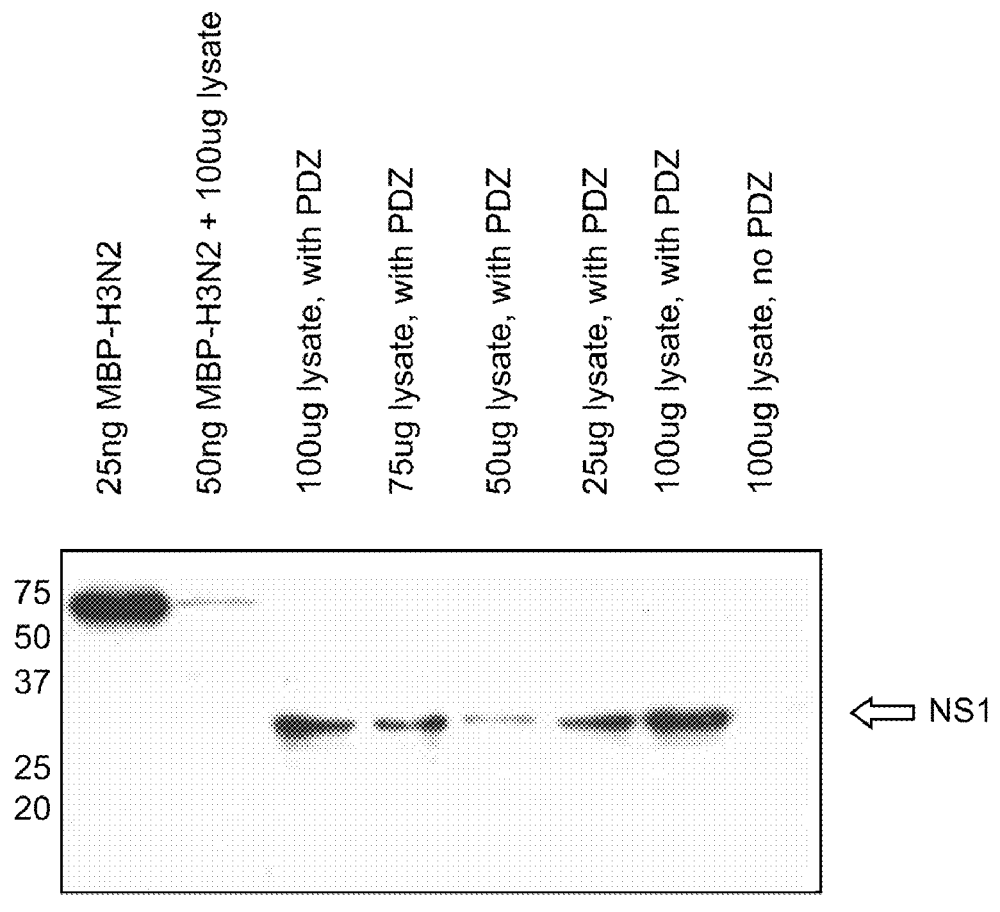

To verify that NS1 interacts with PDZ proteins in cells, a series of PDZ pull-down experiments were performed. 293 HEK cells were transfected with plasmids containing HA-NS1-H5N1B or with HA-NS1-H3N2. Lysates were prepared as described herein. Glutathione-sepharose-PDZ beads were prepared (10 ug of DLG1d 1,2, 10 ug of NeDLGd 1,2, and 10 ug PSD95d1,2,3) and used to pulldown 150 ug of lysate from transfected 293ET cells as shown in FIGS. 6 and 7. Following an overnight incubation at 4° C. and multiple washes with HNTG buffer, a membrane was prepared with the pulldowns. The membrane was probed with F63-3G1 supernatant (1:5). All 3 of the PDZs tested successfully pulldown NS1 from cell expressing HA-H5N1B (see FIG. 6).

Similarly, glutathione-sepharose-PDZ beads were prepared (40 ug of INADLd8) and used to pulldown 150 ug of lysate from 293ET cells transfected with H3N2. Following an overnight incubation at 4° C. and multiple washes with PBS, a western blot was prepared and probed a-HA (1:500) (Roche). INADL d8 successfully pulldown HA-H3N2 NS1 from cell lysate (FIG. 7).

The conclusion is that the NS1 PL is functional within the cell and can interact with PDZ domains as determined by the MATRIX assay.

Example 5

Monoclonal Antibodies to NS1

Monoclonal antibodies were prepared to specifically bind to subtype NS1 proteins, NS1 PL classes and for pan-specificity. The strategy for the generation of monoclonal antibodies to NS1 is as follows and the results are shown in Tables 5, 6, and 7:

1. GST and MBP fusion proteins of NS1 were generated for the subtypes summarized in Table 5. The cloning vectors were obtained from Pharmacia (GST) or New England Biolabs (MBP). The NS1 coding regions were synthesized using overlapping oligonucleotides by DNA 2.0 (Menlo Park, Calif.).
2. Mice were immunized with MBP-NS1 fusion proteins at doses ranging from 10-100 ug per dose in CFA then IFA and PBS.
3. Spenocytes and lymphocytes were harvested 3 days after the last boost with the corresponding GST-NS1 fusion protein and fused with FOX-NY myeloma cells according to Kohler and Milstein (Nature 1975).
4. The hybridomas were screened first with MBP-NS1 in an ELISA (see direct ELISA in tables 5-7) The positive wells were cloned and rescreened with a panel of MBP and GST NS1 and classified into pan-reactive or subtype reactive.
5. Further screenings were done using Western blots to verify the molecular weight of the target protein that is consistent with NS1.
6. An additional screening was performed using a S2 assay format (see Example 4) for compatibility with PDZ capture. (see S2 ELISA in Tables 5-7).
7. Steps 5 and 6 were repeated with eukaryotic expressed NS1 in the form of a cell lysate.
8. The antibodies are checked for compatibility with a lateral flow format described in Example 6.
9. Finally, the antibodies are checked for the ability to detect NS1 in a clinical specimen.

This workflow is critical to obtain an antibody that will recognize a human clinical specimen.

TABLE 5

| | | Direct ELISA with MBP-NS1 | | | | S2 ELISA with MBP-NS1 | | | |
|---|---|---|---|---|---|---|---|---|---|
| | | H1N1 | H3N2 | H5N1A | H5N1B | H1N1 | H3N2* | H5N1A | H5N1B |
| F63 | 1C6 | − | + | ++++ | − | − | − | N/A | − |
| | 1F9 | ++ | − | +++ | +++ | − | − | N/A | − |
| | 2C3 | − | − | +++ | − | − | − | N/A | − |
| | 3C1 | − | − | +++ | + | − | − | N/A | − |
| | 3G1 | ++ | + | +++ | +++ | − | − | N/A | − |
| | 5E11 | − | − | +++ | − | − | − | N/A | − |
| F64 | 1A10 | ++++ | ++++ | ++++ | ++++ | − | − | N/A | − |
| | 1D6 | + | ++++ | − | ++ | + | − | N/A | ++++ |
| | 2H6 | ++ | − | − | ++ | +++ | − | N/A | ++++ |
| | 2H9 | ++ | − | − | ++ | +++ | − | N/A | ++++ |
| | 3H3 | +++ | ++ | ++ | ++++ | ++++ | + | N/A | ++++ |
| | 4C4 | + | − | +++ | +++ | ++ | − | N/A | ++++ |
| | 5B4 | + | + | − | ++ | + | − | N/A | +++ |
| | 5G12 | ++++ | − | +++ | ++++ | ++++ | − | N/A | ++++ |
| | 5H10 | ++ | − | + | +++ | +++ | − | N/A | ++++ |
| | 6C1 | − | − | − | + | + | − | N/A | +++ |
| | 6G12 | + | ++ | + | +++ | +++ | ++ | N/A | ++++ |
| | 7A8 | ++ | − | − | ++++ | ++++ | − | N/A | ++++ |
| | 7B1 | − | − | − | + | − | + | N/A | +++ |
| | 7B5 | +++ | ++++ | +++ | +++ | + | − | N/A | + |
| | 7D1 | +++ | − | +++ | ++++ | +++ | − | N/A | ++++ |
| | 7H2 | − | − | − | + | − | − | N/A | + |
| | 8B3 | + | − | − | ++ | + | − | N/A | ++++ |
| | 8C11 | ++ | − | − | − | − | − | N/A | ++++ |
| F68 | 1D10 | ++++ | ++++ | ++++ | ++++ | + | + | N/A | + |
| | 1E5 | +++ | − | − | − | +++ | − | N/A | − |
| | 2C3 | − | − | ++++ | − | − | − | N/A | − |
| | 3G5 | +++ | − | − | − | + | − | N/A | ++++ |
| | 3H5 | ++ | − | − | +++ | ++ | − | N/A | ++++ |
| | 4B2 | ++ | +++ | − | + | ++++ | ++++ | N/A | ++++ |
| | 4C1 | ++++ | − | − | − | ++ | − | N/A | − |
| | 4H9 | ++ | +++ | − | ++ | +++ | ++++ | N/A | ++++ |
| | 5B5 | ++++ | ++++ | +++ | ++++ | − | − | N/A | − |
| | 6A12 | +++ | +++ | +++ | +++ | + | − | N/A | + |
| | 6B7 | ++++ | ++++ | ++++ | ++++ | + | + | N/A | + |
| | 6C6 | ++ | − | − | ++ | +++ | + | N/A | ++++ |
| | 6D6 | ++ | +++ | − | ++ | +++ | +++ | N/A | ++++ |
| | 7B10 | +++ | +++ | +++ | +++ | + | − | N/A | + |
| | 9A6 | ++ | − | − | − | − | − | N/A | − |
| F70 | 1A3 | +++ | ++++ | +++ | +++ | − | − | N/A | − |
| | 1B2 | − | + | − | − | − | + | N/A | − |
| | 2C4 | ++++ | ++++ | ++++ | ++++ | + | + | N/A | + |

TABLE 5-continued

|   |   | Direct ELISA with MBP-NS1 | | | | S2 ELISA with MBP-NS1 | | | |
|---|---|---|---|---|---|---|---|---|---|
|   |   | H1N1 | H3N2 | H5N1A | H5N1B | H1N1 | H3N2* | H5N1A | H5N1B |
|   | 2D12 | − | ++ | − | + | + | ++++ | N/A | ++++ |
|   | 2G12 | ++ | ++++ | +++ | + | − | − | N/A | − |
|   | 2H1 | + | + | − | + | ++ | ++++ | N/A | ++++ |
|   | 3A6 | + | +++ | − | + | − | − | N/A | − |
|   | 3C2 | ++ | +++ | ++ | +++ | − | − | N/A | − |
|   | 3F6 | ++ | +++ | + | + | − | − | N/A | − |
|   | 3G7 | − | + | − | + | + | +++ | N/A | ++++ |
|   | 4G9 | ++ | ++ | + | ++ | − | − | N/A | − |
|   | 4H12 | ++ | ++ | + | ++ | − | − | N/A | − |
| F72 | 1B11 | +++ | +++ | ++ | +++ | + | + | N/A | ++ |
|   | 1C1 | +++ | +++ | ++ | +++ | − | − | N/A | − |
|   | 1G4 | − | − | +++ | + | − | − | N/A | − |
|   | 1H7 | ++ | ++ | + | ++ | − | − | N/A | − |
|   | 2A8 | ++ | +++ | ++ | ++ | − | − | N/A | − |
|   | 3D7 | +++ | − | ++ | +++ | + | − | N/A | + |

TABLE 6

|   |   | Western with GST-NS1 | | | | Western with HA-NS1 lysate | | | |
|---|---|---|---|---|---|---|---|---|---|
|   |   | H1N1 | H3N2 | H5N1A | H5N1B | H1N1 | H3N2 | H5N1A | H5N1B |
| F63 | 3G1 | − | + | +++ | +++ | − | − | +++ | +++ |
| F64 | 1A10 | +++ | +++ | +++ | +++ | +++ | +++ | +++ | +++ |
|   | 1D6 | + | + | − | + | + | − | − | − |
|   | 2H6 | − | − |   | ++ |   |   |   | − |
|   | 3H3 | +++ | ++ | ++ | ++ | +++ | − | + | +++ |
|   | 4C4 | + | − |   | +++ |   |   |   | ++ |
|   | 5B4 | + | − | − | + | − | − | − | − |
|   | 5H10 | + | − |   | +++ |   |   |   | ++ |
|   | 6C1 | + | − | − | − | − | − | − | − |
|   | 6G12 | +++ | +++ | +++ | +++ | +++ | +++ | +++ | +++ |
|   | 7A8 | − | ++ | − | +++ | − | − | − | ++ |
|   | 7B5 | +++ | ++ | +++ | +++ | +++ | + | +++ | +++ |
|   | 7D1 | +++ | − | +++ | +++ | − | − | − | +++ |
|   | 7H2 | + | − |   | ++ |   |   |   | − |
|   | 8B3 | ++ | − | − | +++ | ++ | + | ++ | +++ |
| F68 | 1D10 | +++ | ++ | +++ | +++ | +++ | ++ | +++ | +++ |
|   | 4B2 | +++ | +++ | − | ++ | +++ | − | − | ++ |
|   | 4H9 | +++ | ++ | + | + | +++ | − | + | + |
|   | 5B5 | +++ | +++ | +++ | +++ | +++ | +++ | +++ | +++ |
|   | 6A12 | +++ | +++ | +++ | ++ | +++ | ++ | +++ | +++ |
|   | 6B7 | +++ | +++ | +++ | +++ | +++ | ++ | +++ | +++ |
|   | 6D6 | +++ | ++ | + | + | +++ | − | + | + |
|   | 7B10 | +++ | +++ | +++ | +++ | +++ | +++ | +++ | +++ |
| F70 | 1A3 | + | + | + | + | + | + | + | + |
|   | 2C4 | +++ | +++ | +++ | +++ | +++ | +++ | +++ | +++ |
|   | 2D12 | − | ++ | + | + | − | ++ | + | + |
|   | 2G12 | ++ | ++ | ++ | + | + | ++ | ++ | + |

TABLE 7

|   |   | S2 ELISA with HA-NS1 lysate | | | |
|---|---|---|---|---|---|
|   |   | H1N1 | H3N2* | H5N1A | H5N1B |
| F64 | 1D6 | − | − | N/A | ++ |
|   | 3H3 | ++ | − | N/A | ++++ |
|   | 5B4 | − | − | N/A | + |
|   | 6C1 | − | − | N/A | − |
|   | 6G12 | − | + | N/A | ++++ |
|   | 7A8 | − | − | N/A | ++++ |
|   | 7B5 | − | − | N/A | − |
|   | 7D1 | − | − | N/A | ++++ |
|   | 7H2 |   | − | N/A | − |
|   | 8B3 | − | − | N/A | ++++ |
| F68 | 1D10 | − | − | N/A | − |
|   | 4B2 | + | + | N/A | ++++ |
|   | 4H9 | + | + | N/A | ++++ |
|   | 5B5 | − | − | N/A | − |
|   | 6A12 | − | − | N/A | − |
|   | 6B7 | − | − | N/A | − |
|   | 6D6 | + | − | N/A | ++++ |
|   | 7B10 | − | − | N/A | − |

Example 6

Lateral Flow

Figure 9:
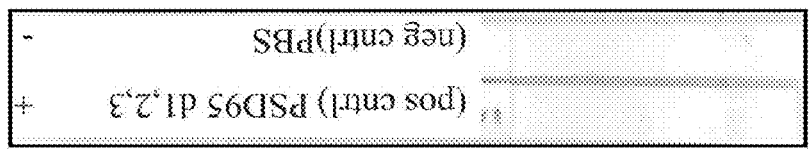
FIG. 9 shows a lateral flow format using a monoclonal antibody capture agent and a monoclonal antibody detect agent AU-4B2.
Figure 9:
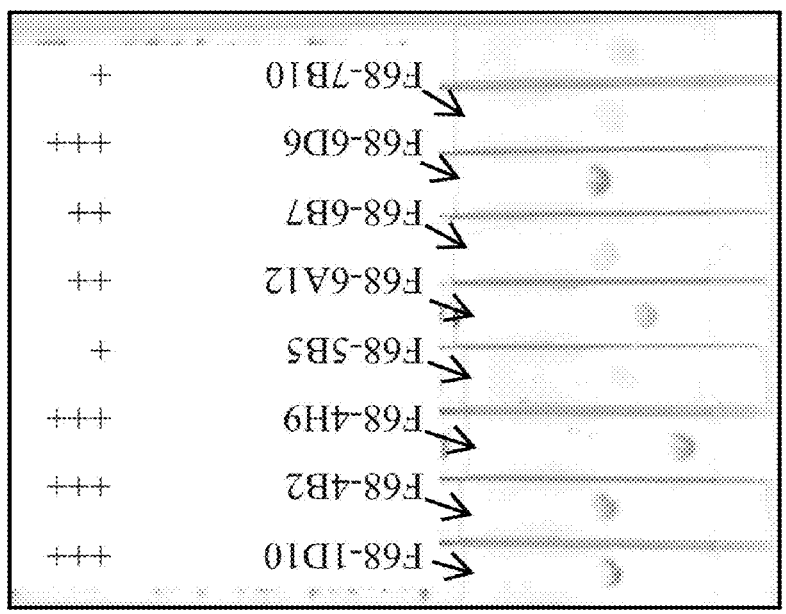
Figure 9:
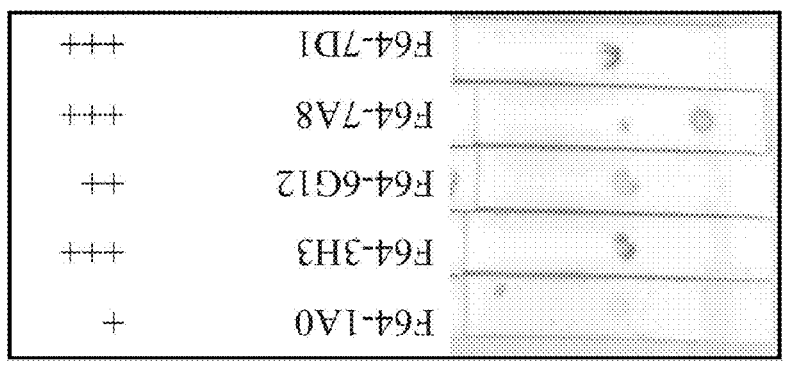

Examples of lateral flow formats for detection of NS1 are provided in FIGS. 8, 9 and 11. FIG. 8 provides a lateral flow using PDZ capture followed by monoclonal antibody detection. For all cases, recombinant PDZ domain proteins or antibodies were deposited on RF120 Millipore membrane using a striper. For FIG. 8, the PDZ proteins PSD95D1-3, and INADL D8 were deposited at a concentration of 0.5 mg/ml. A control band was also deposited composed of goat anti-mouse antibody (GAM) also at 0.5 mg/ml. NS1 protein was combined with gold conjugated monoclonal anti-NS1 such as 4B2 in 100 ul volume in TBS-T buffer. The NS1 proteins used were from H1N1, H3N2, H5N197, H5N1, and a control lane did not contain NS1. In all cases, human nasal aspirates were diluted and stored in saline or M4, as indicated. The samples were directly mixed with gold conjugated antibody in the amounts described below.

The PDZ striped membrane was inserted into the NS1/anti-NS1 protein solution and flow initiated by capillary action and a wicking pad. NS1 was subtyped based on the pattern of PDZ reactivity; H1N1 binds to both PSD95 and INADL d8; H3N2 binds to INADL d8 only; H5N1 binds to PSD95 only. Influenza A subtyping was perfomed based on the results of the NS1 lateral flow using reactivity to PDZ and detection with a gold conjugated pan-reactive anti-NS1 monoclonal antibody.

In FIG. 9, 13 different monoclonal antibodies were deposited on the lateral flow device. The 13 antibodies used were F64-1A0, F64-3H3, F64-6G12, F64-7A8, F64-7D1, F68-1D10, F68-4B2, F68-4H9, F68-6A12, F68-6B7, F68-6D6, F68-7B10. A subtype specific gold conjugated pan-NS1 antibody was added to a sample containing H1N1 influenza virus. The sample was applied to the lateral flow device and the results are shown in FIG. 9. The results show that a pan-specific antibody can be used for the test and the assay identified which antibodies were the best for binding to H1N1. The binding strength is quantified by using the following symbols: (−) for no binding, (+) for weak binding, (+++) for strong binding and (++) for moderate binding.

A lateral flow assay to identify pathogenic Influenza A in a patient sample is produced having pan-specific antibodies deposited on the membrane. The patient sample is admixed with a mixture of gold-labeled antibodies that recognize all NS1 PL's. The sample is applied to the lateral flow test strip and if a pathogenic strain of influenza A is present a line is formed on the strip.

The strip tests were run using the following protocol and materials: The materials that were used included: strips previously striped with goat anti-mouse/PSD95 d1,2,3/INADL d8; TBST/2% BSA/0.25% Tween 20 buffer; Stocks of NS1 proteins MBP-H1N1, MBP-H3N2, MBP-H5N1A, and MBP-H5N1B "old" (Jon's) fast gold-conjugated F68-4B2 antibody; and Maxisorp ELISA plates. The procedure was performed as follows:

1) Stock NS1 proteins were diluted down in TBST/2% BSA/0.25% Tween 20 to 100 ng/uL (using no less than 5 uL of proteins to perform the dilutions)
2.) The 100 ng/uL dilution was diluted down to 50 ng/uL by adding 10 uL of the protein to 10 uL of TBST/2% BSA/0.25% Tween 20
3.) A stock solution of gold-conjugated antibody in TBST/2% BSA/0.25% Tween 20 buffer was prepared. Four uL of the antibody was added to every 100 uL of the buffer, and enough buffer was prepared for 6 100 uL reactions (which provides extra dead volume).
4.) 98 uL of the antibody/buffer mix was added to separate wells in the ELISA plate
5.) 2 uL of the NS1 dilutions were added to the buffer-containing wells (one NS1 per well)
6.) One well was left with just antibody and buffer to serve as a negative "no NS1" control
7.) The ELISA plate was tapped several times to mix the contents of the wells
8.) The pre-striped strips were added to the wells and observed during development.

After approximately 15 minutes (when all of the liquid had been absorbed, but the strip was not yet dry) the strips were removed from the wells and scanned into the computer.

The test provided in FIGS. 10a and 10b was prepared as follows: a GST-PSD95 d1,2,3 protein was striped onto the membrane at 3 mg/mL for the avian test, or alternatively a mixture of two monoclonal antibodies can be used (1.1 mg/mL F64-3H3 and 0.075 mg/mL F68-4H9 for the pan-flu A test. A second line of 1 mg/mL polyclonal goat anti-mouse antibody was used for the test capture line. The steps are set out below.

1. Prepare cards with a sample membrane and sink pad.
2. Stripe membrane with the PDZ protein and/or antibodies (see above for conc.)
3. Dry the membrane overnight at 56 degrees, then cut the cards into strips 4.26 mm wide.
4. Attach a glass fiber sample pad to the bottom of the strip and place the entire strip inside a cassette for testing.
5. Thaw sample to be tested and add 80 µl of sample to 20 µl of buffer. Pipette up and down several times to mix.
6. Spike 8 µl of the gold-conjugated (Au—) detector mix into the sample/buffer solution. This detector mix is 4 µl of Au—F68-4B2 with 4 µl of Au—F68-3D5. Pipette up and down several times to mix.
7. Add 100 µl of the prepared sample to the sample well on the cassette.
8. Read the test and control lines on the cassette at 15 minutes post-addition of sample. The control line is clearly visible for any test results to be read reliably. Flu A positive samples are noted with (+). Flu A negative samples are noted with (−). The top arrow is pointing to the control and the bottom arrow is pointing to the test. In both cases the top line is a control line (goat anti-mouse mAb), the second line down is the test line (mixture of F64-3H3 and F68-4H9 mAbs for the Pan-Flu A Test and PSD95 d1,2,3 for the Avian test). 2 ng of H5N1 protein was tested for the Avian test. The bottom circular spot is the sample well. In FIG. 10a, both test are positives.

Figure 10A:
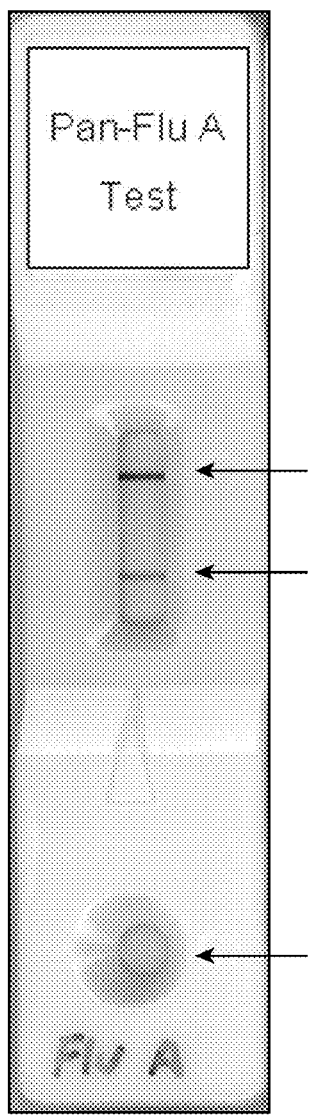
FIGS. 10a-f are exemplary lateral flow Influenza test formats.
Figure 10B:
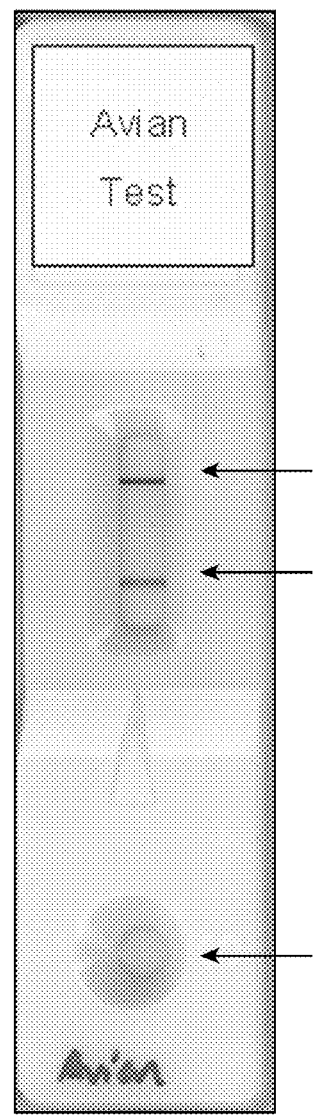
Figure 10C:
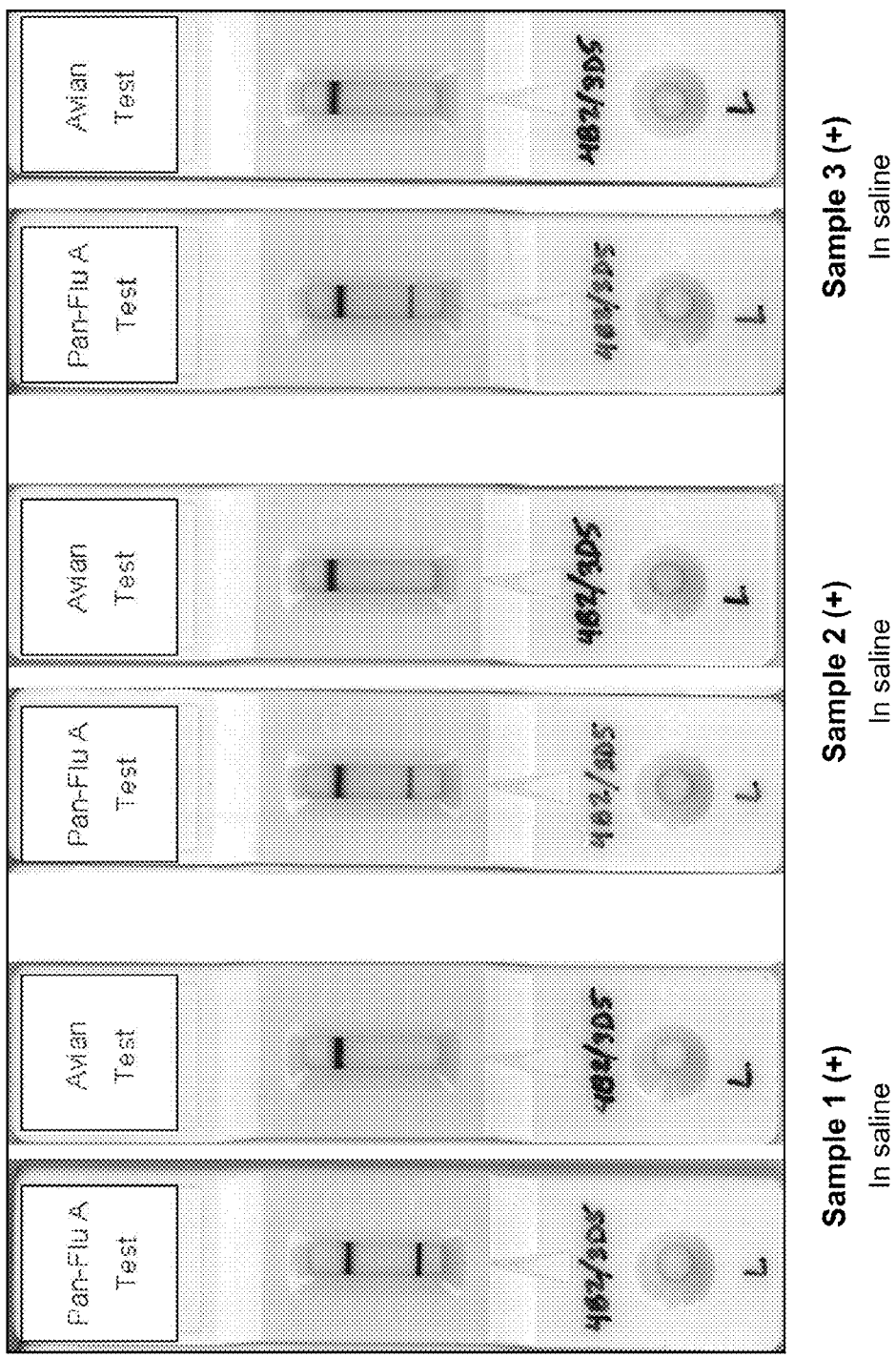
Figure 10D:
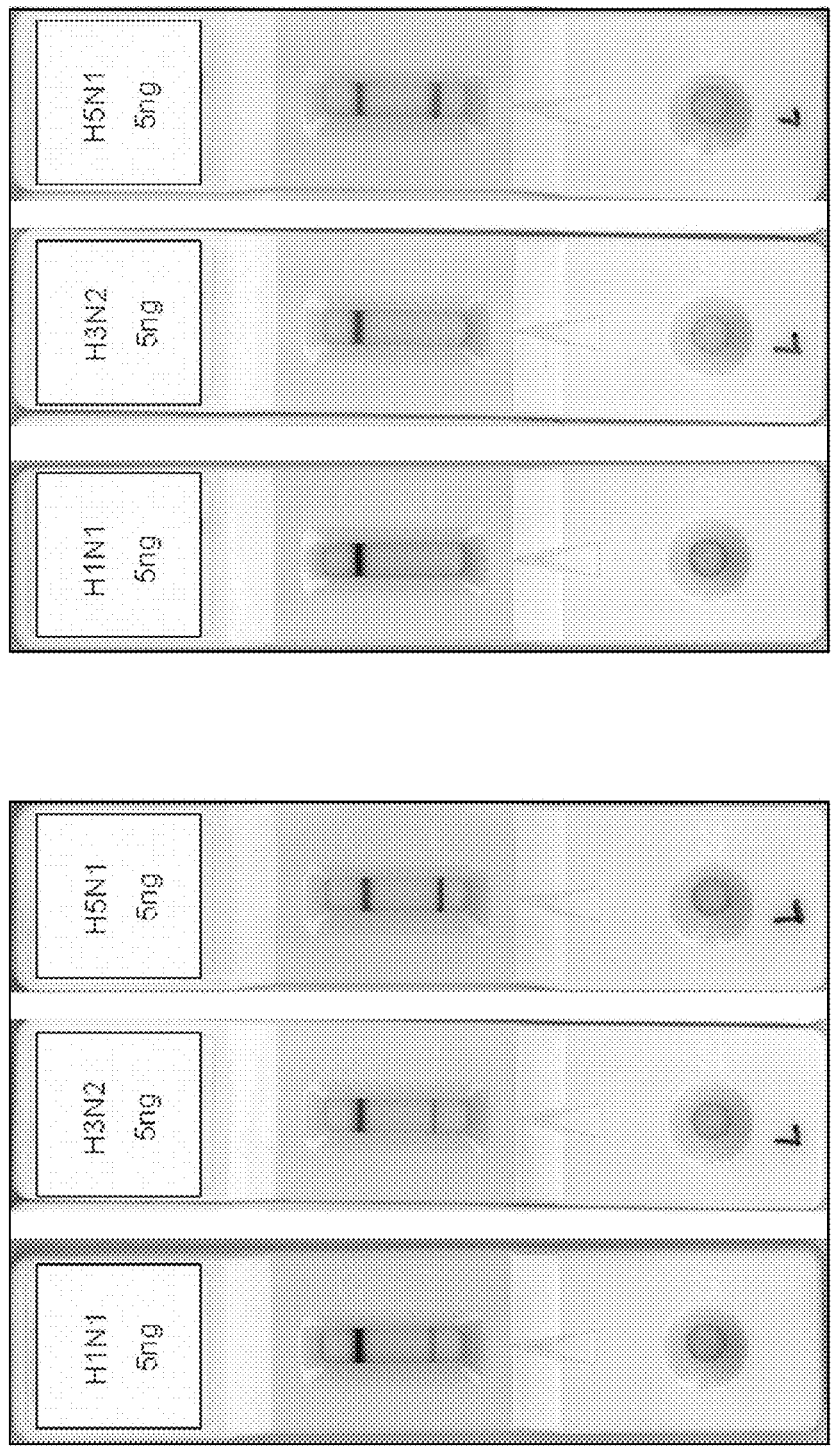
Figure 10E:
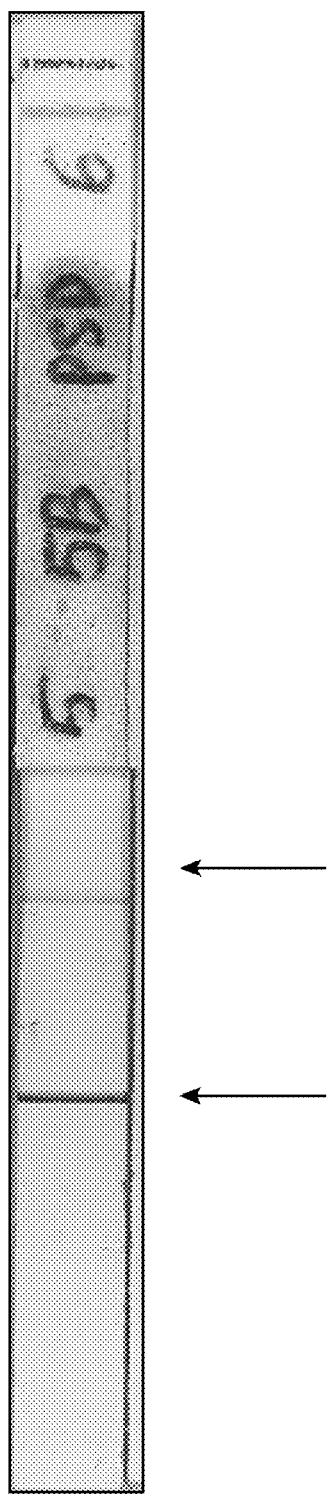

FIG. 10c shows three of twenty human samples that were tested with the format shown in FIGS. 10a and 10b using 80% M4 media, 20% buffer B3. The left two panels are a Pan-Flu A test and an Avian test lateral flow format for human Sample 1. The middle two are the same but for human Sample 2 and the right two are the same but for human Sample 3. The samples showed a variety of outcomes, for example, Sample 1 was positive for Flu A, but negative for Avian Flu A and Sample 14 was negative for both. FIG. 10d shows the same test for H1N1, H3N2, and H5N1 recombinant proteins. The Pan-FluA test shown in the left three panels was positive for all three. The Avian Flu test shown in the right three panels was positive for only H5N1. In FIG. 10e, Gold-conjugated PDZs were used as detectors and single or multiple mAbs were used for capture. FIG. 10e had liquid gold added in the form of Au-PSD95 d1,2,3 with a F68-4B2 mAb capture. 1.7 ng of NS1 H5N1 protein tested positively. This was an Avian Flu specific test. The top line with the goat anti-mouse mAb will not show a strong signal with this detector. The bottom line is the test line of F68-4B2 mAb capture.

Figure 10F:
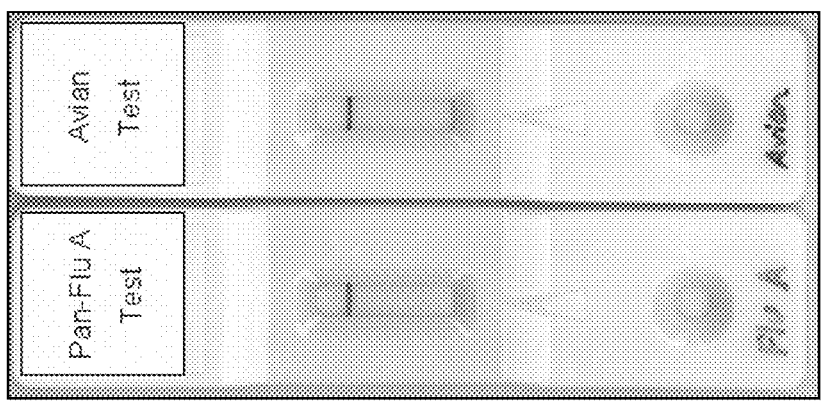
Figure 10F:
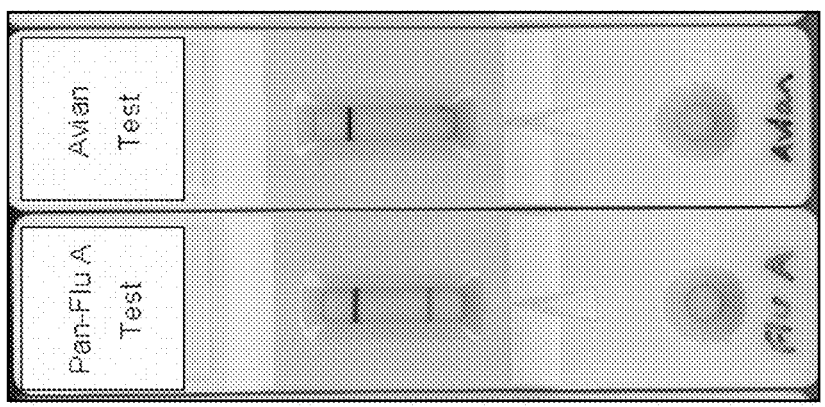
Figure 10F:
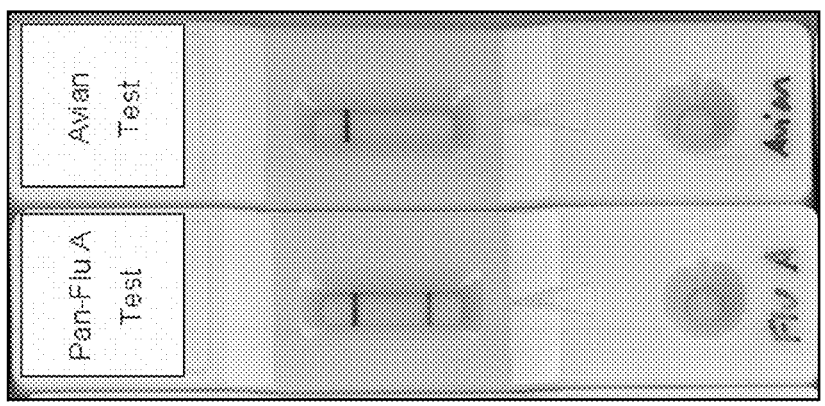

In FIG. 10f, a dried gold method was used. The left two panels are the Pan-FluA test and the Avian test for Sample 7, the middle two panels are the same tests for Sample 9 and the right two panels are the same two tests for Sample 12. The preparation of the cards proceeded the same as in the liquid gold protocol, with the exception of the sample pad being affixed to the card before any striping was performed. When the captures were striped down, the gold-conjugated detector mix (which here also contained a conjugate diluent) was sprayed on the sample pad at the base of the card. The cards were dried, cut, and placed in cassettes as with the liquid test. When the human samples were prepared, they were treated with only the buffer solution in M4 media before 100μl was run on the cassette (no additional gold-conjugated detector mix was added). The Flu A positive samples are noted with a (+), the Flu A negative samples are noted with a (−). These cassettes were designed and read in the same way as the liquid gold cassettes. In FIG. 10f, Sample 7 and 9 were positive for both Flu A and Avian flu and sample 12 was negative for both Flu A and Avian flu.

Example 7

Inhibitors of PDZ/PDZ Ligand Interactions

In this example, compounds were selected for analysis as inhibitors of PDZ/PDZ ligand interactions. The following 23 drugs were screened against select PDZ/PL pairs (numbers 1-17 are COX inhibitors). 1. Niflumic acid, 2. Ibuprofen, 3. Naproxen sodium, 4. Diclofenac sodium salt, 5. Acetylsalicylic acid, 6. Salicylic acid, 7. Flurbiprofen, 8. Sulindac sulphide, 9. Sulindac, 10. Etodolac, 11. Indomethacin, 12. Ketorolac Tris salt, 13. Ketoprofen, 14. Mefenamic acid, 15. Carprofen, 16. Baclofen, 17. Fenoprofen, 18. Benztropine mesylate, 19. Amitriptyline HCl, 20. Cromolyn sodium, 21. Desipramine HCl, 22. Clomipramine HCl, and 23. Nortriptyline HCl. In the description below, Section A provides the experiments that were performed using COX inhibitors, Section B provides the experiments that were performed using small molecule inhibitors and Section C provides the experiments that were performed using peptide inhibitors. Table 8 provides the PDZ/PL interactions that were used to identify inhibitors in sections A-C. The PL sequences used were SEQ ID NOS:54-59. The results are shown in Table 11-13.

TABLE 8

PDZ/PL Interactions used in drug screens

| PDZ | PL sequence | Sequence Number |
|---|---|---|
| Magi d1 (AVC 88) | GRWTGRSMSSWKPTRRETEV (AVC 1857) | SEQ ID NO: 54 |
| TIP1 (AVC 54) | QISPGGLEPPSEKHFRETEV (AVC AA56) | 55 |
| SHANK1 (AVC 235) | YGRKKRRQRRRYIPEAQTRL (AVC 1965) | 56 |
| PSD95 d1 (AVC 143) | YGRKKRRQRRRRISSIETDV (AVC 1912) | 57 |
| PSD95 d2 (AVC 265) | YGRKKRRQRRRKLSSIESDV (AVC AA348) | 58 |
| PSD95 d3 (AVC 466) | YGRKKRRQRRRTKNYKQTSV (AVC 1916) | 59 |

A. COX inhibitors were selected based on two criteria: 1. The presence of a carboxylate group which may interact favorably at the position zero of the PDZ, and 2. a hydrophobic or aromatic group near the carboxylate which may be placed at the position zero of the PDZ. The hydrophobic or aromatic group was not absolutely necessary but was preferred.

COX molecules were subject to screening in a matrix/array competition assay format at 250 uM drug concentration, i.e., assays where docking of ligands to solid phase PDZ domain in fusion proteins was assessed in the presence and absence of the small molecule competitor as described previously. The results are as follows. MAGI1 d1/AVC1857 was inhibited by Sulindac sulphide. The PSD95 d1/AVC1912 interaction was inhibited by Fenoprofen. The PSD95 d2/AVCAA345 interaction was not significantly inhibited by any of the drugs in the assay. The PSD95 d2/AVCAA348 interaction was inhibited by Fenoprofen. The PSD95 d3/AVC1916 interaction was inhibited by Fenoprofen. The SHANK1/AVC1965 interaction was inhibited by Fenoprofen. The TIP1/AVCAA56 interaction was inhibited by Sulindac sulphide. The other drugs did not show significant inhibition in this assay. The two main small molecule hits were Sulindac Sulphide and Fenoprofen.

The results show that COX inhibitors can be used as inhibitors of PDZ/PDZ ligand interactions and derivatives of these can be useful therapeutics for PDZ based targets and that of those tested, Sulindac Sulphide and Fenoprofen showed the strongest inhibition.

B. Small Molecule Inhibitors of PDZ/PDZ ligand interactions were predicted from molecular modeling. In silico screening with Accelrys software (Accelrys, San Diego, Calif.) was used to model and dock a 650,000 molecule library (ChemDiv, San Diego, Calif.; Blanca Pharmaceuticals, Mountain View, Calif.) with 4 different PDZ domain mimics. The molecular modeling was based on finding compounds that had the capability of interacting with the PDZ via electrostatic, hydrogen bonding and hydrophobic interactions.

The best hits from in silico screening were subject to screening in a matrix/array competition assay format, i.e., assays where docking of ligands to solid phase PDZ domain in fusion proteins was assessed in the presence and absence of the small molecule competitor as described elsewhere. The small molecules were screened for inhibition of the PDZ/PDZ ligand interactions listed in Table 9. The chemical structures and formulas of the small molecule inhibitors tested can be found with reference to any public database of small molecules known to one of skill in the art. Other examples of small molecule inhibitors can be found in U.S. Provisional application 60/755,315, entitled "Small Molecule Inhibitors of PDZ Interactions," filed Dec. 30, 2005, herein incorporated by reference in its entirety. The small molecule concentration used in the screen was about 250 uM. The results of these screens are shown in Table 10.

TABLE 9

| Molecule name | Magil d1/ 1857 | PSD95 d1/ 1912 | PSD95 d2/ AA348 | PSD95 d3/ 1916 | Shank1/ 1965 |
|---|---|---|---|---|---|
| | Relative Strength of Hits for hits in Drug Screen @ 250 uM Small Molecule Concentration | | | | |
| D008-0168 | | STRONG | STRONG | STRONG | MEDIUM |
| 2357-3224 | WEAK | STRONG | STRONG | STRONG | STRONG |
| E544-0129 | MEDIUM | MEDIUM | STRONG | STRONG | STRONG |
| 0620-0057 | | | STRONG | STRONG | STRONG |
| 7291-0042 | STRONG | | | | |
| 3289-2331 | STRONG | STRONG | | | |
| 1193-0076 | | STRONG | STRONG | WEAK | WEAK |
| 3807-2058 | MEDIUM | | | | |
| 2817-0095 | WEAK | MEDIUM | WEAK | STRONG | |
| C450-0454 | | MEDIUM | MEDIUM | MEDIUM | |
| 3558-0042 | WEAK | | | | |
| 6623-2002 | | | | | WEAK |
| 8003-6598 | | | | STRONG | MEDIUM |
| 5786-0525 | MEDIUM | | | | |
| 2054-0616 | | MEDIUM | | | |
| MC 319743 | STRONG | | | | |
| MC 272352 | STRONG | STRONG | MEDIUM | STRONG | STRONG |
| 3699-1081 | WEAK | | | | |
| K906-1419 | WEAK | | | | |
| 3254-1829 | MEDIUM | | MEDIUM | | |
| MC 319405 | | MEDIUM | | MEDIUM | |
| 3019-0348 | WEAK | | | | |
| 8009-5039 | WEAK | | | | |
| 4998-2792 | WEAK | | | | |
| 8014-1258 | WEAK | | | | |
| MC 285172 | STRONG | MEDIUM | MEDIUM | MEDIUM | MEDIUM |
| MC 247808 | MEDIUM | | MEDIUM | MEDIUM | MEDIUM |

With reference to Tables 10 and 11 which summarize the results, the small molecules were considered as hits based on the OD (450) readout of the assay either as weak, medium or strong: Weak hit: >40% reduction in OD relative to control, Medium Hit: ~40-60% reduction in OD relative to control, Strong Hit: >40% reduction in OD.

The best of the hits in this latter analysis were then subject to titration binding studies, i.e., titration of small molecule in the same competition assay to estimate and IC50 value and the results are summarized Table 10.

Based on in silico screening, various small molecule inhibitors of PDZ/PL interactions were identified. These molecules can be used to block PDZ/PL interactions of therapeutic value, including Influenza A NS1/PDZ interactions.

C. Peptide therapeutic inhibitors were identified and tested (see Table 11). Each influenza A NS1 protein type containing a PL (H5N1, H3N2 and H1N1) has the potential to interact with several PDZs. Each of these PDZ's may in itself be a potential therapeutic target against the relevant Influenza A strain, and as such, blocking the PDZ with a peptide may have therapeutic utility. In order to identify potential therapeutic peptides, an AVC proprietary database was searched for PDZ ligands of each of the PDZ's. The AVC database contained PL/PDZ interactions that were identified as such based on a proprietary ELISA based assay (G assay) previously described. The criterion used to identify promising PL's was based on the following three criteria: 1) OD(450 nm)>=0.5, 2) Relative standard deviation of measurements<0.25, 3) Peptide concentration=<20 micromolar.

Based on a database of PDZ/PL binding interactions, structure and binding data, C-terminal sequences were identified as most likely to bind to the PSD95 d2 structure (SEQ ID NO:1, for example) based on PSD95 d2 structure and binding

TABLE 10

| Molecule name | Magi1 d1/ 1857 | PSD95 d1/1912 | PSD95 d2/ AA348 | PSD95 d3/ 1916 | Shank1/ 1965 | Tip1/ AA56 | PDZ Modeled From |
|---|---|---|---|---|---|---|---|
| D008-0168 | >250 | 159 | 177 | >250 | 212 | >250 | hDVL1 |
| 2357-3224 | 160 | >250 | >250 | 210 | 211 | >250 | hDVL1 |
| E544-0129 | 61 | 2.5 | 5.0 | 3.5 | 9.1 | >250 | hDVL1 |
| 0620-0057 | 237 | 2.7 | 14.9 | 8.2 | >250 | >250 | PSD95 d3 |
| 7291-0042 | 87 | >250 | >250 | >250 | >250 | >250 | PSD95 d2 (DPi) |
| 3289-2331 | 130 | >250 | >250 | >250 | >250 | >250 | PSD95 d1 |
| 1193-0076 | >250 | >250 | >250 | >250 | >250 | >250 | PSD95 d1 |
| 3807-2058 | >250 | >250 | >250 | >250 | >250 | >250 | PSD95 d1 |
| 2817-0095 | 86 | 183 | >250 | 99.9 | >250 | >250 | hDVL1 |
| C450-0454 | >250 | 206 | >250 | >250 | >250 | >250 | PSD95 d3 |
| 3558-0042 | >250 | >250 | >250 | >250 | >250 | >250 | |
| 6623-2002 | >250 | >250 | >250 | >250 | >250 | >250 | |
| 8003-6598 | >250 | >250 | >250 | 6.3 | 10.9 | >250 | hDVL1 |
| 5786-0525 | >250 | >250 | >250 | >250 | >250 | >250 | |
| 2054-0616 | >250 | >250 | >250 | >250 | >250 | >250 | |
| MC 319743 | 113 | >250 | >250 | >250 | >250 | >250 | PSD95 d2 |
| MC 272352 | 233 | 213 | 223 | 181 | 161 | >250 | (1QLC) |
| 3699-1081 | >250 | >250 | >250 | >250 | >250 | >250 | PSD95 d2 |
| K906-1419 | >250 | >250 | >250 | >250 | >250 | >250 | (1QLC) |
| 3254-1829 | >250 | >250 | >250 | >250 | >250 | >250 | |
| MC 310405 | >250 | >250 | >250 | >250 | >250 | >250 | |
| 3019-0348 | >250 | >250 | >250 | >250 | >250 | >250 | |
| 8009-5039 | >250 | >250 | >250 | >250 | >250 | >250 | |
| 4998-2792 | >250 | >250 | >250 | >250 | >250 | >250 | |
| 8014-1258 | >250 | >250 | >250 | >250 | >250 | >250 | |
| MC 285172 | >250 | >250 | >250 | >250 | >250 | >250 | |
| MC 247808 | >250 | >250 | 220.8 | >250 | >250 | >250 | hDVL1 | data. Thus, preferred peptide therapeutic inhibitors for the Avian FluA (H5N1) are based on peptides that bind to PSD95 d2 and, the optimum and preferred peptide sequences that bind to PSD95 d2 conform to the concensus sequence: E/D/N/Q-S/T-D/E/Q/N-V/L (SEQ ID NO:48)

Using this consensus sequence, the following are examples of preferred C-terminal sequences for peptide inhibitors that bind to the PSD95 d2 domain:
1) ESDV (SEQ ID NO:49)
2) ESEV (SEQ ID NO:2)
3) ETDV (SEQ ID NO:50)
4) ETEV (SEQ ID NO:51)
5) DTDV (SEQ ID NO:52)
6) DTEV (SEQ ID NO:53)
7) DSDV (SEQ ID NO:996)
8) DSEV (SEQ ID NO:997)

Potential PDZ ligand therapeutic peptides for each PDZ are summarized in Table 11. Table 11 sets out the PL peptide identifier (AVC ID) in the first column, the PL peptide name (derived from the protein from which it was derived) in the second column, the peptide sequence in the third column and the sequence identification number in the last column. Each part of the Table contains a heading identifying the PDZ protein that the PLs will bind. The peptides shown in table 11 or truncations thereof that leave the C-terminal PL are agents suitable for treating influenza. The PL peptide therapeutics that block binding of a pathogenic influenza PL to the PDZ are useful for treating pathogenic influenza. For example, the C-terminal sequences (3 to 20 amino acids long) of each of these peptides (SEQ ID NOS:89-987) is converted into a therapeutic by attaching a transporter peptide (protein transduction domain) to the N-terminus of the peptide sequence. Subfragments of these peptides of at least 5 amino acids long with the C-terminal 3 amino acids conserved are used as therapeutic inhibitors of the viral PL/PDZ interaction for each PDZ listed in Table 11, preferably, at least 6 amino acids long, 7 amino acids long, 8 amino acids long, 9 amino acids long, and 10 amino acids long. Preferably at least the C-terminal 4 amino acids are conserved, more preferably, the C-terminal 5 amino acids are conserved, the C-terminal 6 amino acids, or the C-terminal 7 amino acids. The peptide therapeutics also include peptides containing conservative substitutions of the amino acids in the peptide mimetics. However, preferably the conservative substitution is in a region other than the last 3 or 4 amino acids. Several transporter peptide sequences are used, including Tat and antennapedia. The peptides are subjected to further analysis by identifying those peptides that inhibit PDZ/PL interactions using the A or G PDZ assays as described in Example 2. Those peptides that are shown to be inhibitory are subjected to further studies in vitro and in an animal model of influenza.

Example 8

NS2 Motif Associated with Virulence

In previous sections, the NS1 PL motif, ESEV (SEQ ID NO:2), was associated with the highly virulent/lethal phenotype seen in avian subtypes such as H5N1. Since the PL portion of NS1 overlaps with NS2, the impact of avian PL conservation on NS2 sequence in the overlap region were analyzed. NS1 and NS2 use different reading frames over the overlapping region and this places constraints on the choice of codons that can be used. The analysis identified that the sequence variation in this region changes the protein sequence of NS1 but not NS2 (see Tables 12 and 13—In Table 12 STYPE refers to the Subtype of the virus). Specifically, in H5N1 the PL sequences ESEV (SEQ ID NO:2), EPEV (SEQ ID NO:27) and ESKV (SEQ ID NO:4) did not change the protein sequence in NS2, maintaining a serine (S or Ser) at position 70 of NS2. In contrast, benign subtypes such as H3N2 contained nucleotide sequences that led to a glycine at position 70. The only exception to this was the 1918 strain H1N1, responsible for the lethal pandemic of 1918, expressed the PL, KSEV (SEQ ID NO:41), that resulted in a serine at position 70 like the H5N1 strain. The NS1 PL sequences shown in Table 12 are ESEV (SEQ ID NO:2), EPEV (SEQ ID NO:27), ESKV (SEQ ID NO:4), RSKV (SEQ ID NO:8), KSEV (SEQ ID NO:41), and RSEV (SEQ ID NO:7), the SEQ ID NOs for the NS1 C-Terminal coding region are identified in the Table as are the SEQ ID NOs for the NS2 REGION (See Tables 12 and 13). Therefore, a serine at position 70 in the Influenza A virus NS2 protein correlates with the virulence of the virus. As a result, the serine at position 70 can be used as a marker for high virulence while a glycine at position 70 in NS2 can be used as a marker for a more benign clinical course. The variation at position 70 of NS2 is used as a diagnostic marker and a therapeutic target below. The serine substitution permits this sequence to be phosphorylated and possibly regulated by kinases.

TABLE 12

S70 is associated with a highly virulent clinical course

| VIRUS | STYP | NS1 C-TERM CODING REGION | SEQ ID NO. | NS1 PL | NS2 REGION | SEQ ID NO. |
|---|---|---|---|---|---|---|
| A/chicken/Viet Nam/DT-015/2004(H5N1) | H5N1 | attgagtcagaagtttgaaga | 988 | ESEV | QLSQKFE | 994 |
| A/Chicken/HongKong/FY 150/01(H5N1) | H5N1 | attgagtcagaagtttgaaga | 988 | ESEV | QLSQKFE | 994 |
| A/Ck/YN/374/2004(H5N1) | H5N1 | attgagtcagaagtttgaaga | 988 | ESEV | QLSQKFE | 994 |
| A/ck/Nakhon Sawan/Thailand/CU-39/04(H5N1 | H5N1 | attgagtcagaagtttgaaga | 988 | ESEV | QLSQKFE | 994 |
| A/Duck/Hong Kong/ww461/2000(H5N1) | H5N1 | gttgagtcagaagtttgaaga | 988 | ESEV | QLSQKFE | 994 |

TABLE 12-continued

S70 is associated with a highly virulent clinical course

| VIRUS | STYP | NS1 C-TERM CODING REGION | SEQ ID NO. | NS1 PL | NS2 REGION | SEQ ID NO. |
|---|---|---|---|---|---|---|
| A/Duck/Hong/Kong/2986.1/2000(H5N1) | H5N1 | attgagtcagaagtttgaaga | 988 | ESEV | QLSQKFE | 994 |
| A/Duck/Hong Kong/p46/97 (H5N1) EPEV | H5N1 | attgag<u>cc</u>agaagtttgaaga | 989 | E<u>P</u>EV | QLSQKFE | 994 |
| A/grebe/Novosibirsk/29/2005(H5N1) ESKV | H5N1 | attgagtca<u>a</u>aagtttgaaga | 990 | ES<u>K</u>V | QLSQKFE | 994 |
| A/Bar-headed Goose/Qinghai/60/05(H5N1) | H5N1 | attgagtca<u>a</u>aagtttgaaga | 990 | ES<u>K</u>V | QLSQKFE | 994 |
| A/Hong Kong/213/03(H5N1) | H5N1 | attgagtcagaagtttgaaga | 988 | ESEV | QLSQKFE | 994 |
| A/Hong Kong/481/97(H5N1) EPEV | H5N1 | attgag<u>cc</u>agaagtttgaaga | 989 | E<u>P</u>EV | QLSQKFE | 994 |
| A/Thailand/2(SP-33)/2004(H5N1) | H5N1 | attgagtcagaagtttgaaga | 988 | ESEV | QLSQKFE | 994 |
| A/tiger/Suphanburi/Thailand/Ti-1/04(H5N1 | H5N1 | attgagtcagaagtttgaaga | 988 | ESEV | QLSQKFE | 994 |
| A/leopard/Suphanburi/Thailand/Leo-1/04(H5N | H5N1 | attgagtcagaagtttgaaga | 988 | ESEV | QLSQKFE | 994 |
| A/HongKong/97/98(H5N1) EPEV | H5N1 | attgag<u>cc</u>agaagtttgaaga | 989 | E<u>P</u>EV | QLSQKFE | 994 |
| A/Viet Nam/1203/2004(H5N1) del PL* | H5N1 | attgagtcagaagtttgaaga | 988 | DEL PL | QLSQKFE | 994 |
| A/New York/393/2005(H3N2 | H3N2 | gct<u>ag</u>gtca<u>a</u>aagtttgaaga | 991 | RS<u>K</u>V | QLG<u>Q</u>KFE | 995 |
| A/Brevig Mission/1/1918(H1N1) | H1N1 | att<u>a</u>agtcagaagtttgaaga | 992 | <u>K</u>SEV | QLSQKFE | 994 |
| A/New York/227/2003(H1N1) | H1N1 | att<u>ag</u>gtcagaagtttgaaga | 993 | <u>R</u>SEV | QLG<u>Q</u>KFE | 995 |

Use as a Diagnostic Marker

A mucous sample is taken from a patient that presents with symptoms of influenza A. The sample is treated to be more fluid for use in a lateral flow format. A lateral flow format is produced using the protocol presented in Example 6, except that a nucleic acid that is complementary to the sequence comprising the overlap and containing the serine 70 in the NS2 protein from Table 12 is used to identify capture agents to capture any NS2 containing a serine at position 70 present in the sample. The capture agent includes complementary nucleic acids for all known virulent influenza A strains. A positive result indicates that the patient should be treated for a highly virulent form of Influenza A virus.

TABLE 13

S70 is associated with a highly virulent clinical course

| NS2 | | | | | NUCLEOTIDE SEQUENCE | | | | | | NS1 | | SUBTYPE |
|---|---|---|---|---|---|---|---|---|---|---|---|---|---|
| | | | | | | ag | a | | | | R | K | H3N2 |
| | G | | | | | ag | | | | | R | | H1N1 |
| L | S | Q | K | F | att | gag | tca gaa gtt tga | I | E | S | E | V | H5N1 |
| | | | | | | | a | | | | | I | H5N1 |
| | | | | | | | a | | | | | K | H5N1 |
| | | | | | | c | | | | | P | | H5N1 |
| | | | | | | a | | | | | K | | H1N1 (1918) |

A monoclonal antibody based test is identical except that a series of antibodies that specifically recognize the NS2 overlap regions including the serine 70 from Table 12 are used as capture agents.

Use for Therapeutic Design

A therapeutic agent that blocks the interaction between the NS2 and a target is used. Specifically, the therapeutic agents block the binding at the serine 70 position of the NS2 protein. Peptides or small molecules therapeutic agents are administered to a patient that has been infected with Influenza A or prior to infection in an amount sufficient to block the interaction between NS2 and its target. The administration is via inhalation and the treatment is continued until the patient is free of symptoms and/or the patient is no longer in danger of contracting the disease.

All publications and patents cited in this specification are herein incorporated by reference as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All publications and patent applications mentioned in this specification are herein incorporated by reference to the same extent as if each individual publication or patent application was specifically and individually indicated to be incorporated by reference.

TABLE 11

PL sequences binding DLG2 d1

| AVC ID | Peptide | Sequence | Seq. ID No. |
|---|---|---|---|
| AA72.1 | HPV E6 33 (modified) | AAGGRSARGGRLQGRRETAL | 60 |
| AA206L | CITRON protein | AGAVRTPLSQVNKVWDQSSV | 61 |
| AA75.1 | HPV E6 58 (modified) | AVGGRPARGGRLQGRRQTQV | 62 |
| AA245 | alpha-2C Adrenergic receptor | DFRPSFKHILFRRARRGFRQ | 63 |
| AA233L | serotonin receptor 5HT-2B | DTLLLTENEGDKTEEQVSYV | 64 |
| AA80.1 | HPV E6 #35 (cysteine-free) | GRWTGRAMSAWKPTRRETEV | 65 |
| AA258 | noradrenaline transporter | HHLVAQRDIRQFQLQHWLAI | 66 |
| AA327 | PAR-2 | KHSRKSSSYSSSSTTVKTSY | 67 |
| 1820 | TRPM7 | KKKKQPGNSTKESESTNSVRLML | 68 |
| AA250 | Serotonin receptor 3a | LAVLAYSITLVMLWSIWQYA | 69 |
| AA34.2 | NMDA | LNSCSNRRVYKKMPSIESDV | 70 |
| AA345 | NMDA R2A | LNSCSNRRVYKKMPSIESDV | 71 |
| AA140 | KIAA 1481 | PIPAGGCTFSGIFPTLTSPL | 72 |
| AA217 | catenin-delta 2 | PYSELNYETSHYPASPDSWV | 73 |
| AA244 | alpha-2B Adrenergic receptor | QDFRRAFRRILARPWTQTAW | 74 |
| AA56 | TAX | QISPGGLEPPSEKHFRETEV | 75 |
| AA240 | Dopamine transporter | RELVDRGEVRQFTLRHWLKV | 76 |
| AA095 | GluR5-2 (rat) | SFTSILTCHQRRTQRKETVA | 77 |
| AA214L | ErbB-4 receptor | SLKPGTVLPPPPYRHRNTVV | 78 |
| AA23.3 | Fas Ligand | SSKSKSSEESQTFFGLYKL | 79 |
| AA223 | claudin 1 | SYPTPRPYPKPAPSSGKDYV | 80 |
| AA66.1 | HPV E6 #66 (cysteine-free) | TGSALQAWRHTSRQATESTV | 81 |
| AA180 | NMDA Glutamate Receptor 2C | TQGFPGPATWRRISSLESEV | 82 |
| AA82 | AdenoE4 typ9 | VGTLLLERVIFPSVKIATLV | 83 |
| AA77 | HPV-E6 #63 | VHKVRNKFKAKCSLCRLYII | 84 |
| 1775 | Tat-N-protein-SARS | YGRKKRRQRRRGASADSTQA | 85 |
| AA348 | TATNMDA2B9 | YGRKKRRQRRRKLSSIESDV | 86 |
| 1777 | Tat-M-Protein-SARS | YGRKKRRQRRRNDNIALLVQ | 87 |
| 1776 | Tat-E-protein-SARS | YGRKKRRQRRRSEGVPDLLV | 88 |

TABLE 11-continued

PL sequences binding GORASP d1

| AVC ID | Peptide | Sequence | Seq ID No. |
|---|---|---|---|
| 1927 | X = L-phenyl glycine | | |
| 1754 | Nucleocapsid, SARS | DFSRQLQNSMSGASADSTQA | 89 |
| 1820 | TRPM7 | KKKKQPGNSTKESESTNSVRLML | 90 |
| 1750 | M protein, SARS | NYKLNTDHAGSNDNIALLVQ | 91 |
| AA70.1 | HPV E6 #18 | SGGNRARQERLQRRRETQV | 92 |
| 1795 | Tat-A2A Adrenergic receptor | YGRKKRRQRRRARGDRKRIV | 93 |
| 1791 | Tat-MUC1 Ile-2 | YGRKKRRQRRRAVAATSINL | 94 |
| 1940 | Tat-CLCA-3 (murine) | YGRKKRRQRRREMQVTLGLH | 95 |
| 1775 | Tat-N-protein-SARS | YGRKKRRQRRRGASADSTQA | 96 |
| 1947 | Tat-hCLCA1 | YGRKKRRQRRRIGELQLSIA | 97 |
| 1922 | X = L-alpha-aminobutyric acid | YGRKKRRQRRRKLSSIESDX | 98 |
| 1777 | Tat-M-Protein-SARS | YGRKKRRQRRRNDNIALLVQ | 99 |
| 1789 | Tat-ERC1b | YGRKKRRQRRRQDEEEGIWA | 100 |
| 1776 | Tat-E-protein-SARS | YGRKKRRQRRRSEGVPDLLV | 101 |
| 1752 | E protein, SARS | YVYSRVKNLNSSEGVPDLLV | 102 |

PL sequences binding GRIP1 d4

| AVC ID | Peptide | Sequence | Seq ID. No. |
|---|---|---|---|
| AA75.1 | HPV E6 58 (modified) | AVGGRPARGGRLQGRRQTQV | 103 |
| AA245 | alpha-2C Adrenergic receptor | DFRPSFKHILFRRARRGFRQ | 104 |
| AA258 | noradrenaline transporter | HHLVAQRDIRQFQLQHWLAI | 105 |
| AA70 | HPV-E6 #18 | HSCCNRARQERLQRRRETQV | 106 |
| AA327 | PAR-2 | KHSRKSSSYSSSSTTVKTSY | 107 |
| 1820 | TRPM7 | KKKKQPGNSTKESESTNSVRLML | 108 |
| AA229 | claudin 5 | KYSAPRRPTATGDYDKKNYV | 109 |
| AA250 | Serotonin receptor 3a | LAVLAYSITLVMLWSIWQYA | 110 |
| AA244 | alpha-2B Adrenergic receptor | QDFRRAFRRILARPWTQTAW | 111 |
| AA23.3 | Fas Ligand | SSKSKSSEESQTFFGLYKL | 112 |
| AA228 | Nectin 2 | SSPDSSYQGKGFVMSRAMYV | 113 |
| AA114 | GLUR7 (metabotropic glutamateR) | VDPNSPAAKKKYVSYNNLVI | 114 |
| AA77 | HPV-E6 #63 | VHKVRNKFKAKCSLCRLYII | 115 |
| 1775 | Tat-N-protein-SARS | YGRKKRRQRRRGASADSTQA | 116 |
| 1777 | Tat-M-Protein-SARS | YGRKKRRQRRRNDNIALLVQ | 117 |
| 1776 | Tat-E-protein-SARS | YGRKKRRQRRRSEGVPDLLV | 118 |

TABLE 11-continued

PL sequences binding INADL d8

| AVC ID | Peptide | Sequence | Seq ID No. |
|---|---|---|---|
| AA206L | CITRON protein | AGAVRTPLSQVNKVWDQSSV | 119 |
| AA121 | CD68 | ALVLIAFCIIRRRPSAYQAL | 120 |
| AA115 | presenilin-1 | ATDYLVQPFMDQLAFHQFYI | 121 |
| AA75.1 | HPV E6 58 (modified) | AVGGRPARGGRLQGRRQTQV | 122 |
| AA245 | alpha-2C Adrenergic receptor | DFRPSFKHILFRRARRGFRQ | 123 |
| AA59 | PTEN | DSDPENEPFDEDQHTQITKV | 124 |
| AA233L | serotonin receptor 5HT-2B | DTLLLTENEGDKTEEQVSYV | 125 |
| AA218 | CSPG4(chondroitinSO4 proteoglyc4) | ELLQFCRTPNPALKNGQYWV | 126 |
| AA210L | APC-adenomatous polyposis coli | ESSGTQSPKRHSGSYLVTSV | 127 |
| AA36.2 | Neuroligin (linker 12aa) | GGGGGSGGGGSGLPHSTTRV | 128 |
| AA22.2 | DNAM-1 (linker 12 aa) | GGGGGSGGGGSGSRRPKTRV | 129 |
| AA80.1 | HPV E6 #35 (cysteine-free) | GRWTGRAMSAWKPTRRETEV | 130 |
| AA258 | noradrenaline transporter | HHLVAQRDIRQLQLQHWLAI | 131 |
| AA70 | HPV-E6 #18 | HSCCNRARQERLQRRRETQV | 132 |
| AA177L | c-kit receptor | INSVGSTASSSQPLLVHDDV | 133 |
| AA226 | claudin 7 | KAGYRAPRSYPKSNSSKEYV | 134 |
| AA327 | PAR-2 | KHSRKSSSYSSSSTTVKTSY | 135 |
| 1820 | TRPM7 | KKQPGNSTKESESTNSVRLML | 136 |
| AA118 | MINT-1 | KTMPAAMYRLLTAQEQPVYI | 137 |
| AA250 | Serotonin receptor 3a | LAVLAYSITLVMLWSIWQYA | 138 |
| AA225 | claudin 9 | LGYSIPSRSGASGLDKRDYV | 139 |
| AA34.2 | NMDA | LNSCSNRRVYKKMPSIESDV | 140 |
| AA345 | NMDA R2A | LNSSSNRRVYKKMPSIESDV | 141 |
| AA140 | KIAA 1481 | PIPAGGCTFSGIFPTLTSPL | 142 |
| AA217 | catenin-delta 2 | PYSELNYETSHYPASPDSWV | 143 |
| AA244 | alpha-2B Adrenergic receptor | QDFRRAFRRILARPWTQTAW | 144 |
| AA240 | Dopamine transporter | RELVDRGEVRQFTLRHWLKV | 145 |
| AA207L | Nedasin (s-form) | RNIEEVYVGGKQVVPFSSSV | 146 |
| AA095 | GluR5-2 (rat) | SFTSILTCHQRRTQRKETVA | 147 |
| AA06 | CD6 | SPQPDSTDNDDYDDISAA | 148 |
| AA23.3 | Fas Ligand | SSKSKSSEESQTFFGLYKL | 149 |
| AA228 | Nectin 2 | SSPDSSYQGKGFVMSRAMYV | 150 |
| AA223 | claudin 1 | SYPTPRPYPKPAPSSGKDYV | 151 |

TABLE 11-continued

| AVC ID | Peptide | Sequence | Seq. ID No. |
|---|---|---|---|
| AA36 | Neuroligin | TFAAGFNSTGLPHSTTRV | 152 |
| AA200L | HER2 receptor | TFKGTPTAENPEYLGLDVPV | 153 |
| AA66.1 | HPV E6 #66 (cysteine-free) | TGSALQAWRHTSRQATESTV | 154 |
| AA180 | NMDA Glutamate Receptor 2C (cys-free | TQGFPGPATWRRISSLESEV | 155 |
| AA22 | DNAM-1 | TREDIYVNYPTFSRRPKTRV | 156 |
| AA33 | KV1.3 | TTNNNPNSAVNIKKIFTDV | 157 |
| AA114 | GLUR7 (metabotropic glutamateR) | VDPNSPAAKKKYVSYNNLVI | 158 |
| AA82 | AdenoE4 typ9 | VGTLLLERVIFPSVKIATLV | 159 |
| AA77 | HPV-E6 #63 | VHKVRNKFKAKCSLCRLYII | 160 |
| 1775 | Tat-N-protein-SARS | YGRKKRRQRRRGASADSTQA | 161 |
| AA348 | TATNMDA2B9 | YGRKKKRRQRRRKLSSIESDV | 162 |
| 1966 | Tat-H3N2 | YGRKKRRQRRRMARTARSKV | 163 |
| 1777 | Tat-M-Protein-SARS | YGRKKRRQRRRNDNIALLVQ | 164 |

PL sequenced binding KIAA1284 d1

| AVC ID | Peptide | Sequence | Seq. ID No. |
|---|---|---|---|
| 1927 | X = L-phenyl glycine | YGRKKRRQRRRKLSSIESDX | 165 |
| AA75.1 | HPV E6 58 (modified) | AVGGRPARGGRLQGRRQTQV | 166 |
| AA245 | alpha-2C Adrenergic receptor | DFRPSFKHILFRRARRGFRQ | 167 |
| AA222 | claudin 18 | DGGARTEDEVQSYPSKHDYV | 168 |
| 1761 | FGF receptor 3 IIIc isoform 1 | FHSKTAGANTTDKELEVLSL | 169 |
| AA220 | claudin 10 | GGEDFKTTNPSKQFDKNAYV | 170 |
| AA80.1 | HPV E6 #35 (cysteine-free) | GRWTGRAMSAWKPTRRETEV | 171 |
| AA243 | alpha-2A Adrenergic receptor | HDFRRAFKKILARGDRKRIV | 172 |
| AA258 | noradrenaline transporter | HHLVAQRDIRQFQLQHWLAI | 173 |
| AA70 | HPV-E6 #18 | HSCCNRARQERLQRRRETQV | 174 |
| AA182L | ephrin B2 | ILNSIQVMRAQMNQIQSVEV | 175 |
| AA226 | claudin 7 | KAGYRAPRSYPKSNSSKEYV | 176 |
| AA327 | PAR-2 | KHSRKSSSYSSSSTTVKTSY | 177 |
| 1820 | TRPM7 | KKKKQPGNSTKESESTNSVRLML | 180 |
| AA250 | Serotonin receptor 3a | LAVLAYSITLVMLWSIWQY | 181 |
| AA225 | claudin 9 | LGYSIPSRSGASGLDKRDYV | 180 |
| AA34.2 | NMDA | LNSCSNRRVYKKMPSIESDV | 181 |

TABLE 11-continued

PL sequences binding KIAA1284 d1

| AVC ID | Peptide | Sequence | Seq. ID No. |
|---|---|---|---|
| AA05.1 | CD4 (modified) | LSEKKTSQSPHRFQKTASPI | 182 |
| AA227 | claudin 2 | PGQPPKVKSEFNSYSLTGYV | 183 |
| AA140 | KIAA 1481 | PIPAGGCTFSGIFPTLTSPL | 184 |
| AA244 | alpha-2B Adrenergic receptor | QDFRRAFRRILARPWTQTAW | 185 |
| AA240 | Dopamine transporter | RELVDRGEVRQFTLRHWLKV | 186 |
| AA23.3 | Fas Ligand | SSKSKSSEESQTFFGLYKL | 187 |
| AA228 | Nectin 2 | SSPDSSYQGKGFVMSRAMYV | 188 |
| AA200L | HER2 receptor | TFKGTPTAENPEYLGLDPV | 189 |
| AA33 | KV1.3 | TTNNNPNSAVNIKKIFTDV | 190 |
| AA114 | GLUR7(metabotropic glutamate | VDPNSPAAKKKYVSYNNLVI | 191 |
| AA77 | HPV-E6 #63 | VHKVRNKFKAKCSLCRLYII | 192 |
| 1940 | Tat-CLCA-3 (murine) | YGRKKRRQRRREMQVTLGLH | 193 |
| 1775 | Tat-N-protein-SARS | YGRKKRRQRRRGASADSTQA | 194 |
| 1947 | Tat-hCLCA1 | YGRKKRRQRRRIGELQLSIA | 195 |
| AA348 | TATNMDA2B9 | YGRKKRRQRRRKLSSIESDV | 196 |
| 1922 | X = L-alpha-aminobutyric acid | YGRKKRRQRRRKLSSIESDX | 197 |
| 1777 | Tat-M-Protein-SARS | YGRKKRRQRRRNDNIALLVQ | 198 |
| 1776 | Tat-E-protein-SARS | YGRKKRRQRRRSEGVPDLLV | 199 |

PL sequences binding KIAA1415 d1

| AVC ID | Peptide | Sequence | Seq. ID No. |
|---|---|---|---|
| AA245 | alpha-2C Adrenergic receptor | DFRPSFKHILFRRARRGFRQ | 200 |
| AA222 | claudin 18 | DGGARTEDEVQSYPSKHDYV | 201 |
| AA248 | somatostatin receptor 4 | EALQPEPGRKRIPLTRTTTF | 202 |
| 1761 | FGF receptor 3 IIIc isoform 1 | FHSKTAGANTTDKELEVLSL | 203 |
| AA220 | claudin 10 | GGEDFKTTNPSKQFDKNAYV | 204 |
| AA258 | noradrenaline transporter | HHLVAQRDIRQFQLQHWLAI | 205 |
| AA70 | HPV-E6 #18 | HSCCNRARQERLQRRRETQV | 206 |
| AA182L | ephrin B2 | ILNSIQVMRAQMNQIQSVEV | 207 |
| AA226 | claudin 7 | KAGYRAPRSYPKSNSSKEYV | 208 |
| AA327 | PAR-2 | KHSRKSSSYSSSSTTVKTSY | 209 |
| 1820 | TRPM7 | KKQPGNSTKESESTNSVRLML | 210 |
| AA250 | Serotonin receptor 3a | LAVLAYSITLVMLWSIWQYA | 211 |
| AA225 | claudin 9 | LGYSIPSRSGASGLDKRDYV | 212 |

TABLE 11-continued

| AVC ID | Peptide | Sequence | Seq. ID No. |
|---|---|---|---|
| AA34.2 | NMDA | LNSCSNRRVYKKMPSIESDV | 213 |
| AA227 | claudin 2 | PGQPPKVKSEFNSYSLTGYV | 214 |
| AA140 | KIAA 1481 | PIPAGGCTFSGIFPTLTSPL | 215 |
| AA244 | alpha-2B Adrenergic receptor | QDFRRAFRRILARPWTQTAW | 216 |
| AA240 | Dopamine transporter | RELVDRGEVRQFTLRHWLKV | 217 |
| AA23.3 | Fas Ligand | SSKSKSSEESQTFFGLYKL | 218 |
| AA228 | Nectin 2 | SSPDSSYQGKGFVMSRAMYV | 219 |
| AA124 | CXCR3 | SSSRRDSSWSETSEASYSGL | 220 |
| 1759 | EGFR | TAENAEYLRVAPQSSEFIGA | 221 |
| AA33 | KV1.3 | TTNNNPNSAVNIKKIFTDV | 222 |
| AA114 | GLUR7 (metabotropic glutama | VDPNSPAAKKKYVSYNNLVI | 223 |
| AA77 | HPV-E6 #63 | VHKVRNKFKAKCSLCRLYII | 224 |
| 1775 | Tat-N-protein-SARS | YGRKKRRQRRGASADSTQA | 225 |
| 1777 | Tat-M-Protein-SARS | YGRKKRRQRRRNDNIALLVQ | 226 |
| 1776 | Tat-E-protein-SARS | YGRKKRRQRRRSEGVPDLLV | 227 |

PL sequences binding KIAA1719 d4

| AVC ID | Peptide | Sequence | Seq. ID No. |
|---|---|---|---|
| AA222 | claudin 18 | DGGARTEDEVQSYPSKHDYV | 228 |
| 1761 | FGF receptor 3 IIIc isoform 1 | FHSKTAGANTTDKELEVLSL | 229 |
| AA243 | alpha-2A Adrenergic receptor | HDFRRAFKKILARGDRKRIV | 230 |
| AA258 | noradrenaline transporter | HHLVAQRDIRQFQLQHWLAI | 231 |
| AA70 | HPV-E6 #18 | HSCCNRARQERLQRRRETQV | 232 |
| AA226 | claudin 7 | KAGYRAPRSYPKSNSSKEYV | 233 |
| AA327 | PAR-2 | KHSRKSSSYSSSSTTVKTSY | 234 |
| 1820 | TRPM7 | KKKKQPGNSTKESESTNSVRLML | 235 |
| AA250 | Serotonin receptor 3a | LAVLAYSITLVMLWSIWQYA | 236 |
| AA300 | TRAF2 | NSYVRDDAIFIKAIVDLTGL | 237 |
| AA227 | claudin 2 | PGQPPKVKSEFNSYSLTGYV | 238 |
| AA244 | alpha-2B Adrenergic receptor | QDFRRAFRRILARPWTQTAW | 239 |
| AA328 | GPR5 | SPASIPHSPGAFAYEGASFY | 240 |
| AA23.3 | Fas Ligand | SSKSKSSEESQTFFGLYKL | 241 |
| AA124 | CXCR3 | SSSRRDSSWSETSEASYSGL | 242 |
| AA77 | HPV-E6 #63 | VHKVRNKFKAKCSLCRLYII | 243 |
| 1940 | Tat-CLCA-3 (murine) | YGRKKRRQRRREMQVTLGLH | 244 |
| 1777 | Tat-M-Protein-SARS | YGRKKRRQRRRNDNIALLVQ | 245 |

TABLE 11-continued

| | | | |
|---|---|---|---|
| 1912 | Biotin-Tat-NMDAR2special1 | YGRKKRRQRRRRISSIETDV | 246 |
| 1917 | 1917 | YGRKKRRQRRRRISSLETQV | 247 |
| 1776 | Tat-E-protein-SARS | YGRKKRRQRRRSEGVPDLLV | 248 |

PL sequences binding Lim Mystique d1

| AVC ID | Peptide | Sequence | Seq. ID No. |
|---|---|---|---|
| AA72.1 | HPV E6 33 (modified) | AAGGRSARGGRLQGRRETAL | 249 |
| AA115 | presenilin-1 | ATDYLVQPFMDQLAFHQFYI | 250 |
| AA245 | alpha-2C Adrenergic receptor | DFRPSFKHILFRRARRGFRQ | 251 |
| AA178L | PDZ-binding kinase (PBK) | EDPKDRPSAAHIVEALETDV | 252 |
| AA218 | CSPG4 (chondroitinSO4-proteoglyc 4) | ELLQFCRTPNPALKNGQYWV | 253 |
| 1761 | FGF receptor 3 IIIc isoform 1 | FHSKTAGANTTDKELEVLSL | 254 |
| AA346 | NMDA R2B | FNGSSNGHVYEKLSSIESDV | 255 |
| AA80.1 | HPV E6 #35 (cysteine-free) | GRWTGRAMSAWKPTRRETEV | 256 |
| AA243 | alpha-2A Adrenergic receptor | HDFRRAFKKILARGDRKRIV | 257 |
| AA258 | noradrenaline transporter | HHLVAQRDIRQFQLQHWLAI | 258 |
| AA70 | HPV-E6 #18 | HSCCNRARQERLQRRRETQV | 259 |
| AA182L | ephrin B2 | ILNSIQVMRAQMNQIQSVEV | 260 |
| AA327 | PAR-2 | KHSRKSSSYSSSSTTVKTSY | 261 |
| 1820 | TRPM7 | KKKKQPGNSTKESESTNSVRLML | 262 |
| AA40 | DOCK2 | LASKSAEEGKQIPDSLSTDL | 263 |
| AA250 | Serotonin receptor 3a | LAVLAYSITLVMLWSIWQYA | 264 |
| AA311 | Beta-1 catenin | LMDGLPPGDSNQLAWFDTDL | 265 |
| AA34.2 | NMDA | LNSCSNRRVYKKMPSIESDV | 266 |
| AA345 | NMDA R2A | LNSSSNRRVYKKMPSIESDV | 267 |
| AA140 | KIAA 1481 | PIPAGGCTFSGIFPTLTSPL | 268 |
| AA217 | catenin-delta 2 | PYSELNYETSHYPASPDSWV | 269 |
| AA244 | alpha-2B Adrenergic receptor | QDFRRAFRRILARPWTQTAW | 270 |
| AA56 | TAX | QISPGGLEPPSEKHFRETEV | 271 |
| AA240 | Dopamine transporter | RELVDRGEVRQFTLRHWLKV | 272 |
| AA328 | GPR5 | SPASIPHSPGAFAYEGASFY | 273 |
| AA23.3 | Fas Ligand | SSKSKSSEESQTFFGLYKL | 274 |
| AA124 | CXCR3 | SSSRRDSSWSETSEASYSGL | 275 |
| AA223 | claudin 1 | SYPTPRPYPKPAPSSGKDYV | 276 |
| AA200L | HER2 receptor | TFKGTPTAENPEYLGLDVPV | 277 |

TABLE 11-continued

| | | | |
|---|---|---|---|
| AA180 | NMDA GlutR2C (cysteine-free) | TQGFPGPATWRRISSLESEV | 278 |
| AA114 | GLUR7 (metabotropic glutR) | VDPNSPAAKKKYVSYNNLVI | 279 |
| AA125 | zona occludens 3 (ZO-3) | VHDAESSDEDGYDWGPATDL | 280 |
| AA77 | HPV-E6 #63 | VHKVRNKFKAKCSLCRLYII | 281 |
| AA123 | a-actinin 2 | VPGALDYAAFSSALYGESDL | 282 |
| 1784 | Tat-MUC1 (Ala variant) | YGRKKRRQRRRAVAAASANL | 283 |
| 1763 | Tat-MUC1 | YGRKKRRQRRRAVAATSANL | 284 |
| 1791 | Tat-MUC1 Ile-2 | YGRKKRRQRRRAVAATSINL | 285 |
| 1764 | Tat-HER2 | YGRKKRRQRRREYLGLDVPV | 286 |
| AA348 | TATNMDA2B9 | YGRKKRRQRRRKLSSIESDV | 287 |
| 1777 | Tat-M-Protein-SARS | HGRKKRRQRRRNDNIALLVQ | 288 |

PL sequences binding MAGI1 d1

| AVC ID | Peptide | Sequence | Seq ID No |
|---|---|---|---|
| AA72.1 | HPV E6 33 (modified) | AAGGRSARGGRLQGRRETAL | 289 |
| AA121 | CD68 | ALVLIAFCIIRRRPSAYQAL | 290 |
| AA29.3 | IL-8RA | ARHRVTSYTSSSVNVSSNL | 291 |
| AA115 | presenilin-1 | ATDYLVQPFMDQLAFHQFYI | 292 |
| AA75.1 | HPV E6 58 (modified) | AVGGRPARGGRLQGRRQTQV | 293 |
| AA30 | LPAP | AWDDSARAAGGQGLHVTAL | 294 |
| AA245 | alpha-2C Adrenergic receptor | DFRPSFKHILFRRARRGFRQ | 295 |
| AA218 | CSPG4 (chondroitinSO4-proteoglyc4) | ELLQFCRTPNPALKNGQYWV | 296 |
| AA210L | APC-adenomatous polyposis coli | ESSGTQSPKRHSGSYLVTSV | 297 |
| AA346 | NMDA R2B | FNGSSNGHVYEKLSSIESDV | 298 |
| AA108.1 | GLUR2 (glutamate R 2-modified) | GGGGGSGGGGGSGIESVKI | 299 |
| AA36.3 | Neuroligin (linker 14aa) | GGGGGSGGGGSGGGHSTTRV | 300 |
| AA36.2 | Neuroligin (linker 12aa) | GGGGGSGGGGSGLPHSTTRV | 301 |
| AA22.2 | DNAM-1 (linker 12 aa) | GGGGGSGGGGSGSRRPKTRV | 302 |
| AA22.1 | DNAM-1 (linker 10aa) | GGGGGSGGGGTFSRRPKTRV | 303 |
| 1859 | HPV E6 #33 (Cys->Ser) | GRWAGRSAASWRSRRRETAL | 304 |
| AA80.1 | HPV E6 #35 (cysteine-free) | GRWTGRAMSAWKPTRRETEV | 305 |
| 1858 | HPV E6 #58 (mod Cys->Ser) | GRWTGRSAVSWRPRRRTQV | 306 |
| 1857 | HPV E6 #35 (mod Cys->Ser) | GRWTGRSMSSWKPTRRETEV | 307 |
| AA258 | noradrenaline transporter | HHLVAQRDIRQFQLQHWLAI | 308 |
| AA70 | HPV-E6 #18 | HSCCNRARQERLQRRRETQV | 309 |

TABLE 11-continued

| | | | |
|---|---|---|---|
| AA02.1 | Clasp-2 | ISGTPTSTMVHGMTSSSSVV | 310 |
| AA226 | claudin 7 | KAGYRAPRSYPKSNSSKEYV | 311 |
| AA29.2 | CDw128B | KDSRPSFVGSSSGHTSTTL | 312 |
| AA327 | PAR-2 | KHSRKSSSYSSSSTTVKTSY | 313 |
| 1820 | TRPM7 | KKKKQPGNSTKESESTNSVRLML | 314 |
| AA250 | Serotonin receptor 3a | LAVLAYSITLVMLWSIWQYA | 315 |
| AA106 | Kir2.1 (inwardly rect. K+ channel) | LHNQASVPLEPRPLRRESEI | 316 |
| AA113 | SSTR2 (somatostatin recepor 2) | LNETTETQRTLLNGDLQTSI | 317 |
| AA34.2 | NMDA | LNSCSNRRVYKKMPSIESDV | 318 |
| AA345 | NMDA R2A | LNSSSNRRVYKKMPSIESDV | 319 |
| 1860 | HPV E6 #52 (Cys->Ser) | MGRWTGRSSESWRPRPVTQV | 320 |
| 1861 | HPV E6 #45 (Cys->Ser) | NTSSDQARQERLRRRRETQV | 321 |
| AA227 | claudin 2 | PGQPPKVKSEFNSYSLTGYV | 322 |
| AA140 | KIAA 1481 | PIPAGGCTFSGIFPTLTSPL | 323 |
| AA244 | alpha-2B Adrenergic receptor | QDFRRAFRRILARPWTQTAW | 324 |
| AA56 | TAX | QISPGGLEPPSEKHFRETEV | 325 |
| AA252 | muscarinic Ach receptor M4 | QQYQQRQSVIFHKRAPEQAL | 326 |
| AA240 | Dopamine transporter | RELVDRGEVRQFTLRHWLKV | 327 |
| AA207L | Nedasin (s-form) | RNIEEVYVGGKQVVPFSSSV | 328 |
| AA74.1 | HPV E6 52 (modified) | SEGGRPTRGPRLQGRRVTQV | 329 |
| AA095 | GluR5-2 (rat) | SFTSILTCHQRRTQRKETVA | 330 |
| AA70.1 | HPV E6 #18 | SGGNRARQERLQRRRETQV | 331 |
| AA253 | Clasp-3 | SLIGPVQKEYQRELGKLSSP | 332 |
| AA214L | ErbB-4 receptor | SLKPGTVLPPPPVRHRNTVV | 333 |
| AA06 | CD6 | SPQPDSTDNDDYDDISAA | 334 |
| AA23.3 | Fas Ligand | SSKSKSSEESQTFFGLYKL | 335 |
| AA228 | Nectin 2 | SSPDSSYQGKGFVMSRAMYV | 336 |
| AA124 | CXCR3 | SYPTPRPYPKPAPSSGKDYV | 337 |
| AA223 | claudin 1 | SYPPRPYPKPAPSSGKDYV | 338 |
| AA36 | Neuroligin | TFAAGFNSTGLPHSTTRV | 339 |
| AA69.1 | HPV E6 #16 (Modified) | TGRGMSGGRSSRTRRETQL | 340 |
| AA66.1 | HPV E6 #66 (cysteine-free) | TGSALQAWRHTSRQATESTV | 341 |
| AA180 | NMDA GlutamateR 2C (cys-free) | TQGFPGPATWRRISSLESEV | 342 |
| AA22 | DNAM-1 | TREDIYVNYPTFSRRPKTRV | 343 |
| AA33 | KV1.3 | TTNNNPNSAVNIKKIFTDV | 344 |
| AA114 | GLUR7 (metabotropic-glutamateR | VDPNSPAAKKKYVSYNNLVI | 345 |

TABLE 11-continued

| | | | |
|---|---|---|---|
| AA82 | AdenoE4 typ9 | VGTLLLERVIFPSVKIATLV | 346 |
| AA77 | HPV-E6 #63 | VHKVRNKFKAKCSLCRLYII | 347 |
| 1862 | HPV E6 #82 | WTGQSANSRKPPRQRSETQV | 348 |
| AA353 | bTAT-TAX | YGRKKRRQRRREKHFRETEV | 349 |
| 1775 | Tat-N-protein-SARS | YGRKKRRQRRRGASADSTQA | 350 |
| AA348 | TATNMDA2B9 | YGRKKRRQRRRKLSSIESDV | 351 |
| 1777 | Tat-M-Protein-SARS | YGRKKRRQRRRNDNIALLVQ | 352 |
| 1912 | Biotin-Tat-NMDAR2-special1 | YGRKKRRQRRRRISSIETDV | 353 |
| AA25 | FceR1b | YSATYSELEDPGEMSPPIDL | 354 |

PL sequences binding MAGI2 d5

| AVC ID | Peptide | Sequence | Seq ID No. |
|---|---|---|---|
| AA72.1 | HPV E6 33 (modified) | AAGGRSARGGRLQGRRETAL | 355 |
| AA115 | presenilin-1 | ATDYLVQPFMDQLAFHQFYI | 356 |
| AA75.1 | HPV E6 58 (modified) | AVGGRPARGGRLQGRRQTQV | 357 |
| AA30 | LPAP | AWDDSARAAGGQGLHVTAL | 358 |
| AA245 | alpha-2C Adrenergic receptor | DFRPSFKHILFRRARRGFRQ | 359 |
| AA222 | claudin 18 | DGGARTEDEVQSYPSKHDYV | 360 |
| AA59 | PTEN | DSDPENEPFDEDQHTQITKV | 361 |
| AA218 | CSPG4 (chondroitinSO4-proteoglycan4) | ELLQFCRTPNPALKNGQYVV | 362 |
| AA210L | APC-adenomatous polyposis coli protein | ESSGTQSPKRHSGSYLVTSV | 363 |
| 1761 | Fibroblast growth factor R 3 IIIc isoform 1 | FHSKTAGANTTDKELEVLSL | 364 |
| AA346 | NMDA R2B | FNGSSNGHVYEKLSSIESDV | 365 |
| AA220 | claudin 10 | GGEDFKTTNPSKQFDKNAYV | 366 |
| AA80.1 | HPV E6 #35 (cysteine-free) | GRWTGRAMSAWKPTRRETEV | 367 |
| AA243 | alpha-2A Adrenergic receptor | HDFRRAFKKILARGDRKRIV | 368 |
| AA258 | noradrenaline transporter | HHLVAQRDIRQFQLQHWLAI | 369 |
| AA70 | HPV-E6 #18 | HSCCNRARQERLQRRRETQV | 370 |
| AA182L | ephrin B2 | ILNSIQVMRAQMNQIQSVEV | 371 |
| AA226 | claudin 7 | KAGYRAPRSYPKSNSSKEYV | 372 |
| AA327 | PAR-2 | KHSRKSSSYSSSSTTVKTSY | 373 |
| 1820 | TRPM7 | KQPGNSTKESESTNSVRLML | 374 |
| AA229 | claudin 5 | KYSAPRRPTATGDYDKKNYV | 375 |
| AA40 | DOCK2 | LASKSAEEGKQIPDSLSTDL | 376 |
| AA250 | Serotonin receptor 3a | LAVLAYSITLVMLWSIWQYA | 377 |

TABLE 11-continued

| AVC ID | Peptide | Sequence | Seq. ID No. |
|---|---|---|---|
| AA225 | claudin 9 | LGYSIPSRSGASGLDKRDYV | 378 |
| AA311 | Beta-1 catenin | LMDGLPPGDSNQLAWFDTDL | 379 |
| AA34.2 | NMDA | LNSCSNRRVYKKMPSIESDV | 380 |
| AA345 | NMDA R2A | LNSSSNRRVYKKMPSIESDV | 381 |
| AA227 | claudin 2 | PGQPPKVKSEFNSYSLTGYV | 382 |
| AA140 | KIAA 1481 | PIPAGGCTFSGIFPTLTSPL | 383 |
| AA217 | catenin-delta 2 | PYSELNYETSHYPASPDSWV | 384 |
| AA07 | CD34 | QATSRNGHSARQHVVADTEL | 385 |
| AA244 | alpha-2B Adrenergic receptor | QDFRRAFRRILARPWTQTAW | 386 |
| AA56 | TAX | QISPGGLEPPSEKHFRETEV | 387 |
| AA240 | Dopamine transporter | RELVDRGEVRQFTLRHWLKV | 388 |
| AA207L | Nedasin (s-form) | RNIEEVYVGGKQVVPFSSSV | 389 |
| AA328 | GPR5 | SPASIPHSPGAFAYEGASFY | 390 |
| AA23.3 | Fas Ligand | SSKSKSSEESQTFFGLYKL | 391 |
| AA228 | Nectin 2 | SSPDSSYQGKGFVMSRAMYV | 392 |
| AA124 | CXCR3 | SSSRRDSSWSETSEASYSGL | 393 |
| AA66.1 | HPV E6 #66 (cysteine-free) | TGSALQAWRHTSRQATESTV | 394 |
| AA180 | NMDA Glutamate R 2C (cys-free) | TQGFPGPATWRRISSLESEV | 395 |
| AA33 | KV1.3 | TTNNNPNSAVNIKKIFTDV | 396 |
| AA114 | GLUR7 (metabotropic glutamate | VDPNSPAAKKKYVSYNNLVI | 397 |
| AA82 | AdenoE4 typ9 | VGTLLLERVIFPSVKIATLV | 398 |
| AA125 | zona occludens 3 (ZO-3) | VHDAESSDEDGYDWGPATDL | 399 |
| AA77 | HPV-E6 #63 | VHKVRNKFKAKCSLCRLYII | 400 |
| AA123 | a-actinin 2 | VPGALDYAAFSSALYGESDL | 401 |
| 1763 | Tat-MUC1 | YGRKKRRQRRRAVAATSANL | 402 |
| 1764 | Tat-HER2 | YGRKKRRQRRREYLGLDVPV | 403 |
| 1775 | Tat-N-protein-SARS | YGRKKRRQRRRGASADSTQA | 404 |
| AA348 | TATNMDA2B9 | YGRKKRRQRRRKLSSIESDV | 405 |
| 1777 | Tat-M-Protein-SARS | YGRKKRRQRRRNDNIALLVQ | 406 |
| 1776 | Tat-E-protein-SARS | YGRKKRRQRRRSEGVPDLLV | 407 |

PL sequences binding MAGI3 d1

| AVC ID | Peptide | Sequence | Seq. ID No. |
|---|---|---|---|
| AA72.1 | HPV E6 33 (modified) | AAGGRSARGGRLQGRRETAL | 408 |
| AA121 | CD68 | ALVLIAFCIIRRRPSAYQAL | 409 |
| AA29.3 | IL-8RA | ARHRVTSYTSSSVNVSSNL | 410 |
| AA115 | presenilin-1 | ATDYLVQPFMDQLAFHQFYI | 411 |
| AA75.1 | HPV E6 58 (modified) | AVGGRPARGGRLQGRRQTQV | 412 |

TABLE 11-continued

| | | | |
|---|---|---|---|
| AA245 | alpha-2C Adrenergic receptor | DFRPSFKHILFRRARRGFRQ | 413 |
| AA218 | CSPG4 (chondroitinSO4-proteoglyc4) | ELLQFCRTPNPALKNGQYWV | 414 |
| AA19 | CD148 | ENLAPVTTFGKTNGYIA | 415 |
| AA210L | APC-adenomatous polyposis coli | ESSGTQSPKRHSGSYLVTSV | 416 |
| AA346 | NMDA R2B | FNGSSNGHVYEKLSSIESDV | 417 |
| AA347 | NMDA R2D | GGDLGTRRGSAHFSSLESEV | 418 |
| AA220 | claudin 10 | GGEDFKTTNPSKQFDKNAYV | 419 |
| AA108.1 | GLUR2 (glutamateR 2-modified) | GGGGGSGGGGGSGIESVKI | 420 |
| AA36.3 | Neuroligin (linker 14aa) | GGGGGSGGGGSGGHSTTRV | 421 |
| AA36.2 | Neuroligin (linker 12aa) | GGGGGSGGGGSGLPHSTTRV | 422 |
| AA22.2 | DNAM-1 (linker 12 aa) | GGGGGSGGGGSGSRRPKTRV | 423 |
| 1859 | HPV E6 #33 (Cys->Ser) | GRWAGRSAASWRSRRRETAL | 424 |
| AA80.1 | HPV E6 #35 (cysteine-free) | GRWTGRAMSAWKPTRRETEV | 425 |
| AA80 | HPV-E6 #35 | GRWTGRCMSCWKPTRRETEV | 426 |
| 1858 | HPV E6 #58 (mod Cys->Ser) | GRWTGRSAVSWRPRRRQTQV | 427 |
| 1857 | HPV E6 #35 (mod Cys->Ser) | GRWTGRSMSSWKPTRRETEV | 428 |
| AA67.1 | HPV E6 #57 (cysteine-free) | HAMNAAPRAMENAPALRTSH | 429 |
| AA258 | noradrenaline transporter | HHLVAQRDIRQFQLQHWLAI | 430 |
| AA02.1 | Clasp-2 | ISGTPTSTMVHGMTSSSSVV | 431 |
| AA26 | Galectin3 | ISKLGISGDIDLTSASYTMI | 432 |
| AA226 | claudin 7 | KAGYRAPRSYPKSNSSKEYV | 433 |
| AA327 | PAR-2 | KHSRKSSSYSSSSTTVKTSY | 434 |
| 1820 | TRPM7 | KKKQPGNSTKESESTNSVRLML | 435 |
| AA40 | DOCK2 | LASKSAEEGKQIPDSLSTDL | 436 |
| AA250 | Serotonin receptor 3a | LAVLAYSITLVMLWSIWQYA | 437 |
| AA106 | Kir2.1 (inwardly rect. K+ channel) | LHNQASVPLEPRPLRRESEI | 438 |
| AA34.2 | NMDA | LNSCSNRRVYKKMPSIESDV | 439 |
| AA345 | NMDA R2A | LNSSSNRRVYKKMPSIESDV | 440 |
| AA05.2 | CD4 (modified) C->S | LSEKKTSQSPHRFQKTSSPI | 441 |
| 1860 | HPV E6 #52 (Cys->Ser) | GRWTGRSSESWRPRPVTQV | 442 |
| 1861 | HPV E6 #45 (Cys->Ser) | NTSSDQARQERLRRRRETQV | 443 |
| AA227 | claudin 2 | PGQPPKVKSEFNSYSLTGYV | 444 |
| AA140 | KIAA 1481 | PIPAGGCTFSGIFPTLTSPL | 445 |
| AA217 | catenin-delta 2 | YSELNYETSHYPASPDSWV | 446 |

TABLE 11-continued

| AVC ID | Peptide | Sequence | Seq. ID No. |
|---|---|---|---|
| AA244 | alpha-2B Adrenergic receptor | QDFRRAFRRILARPWTQTAW | 447 |
| AA56 | TAX | QISPGGLEPPSEKHFRETEV | 448 |
| AA240 | Dopamine transporter | RELVDRGEVRQFTLRHWLKV | 449 |
| AA207L | Nedasin (s-form) | RNIEEVYVGGKQVVPFSSSV | 450 |
| AA095 | GluR5-2 (rat) | SFTSILTCHQRRTQRKETVA | 451 |
| AA70.1 | HPV E6 #18 | SGGNRARQERLQRRRETQV | 452 |
| AA253 | Clasp-3 | SLIGPVQKEYQRELGKLSSP | 453 |
| AA214L | ErbB-4 receptor | SLKPGTVLPPPPYRHRNTVV | 454 |
| AA06 | CD6 | SPQPDSTDNDDYDDISAA | 455 |
| AA23.3 | Fas Ligand | SSKSKSSEESQTFFGLYKL | 456 |
| AA228 | Nectin 2 | SPDSSYQGKGFVMSRAMYV | 457 |
| AA117 | presenilin-2 | STDNLVRPFMDTLASHQLYI | 458 |
| AA223 | claudin 1 | SYPTPRPYPKPAPSSGKDYV | 459 |
| AA36 | Neuroligin | TFAAGFNSTGLPHSTTRV | 460 |
| AA200L | HER2 receptor | TFKGTPTAENPEYLGLDVPV | 461 |
| AA69.1 | HPV E6 #16 (Modified) | TGRGMSGGRSSRTRRETQL | 462 |
| AA66.1 | HPV E6 #66 (cysteine-free) | TGSALQAWRHTSRQATESTV | 463 |
| AA180 | NMDA Glutamate R2C (cysteine-free) | TQGFPGPATWRRISSLESEV | 464 |
| AA22 | DNAM-1 | TREDIYVNYPTFSRRPKTRV | 465 |
| AA33 | KV1.3 | TTNNNPNSAVNIKKIFTDV | 466 |
| AA114 | GLUR7 (metabotropic glutamate recept | VDPNSPAAKKKYVSYNNLVI | 467 |
| AA82 | AdenoE4 typ9 | VGTLLLERVIFPSVKIATLV | 468 |
| AA77 | HPV-E6 #63 | VHKVRNKFKAKCSLCRLYII | 469 |
| 1862 | HPV E6 #82 | TGQSANSRKPPRQRSETQV | 470 |
| AA348 | TATNMDA2B9 | YGRKKRRQRRRKLSSIESDV | 471 |
| 1777 | Tat-M-Protein-SARS | YGRKKRRQRRRNDNIALLVQ | 472 |
| AA25 | FceRlb | YSATYSELEDPGEMSPPIDL | 473 |

PL sequences binding MAGI3 d2

| AVC ID | Peptide | Sequence | Seq. ID No. |
|---|---|---|---|
| AA115 | presenilin-1 | ATDYLVQPFMDQLAFHQFYI | 474 |
| AA75.1 | HPV E6 58 (modified) | AVGGRPARGGRLQGRRQTQV | 475 |
| AA245 | alpha-2C Adrenergic receptor | DFRPSFKHILFRRARRGFRQ | 476 |
| AA59 | PTEN | DSDPENEPFDEDQHTQITKV | 477 |
| AA233L | serotonin receptor 5HT-2B | DTLLLTENEGDKTEEQVSYV | 478 |
| AA178L | PDZ-binding kinase (PBK) | EDPKDRPSAAHIVEALETDV | 479 |

TABLE 11-continued

| | | | |
|---|---|---|---|
| AA210L | APC-adenomatous polyposis coli | ESSGTQSPKRHSGSYLVTSV | 480 |
| AA36.3 | Neuroligin (linker 14aa) | GGGGGSGGGGSGGGHSTTRV | 481 |
| AA36.2 | Neuroligin (linker 12aa) | GGGGGSGGGGSGLPHSTTRV | 482 |
| AA80.1 | HPV E6 #35 (cysteine-free) | GRWTGRAMSAWKPTRRETEV | 483 |
| AA80 | HPV-E6 #35 | GRWTGRCMSCWKPTRRETEV | 484 |
| AA243 | apha-2A Adrenergic receptor | HDFRRAFKKILARGDRKRIV | 485 |
| AA258 | noradrenaline transporter | HHLVAQRDIRQFQLQHWLAI | 486 |
| AA216 | NMDA R2C | HPTDITGLPNLSDPSVSTVV | 487 |
| AA182L | ephrin B2 | ILNSIQVMRAQMNQIQSVEV | 488 |
| AA02.1 | Clasp-2 | ISGTPTSTMVHGMTSSSSVV | 489 |
| AA152L | ActRIIA | IVTVVTMVTNVDFPPKESSL | 490 |
| AA226 | claudin 7 | KAGYRAPRSYPKSNSSKEYV | 491 |
| AA327 | PAR-2 | KHSRKSSSYSSSSTTVKTSY | 492 |
| 1820 | TRPM7 | KQPGNSTKESESTNSVRLML | 493 |
| AA40 | DOCK2 | LASKSAEEGKQIPDSLSTDL | 494 |
| AA250 | Serotonin receptor 3a | LAVLAYSITLVMLWSIWQYA | 495 |
| AA34.2 | NMDA | LNSCSNRRVYKKMPSIESDV | 496 |
| AA227 | claudin 2 | PGQPPKVKSEFNSYSLTGYV | 497 |
| | claudin 2 | PGQPPKVKSEFNSYSLTGYV | 497 |
| | KIAA 1481 | PIPAGGCTFSGIFPTLTSPL | 498 |
| | RA-GEF (ras/rap 1A-assoc.-GEF) | PYQSQGFSTEEDEDEQVSAV | 499 |
| | alpha-2B Adrenergic receptor | QDFRRAFRRILARPWTQTAW | 500 |
| | TAX | QISPGGLEPPSEKHFRETEV | 501 |
| | Dopamine transporter | RELVDRGEVRQFTLRHWLKV | 502 |
| | BA1-1 (brain-sp angiogenesis inhib1 | RSGATIPLVGQDIIDLQTEV | 503 |
| | GluR5-2 (rat) | SFTSILTCHQRRTQRKETVA | 504 |
| | ErbB-4 receptor | SLKPGTVLPPPPYRHRNTVV | 505 |
| | CD6 | SPQPDSTDNDDYDDISAA | 506 |
| | Fas Ligand | SSKSKSSEESQTFFGLYKL | 507 |
| | CXCR3 | SSSRRDSSWSETSEASYSGL | 508 |
| | claudin 1 | SYPTPRPYPKPAPSSGKDYV | 509 |
| | Neuroligin | TFAAGFNSTGLPHSTTRV | 510 |
| | HPV E6 #66 (cysteine-free) | TGSALQAWRHTSRQATESTV | 511 |
| | NMDA Glutamate R2C (cys-free) | TQGFPGPATWRRISSLESEV | 512 |
| | DNAM-1 | TREDIYVNYPTFSRRPKTRV | 513 |

TABLE 11-continued

| | | | |
|---|---|---|---|
| | KV1.3 | TTNNNPNSAVNIKKIFTDV | 514 |
| | GLUR7 (metabotropic glutamateR) | VDPNSPAAKKKYVSYNNLVI | 515 |
| | AdenoE4 typ9 | VGTLLLERVIFPSVKIATLV | 516 |
| | HPV-E6 #63 | VHKVRNKFKAKCSLCRLYII | 517 |
| | 1854 | YGRKKRRQRRRARGRRETWV | 518 |
| | TATNMDA2B9 | YGRKKRRQRRRKLSSIESDV | 519 |
| | Tat-M-Protein-SARS | YGRKKRRQRRRNDNIALLVQ | 520 |
| | Tat-E-protein-SARS | YGRKKRRQRRRSEGVPDLLV | 521 |

PL sequences binding NeDLG d1

| AVC ID | Peptide | Sequence | Seq. ID No. |
|---|---|---|---|
| AA72.1 | HPV E6 33 (modified) | AAGGRSARGGRLQGRRETAL | 522 |
| AA206L | CITRON protein | AGAVRTPLSQVNKVWDQSSV | 523 |
| AA29.3 | IL-8RA | ARHRVTSYTSSSVNVSSNL | 524 |
| AA75.1 | HPV E6 58 (modified) | AVGGRPARGGRLQGRRQTQV | 525 |
| AA245 | alpha-2C Adrenergic receptor | DFRPSFKHILFRRARRGFRQ | 526 |
| AA28.1 | CDW125 (modified) | EVIGYIEKPGVETLEDSVF | 527 |
| AA220 | claudin 10 | GGEDFKTTNPSKQFDKNAYV | 528 |
| AA80.1 | HPV E6 #35 (cysteine-free) | GRWTGRAMSAWKPTRRETEV | 529 |
| AA80 | HPV-E6 #35 | GRWTGRCMSCWKPTRRETEV | 530 |
| AA258 | noradrenaline transporter | HHLVAQRDIRQFQLQHWLAI | 531 |
| AA70 | HPV-E6 #18 | HSCCNRARQERLQRRRETQV | 532 |
| AA226 | claudin 7 | KAGYRAPRSYPKSNSSKEYV | 533 |
| AA327 | PAR-2 | KHSRKSSYSSSSTTVKTSY | 534 |
| 1820 | TRPM7 | KKKQPGNSTKESESTNSVRLML | 535 |
| AA229 | claudin 5 | KYSAPRRPTATGDYDKKNYV | 536 |
| AA250 | Serotonin receptor 3a | LAVLAYSITLVMLWSIWQYA | 537 |
| AA311 | Beta-1 catenin | LMDGLPPGDSNQLAWFDTDL | 538 |
| AA34.2 | NMDA | LNSCSNRRVYKKMPSIESDV | 539 |
| AA227 | claudin 2 | PGQPPKVKSEFNSYSLTGYV | 540 |
| AA140 | KIAA 1481 | PIPAGGCTFSGIFPTLTSPL | 541 |
| AA217 | catenin-delta 2 | PYSELNYETSHYPASPDSWV | 542 |
| AA244 | alpha-2B Adrenergic receptor | QDFRRAFRRILARPWTQTAW | 543 |
| AA240 | Dopamine transporter | RELVDRGEVRQFTLRHWLKV | 544 |
| AA240 | Dopamine transporter | RELVDRGEVRQFTLRHWLKV | 545 |
| AA253 | Clasp-3 | SLIGPVQKEYQRELGKLSSP | 546 |
| AA23.3 | Fas Ligand | SSKSKSSEESQTFFGLYKL | 547 |

TABLE 11-continued

| AVC ID | Peptide | Sequence | Seq. ID No. |
|---|---|---|---|
| AA228 | Nectin 2 | SSPDSSYQGKGFVMSRAMYV | 548 |
| 1759 | EGFR | TAENAEYLRVAPQSSEFIGA | 549 |
| AA66.1 | HPV E6 #66 (cysteine-free) | TGSALQAWRHTSRQATESTV | 550 |
| AA180 | NMDA GlutamateR2C (cys-free) | TQGFPGPATWRRISSLESEV | 551 |
| AA33 | KV1.3 | TTNNNPNSAVNIKKIFTDV | 552 |
| AA114 | GLUR7 (metabotropic glutamateR) | VDPNSPAAKKKYVSYNNLVI | 553 |
| AA251 | v-AKT1 | VDSERRPHFPQFSYSASGTA | 554 |
| AA82 | AdenoE4 typ9 | VGTLLLERVIFPSVKIATLV | 555 |
| AA77 | HPV-E6 #63 | VHKVRNKFKAKCSLCRLYII | 556 |
| 1777 | Tat-M-Protein-SARS | YGRKKRRQRRRNDNIALLVQ | 557 |

PL sequences binding NeDLG d2

| AVC ID | Peptide | Sequence | Seq. ID No. |
|---|---|---|---|
| AA72.1 | HPV E6 33 (modified) | AAGGRSARGGRLQGRRETAL | 558 |
| AA206L | CITRON protein | AGAVRTPLSQVNKVWDQSSV | 559 |
| AA115 | presenilin-1 | ATDYLVQPFMDQLAFHQFYI | 560 |
| AA75.1 | HPV E6 58 (modified) | AVGGRPARGGRLQGRRQTQV | 561 |
| AA245 | alpha-2C Adrenergic receptor | DFRPSFKHILFRRARRGFRQ | 562 |
| AA178L | PDZ-binding kinase (PBK) | EDPKDRPSAAHIVEALETDV | 563 |
| AA218 | CSPG4 (chondroitinSO4 proteoglyc4) | ELLQFCRTPNPALKNGQYWV | 564 |
| AA210L | APC-adenomatous polyposis coli | ESSGTQSPKRHSGSYLVTSV | 565 |
| AA346 | NMDA R2B | FNGSSNGHVYEKLSSIESDV | 566 |
| AA347 | NMDA R2D | GGDLGTRRGSAHFSSLESEV | 567 |
| AA80.1 | HPV E6 #35 (cysteine-free) | GRWTGRAMSAWKPTRRETEV | 568 |
| AA80 | HPV-E6 #35 | GRWTGRCMSCWKPTRRETEV | 569 |
| AA258 | noradrenaline transporter | HHLVAQRDIRQFQLQHWLAI | 570 |
| AA70 | HPV-E6 #18 | HSCCNRARQERLQRRRETQV | 571 |
| AA182L | ephrin B2 | ILNSIQVMRAQMNQIQSVEV | 572 |
| AA226 | claudin 7 | KAGYRAPRSYPKSNSSKEYV | 573 |
| AA327 | PAR-2 | KHSRKSSYSSSSTTVKTSY | 574 |
| 1820 | TRPM7 | KKKQPGNSTKESESTNSVRLML | 575 |
| AA229 | claudin 5 | KYSAPRRPTATGDYDKKNYV | 576 |
| AA250 | Serotonin receptor 3a | LAVLAYSITLVMLWSIWQYA | 577 |
| AA225 | claudin 9 | LGYSIPSRSGASGLDKRDYV | 578 |
| AA311 | Beta-1 catenin | LMDGLPPGDSNQLAWFDTDL | 579 |

TABLE 11-continued

| AVC ID | Peptide | Sequence | Seq. ID No. |
|---|---|---|---|
| AA34.2 | NMDA | LNSCSNRRVYKKMPSIESDV | 580 |
| AA345 | NMDA R2A | LNSSSNRRVYKKMPSIESDV | 581 |
| AA227 | claudin 2 | PGQPPKVKSEFNSYSLTGYV | 582 |
| AA140 | KIAA 1481 | PIPAGGCTFSGIFPTLTSPL | 583 |
| AA217 | catenin-delta 2 | PYSELNYETSHYPASPDSWV | 584 |
| AA244 | alpha-2B Adrenergic receptor | QDFRRAFRRILARPWTQTAW | 585 |
| AA56 | TAX | QISPGGLEPPSEKHFRETEV | 586 |
| AA240 | Dopamine transporter | RELVDRGEVRQFTLRHWLKV | 587 |
| AA240 | Dopamine transporter | RELVDRGEVRQFTLRHWLKV | 588 |
| AA207L | Nedasin (s-form) | RNIEEVYVGGKQVVPFSSSV | 589 |
| AA095 | GluR5-2 (rat) | SFTSILTCHQRRTQRKETVA | 590 |
| AA214L | ErbB-4 receptor | SLKPGTVLPPPPYRHRNTVV | 591 |
| AA06 | CD6 | SPQPDSTDNDDYDDISAA | 592 |
| AA23.3 | Fas Ligand | SSKSKSSEESQTFFGLYKL | 593 |
| AA228 | Nectin 2 | SSPDSSYQGKGFVMSRAMYV | 594 |
| 1759 | EGFR | TAENAEYLRVAPQSSEFIGA | 595 |
| AA200L | HER2 receptor | TFKGTPTAENPEYLGLDVPV | 596 |
| AA66.1 | HPV E6 #66 (cysteine-free) | TGSALQAWRHTSRQATESTV | 597 |
| AA180 | NMDA GlutamateR2C (cysteine-free) | TQGFPGPATWRRISSLESEV | 598 |
| AA22 | DNAM-1 | TREDIYVNYPTFSRRPKTRV | 599 |
| AA33 | KV1.3 | TTNNNPNSAVNIKKIFTDV | 600 |
| AA114 | GLUR7 (metabotropic glutamateR) | VDPNSPAAKKKYVSYNNLVI | 601 |
| AA82 | AdenoE4 typ9 | VGTLLLERVIFPSVKIATLV | 602 |
| AA77 | HPV-E6 #63 | VHKVRNKFKAKCSLCRLYII | 603 |
| AA348 | TATNMDA2B9 | YGRKKRRQRRRKLSSIESDV | 604 |
| 1777 | Tat-M-Protein-SARS | YGRKKRRQRRRNDNIALLVQ | 605 |
| 1776 | Tat-E-protein-SARS | YGRKKRRQRRRSEGVPDLLV | 606 |
| AA25 | FceR1b | YSATYSELEDPGEMSPPIDL | 607 |

PL sequences binding Outer Membrane Protein

| AVC ID | Peptide | Sequence | Seq. ID No. |
|---|---|---|---|
| AA72.1 | HPV E6 33 (modified) | AAGGRSARGGRLQGRRETAL | 608 |
| AA206L | CITRON protein | AGAVRTPLSQVNKVWDQSSV | 609 |
| AA75.1 | HPV E6 58 (modified) | AVGGRPARGGRLQGRRQTQV | 610 |
| AA245 | alpha-2C Adrenergic receptor | DFRPSFKHILFRRARRGFRQ | 611 |
| AA222 | claudin 18 | DGGARTEDEVQSYPSKHDYV | 612 |
| AA218 | CSPG4 (chondroitinSO4-proteoglyc4) | ELLQFCRTPNPALKNGQYWV | 613 |

TABLE 11-continued

| | | | |
|---|---|---|---|
| AA210L | APC-adenomatous polyposis coli | ESSGTQSPKRHSGSYLVTSV | 614 |
| AA346 | NMDA R2B | FNGSSNGHVYEKLSSIESDV | 615 |
| AA347 | NMDA R2D | GGDLGTRRGSAHFSSLESEV | 616 |
| AA220 | claudin 10 | GGEDFKTTNPSKQFDKNAYV | 617 |
| AA80.1 | HPV E6 #35 (cysteine-free) | GRWTGRAMSAWKPTRRETEV | 618 |
| AA258 | noradrenaline transporter | HHLVAQRDIRQFQLQHWLAI | 619 |
| AA70 | HPV-E6 #18 | HSCCNRARQERLQRRRETQV | 620 |
| AA02.1 | Clasp-2 | ISGTPTSTMVHGMTSSSSVV | 621 |
| AA226 | claudin 7 | KAGYRAPRSYPKSNSSKEYV | 622 |
| AA58 | PAG | KENDYESISDLQQGRDITRL | 623 |
| AA327 | PAR-2 | KHSRKSSSYSSSSTTVKTSY | 624 |
| 1820 | TRPM7 | KKKKQPGNSTKESESTNSVRLML | 625 |
| AA229 | claudin 5 | KYSAPRRPTATGDYDKKNYV | 626 |
| AA250 | Serotonin receptor 3a | LAVLAYSITLVMLWSIWQYA | 627 |
| AA225 | claudin 9 | LGYSIPSRSGASGLDKRDYV | 628 |
| AA106 | Kir2.1 (inwardly rect. K+ channel) | LHNQASVPLEPRPLRRESEI | 629 |
| AA34.2 | NMDA | LNSCSNRRVYKKMPSIESDV | 630 |
| AA345 | NMDA R2A | LNSSSNRRVYKKMPSIESDV | 631 |
| AA227 | claudin 2 | PGQPPKVKSEFNSYSLTGYV | 632 |
| AA140 | KIAA 1481 | PIPAGGCTFSGIFPTLTSPL | 633 |
| AA217 | catenin-delta 2 | PYSELNYETSHYPASPDSWV | 634 |
| AA07 | CD34 | ATSRNGHSARQHVVADTEL | 635 |
| AA244 | alpha-2B Adrenergic receptor | DFRRAFRRILARPWTQTAW | 636 |
| AA56 | TAX | ISPGGLEPPSEKHFRETEV | 637 |
| AA112 | GluR delta-2 | PTPTLGLNLGNDPDRGTSI | 638 |
| AA240 | Dopamine transporter | ELVDRGEVRQFTLRHWLKV | 639 |
| AA240 | Dopamine transporter | ELVDRGEVRQFTLRHWLKV | 640 |
| AA207L | Nedasin (s-form) | NIEEVYVGGKQVVPFSSSV | 641 |
| AA181 | BAI-1 (brain-sp angiogenesis inhibitor 1) | SGATIPLVGQDIIDLQTEV | 642 |
| AA095 | GluR5-2 (rat) | FTSILTCHQRRTQRKETVA | 643 |
| AA70.1 | HPV E6 #18 | SGGNRARQERLQRRRETQV | 644 |
| AA06 | CD6 | SPQPDSTDNDDYDDISAA | 645 |
| AA23.3 | Fas Ligand | SSKSKSSEESQTFFGLYKL | 646 |
| AA228 | Nectin 2 | SPDSSYQGKGFVMSRAMYV | 647 |
| AA223 | claudin 1 | YPTPRPYPKPAPSSGKDYV | 648 |
| AA36 | Neuroligin | TFAAGFNSTGLPHSTTRV | 649 |

TABLE 11-continued

| | | | |
|---|---|---|---|
| AA200L | HER2 receptor | FKGTPTAENPEYLGLDVPV | 650 |
| AA69.1 | HPV E6 #16 (Modified) | TGRGMSGGRSSRTRRETQL | 651 |
| AA66.1 | HPV E6 #66 (cysteine-free) | GSALQAWRHTSRQATESTV | 652 |
| AA180 | NMDA GlutamateR2C (cys-free) | QGFPGPATWRRISSLESEV | 653 |
| AA22 | DNAM-1 | REDIYVNYPTFSRRPKTRV | 654 |
| AA33 | KV1.3 | TTNNNPNSAVNIKKIFTDV | 655 |
| AA114 | GLUR7 (metabotropic glutamate recepto | DPNSPAAKKKYVSYNNLVI | 656 |
| AA82 | AdenoE4 typ9 | GTLLLERVIFPSVKIATLV | 657 |
| AA125 | zona occludens 3 (ZO-3) | HDAESSDEDGYDWGPATDL | 658 |
| AA77 | HPV-E6 #63 | HKVRNKFKAKCSLCRLYII | 659 |
| AA123 | a-actinin 2 | PGALDYAAFSSALYGESDL | 660 |
| AA348 | TATNMDA2B9 | GRKKRRQRRRKLSSIESDV | 661 |
| 1777 | Tat-M-Protein-SARS | GRKKRRQRRRNDNIALLVQ | 662 |
| 1776 | Tat-E-protein-SARS | GRKKRRQRRRSEGVPDLLV | 663 |

PL sequences binding PICK1 d1

| AVC ID | Peptide | Sequence | Seq. ID No. |
|---|---|---|---|
| 1927 | X = L-phenyl glycine | YGRKKRRQRRRKLSSIESDX | 664 |
| AA121 | CD68 | ALVLIAFCIIRRRPSAYQAL | 665 |
| AA115 | presenilin-1 | ATDYLVQPFMDQLAFHQFYI | 666 |
| AA245 | alpha-2C Adrenergic receptor | DFRPSFKHILFRRARRGFRQ | 667 |
| AA222 | claudin 18 | DGGARTEDEVQSYPSKHDYV | 668 |
| AA218 | CSPG4(chondroitinSO4-proteoglyc4 | ELLQFCRTPNPALKNGQYWV | 669 |
| 1761 | FGF Receptor3 IIIc isoform 1 | FHSKTAGANTTDKELEVLSL | 670 |
| AA80.1 | HPV E6 #35 (cysteine-free) | GRWTGRAMSAWKPTRRETEV | 671 |
| AA243 | alpha-2A Adrenergic receptor | HDFRRAFKKILARGDRKRIV | 672 |
| AA258 | noradrenaline transporter | HHLVAQRDIRQFQLQHWLAI | 673 |
| AA70 | HPV-E6 #18 | HSCCNRARQERLQRRRETQV | 674 |
| AA182L | ephrin B2 | ILNSIQVMRAQMNQIQSVEV | 675 |
| AA226 | claudin 7 | KAGYRAPRSYPKSNSSKEYV | 676 |
| AA327 | PAR-2 | KHSRKSSSYSSSSTTVKTSY | 677 |
| AA118 | MINT-1 | KTMPAAMYRLLTAQEQPVYI | 678 |
| AA229 | claudin 5 | KYSAPRRPTATGDYDKKNYV | 679 |
| AA250 | Serotonin receptor 3a | LAVLAYSITLVMLWSIWQYA | 680 |
| AA05.2 | CD4 (modified) C->S | LSEKKTSQSPHRFQKTSSPI | 681 |

TABLE 11-continued

| AA227 | claudin 2 | PGQPPKVKSEFNSYSLTGYV | 682 |
| AA140 | KIAA 1481 | PIPAGGCTFSGIFPTLTSPL | 683 |
| AA217 | catenin-delta 2 | PYSELNYETSHYPASPDSWV | 684 |
| AA244 | alpha-2B Adrenergic receptor | QDFRRAFRRILARPWTQTAW | 685 |
| AA240 | Dopamine transporter | RELVDRGEVRQFTLRHWLKV | 686 |
| AA06 | CD6 | SPQPDSTDNDDYDDISAA | 687 |
| AA23.3 | Fas Ligand | SSKSKSSEESQTFFGLYKL | 688 |
| AA228 | Nectin 2 | SSPDSSYQGKGFVMSRAMYV | 689 |
| AA223 | claudin 1 | SYPTPRPYPKPAPSSGKDYV | 690 |
| AA33 | KV1.3 | TTNNNPNSAVNIKKIFTDV | 691 |
| AA114 | GLUR7 (metabotropic glutamateR) | VDPNSPAAKKKYVSYNNLVI | 692 |
| AA77 | HPV-E6 #63 | VHKVRNKFKAKCSLCRLYII | 693 |
| 1940 | Tat-CLCA-3 (murine) | YGRKKRRQRRREMQVTLGLH | 694 |
| 1764 | Tat-HER2 | YGRKKRRQRRREYLGLDVPV | 695 |
| 1947 | Tat-hCLCA1 | YGRKKRRQRRRIGELQLSIA | 696 |
| 1922 | X = L-alpha-aminobutyric acid | YGRKKRRQRRRKLSSIESDX | 697 |

PL sequences binding PSD95 d1

| AVC ID | Peptide | Sequence | Seq. ID No. |
| --- | --- | --- | --- |
| AA72.1 | HPV E6 33 (modified) | AAGGRSARGGRLQGRRETAL | 698 |
| AA75.1 | HPV E6 58 (modified) | AVGGRPARGGRLQGRRQTQV | 699 |
| AA245 | alpha-2C Adrenergic receptor | DFRPSFKHILFRRARRGFRQ | 700 |
| AA222 | claudin 18 | DGGARTEDEVQSYPSKHDYV | 701 |
| AA218 | CSPG4 (chondroitinSO4-proteoglyc | ELLQFCRTPNPALKNGQYWV | 702 |
| AA346 | NMDA R2B | FNGSSNGHVYEKLSSIESDV | 703 |
| AA347 | NMDA R2D | GGDLGTRRGSAHFSSLESEV | 704 |
| AA220 | claudin 10 | GGEDFKTTNPSKQFDKNAYV | 705 |
| 1859 | HPV E6 #33 (Cys->Ser) | GRWAGRSAASWRSRRRETAL | 706 |
| AA80.1 | HPV E6 #35 (cysteine-free) | GRWTGRAMSAWKPTRRETEV | 707 |
| AA258 | noradrenaline transporter | HHLVAQRDIRQFQLQHWLAI | 708 |
| AA226 | claudin 7 | KAGYRAPRSYPKSNSSKEYV | 709 |
| AA327 | PAR-2 | KHSRKSSSYSSSSTTVKTSY | 710 |
| 1820 | TRPM7 | KKKQPGNSTKESESTNSVRLML | 711 |
| AA229 | claudin 5 | KYSAPRRPTATGDYDKKNYV | 712 |
| AA250 | Serotonin receptor 3a | LAVLAYSITLVMLWSIWQYA | 713 |
| AA225 | claudin 9 | LGYSIPSRSGASGLDKRDYV | 714 |

TABLE 11-continued

| | | | |
|---|---|---|---|
| A34.2 | NMDA | LNSCSNRRVYKKMPSIESDV | 715 |
| AA345 | NMDA R2A | LNSSSNRRVYKKMPSIESDV | 716 |
| AA227 | claudin 2 | PGQPPKVKSEFNSYSLTGYV | 717 |
| AA140 | KIAA 1481 | PIPAGGCTFSGIFPTLTSPL | 718 |
| AA217 | catenin-delta 2 | PYSELNYETSHYPASPDSWV | 719 |
| AA244 | alpha-2B Adrenergic receptor | QDFRRAFRRILARPWTQTAW | 720 |
| AA56 | TAX | QISPGGLEPPSEKHFRETEV | 721 |
| AA240 | Dopamine transporter | RELVDRGEVRQFTLRHWLKV | 722 |
| AA207L | Nedasin (s-form) | RNIEEVYVGGKQVVPFSSSV | 723 |
| AA095 | GluR5-2 (rat) | SFTSILTCHQRRTQRKETVA | 724 |
| AA23.3 | Fas Ligand | SSKSKSSEESQTFFGLYKL | 725 |
| AA228 | Nectin 2 | SSPDSSYQGKGFVMSRANYV | 726 |
| AA223 | claudin 1 | SYPTPRPYPKPAPSSGKDYV | 727 |
| AA66.1 | HPV E6 #66 (cysteine-free) | TGSALQAWRHTSRQATESTV | 728 |
| AA180 | NMDA GlutamateR2C (cys-free) | TQGFPGPATWRRISSLESEV | 729 |
| AA22 | DNAM-1 | TREDIYVNYPTFSRRPKTRV | 730 |
| AA33 | KV1.3 | TTNNNPNSAVNIKKIFTDV | 731 |
| AA114 | GLUR7 (metabotropic glutamateR) | VDPNSPAAKKKYVSYNNLVI | 732 |
| AA82 | AdenoE4 typ9 | VGTLLLERVIFPSVKIATLV | 733 |
| AA77 | HPV-E6 #63 | VHKVRNKFKAKCSLCRLYII | 734 |
| 1915 | Biotin-Tat-NMDA-optimized | YGRKKRRQRRRALKSIETEV | 735 |
| 1854 | 1854 | YGRKKRRQRRRARGRRETWV | 736 |
| AA353 | bTAT-TAX | YGRKKRRQRRREKHFRETEV | 737 |
| 1775 | Tat-N-protein-SARS | YGRKKRRQRRRGASADSTQA | 738 |
| 1853 | 1853 | YGRKKRRQRRRGMTSSSSVV | 739 |
| 1914 | Biotin-Tat-NMDAR2_short | YGRKKRRQRRRIETEV | 740 |
| AA348 | TATNMDA2B9 | YGRKKRRQRRRKLSSIESDV | 741 |
| AA351 | TAT-NR2B9 | YGRKKRRQRRRKLSSIESDV | 742 |
| 1923 | X = 2-amino-4,4,4-trifluorobutyric acid | YGRKKRRQRRRKLSSIESDX | 743 |
| 1924 | X = L-t-butyl-glycine | YGRKKRRQRRRKLSSIESDX | 744 |
| 1944 | X = norvaline NMDAR2B analogue | YGRKKRRQRRRKLSSIESDX | 745 |
| 1963 | X = 4-amino-Phenylala Tat-NMDAR2B var | YGRKKRRQRRRKLSSIESXV | 746 |
| 1953 | NMDAR2B P-1 Y | YGRKKRRQRRRKLSSIESYV | 747 |
| 1939 | Tat-NMDAR2B S->T P-2 | YGRKKRRQRRRKLSSIETDV | 748 |
| 1945 | X = noraline, S->T P-2 NMDAR2B analog | YGRKKRRQRRRKLSSIETDX | 749 |

TABLE 11-continued

| | | | |
|---|---|---|---|
| 1931 | 1931 | YGRKKRRQRRRKLSSIEYDV | 750 |
| 1777 | Tat-M-Protein-SARS | YGRKKRRQRRRNDNIALLVQ | 751 |
| 1855 | 1855 | YGRKKRRQRRRQDERVETRV | 752 |
| 1918 | TAT-SLO2 | YGRKKRRQRRRQDSREETQL | 753 |
| 1912 | Biotin-Tat-NMDAR2special1 | YGRKKRRQRRRRISSIETDV | 754 |
| 1913 | Biotin-Tat-NMDAR2special2 | YGRKKRRQRRRRISSIQTDV | 755 |
| 1797 | Tat-NMDA 2C9 | YGRKKRRQRRRRISSLESEV | 756 |
| 1911 | Biotin-Tat-NMDAR2C S->T mutant | YGRKKRRQRRRRISSLETEV | 757 |
| 1917 | 1917 | YGRKKRRQRRRRISSLETQV | 758 |
| 1938 | Tat-HPV33E6(cys free) | YGRKKRRQRRRRSRRRETAL | 759 |
| 1916 | Biotin-Tat-CRIPT | YGRKKRRQRRRTKNYKQTSV | 760 |
| AA25 | FceR1b | YSATYSELEDPGEMSPPIDL | 761 |

PL sequences binding PSD95 d1,2

| AVC ID | Peptide | Sequence | Seq. ID No. |
|---|---|---|---|
| AA72.1 | HPV E6 33 (modified) | AAGGRSARGGRLQGRRETAL | 762 |
| AA29.3 | IL-8RA | ARHRVTSYTSSSVNVSSNL | 763 |
| AA75.1 | HPV E6 58 (modified) | AVGGRPARGGRLQGRRQTQV | 764 |
| AA245 | alpha-2C Adrenergic receptor | DFRPSFKHILFRRARRGFRQ | 765 |
| AA178L | PDZ-binding kinase (PBK) | EDPKDRPSAAHIVEALETDV | 766 |
| AA218 | CSPG4 (chondroitinSO4-proteoglyc4) | ELLQFCRTPNPALKNGQYWV | 767 |
| AA210L | APC-adenomatous polyposis coli | ESSGTQSPKRHSGSYLVTSV | 768 |
| AA346 | NMDA R2B | FNGSSNGHVYEKLSSIESDV | 769 |
| AA347 | NMDA R2D | GGDLGTRRGSAHFSSLESEV | 770 |
| AA220 | claudin 10 | GGEDFKTTNPSKQFDKNAYV | 771 |
| AA108.1 | GLU2 (glutamateR2-modified) | GGGGGSGGGGGSGIESVKI | 772 |
| 1859 | HPV E6 #33 (Cys->Ser) | GRWAGRSAASWRSRRRETAL | 773 |
| AA80.1 | HPV E6 #35 (cysteine-free) | GRWTGRAMSAWKPTRRETEV | 774 |
| 1858 | HPV E6 #58 (mod Cys->Ser) | GRWTGRSAVSWRPRRRQTQV | 775 |
| AA258 | noradrenaline transporter | HHLVAQRDIRQFQLQHWLAI | 776 |
| AA216 | NMDA R2C | HPTDITGLPNLSDPSVSTVV | 777 |
| AA70 | HPV-E6 #18 | HSCCNRARQERLQRRRETQV | 778 |
| AA182L | ephrin B2 | ILNSIQVMRAQMNQIQSVEV | 779 |
| AA02.1 | Clasp-2 | ISGTPTSTMVHGMTSSSSVV | 780 |
| AA226 | claudin 7 | KAGYRAPRSYPKSNSSKEYV | 781 |

TABLE 11-continued

| | | | |
|---|---|---|---|
| AA13P | CD95 phosphorylated | KDITSDSENSNFRNEIQSLV | 782 |
| AA13 | CD95 | KDITSDSENSNFRNEIQSLV | 783 |
| AA327 | PAR-2 | KHSRKSSYSSSSTTVKTSY | 784 |
| 1820 | TRPM7 | KKKQPGNSTKESESTNSVRLML | 785 |
| AA250 | Serotonin receptor 3a | LAVLAYSITLVMLWSIWQYA | 786 |
| AA106 | Kir2.1 (inwardly rect. K+ channel) | LHNQASVPLEPRPLRRESEI | 787 |
| AA34.2 | NMDA | LNSCSNRRVYKKMPSIESDV | 788 |
| AA345 | NMDA R2A | LNSSSNRRVYKKMPSIESDV | 789 |
| 1860 | HPV E6 #52 (Cys->Ser) | MGRWTGRSSESWRPRPVTQV | 790 |
| 1861 | HPV E6 #45 (Cys->Ser) | NTSSDQARQERLRRRRETQV | 791 |
| AA217 | catenin-delta 2 | PYSELNYETSHYPASPDSWV | 793 |
| AA244 | alpha-2B Adrenergic receptor | QDFRRAFRRILARPWTQTAW | 794 |
| AA56 | TAX | QISPGGLEPPSEKHFRETEV | 795 |
| AA240 | Dopamine transporter | RELVDRGEVRQFTLRHWLKV | 796 |
| AA207L | Nedasin (s-form) | RNIEEVYVGGKQVVPFSSSV | 797 |
| AA181 | BAI-1 (brain-sp angiogenesis inhib 1) | RSGATIPLVGQDIIDLQTEV | 798 |
| AA095 | GluR5-2 (rat) | SFTSILTCHQRRTQRKETVA | 799 |
| AA253 | Clasp-3 | SLIGPVQKEYQRELGKLSSP | 800 |
| AA214L | ErbB-4 receptor | SLKPGTVLPPPPYRHRNTVV | 801 |
| AA23.3 | Fas Ligand | SSKSKSSEESQTFFGLYKL | 802 |
| AA223 | claudin 1 | SYPTPRPYPKPAPSSGKDYV | 803 |
| AA36 | Neuroligin | TFAAGFNSTGLPHSTTRV | 804 |
| AA200L | HER2 receptor | TFKGTPTAENPEYLGLDVPV | 805 |
| AA69.1 | HPV E6 #16 (Modified) | TGRGMSGGRSSRTRRETQL | 806 |
| AA66.1 | HPV E6 #66 (cysteine-free) | TGSALQAWRHTSRQATESTV | 807 |
| AA180 | NMDA GlutamateR2C (cys-free) | TQGFPGPATWRRISSLESEV | 808 |
| AA22 | DNAM-1 | TREDIYVNYPTFSRRPKTRV | 809 |
| AA33 | KV1.3 | TTNNNPNSAVNIKKIFTDV | 810 |
| AA114 | GLUR7 (metabotropic glutamateR) | VDPNSPAAKKKYVSYNNLVI | 811 |
| AA82 | AdenoE4typ9 | VGTLLLERVIFPSVKIATLV | 812 |
| AA77 | HPV-E6 #63 | VHKVRNKFKAKCSLCRLYII | 813 |
| 1862 | HPV E6 #82 | WTGQSANSRKPPRQRSETQV | 814 |
| 1775 | Tat-N-protein-SARS | YGRKKRRQRRRGASADSTQA | 815 |
| AA348 | TATNMDA2B9 | YGRKKRRQRRRKLSSIESDV | 816 |
| 1967 | Tat-H1N1 | YGRKKRRQRRRMAGTIRSEV | 817 |
| 1961 | H5N1 AAT73368/50296240 | YGRKKRRQRRRMARTIESEI | 818 |

TABLE 11-continued

| | | | |
|---|---|---|---|
| 1959 | H5N1 AAT73457/50296374 | YGRKKRRQRRRMARTIESEV | 819 |
| 1958 | H5N1 AAF02349/6048830 | YGRKKRRQRRRMERTIEPEV | 820 |
| 1777 | Tat-M-Protein-SARS | YGRKKRRQRRRNDNIALLVQ | 821 |

PL sequences binding PSD95 d2

| AVC ID | Peptide | Sequence | Seq. ID No. |
|---|---|---|---|
| AA72.1 | HPV E6 33 (modified) | AAGGRSARGGRLQGRRETAL | 822 |
| AA75.1 | HPV E6 58 (modified) | AVGGRPARGGRLQGRRQTQV | 823 |
| AA346 | NMDA R2B | FNGSSNGHVYEKLSSIESDV | 824 |
| AA347 | NMDA R2D | GGDLGTRRGSAHFSSLESEV | 825 |
| 1859 | HPV E6 #33 (Cys->Ser) | GRWAGRSAASWRSRRRETAL | 826 |
| AA80.1 | HPV E6 #35 (cysteine-free) | GRWTGRAMSAWKPTRRETEV | 827 |
| 1858 | HPV E6 #58 (mod Cys->Ser) | GRWTGRSAVSWRPRRRQTQV | 828 |
| AA13 | CD95 | KDITSDSENSNFRNEIQSLV | 829 |
| AA327 | PAR-2 | KHSRKSSSYSSSSTTVKTSY | 830 |
| 1820 | TRPM7 | KKKQPGNSTKESESTNSVRLML | 831 |
| AA34.2 | NMDA | LNSCSNRRVYKKMPSIESDV | 832 |
| AA345 | NMDA R2A | LNSSSNRRVYKKMPSIESDV | 833 |
| 1861 | HPV E6 #45 (Cys->Ser) | NTSSDQARQERLRRRRETQV | 834 |
| AA56 | TAX | QISPGGLEPPSEKHFRETEV | 835 |
| AA240 | Dopamine transporter | RELVDRGEVRQFTLRHWLKV | 836 |
| AA181 | BA1-1 (brain-sp angiogen inhib 1) | RSGATIPLVGQDIIDLQTEV | 837 |
| AA06 | CD6 | SPQPDSTDNDDYDDISAA | 838 |
| AA124 | CXCR3 | SSSRRDSSWSETSEASYSGL | 839 |
| AA69.1 | HPV E6 #16 (Modified) | TGRGMSGGRSSRTRRETQL | 840 |
| AA180 | NMDA GlutamateR2C (cys-free) | TQGFPGPATWRRISSLESEV | 841 |
| AA33 | KV1.3 | TTNNNPNSAVNIKKIFTDVI | 842 |
| AA77 | HPV-E6 #63 | VHKVRNKFKAKCSLCRLYII | 843 |
| 1915 | Biotin-Tat-NMDA-optimized | YGRKKRRQRRRALKSIETEV | 844 |
| 1854 | 1854 | YGRKKRRQRRRARGRRETWV | 845 |
| 1767 | Tat-FGFR3 IIIIc isoform | YGRKKRRQRRRDKELEVLSL | 846 |
| AA356 | bTAT-TAXAA | YGRKKRRQRRREKHFREAEA | 847 |
| AA353 | bTAT-TAX | YGRKKRRQRRREKHFRETEV | 848 |
| 1764 | Tat-HER2 | YGRKKRRQRRREYLGLDVPV | 849 |
| 1853 | 1853 | YGRKKRRQRRRGMTSSSSVV | 850 |
| 1914 | Biotin-Tat-NMDAR2_short | YGRKKRRQRRRIETEV | 851 |
| 1930 | 1930 | YGRKKRRQRRRKLSSIESDL | 852 |

TABLE 11-continued

| AVC ID | Peptide | Sequence | Seq. ID No. |
|---|---|---|---|
| AA348 | TATNMDA2B9 | YGRKKRRQRRRKLSSIESDV | 853 |
| AA351 | TAT-NR2B9 | YGRKKRRQRRRKLSSIESDV | 854 |
| 1923 | X = 2-amino-4,4,4-trifluorobutyricacid | YGRKKRRQRRRKLSSIESDX | 855 |
| 1924 | X = L-t-butyl-glycine | YGRKKRRQRRRKLSSIESDX | 856 |
| 1926 | X = 3-fluoro-DL-Valine | YGRKKRRQRRRKLSSIESDX | 857 |
| 1929 | X = 4,4,4-trifluoro-DL-valine | YGRKKRRQRRRKLSSIESDX | 858 |
| 1944 | X = norvaline NMDAR2B analogue | YGRKKRRQRRRKLSSIESDX | 859 |
| 1954 | X = propargyl glycineP0 NMDAR2B | YGRKKRRQRRRKLSSIESDX | 860 |
| 1963 | X = 4-amino-PheTat-NMDAR2B var | YGRKKRRQRRRKLSSIESXV | 861 |
| 1953 | NMDAR2B P-1 Y | YGRKKRRQRRRKLSSIESYV | 862 |
| 1939 | Tat-NMDAR2B S->T P-2 | YGRKKRRQRRRKLSSIETDV | 863 |
| 1945 | X = norvaline, S->T P-2 NMDAR2Ban | YGRKKRRQRRRKLSSIETDX | 864 |
| 1946 | X = L-2NH4-3ureidopro-acidP-2TatNMD | YGRKKRRQRRRKLSSIEXDV | 865 |
| 1931 | 1931 | YGRKKRRQRRRKLSSIEYDV | 866 |
| 1961 | H5N1 AAT73368/50296240 | YGRKKRRQRRRMARTIESEI | 867 |
| 1959 | H5N1 AAT73457/50296374 | YGRKKRRQRRRMARTIESEV | 868 |
| 1958 | H5N1 AAF02349/6048830 | YGRKKRRQRRRMERTIEPEV | 869 |
| 1777 | Tat-M-Protein-SARS | YGRKKRRQRRRNDNIALLVQ | 870 |
| 1855 | 1855 | YGRKKRRQRRRQDERVETRV | 871 |
| 1918 | TAT-SLO2 | YGRKKRRQRRRQDSREETQL | 872 |
| 1912 | Biotin-Tat-NMDAR2-special1 | YGRKKRRQRRRRISSIETDV | 873 |
| 1913 | Biotin-Tat-NMDAR2-special2 | YGRKKRRQRRRRISSIQIDV | 874 |
| 1797 | Tat-NMDA 2C9 | YGRKKRRQRRRRISSLESEV | 875 |
| 1911 | Biotin-Tat-NMDAR2C S->T mut | YGRKKRRQRRRRISSLETEV | 876 |
| 1917 | 1917 | YGRKKRRQRRRRISSLETQV | 877 |
| 1938 | Tat-HPV33E6(cys free) | YGRKKRRQRRRRSRRRETAL | 878 |
| 1916 | Biotin-Tat-CRIPT | YGRKKRRQRRRTKNYKQTSV | 879 |

| PL sequences binding PTN-3 | | | |
|---|---|---|---|
| AVC ID | Peptide | Sequence | Seq. ID No. |
| 1820 | TRPM7 | KKKQPGNSTKESESTNSVRLML | 880 |
| AA311 | Beta-1 catenin | LMDGLPPGDSNQLAWFDTDL | 881 |
| 1763 | Tat-MUC1 | YGRKKRRQRRRAVAATSANL | 882 |
| 1764 | Tat-HER2 | YGRKKRRQRRREYLGLDVPV | 883 |
| 1775 | Tat-N-protein-SARS | YGRKKRRQRRRGASADSTQA | 884 |

TABLE 11-continued

| | | | |
|---|---|---|---|
| 1777 | Tat-M-Protein-SARS | YGRKKRRQRRRNDNIALLVQ | 885 |
| 1776 | Tat-E-protein-SARS | YGRKKRRQRRRSEGVPDLLV | 886 |

PL sequences binding SHANK 1

| AVC ID | Peptide | Sequence | Seq. ID No. |
|---|---|---|---|
| AA72.1 | HPV E6 33 (modified) | AAGGRSARGGRLQGRRETAL | 887 |
| AA121 | CD68 | ALVLIAFCIIRRRPSAYQAL | 888 |
| AA30 | LPAP | AWDDSARAAGGQGLHVTAL | 889 |
| AA261 | GABA transporter 3 | DAKLKSDGTIAAITEKETHF | 890 |
| AA245 | alpha-2C Adrenergic receptor | DFRPSFKHILFRRARRGFRQ | 891 |
| AA222 | claudin 18 | DGGARTEDEVQSYPSKHDYV | 892 |
| AA59 | PTEN | DSDPENEPFDEDQHTQITKV | 893 |
| AA248 | somatostatin receptor 4 | EALQPEPGRKRIPLTRTTTF | 894 |
| AA218 | CSPG4 (chondroitinSO4-proteo4) | ELLQFCRTPNPALKNGQYWV | 895 |
| AA220 | claudin 10 | GGEDFKTTNPSKQFDKNAYV | 896 |
| AA36.3 | Neuroligin (linker 14aa) | GGGGGSGGGGSGGGHSTTRV | 897 |
| AA36.2 | Neuroligin (linker 12aa) | GGGGGSGGGGSGLPHSTTRV | 898 |
| AA22.2 | DNAM-1 (linker 12 aa) | GGGGGSGGGGSGSRRPKTRV | 899 |
| AA258 | noradrenaline transporter | HHLVAQRDIRQFQLQHWLAI | 900 |
| AA70 | HPV-E6 #18 | HSCCNRARQERLQRRRETQV | 901 |
| AA226 | claudin 7 | KAGYRAPRSYPKSNSSKEYV | 902 |
| AA29.2 | CDw128B | KDSRPSFVGSSSGHTSTTL | 903 |
| AA58 | PAG | KENDYESISDLQQGRDITRL | 904 |
| AA327 | PAR-2 | KHSRKSSSYSSSSTTVKTSY | 905 |
| 1820 | TRPM7 | KKKQPGNSTKESESTNSVRLML | 906 |
| AA148L | CFTCR (CysticF transmemconductancereg) | KPQIAALKEETEEEVQDTRL | 907 |
| AA229 | claudin 5 | KYSAPRRPTATGDYDKKNYV | 908 |
| AA40 | DOCK2 | LASKSAEEGKQIPDSLSTDL | 909 |
| AA250 | Serotonin receptor 3a | LAVLAYSITLVMLWSIWQYA | 910 |
| AA225 | claudin 9 | LGYSIPSRSGASGLDKRDYV | 911 |
| AA311 | Beta-1 catenin | LMDGLPPGDSNQLAWFDTDL | 912 |
| AA113 | SSTR2 (somatostatin recepor 2) | LNETTETQRTLLNGDLQTSI | 913 |
| AA34.2 | NMDA | LNSCSNRRVYKKMPSIESDV | 914 |
| AA329 | VIPS_human | LQFHRGSRAQSFLQTETSVI | 915 |
| AA227 | claudin 2 | PGQPPKVKSEFNSYSLTGYV | 916 |
| AA140 | KIAA 1481 | PIPAGGCTFSGIFPTLTSPL | 917 |
| AA147 | Na+/Pi cotransporter 2 | PPATPSPRLALPAHHNATRL | 918 |

TABLE 11-continued

| AVC ID | Peptide | Sequence | Seq. ID No. |
|---|---|---|---|
| AA45 | BLR-1 | PSWRRSSLSESENATSLTTF | 919 |
| AA217 | catenin-delta 2 | PYSELNYETSHYPASPDSWV | 920 |
| AA244 | alpha-2B Adrenergic receptor | QDFRRAFRRILARPWTQTAW | 921 |
| AA240 | Dopamine transporter | RELVDRGEVRQFTLRHWLKV | 922 |
| 1895 | TAMRA-sticky class I (Val 0) | RRASTSRETWV | 923 |
| AA181 | BA1-1 (brain-sp angiogenesis inhib 1) | RSGATIPLVGQDIIDLQTEV | 924 |
| AA23.3 | Fas Ligand | SSKSKSSEESQTFFGLYKL | 925 |
| AA228 | Nectin 2 | SSPDSSYQGKGFVMSRAMYV | 926 |
| AA124 | CXCR3 | SSSRRDSSWSETSEASYSGL | 927 |
| AA36 | Neuroligin | TFAAGFNSTGLPHSTTRV | 928 |
| AA69.1 | HPV E6 #16 (Modified) | TGRGMSGGRSSRTRRETQL | 929 |
| AA22 | DNAM-1 | TREDIYVNYPTFSRRPKTRV | 930 |
| AA114 | GLUR7 (metabotropic glutamateR) | VDPNSPAAKKKYVSYNNLVI | 931 |
| AA77 | HPV-E6 #63 | VHKVRNKFKAKCSLCRLYII | 932 |
| AA123 | a-actinin 2 | VPGALDYAAFSSALYGESDL | 933 |
| 1767 | Tat-FGFR 3 IIIc isoform | YGRKKRRQRRRDKELEVLSL | 934 |
| 1956 | Tat-COX-2 | YGRKKRRQRRRLLKERSTEL | 935 |
| 1777 | Tat-M-Protein-SARS | YGRKKRRQRRRNDNIALLVQ | 936 |
| 1950 | Tat-TIAM 1 | YGRKKRRQRRRPSRKLNTEI | 937 |
| 1965 | Tat-hGKAP | YGRKKRRQRRRYIPEAQTRL | 938 |

PL sequences binding TIP43 d1

| AVC ID | Peptide | Sequence | Seq. ID No. |
|---|---|---|---|
| AA72.1 | HPV E6 33 (modified) | AAGGRSARGGRLQGRRETAL | 939 |
| 1761 | FGFR3 IIIc isoform 1 | FHSKTAGANTTDKELEVLSL | 940 |
| AA346 | NMDA R2B | FNGSSNGHVYEKLSSIESDV | 941 |
| AA347 | NMDA R2D | GGDLGTRRGSAHFSSLESEV | 942 |
| AA80.1 | HPV E6 #35 (cysteine-free) | GRWTGRAMSAWKPTRRETEV | 943 |
| AA327 | PAR-2 | KHSRKSSSYSSSSTTVKTSY | 944 |
| 1820 | TRPM7 | KKKQPGMSTKESESTNSVRLML | 945 |
| AA40 | DOCK2 | LASKSAEEGKQIPDSLSTDL | 946 |
| AA345 | NMDA R2A | LNSSSNRRVYKKMPSIESDV | 947 |
| AA181 | BA1-1 (brain-sp angiogenesis inhib 1) | RSGATIPLVGQDIIDLQTEV | 948 |
| AA095 | GluR5-2 (rat) | SFTSILTCHQRRTQRKETVA | 949 |
| AA124 | CXCR3 | SSSRRDSSWSETSEASYSGL | 950 |
| AA180 | NMDA GlutamateR2C (cys-free) | TQGFPGPATWRRISSLESEV | 951 |

TABLE 11-continued

| | | | |
|---|---|---|---|
| AA33 | KV1.3 | TTNNNPNSAVNIKKIFTDV | 952 |
| AA77 | HPV-E6 #63 | VHKVRNKFKAKCSLCRLYII | 953 |
| 1764 | Tat-HER2 | YGRKKRRQRRREYLGLDPV | 954 |
| 1775 | Tat-N-protein-SARS | YGRKKRRQRRRGASADSTQA | 955 |
| AA348 | TATNMDA2B9 | YGRKKRRQRRRKLSSIESDV | 956 |
| 1777 | Tat-M-Protein-SARS | YGRKKRRQRRRNDNIALLVQ | 957 |

PL sequences binding Vartul d2

| AVC ID | Peptide | Sequence | Seq. ID No. |
|---|---|---|---|
| AA72.1 | HPV E6 33 (modified) | AAGGRSARGGRLQGRRETAL | 958 |
| AA206L | CITRON protein | AGAVRTPLSQVNKVWDQSSV | 959 |
| AA29.3 | IL-8RA | ARHRVTSYTSSSVNVSSNL | 960 |
| AA115 | presenilin-1 | ATDYLVQPFMDQLAFHQFYI | 961 |
| AA245 | alpha-2C Adrenergic receptor | DFRPSFKHILFRRARRGFRQ | 962 |
| AA218 | CSPG4 (chondroitinSO4-proteoglyc4 | ELLQFCRTPNPALKNGQYWV | 963 |
| AA210L | APC-adenomatous polyposis coli | ESSGTQSPKRHSGSYLVTSV | 964 |
| AA80.1 | HPV E6 #35 (cysteine-free) | GRWTGRAMSAWKPTRRETEV | 965 |
| AA258 | noradrenaline transporter | HHLVAQRDIRQFQLQHWLAI | 966 |
| AA327 | PAR-2 | KHSRKSSSYSSSSTTVKTSY | 967 |
| 1820 | TRPM7 | KKQPGNSTKESESTNSVRLML | 968 |
| AA250 | Serotonin receptor 3a | LAVLAYSITLVMLWSIWQYA | 969 |
| AA34.2 | NMDA | LNSCSNRRVYKKMPSIESDV | 970 |
| AA140 | KIAA 1481 | PIPAGGCTFSGIFPTLTSPL | 971 |
| AA190L | ephrin B1 | PVYIVQEMPPQSPANIYYKV | 972 |
| AA217 | catenin-delta 2 | PYSELNYETSHYPASPDSWV | 973 |
| AA244 | alpha-2B Adrenergic receptor | QDFRRAFRRILARPWTQTAW | 974 |
| AA56 | TAX | QISPGGLEPPSEKHFRETEV | 975 |
| AA240 | Dopamine transporter | RELVDRGEVRQFTLRHWLKV | 976 |
| AA253 | Clasp-3 | SLIGPVQKEYQRELGKLSSP | 977 |
| AA23.3 | Fas Ligand | SSKSKSSEESQTFFGLYKL | 978 |
| AA223 | claudin 1 | SYPTPRPYPKPAPSSGKDYV | 979 |
| AA180 | NMDA Glutamate R 2C (cys-free) | TQGFPGPATWRRISSLESEV | 980 |
| AA33 | KV1.3 | TTNNNPNSAVNIKKIFTDV | 981 |
| AA114 | GLUR7 (metabotropic glutamateR) | VDPNSPAAKKKYVSYNNLVI | 982 |
| AA77 | HPV-E6 #63 | VHKVRNKFKAKCSLCRLYII | 983 |

TABLE 11-continued

| 1775 | Tat-N-protein-SARS | YGRKKRRQRRRGASADSTQA | 984 |
| AA348 | TATNMDA2B9 | YGRKKRRQRRRKLSSIESDV | 985 |
| 1777 | Tat-M-Protein-SARS | YGRKKRRQRRRNDNIALLVQ | 986 |
| AA25 | FceR1b | YSATYSELEDPGEMSPPIDL | 987 |

CITATIONS

1. Fauci, 2005, *Nature* 435 (7041): 423-424.
2. Normile, 2005, *Science* 308 (5726): 1234-1235.
3. Guan, 2002, *PNAS* 99 (13): 8950-8955.
4. Jin, 2004, *Avian Dis.* 48 (4): 870-878.
5. Webster, 2004, *Rev. Sci. Tech.* 23 (2): 453-465.
6. Noah, 2003 *Virology* 307(2):386-395.
7. Chien, *Biochemistry* 43(7): 1950-62.
8. Dauber, *J. Virol.* 78(4):1865-1872.
9. Quinlivan, 2005 *J. Virol.* 79(13):8431-8439.
10. Solorzano, 2005 *J Virol.* 79(12):7535-7543.
11. Stasakova, 2005, *J Gen Virol.* 86(Pt 1): 185-195.
12. Diebold, 2003, *Nature* 424(6946):324-328.
13. Theofilopoulos, 2005, *Ann. Rev. Immunol.* 23: 307-336.
14. Yang, 2005 *J. Biol. Chem.* 280(36): 31530-31536.
15. Uddin, 2002. *J. Biol. Chem.* 277 (17): 14408-14416.
16. Voss, 2005 *J. Biol. Chem.* 280: 17371-17379.
17. DeVries 2004 *J. Biol. Chem.* 279 (44): 45603-45612.
18. Page 2003 *J. Immunol.* 170(11): 5681-5689.
19. Farshori, 2003, *J. Steroid Biochem. Mol. Biol.* 85 (2-5): 337-347.
20. Akca, 2003, *Growth Factors* 21 (1): 31-39.
21. Minami 2003, *J. Biol. Chem.* 278 (9): 6976-6984.
22. Greenspan, 1988 *J. Virol.* 62: 3020-3026.
23. Compans, 1973, *Virology* 51: 56-70.
24. Krug, 1973, *Virology* 56: 334-348.
25. Seo 2004, *Virus Res.* 103(1-2):107-13
26. Solorzano, 2005, *J. Virol.* 79(12): 7535-7543.
27. Quinlivan, 2005 *J. Virol.* 79 (13): 8431-8439.
28. Garcia-Sastre, 1998, *Virology* 252: 324-330.
29. Lipatov, 2005, *J. Gen. Virol.* 86(4): 1121-1130.
30. Usacheva, 2001, *J. Biol. Chem.* 276 (25): 22948-22953.
31. Usacheva, 2003 *J. Immunol.* 171 (6): 2989-2994.
32. Osmanagic-Myers; 2004. Plectin-RACK1, *J. Biol. Chem.* 279(8): 18701-18710.
33. Litjens, 2005, *J. Biol. Chem.* 280 (23): 22270-7.
34. Kubota, 2002, *J. Virology* 76 (24): 12676-12682.
35. Yokota, 2003, *Virology* 306 (1): 135-146.
36. Spackman, 2005, *J. Vet. Diagn. Invest.* 17 (1): 76-80.
37. Lee, *J. Virol. Methods* 119(2): 151-158.
38. Munch, 2001, *Arch. Virol.* 146 (1): 87-97.
39. Xu, 2005, *J. Clin. Microbiol.* 43 (4): 1953-1955.
40. Tumpey, 2005, *J. Clin. Microbiol.* 43 (2): 676-682.
41. Steininger, 2002, *J. Clin. Microbiol.* 40 (6): 2051-2056.
42. Cattoli, 2004, *Avian Pathol.* 33 (4): 432-437.
43. Kaiser, 1999, *J. Clin. Virol.* 14 (3): 191-197.
44. Tucker, 2001. *Philos. Trans. R. Soc. Lond B Biol.Sci.* 356 (1416): 1915-1924.
45. Sharma, 2002, *Arch. Pediatr. Adolesc. Med.* 156(1):41-43.
50. Brown, 1983, NS1. *Virology* 130(1):134-143.
51. Seo, 2000, *Nature Medicine* 8 (9): 950-954.
52. Govorkova, 2005 *J. Virol.* 79 (4): 2191-2198.

What is claimed is:

1. A method for identifying whether a patient is infected with influenza virus type A, comprising:
   determining whether NS1 protein of influenza virus type A is present in a patient sample, presence indicating the patient is infected with influenza virus type A, wherein the determining comprises:
   (a) contacting a patient sample with an agent comprising at least one PDZ polypeptide that specifically binds to influenza virus type A protein NS1; and
   (b) detecting specific binding between the agent and the NS1 protein, specific binding indicating presence of the influenza virus type A.

2. The method of claim 1, wherein the NS1 protein comprises a PDZ ligand motif (PL) that has a motif S/T-X-V/I/L where the S is serine, T is threonine, V is valine, I is isoleucine, L is leucine and X is any amino acid.

3. The method of claim 1, wherein:
   (i) the contacting step comprises contacting the patient sample with first and second agents that specifically bind to different sites of influenza virus type A protein NS1,
   (ii) the first agent or the second agent comprises the at least one PDZ polypeptide,
   (iii) the first agent is immobilized on a support, and
   (iv) the detecting step detects a sandwich in which the first and second agents are specifically bound to the NS1 protein to indicate presence of the virus.

4. The method of claim 3, wherein the first agent comprises one or more PDZ polypeptides and the second agent comprises one or more antibodies.

5. The method of claim 3 wherein the first agent comprises a mixture of one or more PDZ polypeptides and one or more antibodies.

6. The method of claim 1, wherein the at least one PDZ polypeptide is comprises a PL-binding domain of a PDZ protein selected from the group consisting of: Outer Membrane, PSD95 (PDZ # 2), PSD95 (PDZ #1,2,3), DLG1 (PDZ #1), DLG1 (PDZ #1,2), DLG1 (PDZ #2), DLG2 (PDZ #1), DLG2 (PDZ #2), Magi3 (PDZ #1), PTN3 (PDZ #1), MAST2 (PDZ #1), NeDLG (PDZ #1,2), Shank1 d1, Shank2 d1, Shank3 d1, Syntrophin1 alpha, Syntrophin gamma 1, Magi1 (PDZ #1), Magi1 (PDZ #4), Tip1; PTPL1 (PDZ #1), Mint3 (PDZ #1), Lym Mystique (PDZ #1), DLG2 (PDZ #3), MUPP1 (PDZ #8), NeDLG (PDZ #1), DLG5 (PDZ #1), PSD95 (PDZ #1), NumBP (PDZ #3), LIMK1 (PDZ #1), KIAA0313, DLG1 (PDZ #2), Syntenin (PDZ #2), Pick1, MAST2, PTN3 (PDZ #1), NOS1 (PDZ # 1, 2, 3), MINT1 (PDZ # 2), ZO-1 (PDZ #2), NSP and RIM2 d2.

7. The method of claim 1, wherein said patient sample is selected from the group consisting of blood, tissue, a nasal secretion, a lung exudate, a throat swab and saliva.

8. The method of claim 1, wherein said patient is selected from the group consisting of: a human, a bird, a swine, a horse, and a mammal.

9. The method of claim 3, wherein said PDZ polypeptide comprises a PL-binding domain from PSD95 d2.

10. The method of claim 1, wherein said PDZ polypeptide comprises a PL-binding domain of a PDZ protein selected from the group consisting of: PSD95 d1, PSD95 d2, PSD95 d3, INADL8d1, Magi1 d1, DLG1d2, DLG1d3, NeDLG1d1, and NeDLG1d2.

11. The method of claim 1, comprising:

determining whether NS1 protein of influenza virus type A is present in a nasal secretion, a sputum sample or a throat swab from the patient, presence indicating the patient is infected with influenza virus type A.

12. A method for identifying whether a patient is infected with a pathogenic avian influenza virus type A, comprising:

contacting a patient sample with a PSD-95 PDZ protein; and detecting specific binding between the PSD-95 PDZ protein and the sample, specific binding indicating presence of the influenza virus type A, presence indicating the patient is infected with a pathogenic avian influenza virus type A.

13. The method of claim 12, wherein the pathogenic influenza virus type A is H5N1.

14. The method of claim 12, wherein the PSD-95 PDZ protein comprises a PDZ domain from domain 2 of PSD-95.

15. The method of claim 12, wherein the influenza NS1 protein PL has a motif of ESKV (SEQ ID NO:4), ESLI (SEQ ID NO:3), or ESEV (SEQ ID NO:2).

16. The method of claim 12, wherein the contacting step comprises contacting the patient sample with the PSD-95 PDZ protein and an antibody that specifically binds to a different site of influenza virus type A protein NS1 than the PSD-95 PDZ protein, and the PSD-95 is immobilized on a support, and the detecting step detects the NS1 protein specifically bound to the antibody.

17. A method for identifying whether a patient is infected with a pathogenic avian influenza virus type A, comprising:

contacting a patient sample with a PSD-95 PDZ protein;

detecting specific binding between the PSD-95 PDZ protein and the sample;

contacting the patient sample with a second PDZ protein, INADL d8 as a control; and determining specific binding between the INADL d8 protein and the sample, a greater specific binding of the first PSD-95 protein relative to the second PDZ INADL d8 protein indicating that the patient is infected with a pathogenic avian influenza virus type A.

18. The method of claim 3, wherein the first agent comprises a plurality of PDZ polypeptides immobilized on a support.

19. The method of claim 18, wherein the first agent comprises an array of PDZ polypeptides.

20. The method of claim 19, wherein the second agent comprises at least one anti-NS1 antibody.

21. The method of claim 18, wherein the first agent comprises a plurality of PDZ polypeptides immobilized on beads.

22. The method of claim 21, wherein the second agent comprises at least one anti-NS1 antibody.

23. The method of claim 3, wherein the first agent comprises at least one anti-NS1 antibody immobilized on a support.

24. The method of claim 23, wherein the first agent comprises an array of antibodies.

25. The method of claim 24, wherein the second agent comprises at least one PDZ polypeptide.

26. The method of claim 23, wherein the first agent comprises a plurality of anti-NS1 antibodies immobilized on beads and the second agent comprises at least one PDZ polypeptide.

27. The method of claim 3, wherein the solid support is a component of a lateral flow device.

28. The method of claim 12, wherein the solid support is a component of a lateral flow device.

29. The method of claim 17, wherein the solid support is a component of a lateral flow device.

30. The method of claim 3, wherein the patient is human.

31. The method of claim 12, wherein the patient is human.

32. The method of claim 17, wherein the patient is human.

* * * * *